Figure 1:
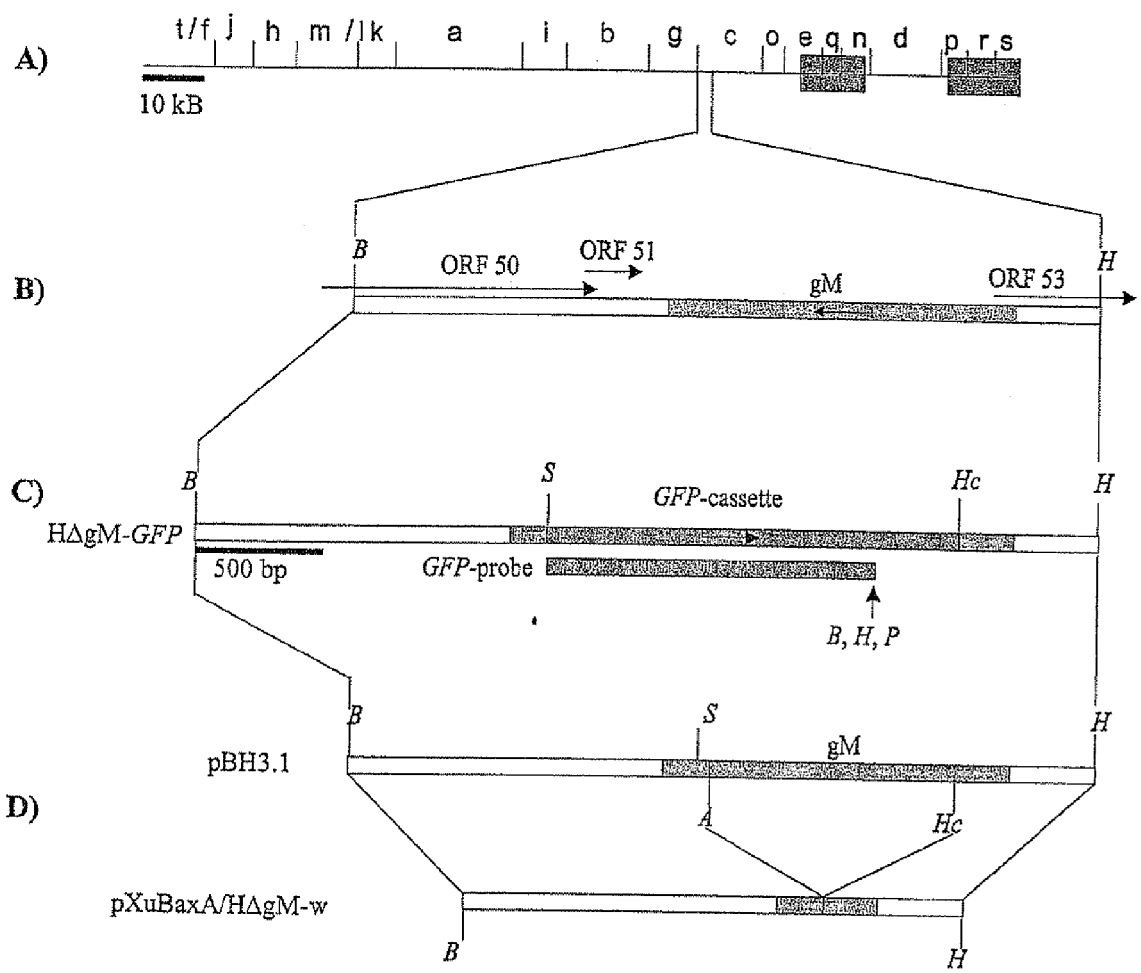

(12) United States Patent
Neubauer et al.

(10) Patent No.: US 7,524,506 B2
(45) Date of Patent: Apr. 28, 2009

(54) GM-NEGATIVE EHV-MUTANTS WITHOUT HETEROLOGOUS ELEMENTS

(75) Inventors: Antonie Neubauer, Munich (DE); Christina Ziegler, Munich (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 0 days.

(21) Appl. No.: 11/550,934

(22) Filed: Oct. 19, 2006

(65) Prior Publication Data

US 2007/0166330 A1    Jul. 19, 2007

Related U.S. Application Data

(62) Division of application No. 10/624,149, filed on Jul. 21, 2003, now Pat. No. 7,141,243.

(60) Provisional application No. 60/403,282, filed on Aug. 14, 2002.

(30) Foreign Application Priority Data

| Jul. 19, 2002 | (DE) | ............................... 102 33 064 |
| Apr. 11, 2003 | (DE) | ............................... 103 17 008 |

(51) Int. Cl.
*A61K 39/12* (2006.01)

(52) U.S. Cl. ................................... 424/199.1
(58) Field of Classification Search ............... 424/199.1
See application file for complete search history.

(56) References Cited

U.S. PATENT DOCUMENTS

| 5,674,735 | A | 10/1997 | Onions et al. |
| 5,853,715 | A | 12/1998 | Macek et al. |
| 6,083,511 | A | 7/2000 | Onions et al. |
| 6,187,320 | B1 | 2/2001 | Darai et al. |
| 6,193,983 | B1 | 2/2001 | Crabb et al. |
| 6,387,685 | B1 | 5/2002 | Markham et al. |
| 6,703,231 | B2 | 3/2004 | Elbers et al. |
| 7,309,598 | B2 * | 12/2007 | Elbers et al. ............. 435/235.1 |

FOREIGN PATENT DOCUMENTS

| EP | 1129722 | 9/2001 |
| WO | WO9826049 | 6/1998 |
| WO | WO0008165 | 2/2000 |
| WO | WO0117553 | 3/2001 |
| WO | WO0209750 | 2/2002 |

OTHER PUBLICATIONS

Elizabeth A.R. Telford et al; The DNA Sequence of Equine Herpesvirus—1; Virology (1992) vol. 189 p. 304-316; Institute of Virology University of Glasgow, Church Street, Glasgow G11 5JR United Kingdom.

Elizabeth A.R. Telford; The DNA sequence of equine herpesvirus—4; Journal of General Virology (1998) vol. 79 p. 1197-1203; Institute of Virology University of Glasgow Church Street, Glasgow G11 5JR UK.

D.R. Fitzpatrick et al; Immunologic relationships between equine herpersvirus type 1 (equine abortion virus) and type 4 (equine rhinopneumonitis virus); Am J. Vet Res. (1984) vol. 45 No. 10 p. 1947-1952; School of Veterinary Science, University of Melbourne Parkville, Victoria 3052 Australia.

Jacobus G.M. Heldens et al; Clinical and virological evaluation of the efficacy of an inactivated EHV1 and EHV4 whole virus vaccine (Duvaxyn EHV 1,4). Vaccination/challenge experiments in foals and pregnant mares; Vaccine (2001) vol. 19 p. 4307-4317; Ford Dodge Animal Health Dept. of Bio R&D.

Nikolaus Osterrieder et al; The Equine Herpesvirus 1 Glycoprotein gp21/22a, the Herpes Simplex Virus Type 1 gM Homolog, Is Involved in Virus Penetration and Cell-to-Cell Spread of Virions; Journal of Virology Jun. 1996 vol. 70 No. 6 p. 4110-4115; American Cancer Society for Microbiology.

Antonie Neubauer et al; Equine Herpesvirus 1 Mutants Devoid of Glycoprotein B or M Are Apathogenic for Mice but Induce Protection against Challenge Infection; Virology 1997 vol. 239 pp. 36-45; Institute for Medical Microbiology, Munich, Germany.

Christian Seyboldt et al; Equine Herpesvirus 1 (EHV-1) Glycoprotein M: Effect of Deletions of Transmembrane Domains; Virology 2000 vol. 278 pp. 477-489; Institute of Molecular Biology and Infectology, Ins Figure 6:
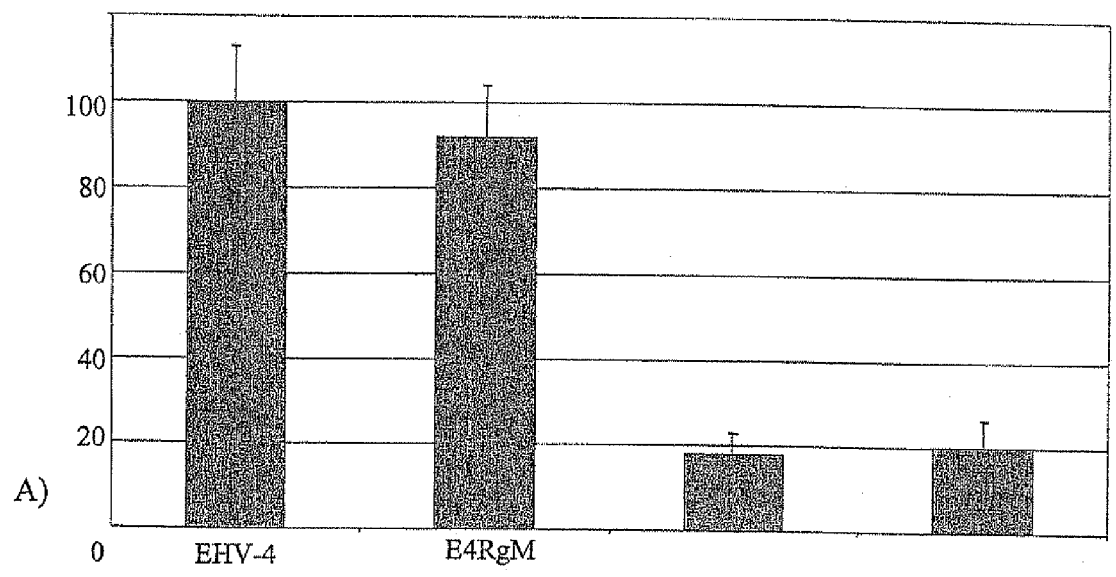
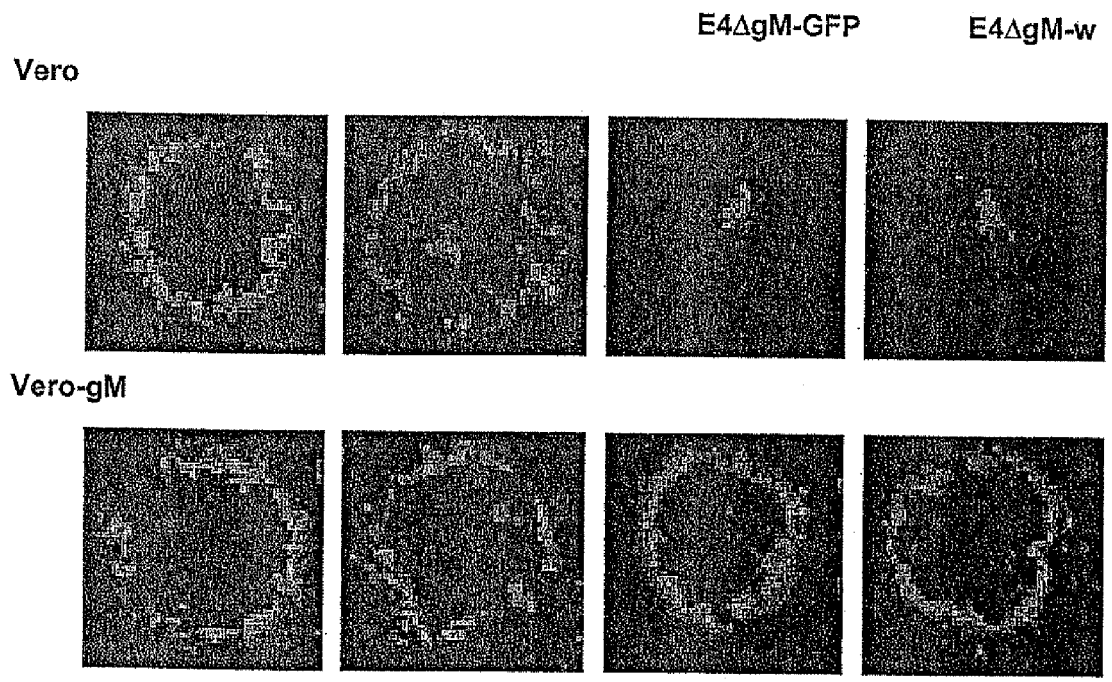

Figure 8:

| Resulting Plasmid: | 5' primer | 3' primer | Length of product (location) |
|---|---|---|---|
| pCgM4 vector: pCDNAI/Amp | 5'gcctctagattaacggtaa tctctgcgc3'; *Xba*I | 5'aaggatccatggcacgacg tggcg3'; *Bam*HI | 1352 bp (nt 92681-94033) |
| pgM4R vector: pGEM3Zf+ | 5'aatctgcaggtagctacgg cctatg 3'; *Pst*I | 5'aagaattcccgcaatacgtc cgtcc3'; *Eco*RI | 3113 bp (nt 91699-94808) |
| pgM4Del1 vector: pTZ18R | 5'ccggatccctaccagaga cccataa3'; *Bam*HI | 5'aagaattcccgcaatacgtc cgtcc3'; *Eco*RI | 983 bp (nt 93825-94808) |
| pgM4Del2 vector: pTZ18R | 5'aatctgcaggtagctacgg cctatg 3'; *Pst*I | 5'ttaagtcgacatttgaataga aactcg 3'; *Sal*I | 1017 bp (nt 91699-92714) |

Figure 10:
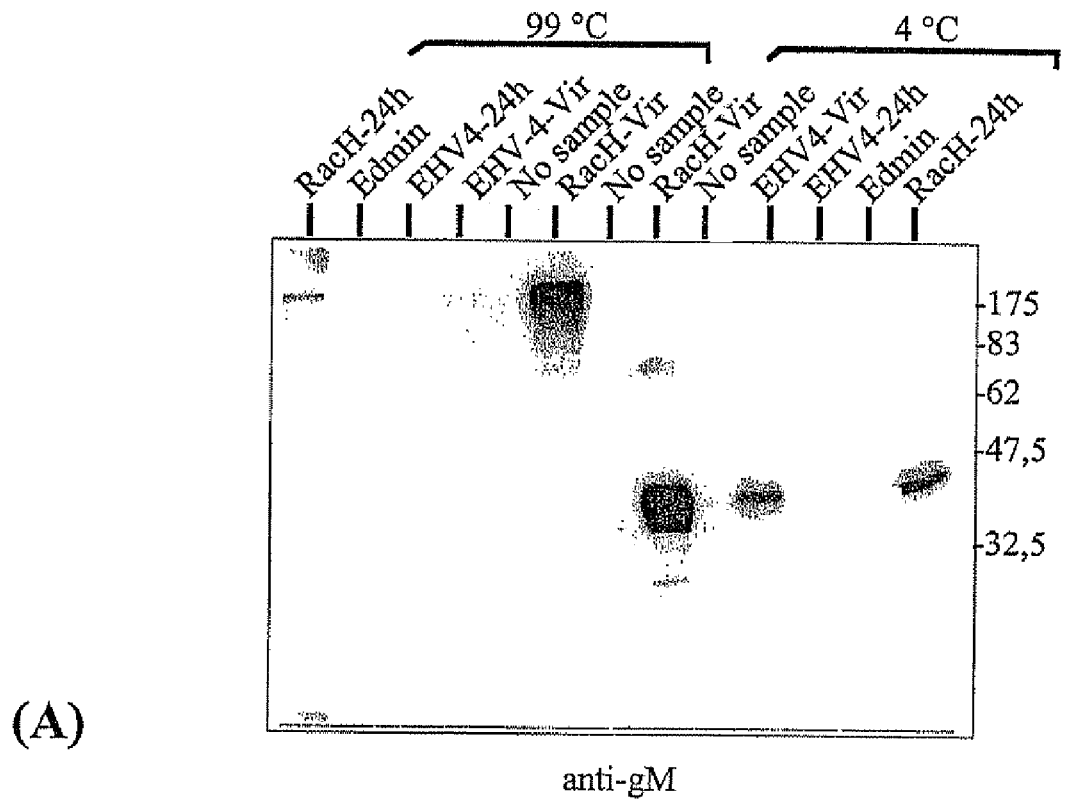
(A)
anti-gM
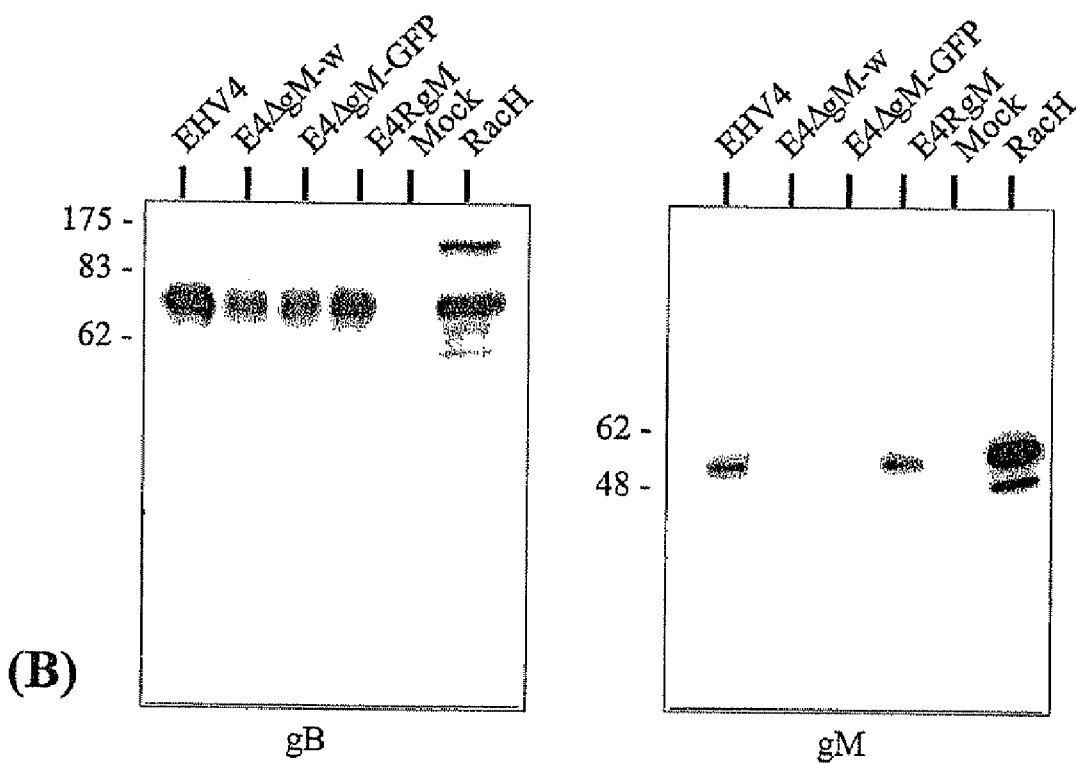
(B)
gB          gM

GM-NEGATIVE EHV-MUTANTS WITHOUT HETEROLOGOUS ELEMENTS

RELATED APPLICATIONS

This application is a division of U.S. application Ser. No. 10/624,149 filed Jul. 21, 2003, which claims the priority benefit of DE 10317008, filed Apr. 11, 2003 and U.S. Provisional Application No. 60/403,282, filed Aug. 14, 2002 and DE 10233064 filed Jul. 19, 2002, are hereby claimed, all of which are incorporated by reference herein.

BACKGROUND OF THE INVENTION

The present invention relates to the field of animal health and in particular of Equine Herpes Viruses (EHV) wherein the gene encoding the protein gM is absent, and which is free of heterologous elements. Further aspects of the invention relate to pharmaceutical compositions comprising said viruses, uses thereof, and methods for the prophylaxis and treatment of EHV infections. The invention also relates to pharmaceutical compositions comprising the combination of EHV-1 and EHV-4 viruses wherein the gene encoding the protein gM is absent and which is free of heterologous elements.

Equine herpesvirus 1 (EHV-1), a member of the Alphaherpesvirinae, is the major cause of virus-induced abortion in equines and causes respiratory and neurological disease. Equine herpesvirus 4 (EHV-4) can also induce respiratory symptoms, abortions or neurological disorder. The entire DNA sequence of both species (EHV-1: Strain Ab4p; EHV-4: Strain NS80567) has been determined (Telford, E. A. R. et al., 1992; Telford, E. A. R. et al., 1998). However, only few genes and gene products have been characterized in regard to their relevance for the virulence and immunogenic properties of EHV.

Herpesvirus glycoproteins are crucially involved in the early stages of infection, in the release of virions from cells, and in the direct cell-to-cell spread of virions by fusion of neighboring cells. To date, 11 herpes simplex virus type 1 (HSV-1)-encoded glycoproteins have been identified and have been designated gB, gC, gD, gE, gG, gH, gI, gJ, gK, gL, and gM. HSV-1 mutants lacking gC, gE, gG, gI, gJ, and gM are viable, indicating that these genes are dispensable for replication in cultured cells. Comparison of the HSV-1 and equine herpesvirus 1 nucleotide sequences revealed that all of the known HSV-1 glycoproteins are conserved in EHV-1. According to the current nomenclature, these glycoproteins are designated by the names of their HSV-1 homologs. It is known that EHV-1 gC, gE and gI are not essential for growth in cell culture, whereas gB and gD are essential for virus growth in cultured cells. The contributions of other EHV-1 glycoproteins to replication in cultured cells are not known (Flowers, C. C. et al., 1992). Transcriptional and protein analyses have shown that the glycoproteins gB, gC, gD, gG, gH, and gK are expressed in EHV-1-infected cells. Glycoprotein gM (encoded by gene UL10 [Baines, J. D. et al., 1991; Baines, J. D. et al., 1993]) is the only reported nonessential glycoprotein which is conserved in all herpesviral subfamilies and has been described for human and murine cytomegalovirus and the Gammaherpesvirinae members EHV-2, herpesvirus saimiri, and Epstein-Barr virus. Like many herpesvirus glycoproteins, HSV-1 gM is present in virions and membranes of infected cells. HSV-1 mutants solely lacking gM grew to titers in cell culture systems reduced approximately 10-fold relative to those of wild-type virus and showed a reduced virulence in a murine model (Baines, J. D. et al., 1991; MacLean, C. A. et al., 1993). The EHV-1 gM homolog (gp21/22a; referred to as EHV-1 gM from now on) was first described by Allen and Yeargan (Allen, G. P. et al, 1987) and was shown to be a major constituent of the virus envelope. Further investigations revealed that gene 52, the gene homologous to HSV-1 UL10, encodes the 450-amino-acid EHV-1 gM polypeptide (Pilling, A. et al., 1994; Telford, E. A. R. et al, 1992). EHV-1 gM represents a multiple hydrophobic protein which contains eight predicted transmembrane domains and has been reported to be present in infected cells and in purified virions as an $M_r$ 45,000 protein (Pilling, A. et al, 1994; Telford, E. A. R. et al, 1992).

For control of EHV-1 infections, two different approaches were followed. First, modified live vaccines (MLVs) have been developed, including the strain RacH (Mayr, A. et al., 1968; Hübert, P. H. et al., 1996), which is widely used in Europe and the United States. Second, inactivated vaccines and subunit vaccines based on recombinant expressed viral glycoproteins such as the glycoproteins (g) B, C, D, and H, which induced partial protection against subsequent challenge EHV-1 infection in a murine model. Subunit vaccines comprising said glycoproteins e.g. gB, gC, gD, and gH only poorly protect against reinfection (Awan et al., 1990, Osterrieder et al., 1995, Tewari et al., 1994, Stokes et al, 1996).

The following U.S. patent applications are also incorporated by reference herein: U.S. patent application Ser. No. 09/789,495, filed Feb. 16, 2001, U.S. patent application Ser. No. 10/105,828, filed Mar. 25, 2002, and U.S. patent application Ser. No. 09/812,720, filed Mar. 20, 2001.

The technical problem underlying this invention was to provide improved vaccines which protect better against EHV infection than prior art vaccines.

FIGURE LEGENDS

FIG. 1: Generation of a gM negative EHV-1 RacH virus without foreign sequences (HΔgM-w)

Figure 2:
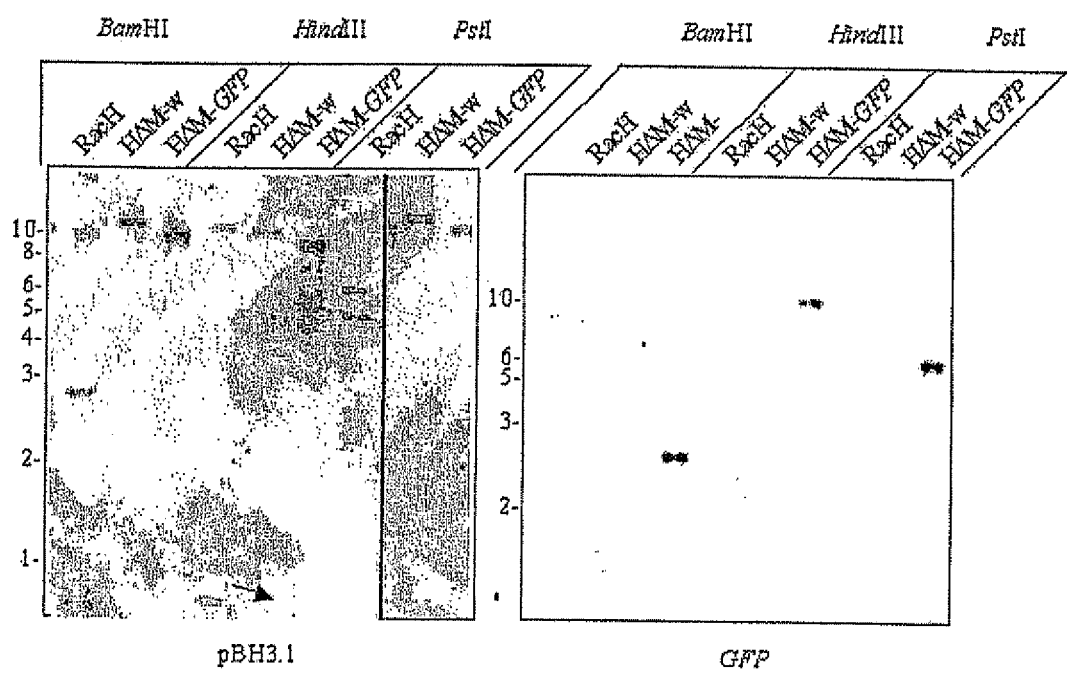

This figure shows the map of viruses and plasmids used for the construction of HΔgM-w. "First-generation" HΔgM virus has previously been constructed by either inserting the *Escherichia coli* lacZ (HΔgM-lacZ) or the green fluorescent protein (GFP) expression cassette (HΔgM-GFP). The BamHI map of EHV-1 strain RacH is shown (A) and the BamHI-HindIII fragment containing the gM-ORF is magnified showing the genomic organization of the region (B). The gM-negative virus, HΔgM-GFP carries a GFP-expression cassette, replacing the major part of the EHV-1 gM gene. The GFP-specific probe, that was used in Southern blots, is depicted (C). Plasmid pBH3.1 carries the EHV-1 BamHI-HindIII fragment of interest and was used to construct plasmid pXuBaxA. After cotransfection of DNA of HΔgM-GFP with plasmid pXuBaxA resulted HΔgM-w (D). Restriction sites: BamHI—B, HindIII—H, SphI—S, HincII—Hc, ApaI—A, PstI—P FIG. 2: Southern blot of gM-deleted EHV-1 virus without foreign sequences (HΔgM-w).

DNA of RacH, HΔgM-GFP and of HΔgM-w was cleaved with BamHI, HindIII or PstI and analyzed with a GFP-specific probe (GFP) or the EHV-1 BamHI-HindIII fragment of pBH3.1 (pBH3.1). DNA-hybrids were detected by chemoluminescence using CSPD. Molecular weight marker sizes (Biolabs) are given in kbp on the left margin. The arrow points to a barely visible specific hybrid.

Figure 3:
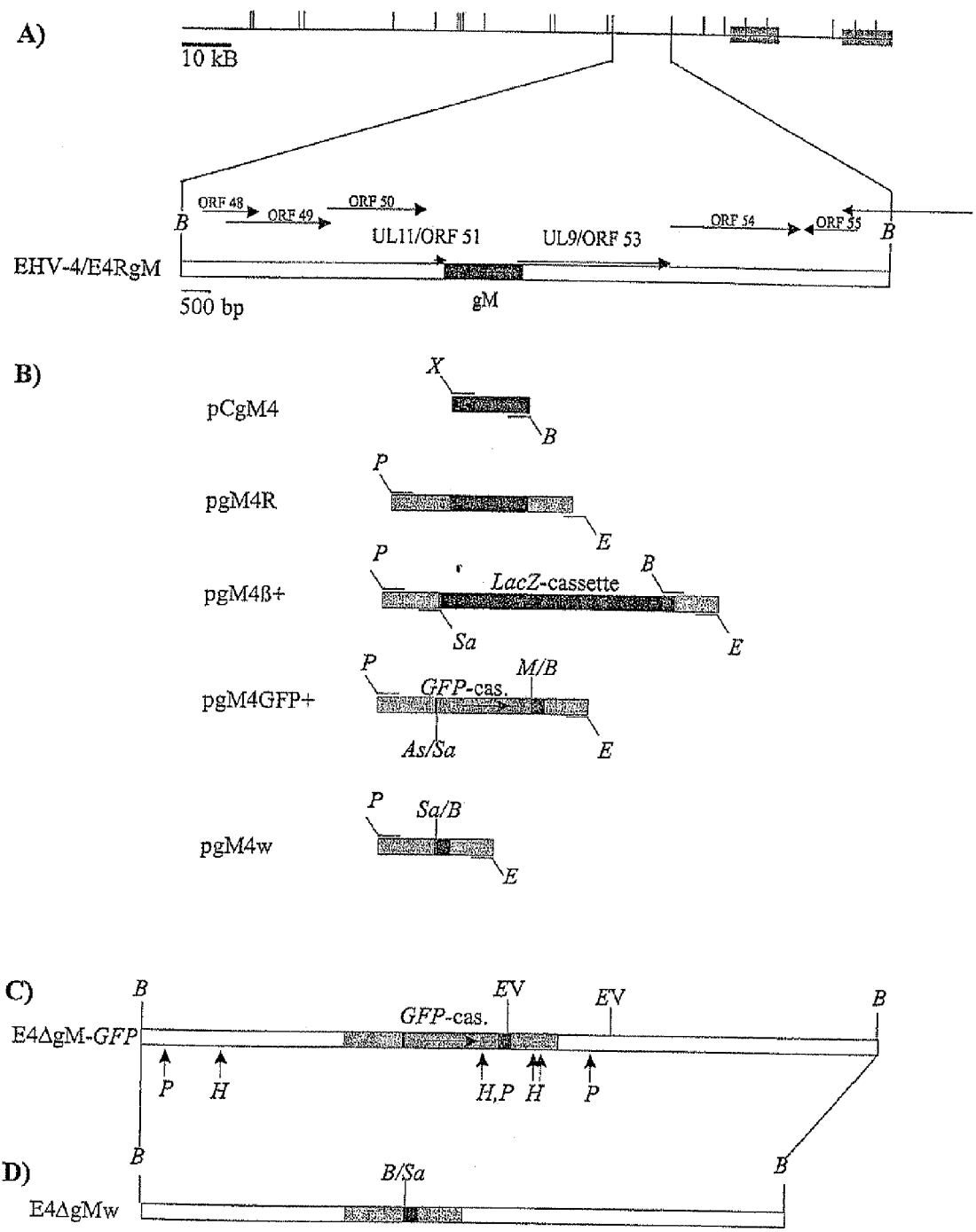

FIG. 3: Generation of a gM negative EHV-4 virus without foreign sequences (E4ΔgM-w).

Figure 4:
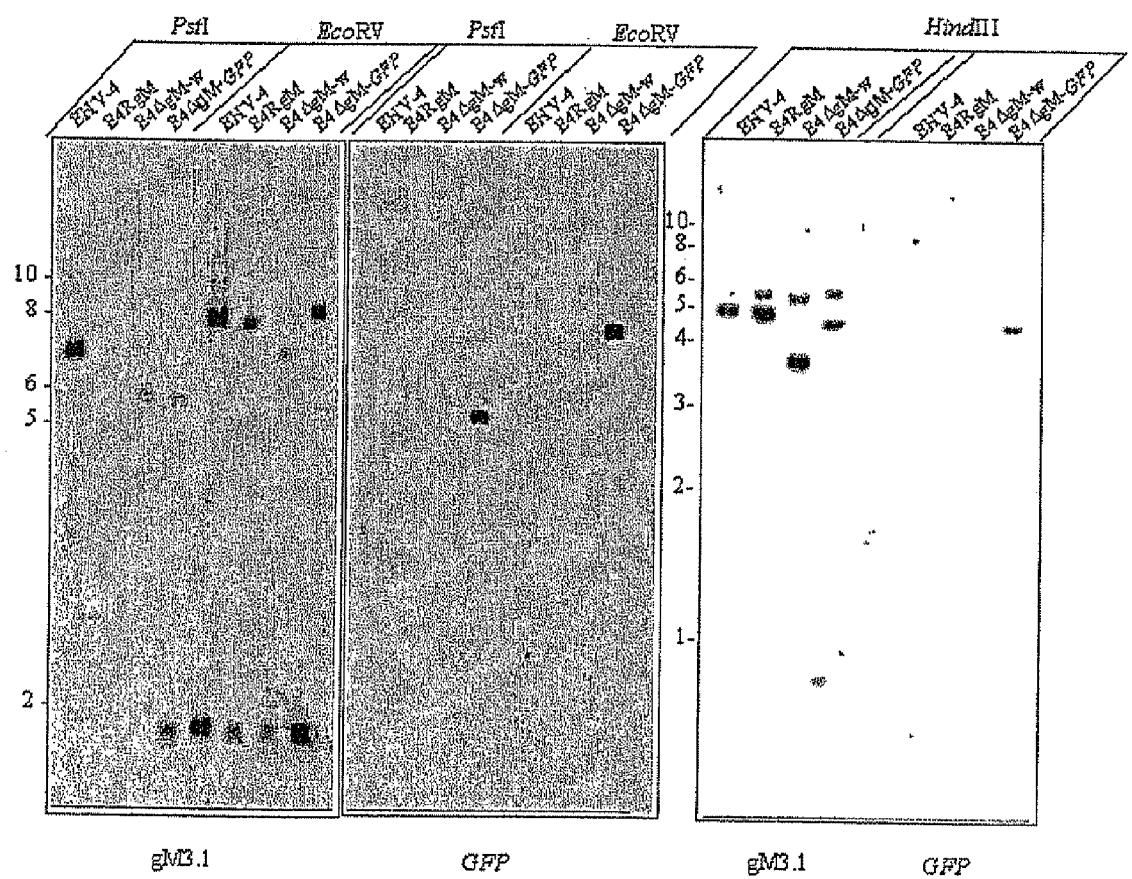
Figure 5:
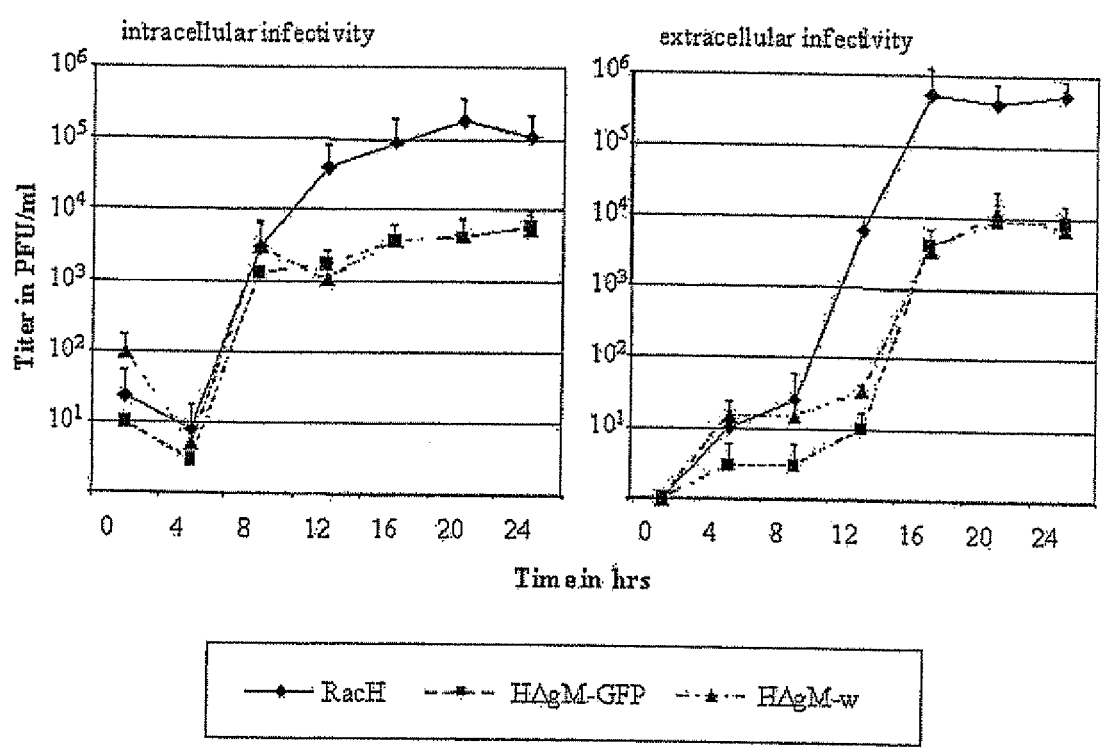
Figure 7:
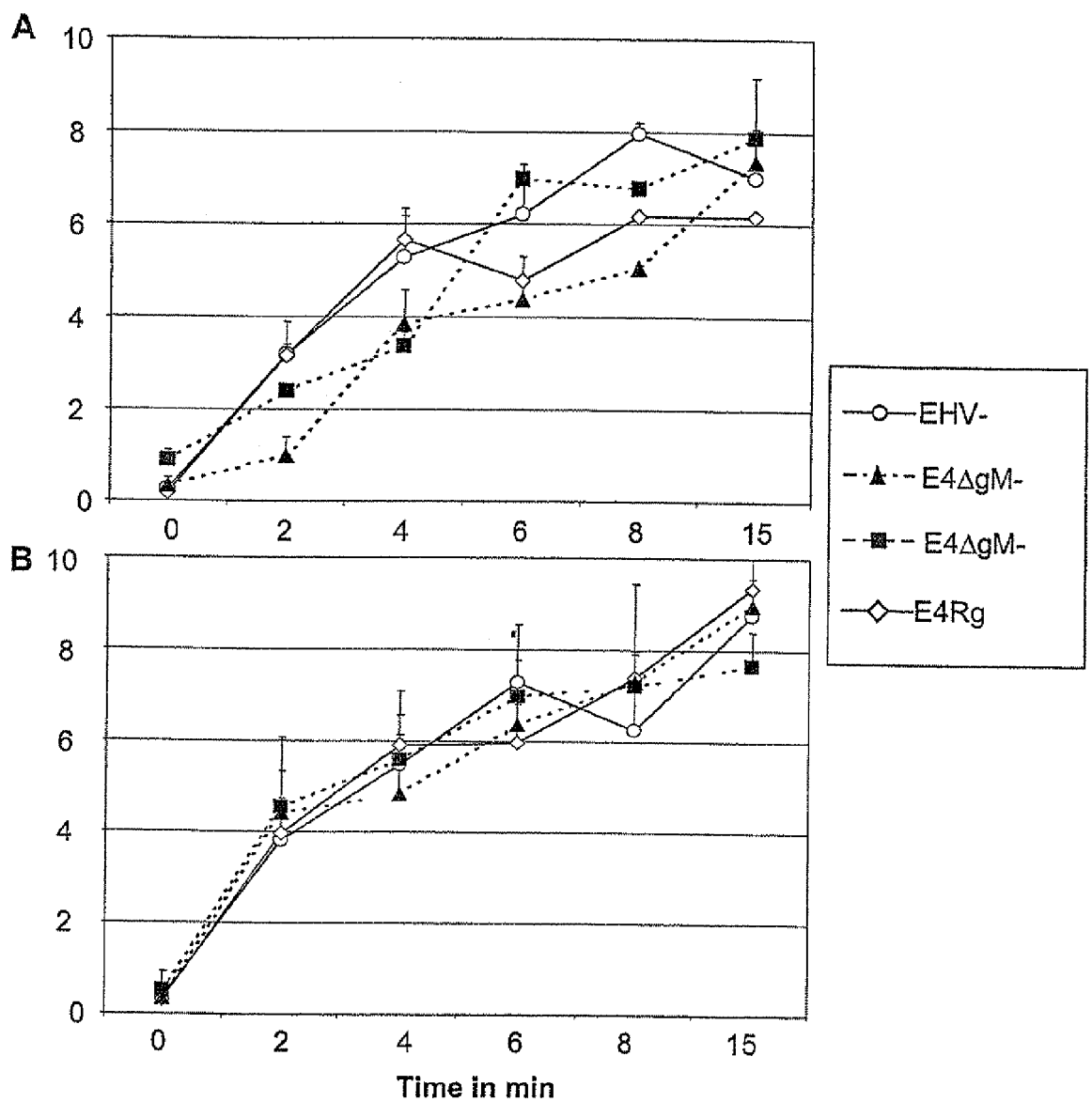
Figure 9:
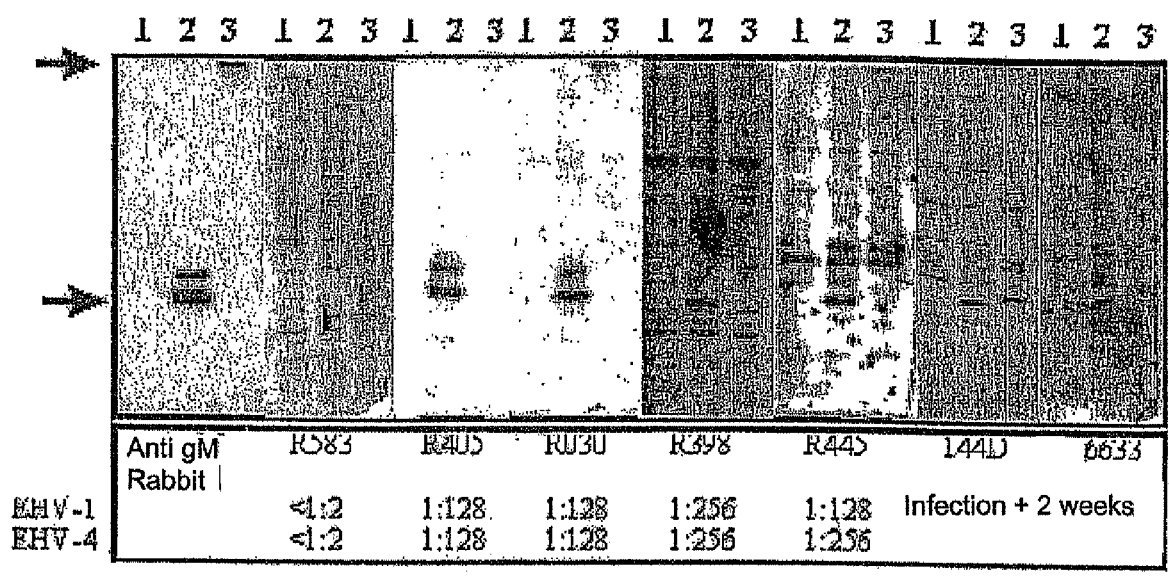

In this figure, a BamHI map of EHV-4 strain NS80567 is depicted. The enlarged BamHI-e fragment encompasses the gM- and neighboring ORFs (A). Plasmid constructs and priming sites are depicted (B). Plasmid pgM4GFP+ was used for the generation of E4ΔgM-GFP, the GFP-positive and gM negative EHV-4 (B, C). Recombination of DNA of E4ΔgM-GFP with either plasmid pgM4R (B), containing 3.109 bp of EHV-4 sequences including the gM-ORF, resulted in E4RgM, the gM-repaired EHV-4 (A), or with plasmid pgM4w (B) resulted in E4ΔgM-w, the GFP- and gM-negative EHV-4 (D). Restriction sites: BamHI—B, PstI—P, EcoRI—E, SalI—Sa, MluI—M, AsnI—As, EcoRV—EV FIG. 4: Southern blot of a gM-deleted EHV-4 virus without foreign sequences (E4ΔgM-w).

DNA of EHV-4, E4RgM, E4ΔgM-w and E4ΔgM-GFP were cleaved with PstI, EcoRV or HindIII as indicated and DNA-fragments blotted onto nylon membranes. Parallel membranes were either hybridized with GFP-specific sequences or with a probe, named gM3.1, containing the EHV-4 specific sequences taken out of plasmid pgM4R (FIG. 3). DNA hybrids were detected by chemoluminescence using CSPD. Molecular weight marker sizes (Biolabs) are given in kbp.

FIG. 5: Growth characteristics of the gM deleted EHV-4 virus, E4ΔgM-w.

Cells were infected with an MOI of 2 of the different viruses, as listed in the box. Kinetics of virus growth are depicted as virus titers determined in supernatants of infected cells (extracellular activity) or within infected cells (intracellular activity) relative to the time point indicated. Shown are the means of two individual experiments, standard deviations are given as error bars.

FIG. 6: Plaque sizes of E4ΔgM-w.

Vero or Vero-gM cells in 6-well plates were infected with 50 PFU of either EHV-4, E4RgM, E4ΔgM-GFP or E4ΔgM-w. Maximal diameters of 150 respective plaques were determined and average plaque sizes are given in %, relative to sizes of wildtype plaques, that were set 100%. Standard deviations are given as error bars (A). Plaques were stained by indirect immunofluorescence (anti-gD Mab 20C4, 1:1000) at day 4 p.i. and analyzed in an Axioscope (×100, Zeiss, Germany). Pictures were scanned and digitally processed (B).

FIG. 7: EHV-4 virus penetration into Vero cells.

Penetration of EHV-4, E4RgM, E4ΔgM-w and E4ΔgM-GFP produced on non complementing Vero cells (A) or on complementing Vero-gM cells (B) into Vero cells. At given time points the penetration efficiency was determined as the percentage of the number of plaques present after citrate treatment relative to that of plaques present after control treatment. Means of two independent experiments are given. Standard deviations are depicted as error bars.

FIG. 8: PCR primer sequences and location of amplificates within the EHV-4 genome.

Sequences representing restriction enzyme recognition sites are printed in bold and the respective enzymes are listed. PCR products were inserted into the given vectors, resulting in plasmids pCgM4, pgM4R pgM4Del1 or pgM4Del2, as indicated. The location of a fragment within the EHV-4 genome is given relative to the sequence determined by Telford et al. (1998) (SEQ ID NO:2).

FIG. 9: Western Blot analysis of horse sera.

Lysates of EHV-1 gM expressing cell line ccgM and Rk13 cells were either heated for 2 min at 56° C. (1,2) or for 5 min at 95° C. (3) (gM is highly hydrophobic and known to aggregate upon boiling, so that it does not enter the separating gel anymore). Identical blots were incubated with various horse sera (1:3000) or the anti-gM rabbit serum. Arrows point to gM specific reactivity in boiled and unboiled samples. Neutralizing test titers (NT) are given for sera, that were obtained from the virological diagnostic unit.

FIG. 10:

(A) Comparison of EHV-1 gM to EHV-4 gM using an anti-EHV-1 gM polyclonal antibody. Cells were infected with the indicated viruses (MOI of 0.5-1) and cell lysates were prepared at the stated time points p.i. EHV-1 or -4 virions were purified by repeated centrifugation through a sucrose cushion (30%) and resuspended in PBS. Samples were mixed with buffer containing 5% 2-mercaptoethanol and then either heated to 99° C. for 5 min or left at 4° C. Proteins were separated by SDS-10% PAGE and blotted onto nitrocellulose filters. Antibody binding was visualized using anti-rabbit immunoglobulin G (IgG) peroxidase conjugate (Sigma) followed by ECLTM detection (Pharmacia-Amersham).

(B) Virions were purified of Edmin337 cells infected with EHV-4, E4ΔgM-w, E4ΔgM-GFP or E4RgM and subjected to Western blot analysis as described in (A). gB reactivity of virions was then compared to gM reactivity using anti EHV-1 gB monoclonal antibody 3F6 or the anti EHV-1 gM polyclonal antibody.

DESCRIPTION OF THE INVENTION

Definitions of Terms Used in the Description:

Before the embodiments of the present invention it must be noted that as used herein and in the appended claims, the singular forms “a”, “an”, and “the” include plural reference unless the context clearly dictates otherwise. Thus, for example, reference to “an EHV virus” includes a plurality of such EHV viruses comprising also all subspecies like EHV1, 4 and others, reference to the “cell” is a reference to one or more cells and equivalents thereof known to those skilled in the art, and so forth. Unless defined otherwise, all technical and scientific terms used herein have the same meanings as commonly understood by one of ordinary skill in the art to which this invention belongs.

Although any methods and materials similar or equivalent to those described herein can be used in the practice or testing of the present invention, the preferred methods, devices, and materials are now described. All publications, patents and patent applications mentioned herein are incorporated herein by reference for the purpose of describing and disclosing the cell lines, vectors, and methodologies as reported which might be used in connection with the invention. Nothing herein is to be construed as an admission that the invention is not entitled to antedate such disclosure by virtue of prior invention.

The term “EHV” as used herein refers to all equine herpes viruses such as species EHV-1 and EHV-4 within the family Alphaherpesvirinae. The terms EH-virus, EH virus EHV virus, EHV-virus and EHV all relate to equine herpes viruses.

Virulence: “virulence” as used herein relates to an EH-virus capable of propagating in the target host species (i.e. horses) with the potential to induce subclinical and clinical disease characterized by respiratory symptoms, abortions or neurological disorders. Examples of virulent EHV are wild-type viruses inducing strong clinical symptoms. Examples of virulence factors are hemolysins (lysing red blood cells) or adhesins (proteins by which the pathogen can adhere to the host and initiate colonisation or invasion). More specifically, “virulence” here means that the gM gene product, a major constituent of the virus envelope, enables the virus to penetrate the host and is involved in cell-to-cell spread.

Attenuation: “An attenuated EH-virus” as used herein is relates to infectious EHV which do not cause EHV-associated subclinical or clinical disease. In particular according to the invention, such attenuated EH-viruses are EHV which can replicate and do not express gM.

A "functional variant" of the EH-virus according to the invention is EHV virus which possesses a biological activity (either functional or structural) that is substantially similar to the EHV according to the invention. The term "functional variant" also includes "a fragment", "a functional variant", "variant based on the degenerative nucleic acid code" or "chemical derivative". Such a "functional variant" e.g. may carry one or several nucleic acid substitutions, deletions or insertions. Said substitutions, deletions or insertions may account for 10% of the entire sequence. Said functional variant at least partially retains its biological activity, e.g. function as an infectious clone or a vaccine strain, or even exhibits improved biological activity.

A "variant based on the degenerative nature of the genetic code" is a variant resulting from the fact that a certain amino acid may be encoded by several different nucleotide triplets. Said variant at least partially retains its biological activity, or even exhibits improved biological activity.

A "fusion molecule" may be the DNA molecule or infectious EHV virus according to the invention fused to e.g. a reporter such as a radiolabel, a chemical molecule such as a fluorescent label or any other molecule known in the art.

As used herein, a "chemical derivative" according to the invention is a DNA molecule or infectious EHV clone according to the invention chemically modified or containing additional chemical moieties not normally part of the molecule. Such moieties may improve the molecule's solubility, absorption, biological half-life etc.

A molecule is "substantially similar" to another molecule if both molecules have substantially similar nucleotide sequences or biological activity. Thus, provided that two molecules possess a similar activity, they are considered variants as that term is used herein if the nucleotide sequence is not identical, and two molecules which have a similar nucleotide sequence are considered variants as that term is used herein even if their biological activity is not identical.

The term "vaccine" as used herein refers to a pharmaceutical composition comprising at least one immunologically active component that induces an immunological response in an animal and possibly but not necessarily one or more additional components that enhance the immunological activity of said active component. A vaccine may additionally comprise further components typical to pharmaceutical compositions. The immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of said organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian or other species plus optionally subsequent isolation and purification procedures, or by induction of said synthetic processes in the animal needing a vaccine by direct incorporation of genetic material using suitable pharmaceutical compositions (polynucleotide vaccination). A vaccine may comprise one or simultaneously more than one of the elements described above.

The term "vaccine" as understood herein is a vaccine for veterinary use comprising antigenic substances and is administered for the purpose of inducing a specific and active immunity against a disease provoked by EHV. The EHV vaccine according to the invention confers active immunity that may be transferred passively via maternal antibodies against the immunogens it contains and sometimes also against antigenically related organisms.

Additional components to enhance the immune response are constituents commonly referred to as adjuvants, like e.g. aluminumhydroxide, mineral or other oils or ancillary molecules added to the vaccine or generated by the body after the respective induction by such additional components, like but not restricted to interferons, interleukins or growth factors.

A "vaccine composition" or "pharmaceutical composition" essentially consists of one or more ingredients capable of modifying physiological e.g. immunological functions of the organism it is administered to, or of organisms living in or on the organism. The terms include, but are not restricted to antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

Disclosure of the Invention

The invention overcomes the difficulties and prejudice in the art that an equine herpes virus cannot be generated free of foreign sequences. The solution to the above technical problem is achieved by the description and the embodiments characterized in the claims. By using the methods according to the invention, EH-viruses of superior quality for use in vaccines are provided. The central coding sequence for the protein gM is eliminated in a way that the remaining gM carboxyterminal sequences are in a different reading frame than the aminoterminal sequences. The neighboring gene for the essential protein UL9 homolog (gene 53), its orientation and overlap with the gene coding for the protein gM requires that a minimal nucleotide sequence of the gene for gM must remain to allow the expression of gene 53 and thereby retain virus viability. Therefore, an EHV according to the invention relates to EHVs that are characterized in that the gene coding for the protein gM is deleted in a way that the expression of the gene coding for the UL9 homolog (gene 53) is not affected. The term "not affected" does not relate to certain quantity or qualitative properties of UL9 but simply means that the expression of the gene is not affected as long as said protein is expressed by the virus and present in an essentially sufficient amount for the viability of the virus.

The long lasting need in the art for a vaccine comprising recombinant equine herpesvirus 4 is satisfied by the present invention which overcomes major difficulties in the art. The EHV-1 and EHV-4 viruses according to the invention may advantageously be used, for example, in a vaccine.

Hence, in a first important embodiment, the invention relates to a recombinant Equine Herpes Virus (EHV) wherein the gene encoding protein gM, and therefore gM itself, is absent, characterized in that it is free of heterologous elements. "Free of heterologous elements" means that no foreign sequence, i.e. no non-EHV sequence, such as a lacZ- or GFP-encoding cassette, is present in the coding sequence for said virus according to the invention (a so-called "white clone"). Thus, the EHV according to the invention is entirely encoded by EHV sequences. The EHV according to the invention is free of bacterial elements or nucleic acids encoding said bacterial elements. Furthermore, almost the entire coding sequence for the gM protein and therefore the encoded above-mentioned gM protein is eliminated. Thus, preferably, said EHV according to the invention is characterized in that the protein gM is absent due to deletion of the gene coding for the protein gM. However, as set out supra, "the gene encoding protein gM is absent" also requires that a minimum gM sequence remains so that at least the overlapping gene 53 sequence is still present, while the remaining gM sequences may be deleted (see infra). This may all be accomplished by molecular biology techniques (see infra) so that recombinant EHV are generated.

The use of lacZ as a marker for successful deletion of the gM gene of EHV-1 or 4 did not lead to successful generation of viruses according to the invention (see Examples 1, 2). The inventors therefore developed an inventive method to obtain said virus. An EH-virus was constructed in which the gM gene was deleted by insertion of a cassette containing the GFP marker. This approach surprisingly allowed the differentiation between input virus (green fluorescent plaques) and new recombinant plaques (non-fluorescent plaques).

Preferred is an EHV obtainable by a method comprising the steps of:

a) isolating a wild-type EHV;
b) establishing a plasmid encoding the EHV gM gene, optionally with flanking sequences;
c) generating a complementing cell line expressing gM or parts thereof;
d) establishing an EH virus carrying a GFP-encoding cassette insert in its gM coding sequence by co-transfecting the complementing cell line of step b) with EHV-nucleic acid and a plasmid encoding gM which is interrupted by a GFP-encoding cassette insert;
e) deleting the GFP-encoding cassette; and
f) selecting for the EHV clones wherein the GFP-encoding cassette is successfully deleted.

"lacZ" is known to the artisan as the gene encoding β-galactosidase. According to the invention, "GFP" relates to green fluorescent protein (GFP) produced by the bioluminescent jellyfish (Chalfie et al., 1994).

"Complementing cell line" refers to a cell line, into which a gene normally not present in the cell line genome is introduced and expressed constitutively. Useful cell lines include, but are not limited to rabbit kidney cell line Rk13, cell line cc (Seyboldt et al., 2000) or the Vero cell lines (ATCC catalogue # CRL-1586), such as clone 1008, as also disclosed in Examples 1 and 2, and any other cell line known to the artisan. Usually it can be selected for cell clones expressing this additional protein. This cell line expresses the gene which is deleted in the virus, complementing this deficiency, and enables the growth of the virus after gene deletion.

Standard molecular biology methods of use of restriction enzymes, ligation, PCR, transfection etc. are known in the art (see e.g. Sambrook et al. (1989). Molecular Cloning: A Laboratory Manual, 2$^{nd}$ ed., Cold Spring Harbor Laboratory Press, Cold Spring Harbor, N.Y.)

Preferably, such EHV according to the invention is characterized in that it is EHV-1. More preferred, the EHV-1 according to the invention is characterized in that 850-1100 bp of the 1332 bp gM open reading frame are deleted. Even more preferred, the EHV-4 according to the invention is characterized in that 900-1000 bp of the gM open reading frame are deleted. More preferred also, the EHV-1 according to the invention is characterized in that 960-970 bp of the gM open reading frame are deleted (960, 961, 962, 963, 964, 965, 966, 967, 968, 969 or 970 bp). Most preferred, the EHV-1 according to the invention is characterized in that 962 bp of the gM open reading frame are deleted.

More preferred, the EHV-1 according to the invention is characterized in that the coding sequence for gM is deleted except for 150-200 base pairs (bp) of the coding sequence encoding the C-terminal portion of gM and 150-250 bp of the coding sequence encoding the N-terminal portion of gM. In this more preferred embodiment, the coding sequence of gM is deleted, only nucleotides 93118-93267 to 93118-93317 of the sequence encoding the C-terminal portion of gM and nucleotides 94223-94472 to 94323-94472 of the coding sequence encoding the N-terminal portion of gM remain. Thus, more preferred is an EHV-1 according to the invention characterized in that nucleotides 93268-93318 to 94222-94322 (encoding the core portion of gM) are deleted (numbering according to Telford, 1992, SEQ ID NO:1). Within the given ranges, any number of nucleotides may be deleted. Thus, according to the invention, the deletions may start no lower than nucleotide position 93268, but has to begin at position 93318. The deletion may end as early as position 94222, but no later than position 94322. Thus, a preferred EHV-1 according to the invention is characterized in that nucleotides 93268 to 94322 of the gM coding sequence as corresponding to SEQ ID NO:1 are deleted. Any combination is within the scope of the invention, such as 93272 to 94312, 93300 to 94300 and so forth.

Even more preferred, the EHV-1 according to the invention is characterized in that the coding sequence for gM is deleted except for 160-190 bp of the coding sequence encoding the C-terminal portion of gM and 190-220 bp of the coding sequence encoding the N-terminal portion of gM. In this more preferred embodiment, the coding sequence of gM is deleted, only nucleotides 93118-93277 to 93118-93307 of the sequence encoding the C-terminal portion of gM and nucleotides 94253-94472 to 94283-94472 of the coding sequence encoding the N-terminal portion of gM remain. Thus, more preferred is an EHV-1 according to the invention characterized in that nucleotides 93278-93308 to 94252-94282 (encoding the core portion of gM) are deleted (numbering according to SEQ ID NO:1).

More preferred also, the EHV-1 according to the invention is characterized in that the coding sequence for gM is deleted except for 180 to 190 (180, 181, 182, 183, 184, 185, 186, 187, 188, 189, 190) bp of the coding sequence encoding the C-terminal portion of gM coding sequence and 200 to 210 (200, 201, 202, 203, 204, 205, 206, 207, 208, 209 or 210) bp of the coding sequence encoding the N-terminal portion of gM. In this more preferred embodiment, the coding sequence of gM is deleted, only nucleotides 93118-93297 to 93118-93307 (93297, 93298, 93299, 93300, 93301, 93302, 93303, 93304, 93305, 93306, 93307) of the sequence encoding the C-terminal portion of gM and nucleotides 94263-94472 to 94273-94472 (94263, 94264, 94265, 94266, 94267, 94268, 94269, 94270, 94271, 94272, 94273) of the coding sequence encoding the N-terminal portion of gM remain. Thus, more preferred is an EHV-1 according to the invention characterized in that nucleotides 94298-94308 to 94262-94272 (encoding the core portion of gM) are deleted (numbering according to SEQ ID NO:1). This means, that any nucleotides inside the above-mentioned remaining nucleotides may be deleted according to the invention, e.g. nucleotides 94299-94263 or 94299-94264 or 94300-94272 or any combination thereof.

Most preferred, the EHV-1 according to the invention is characterized in that the coding sequence for gM is deleted except for 184 bp of the coding sequence encoding the C-terminal portion of gM coding sequence and 209 bp of the coding sequence encoding the N-terminal portion of gM. In this most preferred embodiment, the coding sequence of gM is deleted, only nucleotides 93118-93301 of the sequence encoding the C-terminal portion of gM and nucleotides 94264-94472 of the coding sequence encoding the N-terminal portion of gM remain. Thus, most preferred is an EHV-1 according to the invention characterized in that nucleotides 94263 to 93302 (encoding the core portion of gM) are deleted (numbering according to SEQ ID NO:1). In this most preferred embodiment, 962 nucleotides of the sequence encoding gM are deleted. This is exemplified in a non-limiting manner in Example 1.

Also more preferred is an EHV-1 characterized in that gM is deleted and it is free of heterologous elements and it is a recombinant variant based on a strain selected from the group of AB69 (ATCC VR2581), EHV-1 Ts-mutant ECACC V99061001, KyA, KyD, Ab1, Ab4, RacH, RacL11 or RacM of EHV-1 and no heterologous elements such as GFP- or lacZ-elements are present. Also more preferred, an EHV-1 according to the invention is characterized in that gM is deleted and it is free of heterologous elements such as GFP- or lacZ-elements and it is a recombinant variant based on strain RacH of EHV-1. Most preferred, an EHV-1 according to the invention is characterized in that gM is deleted and it is free of heterologous elements such as GFP- or lacZ-elements and it is the RacH-based recombinant variant isolate HΔgM-w as disclosed in Example 1. Said EHV-1 HΔgM-w according to the invention was deposited at the "Centre for Applied Microbiology and Research (CAMR) and European Collection of Cell Cultures (ECACC)", Salisbury, Wiltshire SP4 0JG, UK, as patent deposit according to the Budapest Treaty. The date of deposit was Oct. 16, 2002, the preliminary identification reference is H-delta-gM-w, and the accession number given by the international depository authority ECACC/CAMR is 02101663. Also preferred are EHV-1 having all of the identifying characteristics of said deposited EHV-1.

All before-mentioned EHV-1 have superior properties over viruses with heterologous elements such as GFP. Said EHV-1 according to the invention have an advantageously higher extracellular infectivity than those still comprising heterologous elements. This is exemplified in FIG. 5 (e.g. between 4 and 12 hours).

Until the present invention was made, no one in the art was able to generate a recombinant EHV-4 virus which may be used as a vaccine. EHV-1 and EHV-4 are homologous and cross-reactive to some degree. However, there was a long need in the art for attenuated EHV-4 viruses as EHV-1 does not appear to provide sufficient protection against EHV-4 infection. Thus, preferably, an EHV according to the invention is characterized in that it is EHV-4. More preferred, the EHV-4 according to the invention is characterized in that 900-1150 bp of the 1332 bp gM open reading frame are deleted. Even more preferred, the EHV-4 according to the invention is characterized in that 1000-1150 bp of the gM open reading frame are deleted. More preferred also, the EHV-1 according to the invention is characterized in that 1110-1115 bp of the gM open reading frame are deleted (1110, 1111, 1112, 1113, 1114 or 1115 bp). Most preferred, the EHV-1 according to the invention is characterized in that 1110 bp of the gM open reading frame are deleted.

More preferred, the EHV-4 according to the invention is characterized in that the coding sequence for gM is deleted except for 0-50 base pairs (bp) of the coding sequence encoding the C-terminal portion of gM and 150-250 bp of the coding sequence encoding the N-terminal portion of gM. In this more preferred embodiment, the coding sequence of gM is deleted, only nucleotides 92681-92680 to 92681-92730 of the sequence encoding the C-terminal portion of gM and nucleotides 93766-94033 to 93866-94033 of the coding sequence encoding the N-terminal portion of gM remain. Thus, more preferred is an EHV-4 according to the invention characterized in that nucleotides 92681-92731 to 93765-93865 (encoding the core portion of gM) are deleted (numbering according to SEQ ID NO:2). Within the given ranges, any number of nucleotides may be deleted. Thus, according to the invention, the deletions may start no lower than nucleotide position 92681, but has to begin at position 92731. The deletion may end as early as position 93765, but no later than position 93865. Thus, preferably, an EHV-4 according to the invention is characterized in that nucleotides 92681 to 93865 of the gM coding sequence as corresponding to Telford positions (1998) (SEQ ID NO:2) are deleted. Any combination is within the scope of the invention, such as 92672 to 93801, 92700 to 93800 and so forth.

Even more preferred, the EHV-4 according to the invention is characterized in that the coding sequence for gM is deleted except for 10-40 bp of the coding sequence encoding the C-terminal portion of gM and 190-220 bp of the coding sequence encoding the N-terminal portion of gM. In this more preferred embodiment, the coding sequence of gM is deleted, only nucleotides 92681-92690 to 92681-92720 of the sequence encoding the C-terminal portion of gM and nucleotides 93806-94033 to 93836-94033 of the coding sequence encoding the N-terminal portion of gM remain. Thus, more preferred is an EHV-4 according to the invention characterized in that nucleotides 92691-92721 to 93805-93835 (encoding the core portion of gM) are deleted (numbering according to SEQ ID NO:2).

More preferred also, the EHV-4 according to the invention is characterized in that the coding sequence for gM is deleted except for 30 to 40 (30, 31, 32, 33, 34, 35, 36, 37, 38, 39 or 40) bp of the coding sequence encoding the C-terminal portion of gM coding sequence and 200 to 210 (200, 201, 202, 203, 204, 205, 206, 207, 208, 209 or 210) bp of the coding sequence encoding the N-terminal portion of gM. In this more preferred embodiment, the coding sequence of gM is deleted, only nucleotides 92681-92710 to 92681-92720 (92710, 92711, 92712, 92713, 92714, 92715, 92716, 92717, 92718, 92719, 92720) of the sequence encoding the C-terminal portion of gM and nucleotides 93816-94033 to 93826-94033 (93824, 93825, 93826, 93827, 93828, 93829, 93830, 93831, 93832, 93833, 93834) of the coding sequence encoding the N-terminal portion of gM remain. Thus, more preferred is an EHV-4 according to the invention characterized in that nucleotides 92711-92721 to 93823-93833 (encoding the core portion of gM) are deleted (numbering according to SEQ ID NO:2). This means, that any nucleotides inside the above-mentioned remaining nucleotides may be deleted according to the invention, e.g. nucleotides 94299-94257 or 94299-94256 or 94300-94257 or any combination thereof.

Most preferred, the EHV-4 according to the invention is characterized in that the coding sequence for gM is deleted except for 34 bp of the coding sequence encoding the C-terminal portion of gM coding sequence and 209 bp of the coding sequence encoding the N-terminal portion of gM. In this most preferred embodiment, the coding sequence of gM is deleted, only nucleotides 92681-92714 of the sequence encoding the C-terminal portion of gM and nucleotides 93825-94033 of the coding sequence encoding the N-terminal portion of gM remain. Thus, most preferred is an EHV-4 according to the invention characterized in that nucleotides 92715 to 93824 (encoding the core portion of gM) are deleted (numbering according to SEQ ID NO:2). In this most preferred embodiment, 1110 nucleotides of the sequence encoding gM are deleted. This is exemplified in a non-limiting manner in Example 2.

Also more preferred, an EHV-4 according to the invention is characterized in that gM is deleted and it is free of heterologous elements such as GFP- or lacZ-elements and it is a recombinant variant based on strain MSV Lot 071398 of EHV-4. Most preferred, an EHV-4 according to the invention is characterized in that gM is deleted and it is free of heterologous elements such as GFP- or lacZ-elements and it is based on strain MSV Lot 071398 and isolate E4ΔgM-4 as disclosed in Example 2. Said EHV-1 HΔgM-w according to the invention was deposited at the "Centre for Applied Microbiology and Research (CAMR) and European Collection of Cell Cultures (ECACC)", Salisbury, Wiltshire SP4 0JG, UK, as patent deposit according to the Budapest Treaty. The date of deposit was Jan. 14, 2003, the preliminary identification reference is EHV-4, and the accession number given by the international depositary authority ECACC/CAMR is 03011401. Also preferred are EHV-4 having all of the identifying characteristics of said deposited EHV-4.

All before-mentioned EHV-4 have superior properties over viruses known in the prior art as there are no recombinant EHV-4 available in the art. Furthermore, said EHV-4 according to the invention have an advantageously higher extracellular infectivity than those still comprising heterologous elements such as GFP. This is exemplified in FIG. 10 (e.g. at 24 hours). In a preferred embodiment, the EHV-4 strain is the EHV-4 deposited with the ECACC/CAMR on Jan. 4, 2003, given accession number 03011401, which was deposited under the terms of the Budapest Treaty, and all restrictions imposed by the depositor on the availability to the public of the deposited material will be irrevocably removed upon the granting of a patent.

Another important element of the invention is a nucleic acid coding for an EHV as disclosed supra. The artisan can easily determine the corresponding sequence by standard molecular biology methods known in the art.

There was a particular difficulty in the art to obtain the EHV according to the invention. The present inventors constructed gM negative EHV viruses by introducing a marker gene (lacZ) into the gM gene. When it was attempted to remove this cassette, in both EHV-1 and EHV-4 mutants produced by lacZ insertion, all clones phenotypically lacZ negative still contained the lacZ cassette. The inventors therefore developed an inventive method to obtain said viruses. An EH virus was constructed in which the gM gene was deleted by insertion of a cassette containing the GFP marker. This approach surprisingly allowed the differentiation between input virus (green fluorescent plaques) and new recombinant plaques (non-fluorescent plaques). Also, a Vero cell line (based on Vero cell clone 1008) constitutively expressing EHV4-gM was generated by the present inventors to overcome the difficulties in the art. Said cell line was generated by transfection of the appropriate gM gene and subsequent selection for gM-expressing Vero cells. Only said cells enabled the inventors to replicate EHV4 gM negative virus. Said gM-complementing Vero cell line according to the invention was deposited at the "Centre for Applied Microbiology and Research (CAMR) and European Collection of Cell Cultures (ECACC)", Salisbury, Wiltshire SP4 0JG, UK, as patent deposit according to the Budapest Treaty. The date of deposit was Jan. 28, 2003, the preliminary identification reference is VERO GM, and the accession number given by the international depositary authority ECACC/CAMR is 03012801. Also preferred are cell lines having all of the identifying characteristics of said deposited VERO GM cell line.

Preferred is a method for obtaining a recombinant EHV, comprising the steps of:

a) isolating a wild-type EHV;

b) establishing a plasmid encoding the EHV gM gene, optionally with flanking sequences;

c) generating a complementing cell line expressing gM or parts thereof;

d) establishing an EH virus carrying a GFP-encoding cassette insert in its gM coding sequence by co-transfecting the complementing cell line of step b) with EHV-nucleic acid and a plasmid encoding gM which is interrupted by a GFP-encoding cassette insert;

e) deleting the GFP-encoding cassette; and f) selecting for the EHV clones wherein the GFP-encoding cassette is successfully deleted.

Said above-captioned cells are an important embodiment of the present invention. Thus, the invention relates to a cell line for use in a method according to the invention, characterized in that the gene encoding the protein gM is transfected into said cell line and said cell line expresses gM. The invention preferably relates to a cell line according to the invention, characterized in that it is a cell line selected from the group of Vero cells (Vero-gM cells), RK-13, and cc (cc-gM).

As disclosed supra for EHV-1, the use of lacZ as a marker instead of GFP in EHV-4 also did not lead to successful generation of viruses according to the invention (see in a non-limiting manner in Example 2). "LacZ-positive" cells generally stained less intense on Vero cells than on Rk13 cells and were thus harder to identify, and the EHV-4 system replicated slower than EHV-1 and thus gave less time between plaque identification and isolation of viable virus progeny. Therefore, the use of GFP represented the only way to obtain said EHV-4 virus. The procedure was carried out as described supra for EHV-1 and surprisingly also led to the successful identification of EHV-4 gM deleted virus by virtue of identifying fluorescent plaques.

The isolation of wild-type EHV is accomplished by collecting lung tissue at necropsy from animals suspected to have been diseased by EHV, and isolating EHV on tissue cells as known in the art. The EHV 1 complete genome sequence has been published by Telford et al. (1992) (SEQ ID NO:1). Likewise, the complete genome sequence for EHV-4 has been published by Telford et al. (1998) (SEQ ID NO:2). The PCR amplification of DNA sequences by use of specific primers binding to complementary strands of target DNA flanking the DNA stretch of interest represents a standard molecular biology method. Methods for ligating appropriate DNA sequences into plasmids suitable for the constructions intended, for DNA transfection into eukaryotic cells, for Southern Blot and Western Blot analyses, for site-directed excision of DNA fragments via restriction enzymes and for selection of cell lines expressing the desired heterologous gene or plasmids harboring the desired gene or virus in which a certain gene is deleted are known to the skilled person. Standard molecular biology methods such as above mentioned techniques are known to the skilled person and can also be found e.g. in Sambrook et al.(1989) Molecular Cloning: A Laboratory Manual, $2^{nd}$ ed., Cold Spring Harbor Laboratory Press, Cold Spring Harbor, N.Y. and Bertram, S. and Gassen, H. G. Gentechnische Methoden, G. Fischer Verlag, Stuttgart, New York, 1991).

"Deletion" means the removal of one or several nucleotides or amino acids.

Another important embodiment of the invention is a pharmaceutical composition or vaccine comprising an EHV according to the invention, optionally in combination with a pharmaceutically acceptable carrier or excipient.

Also an important part of the present invention is a pharmaceutical composition comprising a nucleic acid according to the invention as disclosed supra.

Preferably, a vaccine according to the invention refers to a vaccine as defined above. The term "live vaccine" refers to a vaccine comprising a particle capable of replication, in particular, a replication active viral component.

Preferably, a vaccine according to the invention comprises a gM-deleted EHV-1 according to the invention as disclosed supra combined with a gM-deleted EHV-4 according to the invention as disclosed supra or optionally any other antigenetic group and optionally a pharmaceutically acceptable carrier or excipient. Said vaccine may be administered as a combined vaccine at the same point in time.

Most preferably, said attenuated EHV-1 according to the invention may be administered first followed by administration of an attenuated EHV-4 according to the invention three to four weeks later. Most preferably also, said attenuated EHV-1 according to the invention may be administered in combination with an attenuated EHV-4 according to the invention in a typical vaccination scheme where two or three basic vaccinations are given. A typical vaccination scheme of such a vaccine is two vaccinations four weeks apart (basic vaccination), followed by regular boosts every six months. However, any of said vaccines according to the invention as disclosed supra may also be administered at different intervals, e.g. every three months.

The artisan may choose to divide the administration into two or more applications, which may be applied shortly after each other, or at some other predetermined interval range. Preferably, such interval may be: 1° immunization, 2° immunization approx. 4 weeks thereafter and optionally 3° immunization 5-6 months thereafter. Depending on the desired duration and effectiveness of the treatment, vaccines may be administered once or several times, also intermittently. The vaccines according to the invention may be administered to a mare prior to breeding and again during its pregnancy to prevent EHV-associated abortions. Other horses can be vaccinated, e.g. once a year. Foals may be vaccinated shortly after birth.

The vaccines of the present invention may be applied by different routes of application known to the expert, notably intravenous injection or direct injection into target tissues. For systemic application, the intravenous, intravascular, intramuscular, intraarterial, intraperitoneal, oral, or intramucosal (e.g. nasal or respiratory spray or injection) routes are preferred. A more local application can be effected subcutaneously, intracutaneously, intrapulmonarily or directly in or near the tissue to be treated (connective-, bone-, muscle-, nerve-, epithelial tissue). A vaccine composition according to the invention can also be administered via an implant or orally. Most preferred is the intramuscular administration.

For preparing suitable vaccine preparations for the applications described above, the expert may use known injectable, physiologically acceptable sterile solutions. For preparing a ready-to-use solution for parenteral injection or infusion, aqueous isotonic solutions, such as e.g. saline or corresponding plasma protein solutions are readily available. The vaccine preparations may be present as lyophylisates or dry preparations, which can be reconstituted with a known injectable solution directly before use under sterile conditions, e.g. as a kit of parts. The final preparation of the vaccine preparations of the present invention are prepared for injection, infusion or perfusion by mixing purified virus according to the invention with a sterile physiologically acceptable solution, that may be supplemented with known carrier substances or/and excipient.

The applied dose of each EH-virus according to the invention present in the vaccine formulation preferably may be between $10^4$ and $10^8$ $TCID_{50}$/per animal, between $10^5$ and $10^7$ $TCID_{50}$/per animal, most preferably $10^6$ $TCID_{50}$/per animal.

The invention further relates to the use of EHV according to the invention in the manufacture of a medicament for the prophylaxis and/or treatment of EHV-associated conditions.

The invention further relates to the use of a nucleic acid according to the invention in the manufacture of a medicament for the prophylaxis and/or treatment of EHV-associated conditions.

The invention further relates to a method for the prophylaxis and/or treatment of an animal characterized in that a pharmaceutical composition according to the invention is applied to said animal and the therapeutic success is monitored.

The invention preferably relates to a method of treating an EHV-infected equine animal with a gM-deleted EHV according to the invention as described supra, wherein the said attenuated EHV or the vaccine composition as disclosed supra is administered to the equine animal in need thereof at a suitable dosis as known to the skilled person and the reduction of EHV symptoms such as viremia and leukopenia and/or coughing and/or pyrexia and/or nasal discharge and/or diarrhea and/or depression and/or abortion is monitored. Said treatment preferably may be repeated. Thus, the invention relates to a method for the prophylaxis and/or treatment of an animal characterized in that a pharmaceutical composition according to the invention is applied to said animal and the therapeutic success is monitored. The treatment may be carried out as disclosed for the vaccine composition supra.

The invention preferably relates to a method of detecting antibodies against specific structures of infecting EHV-1 or EHV-4 and to a method of differentiating wild-type infections from the presence of gM deleted EHV-1 or EHV-4 as described above by an immunological method. Immunological methods are known to the expert in the field and include, but are not limited to ELISAs (enzyme-linked immuno-sorbent assay) or Sandwich-ELISAs, dot-blots, immunoblots, radioimmunoassays (Radioimmunoassay RIA), diffusion-based Ouchterlony tests, rocket immunofluorescent assays or Western-blots. Examples for immunological methods are e.g. described in: *An Introduction to Radioimmunoassay and Related Techniques*, Elsevier Science Publishers, Amsterdam. The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

Said ELISA may use, but not be confined to the use of immobilized gM gene product or a part of gM gene product or any other EH virus 1 or EH virus 4 gene product on a plastic surface suitable for ELISA analysis.

An ELISA according to the present invention comprises, but is not limited to the steps of a) immobilizing a gM gene product or a fragment thereof onto a plastic support b) rinsing the plastic surface with an appropriate washing buffer (e.g., PBS-Tween)

c) adding the samples to selected wells and incubating the ELISA plate according to standardized methods d) washing the wells of the ELISA plate and adding a suitable antibody coupled to an enzyme such as HRP (horse radish peroxidase)

detecting bound antibody/HRP conjugate by adding a suitable substrate, followed by photometric read-out of optical density of individual wells. Suitable antibodies, e.g. rabbit anti horse Ig, are known in the field.

The following examples serve to further illustrate the present invention; but the same should not be construed as limiting the scope of the invention disclosed herein.

EXAMPLES

Example 1 gM Deleted EHV-1 Isolates

The gM negative EHV-1 were constructed by either inserting the *Escherichia coli* lacZ (HΔgM-lacZ) or the green fluorescent protein (GFP) expression cassette (HΔgM-GFP) thereby replacing 74.5% of gM-gene sequences. The expression of a marker protein facilitates the identification and subsequent purification of a recombinant virus. To avoid the presence of any "non-EHV-1" sequences within the vaccine virus, it was decided to remove the marker gene sequences and construct another, second generation gM-negative EHV-1, a "white" HΔgM (HΔgM-w).

To this end, plasmid pXuBaxA was constructed (FIG. 1). At first recombination of pXuBaxA-sequences into the lacZ-marked virus HΔgM-lacZ was attempted. In a first step, DNA transfections mediated by the calcium phosphate method were optimized, such that several white plaques resulted after plating of 100-1000 PFU of transfection supernatants. Consequently, several plaques were chosen for purification of progeny virus and subjected to four to five rounds of isolation of single plaques.

Multiple, independently isolated, phenotypically lacZ-negative virus populations were genotypically analyzed by Southern blotting and turned out to still carry sequences of the lacZ-cassette. Difficulties in isolating truly lacZ-negative virus populations due to "lacZ-silencing" had been anticipated and therefore a great number of phenotypically lacZ-negative virus populations were purified and analyzed without success. Therefore, the strategy of generating a "white" gM-negative RacH virus was changed by switching to cotransfections with the gM negative EHV-1, that had been constructed by insertion of a GFP cassette. Using the GFP-expressing virus facilitated the distinction between input virus (green fluorescent plaques) and new recombinant viruses (non fluorescent plaques) and thus increased the efficiency of isolating phenotypically GFP-negative plaques. Changing the "input" gM-negative RacH was not supposed to influence the genotype of the expected recombinant virus as (i) both the first generation HΔgM viruses are, apart from the marker, genetically identical and as (ii) the final genotype in the region of interest is determined by the recombination plasmid (pXuBaxA).

For construction of plasmid pXuBaxA (construct necessary to obtain the "white" gM negative EHV-1) the 962 bp ApaI-HincII fragment within the 1352 bp open reading frame of EHV-1 gM was removed of plasmid pBH3.1 (FIG. 1D). Plasmid pBH3.1 carries the EHV-1 BamHI-HindIII fragment surrounding the gM gene (Seyboldt et al., 2000). To prevent expression of any truncated gM-product, restriction endonucleases ApaI and HincII have been chosen such that after blunt end adjusting and ligation the remaining C-terminal gM sequences (183 bp) were not in frame with the remaining N-terminal sequences (208 bp).

EHV-1 gM expressing cell line ccgM (Seyboldt at al., 2000; obtained from Dr. N. Osterrieder) was maintained in minimal essential medium supplemented with 5-10% fetal calf serum (Biochrom, γ-irradiated). Homologous recombination into EHV-1 was achieved by calcium phosphate mediated co-transfection of ccgM-cells with 5-10 µg of plasmid pXuBaxA (FIG. 1D) and 2 µg of DNA of HΔgM-lacZ or HΔgM-GFP, respectively.

Subsequent analysis of DNA of HΔgM-GFP with a digoxigenin labeled probe specific for the BamHI-HindIII fragment of plasmid pBH3.1 (FIG. 2) revealed
(i) a 2.757 bp and a 9.043 bp fragment on BamHI,
(ii) a 10.006 bp and a 825 bp fragment on HindIII,
(iii) and to a 5.415 bp and a 4.474 bp fragment on PstI digested DNA.

The restriction enzymes used (BamHI, HindIII, PstI) do cut within sequences of the GFP-marker cassette, thereby altering the fragment pattern relative to the respective GFP-marker cassette free DNA.

The GFP-probe bound to the respective first fragments (i-iii) and did not detect GFP-specific sequences on DNA of RacH or of HΔgM-w.

On DNA of RacH the expected BamHI (11.166 bp), HindIII (10.199 bp) and PstI (9.257 bp) fragments were detected, which decreased in size after removal of 962 bp of gM-sequences accordingly (to: 10.204 bp, 9.237 bp and 8.279 bp; FIG. 3B).

Single-step growth kinetics of gM-negative viruses (HΔgM-w or HΔgM-GFP), which had been constructed as described in the legend to FIG. 1, and RacH were performed. Rk13 cells in 24 well plates were infected at an MOI of 2 of the respective viruses. Supernatants and infected cell pellets were harvested separately at various times p.i. (0, 4, 8, 12, 16, 20, 24 h p.i.). Supernatants were cleared of cellular debris by low speed centrifugation and cells were subjected to freeze-thawing before cell-associated infectivity was assayed. All virus titers were determined individually on Rk13 or ccgM cells, respectively, in 24 well plates. The results (data not shown) can be summarized as follows: Cell-associated infectivity of both HΔgM-viruses was reduced between factor 1.6 (4 h p.i.) and 45 (20 h p.i.) on Rk13 cells when compared to titers of cells infected with RacH (intracellular infectivity). Extracellular virus titers of both the HΔgM viruses were maximally reduced by 186 (HΔgM-w) or 650 (HΔgM-GFP) fold (12 h p.i.) compared to those of RacH (extracellular infectivity), supporting a role of gM in virus egress of RacH also.

Example 2 gM Deleted EHV-4 Isolates

To parallel the construction of gM-negative EHV-1, lacZ selection was chosen for selection of EHV-4. To allow the isolation of a gM-negative EHV-4, a Vero cell line constitutively expressing EHV-4 gM was constructed. Vero cell clone C1008 (ATCC number: CRL-1586 was maintained in minimal essential medium supplemented with 5-10% fetal calf serum (Biochrom, γ-irradiated). Recombinant cell line Vero-gM was generated by Effectene™ (Qiagen) mediated transfection of 1 µg of plasmid pCgM4 (FIG. 3B) and 0.1 µg of plasmid pSV2neo (conferring resistance to G418; Neubauer et al., 1997) into Vero cells. Cell clones were first selected for resistance to G418 (Calbiochem), then for trans-complementation of a gM negative EHV-4. G418 was added to the medium of every 5$^{th}$ passage of recombinant cell lines (500 μg/ml). All cells were regularly analyzed for Mycoplasma by PCR and for Bovine Viral Diarrhoe Virus (BVDV) antigen by FACS analysis. The selected cell clone was called Vero-gM and used in the following experiments.

EHV-4 DNA was cotransfected with plasmid pgM4β+ (FIG. 3B) into Vero-gM cells. The recombination resulted in several "lacZ-positive" plaques, that were isolated and replated. But then the purification of a deletion mutant in EHV-4 turned out to be more difficult and slower than in EHV-1 as: (i) "lacZ-positive" plaques generally stained less intense on Vero cells than on Rk13 cells and were thus harder to identify, and as (ii) the EHV-4 system replicated slower than EHV-1 and thus gave less time between plaque identification and isolation of viable virus progeny.

All lacZ-positive plaques, that were isolated, were lost over the first round of purification, which made it imperative to search for another solution. It was therefore attempted to use the GFP-marker for EHV-4 also. In a first step, plasmid pgM4GFP+ (FIG. 3B) was constructed and used for recombination into EHV-4 DNA. Resulting GFP-positive plaques were purified by three rounds of isolating single plaques on cell line Vero-gM. A homogenous GFP-positive virus population was chosen and viral DNA subjected to Southern blot analysis (FIG. 4). DNA of the resulting virus, E4ΔgM-GFP (FIG. 3C), was then cotransfected with either plasmid pgM4R or pgM4w (FIG. 3B). Plasmid pgM4R was used for the construction of an gM-repaired EHV-4, called E4RgM (FIG. 3A). Plasmid pgM4w was the basis to generate the simultaneously gM- and marker gene-negative EHV-4, E4ΔgM-w (FIG. 3D). E4RgM and E4ΔgM-w virus populations were isolated for a GFP-negative phenotype, purified on Vero or on Vero-gM cells and finally analyzed by Southern blot (FIG. 4). To express EHV-4 gM in eurcaryotic cells plasmid pCgM4 was generated (FIG. 3B). The complete ORF of EHV-4 gM was amplified by PCR using primers given in FIG. 8 and the Taq polymerase (MBI-Fermentas). The resulting PCR-product was inserted into vector pcDNAI/Amp (Invitrogene).

Plasmid pgM4R resulted after PCR-amplification of nucleotides 91.699 to 94.808 (Telford et al., 1998) (SEQ ID NO:2) of EHV-4 and insertion of the amplification product into vector pGEM3Zf+ (Promega) (FIG. 3B; FIG. 8). This plasmid was used for the construction of the gM-repaired EHV-4, E4RgM (FIG. 3A).

To construct plasmid pgM4β+ (FIG. 3B), that was designed to initially delete 1110 bp of the 1352 bp EHV-4 gM, a multistep strategy was chosen. In a first step, both the flanking sequences necessary for DNA recombination were amplified independently by PCR using the PFU polymerase (Stratagene). Restriction sites necessary for stepwise cloning were added by primer sequences (FIG. 8). PCR products were inserted into vector pTZ18R (Pharmacia), resulting in plasmids pgM4Del1 and pgM4Del2 (FIG. 8).

In a next step the 3.9 kbp *E-coli* lacZ expression cassette was released from plasmid ptt264A+ (Osterrieder et al., 1996) by SalI and BamHI digest and was inserted into plasmid pgM4Del1 resulting in plasmid pgM4Del1β+. Then, EHV-4 specific sequences, taken out of pgM4Del2, were introduced into pgM4Del1β+ using PstI and SalI, such that the marker gene cassette was flanked by EHV-4 specific sequences in the resulting plasmid pgM4β+ (FIG. 3B).

Plasmid pgM4β+ was then digested with SalI and BamHI, again releasing the lacZ-cassette, the resulting 5'-overhangs were filled in with the Klenow polymerase and the construct resulting from religation was called pgM4w (FIG. 3B). Again a frameshift between the N-terminal 208 nt and the remaining C-terminal 33 nt of the gM-sequence was designed.

To generate plasmid pgM4GFP+ (FIG. 3B), the lacZ-cassette was taken out of pgM4β+ (FIG. 3B) using the SalI and BamHI sites and replaced by the GFP-cassette (including CMV-promoter and SV40-polyA), that had been removed of vector pEGFP-C1 (Clontech) via AsnI and MluI digest. Restriction enzyme generated overhangs were blunt end adjusted by the Klenow polymerase.

Correct amplification of all PCR products was confirmed by cycle sequencing (MWG Biotech) and comparison to the published sequence of EHV-4 strain NS80567 (Telford et al., 1998) (SEQ ID NO:2).

Recombination into EHV-4 was done by using the cell line Vero-gM and either plasmid pgM4β+ or pgM4GFP+ (FIG. 3B) was cotransfected with EHV-4 DNA to generate a first generation gM-negative EHV-4 (FIG. 3C). Plasmid pgM4w (FIG. 3B) in combination with DNA of the gM-negative EHV-4 resulted in E4ΔgM-w (FIG. 3D). Finally, the gM-repaired EHV-4, E4RgM (FIG. 3A), was isolated after co-transfection of plasmid pgM4R (FIG. 3B) with DNA of E4ΔgM-GFP into Vero-cells.

DNA of EHV-4, E4RgM, E4ΔgM-w and E4ΔgM-GFP were cleaved with PstI, EcoRV or HindIII and DNA-fragments blotted onto nylon membranes. Parallel membranes were either hybridized with GFP-specific sequences (identically to FIG. 2) or with a probe, named gM3.1, containing the EHV-4 specific sequences taken out of plasmid pgM4R (FIG. 3B).

Digestion results obtained (FIG. 4) were as follows:

(i) On DNA of E4ΔgM-GFP the GFP-probe recognized fragments at 5.531 bp, when PstI cleaved, at 8.383 bp after EcoRV-digest and at 4.528 bp after HindIII digest. Identical fragments plus fragments at 1.792 bp (PstI), 1.801 bp (EcoRV) and 826 plus 5.487 bp (HindIII) reacted with probe gM3.1.

(ii) Neither parental EHV-4, nor the repaired virus E4RgM or E4ΔgM-w carried any GFP specific sequences.

(iii) The gM3.1 reactive DNA-fragments in EHV-4 and E4RgM were detected at 6.806 bp (PstI), at 7.874 bp plus 1.801 bp (EcoRV) and at 4.837 plus 5.487 bp (HindIII), respectively.

(iv) The gM- and GFP-cassette negative virus E4ΔgM-w, did not hybridize with GFP-sequences, but with the respective EHV-4 specific sequences (gM3.1). The latter probe detected fragments, lacking 1110 bp of gM sequences, when compared to wild type virus, i.e. at 5.696 bp (PstI), at 6.764 bp plus 1.801 bp (EcoRV) and at 3.727 bp plus 5.487 bp (HindIII), respectively.

On HindIII cleaved DNA of all of these viruses another gM3.1 probe specific fragment exists at 126 bp (FIG. 2C), but this fragment is to small to be shown in this Southern blot.

Viruses E4ΔgM-GFP and E4ΔgM-w lost their capacity to express gM and in addition E4ΔgM-w lost the marker gene sequence.

a) Virus growth on culture cells. Virus growth properties of the various mutant viruses as detailed above were compared on Vero and on Vero-gM cells. Cells seeded in 24 well plates were infected at an MOI of 1-2 and extracellular (extracellular infectivity) and intracellular (intracellular infectivity) virus titers were determined at different time points p.i. (FIG. 5). While growth properties of the rescuant E4RgM virus corresponded well to those of EHV-4, there was a surprising inhibition in the production of E4ΔgM-w and E4ΔgM-GFP extracellular virus titers on non-complementing cells. Within this series of experiments (mean of two independent experiments) extracellular infectivity could never be detected before 24 h p.i. Even at 30 hours p.i. only very low titers were extracellularly observed (maximum of 1.5 plaques/ml at the lowest dilution $10^{-1}$), although cells showed severe cytopathic effect. Differences in intracellular infectivity, however, never reached 100 fold and peaked at 24 hours p.i. (84 fold between EHV-4 and E4ΔgM-w). The delay in detecting intracellular infectivity was only one time point (12 h versus 15 h. p.i.). Taken together it could be surprisingly demonstrated that deletion of gM-sequences of the EHV-4 background massively influenced virus replication in vitro, but that expression of gM is not essential for replication. Especially extracellular infectious virus decreased and the ability to directly infect adjacent cells was diminished—as reflected by plaque sizes.

b) Plaque size. Diameters of 150 plaques after infection of Vero or Vero-gM cells with EHV-4, E4RgM, E4ΔgM-w or E4ΔgM-GFP were measured and average plaque sizes were determined relative to sizes of wildtype plaques, that were set 100%. It was clearly demonstrated, that the gM negative viruses were able to infect and replicate in Vero cells, but that the maximal plaque diameters were markedly reduced, to less than 20% of wildtype plaque diameters (FIG. 6). Infection with the parental or the rescuant virus resulted in wild-type-like appearance of plaques, indicating that the observed phenotype was indeed induced by the gM-deletion. This was additionally corroborated by the fact, that plaque formation of E4ΔgM-w and E4ΔgM-GFP was fully restored on cell line Vero-gM (Data not shown).

c) Penetration experiments. In this experiment, the influence of the EHV-4 gM on entry kinetics of EHV-4 was assessed. 100 PFU of the different viruses, parental EHV-4, the gM repaired virus E4RgM, as well as the gM-deletion mutants and E4ΔgM-GFP (see FIG. 3), were allowed to adsorb at 4° C. to Vero cells in 6-well plates. After 90 min, the respective inocula were replaced by fresh medium and penetration was initiated by shifting the incubation temperature to 37° C. At different times after the temperature shift—starting immediately (=0 min)—extracellular infectivity was pH-inactivated by treating cells with a citrate buffer (pH 3.0). Parallel samples were washed accordingly, but the citrate buffer was replaced by PBS, such that at every time point the "adsorbed infectivity" could be compared to the "penetrated infectivity". Numbers of plaques were determined after incubating cells for four days under a methocell overlay.

c) Several sets of experiments were performed: In FIG. 7A results are depicted for genotypically and phenotypically gM-negative viruses after propagation on non complementing Vero cells, whereas FIG. 7B represents kinetics of phenotypically complemented E4ΔgM-w and E4ΔgM-GFP, as viruses had been grown on gM-expressing Vero-gM cells.

A mean of 52.8% (56.7%) of the infectious parental EHV-4 (E4RgM) was protected from extracellular acid treatment at 40 min after initiating penetration (FIG. 7A, open circles) whereas only 33.7% (E4ΔgM-w—closed rectangles) and 38.5% (E4ΔgM-GFP—closed triangles) of gM negative viruses were protected, yet. At later time points of entry kinetics, the different graphs start to variously overlap and a maximal penetration efficiency between 61.7% and 78.9% is reached after 150 min of penetration time, indicating that a certain assay variability may account for the slight differences observed. (FIG. 7A). When gM negative viruses had been prepared on complementing Vero-gM cells no difference at all was observed in their penetration efficiency (7B). As opposed to a delay in entry kinetics of gM-negative EHV-1 of about 20% (strain RacL11; Osterrieder et al., 1996) to up to 40% (strain KyA; Seyboldt et al., 2000), the effect of deleting gM of EHV-4 has to be noted with reservation. Nevertheless the following conclusions can be drawn: (i) A difference was observed in kinetics of phenotypically complemented to non complemented gM-negative viruses (FIG. 7A-B), but (ii) the influence of deleting gM on EHV-4 penetration is virtually neclectable.

Example 3

Analysis of Horse Sera for Anti gM Antibodies using a gM Specific Serological Test To state whether gM can be used as a serological marker for distinction of wild type infection versus vaccination with a gM-negative vaccine, several assumptions had to be tested. Primarily it needed to be assessed whether sera of field virus infected horses contain gM-specific antibodies. For initial analysis a Western blot test was chosen, as this system allowed to identify a specific reaction against background reactivity. When using highly neutralizing sera (EHV-1 and/or -4 neutralizing titers between 1:128 and 256), it was established (data not shown) that lysates of EHV-1 gM expressing cell line ccgM allowed the detection of a specific signal by horse sera and that a dilution of sera to 1:3000 seemed to work best.

Consequently, sera of all 12 foals (6 vaccinates and 6 controls) that had participated in an EHV-1 gM vaccine trial were analyzed for gM reactivity in Western blot. Of each individual horse three different sera were tested: Taken before entering the trial (Pre), 4 weeks after the second vaccination (V2) and two weeks after challenge infection (C), respectively.

In summary by Western blot analyses (FIG. 9) it was shown that (i) sera of horses, exhibiting EHV-1 neutralization activity, all tested positive for gM, that (ii) gM reactivity was never detected in any of the samples analyzed before known contact to EHV-1 or after vaccination with the gM-negative EHV-1 and that (iii) after infection of vaccine trial horses with the gM-positive challenge virus, gM was clearly detectable in 10 out of 12 cases. Finally (iv) it was observed that anti EHV-1 antibody titers and the intensity of gM reactivity seemed not to be directly correlated.

Due to the high background reactivity of horse sera, the establishment of serological tests is difficult. Based on indirect immunofluorescence (IIF) data obtained in horse sera, it was confirmed that either an indirect or a blocking test system will have to be established or highly purified gM-polypeptides need to be used in an ELISA test. To this end, an ELISA was established as follows. Either purified gM polypeptides or the complete gM was immobilised onto the solid support of a 96 well plate which wascoated to ensure good attachment of the capturing protein. For the assay, unspecific binding sites were be blocked by either dry milk or similar substances to prevent unspecific binding. Following this, the plastic surface was rinsed with an appropriate washing buffer (e.g., PBS-Tween) to remove excess blocking agent. Then the test samples were added to selected wells and the ELISA plate was incubated at 37° C. according to standardised methods, allowing antibodies in the test sample to bind to the immobilized capturing protein. In the next step, the wells of the ELISA plate were washed thoroughly by several times rinsing with washing buffer, followed by the addition of a suitable anti-horse antibody coupled to an enzyme such as HRP (horse radish peroxidase). The detection of bound antibody/HRP conjugate was finally performed by adding a suitable substrate, followed by photometric read-out of optical density of individual wells. The value obtained was be compared to positive and negative controls run in the same assay.

Example 4

Identification of EHV-4 gM

Although the predicted aminoacid sequence of EHV-4 gM is calculated to be 86.7% identical to that of EHV-1 gM (Telford et al., 1998), anti EHV-1 gM Mab 13B2 (Allen and Yeargan, 1987) specifically reacts in Western blot with the type-specific protein only (Crabb et al., 1991). To nevertheless identify the EHV-4 homolog in this study, other anti-EHV-1 gM antibodies (Seyboldt et al., 2000; Day, 1999) were tested on purified EHV-4 virions, on lysates of cells infected with EHV-4 or on lysates of Vero-gM cells. The latter being a recombinant cell line developed to synthesize EHV-4 gM under control of the IE-HCMV promoter. The reactivity of all anti-EHV-1 gM monoclonal antibodies against EHV-4 gM was below the detection limit in Western blot, whereas parallel EHV-1 samples were always readily reactive (data not shown). Only the polyclonal antiserum, that had been generated in rabbits against a His-tagged EHV-1 gM derived polypeptide (aminoacid 376-450; Seyboldt et al., 2000), reacted strong enough with the heterologous gM to allow the identification of EHV-4 gM (FIG. 10A). Using this antibody a specific reactivity at an Mr of about 50,000 to 55,000 was observed in purified EHV-4 virions. According to its predicted hydrophobic properties the detected gM-protein aggregated upon boiling. In contrast the form of gM expressed in recombinant Vero-gM cells mainly run at an Mr of about 46,000 to 48,000, indicating that the gM-proteins of EHV-4 are processed similarly as has been shown for EHV-1 (Osterrieder et al., 1997; Rudolph and Osterrieder, 2002).

Several experiments were conducted to analyze the phenotype of the gM-deletion in EHV-4. To compare expression of other glycoproteins, lysates of Vero cells infected with EHV-4, E4RgM, E4ΔgM-w or E4ΔgM-GFP were subjected to Western blot analysis. It is demonstrated that the deletion of gM did not influence the production of the late proteins gB or gD, indicating that early steps in virus replication were not substantially affected by the deletion.

In another experiment it could be demonstrated by analysis of virion preparations of wildtype, repaired or both gM-deleted EHV-4, that no gM reactivity at all was detectable within gM-negative viruses, whereas the protein was readily reactive in control virions. The presence of virions in the respective preparation was shown in a parallel blot probing against gB (FIG. 10B).

REFERENCES

Allen, G. P., Yeargan, M., Costa, L. R. R. and Cross, R., 1995. Major histocompatibility complex class I-restricted cytotoxic T-lymphocyte responses in horses infected with equine herpesvirus 1. J. Virol. 69, 606-612.

Allen, G. P. and Yeargan, M. R., 1987. Use of λgt11 and monoclonal antibodies to map the genes for the six major glycoproteins of equine herpesvirus 1. J. Virol. 61, 2454-2461.

Awan, A. R., Chong, Y.-C. and Field, H. J., 1990. The pathogenesis of equine herpesvirus type 1 in the mouse: A new model for studying host responses to the infection. J. Gen. Virol. 71, 1131-1140.

Baines, J. D. and Roizman, B., 1991. The open reading frames UL3, UL4, UL10 and UL16 are dispensable vor the replication of herpes simplex virus 1 in cell culture. J. Virol. 65, 938-944.

Baines, J. D. and Roizman, B., 1993. The UL10 gene of herpes simplex virus 1 encodes a novel viral glycoprotein, gM, which is present in the virion and in the plasma membrane of infected cells. J. Virol. 67, 1441-1452.

Chalfie M, Tu Y, Euskirchen G, Ward W W, Prasher D C, 1994. Green fluorescent protein as a marker for gene expression. Science 263, 802-805.

Crabb, B. S.; Allen, G. P., Studdert, M. J., 1991. Characterization of the major glycoproteins of equine herpesviruses 4 and 1 and asinine herpesvirus 3 using monoclonal antibodies. J .Gen. Virol. 72, 2075-82.

Day, L. 1999. Characterization of selected glycoproteins of equine herpesvirus-1: immune responses in the murine model. Ph.D. thesis. University of Leeds, Leeds, United Kingdom.

Flowers, C. C. and O'Callaghan, D. J., 1992. The equine herpesvirus type 1 (EHV-1) homolog of herpes simplex virus type 1 US9 and the nature of a major deletion wethin the unique short segment of the EHV-1 KyA strain genome. Virology 190, 307-315.

Hübert, P. H., Birkenmaier, S., Rziha, H. J. and Osterrieder, N., 1996. Alterations in the equine herpesvirus type-1 (EHV-1) strain RacH during attenuation. J. Vet. Med. B 43, 1-14.

Kyhse-Andersen, J., 1984. Electroblotting of multiple gels: a simple apparatus without tank for rapid transfer of proteins from polyacrylamide gels to nitrocellulose. J. Biochem. Biophys. Methods 10, 203-210.

Laemmli, U. K., 1970. Cleavage of structural proteins during the assembly of the head of bacteriophage T4. Nature 227, 680-685.

MacLean, C. A., Robertson, L. M. and Jamieson, F. E., 1993. Characterization of the UL10 gene product of herpes simplex virus type 1 and investigation of ist role in vivo. J. Gen. Virol. 74, 975-983.

Malik, A. K., Martinez, R., Muncy, L., Carmichael, E. P. and Weller, S. K., 1992. Genetic analysis of the herpes simplex virus type 1 UL9 gene: isolation of a LacZ insertion mutant and expression in eukaryotic cells. Virology 190(2), 702-715.

Mayr, A., Pette, J., Petzoldt, K. and Wagener, K., 1968. Untersuchungen zur Entwicklung eines Lebendimpfstoffes gegen die Rhinopneumonitis (Stutenabort) der Pferde. J. Vet. Med. B 15, 406-418.

Neubauer, A., Beer, M., Brandmüller, C., Kaaden, O.-R. and Osterrieder, N., 1997. Equine herpesvirus 1 mutants devoid of glycoprotein B or M are apathogenic for mice but induce protection against challenge infection. Virology 239, 36-45.

Osterrieder, N., Wagner, R., Brandmüller, C., Schmidt, P., Wolf, H. and Kaaden, O.-R., 1995. Protection against EHV-1 challenge infection in the murine model after vaccination with various formulations of recombinant glycoprotein gp14 (gB). Virology 208, 500-510.

Osterrieder, N., Neubauer, A., Brandmüller, C., Braun, B., Kaaden, O.-R. and Baines, J. D., 1996. The equine herpesvirus 1 glycoprotein gp21/22a, the herpes simplex virus type 1 gM homolog, is involved in virus penetration and cell-to-cell spread of virions. Journal of virology, June 1996, p. 4110-4115.

Osterrieder, N.; Neubauer, A.; Fakler, B.; Brandmüller, C.; Seyboldt, C.; Kaaden, O. R.; Baines, J. D., 1997. Synthesis and processing of the equine herpesvirus 1 glykoprotein M. Virology 232, 230-239.

Pilling, A., Davison, A. J., Telford, E. A. R. and Meredith, D. M., 1994. The equine herpesvirus type 1 glycoprotein homologous to herpes simplex virus type 1 glycoprotein M is a major constituent of the virus particle. J. Gen. Virol. 75, 439-442.

Rudolph, J.; Seyboldt, C.; Granzow, H.; Osterrieder, N., 2002. The gene 10 (UL49.5) product of equine herpesvirus 1 is necessary and sufficient for functional processing of glycoprotein M. J. Virology 76, 2952-2963.

Sambrook, J., Fritsch, D. F. and Maniatis, T., 1989. Molecular Cloning: A laboratory manual. $2^{nd}$ ed. Cold Spring Harbor Laboratory Press, Cold Spring Harbor, N.Y.

Seyboldt, C., 2000. Structural and functional analysis of the equine herpesvirus type 1 glycoprotein M. Doctoral thesis, Ludwig-Maximilians-University, Munich, Germany.

Seyboldt, C.; Granzow, H.; Osterrieder, N. 2000. Equine herpesvirus 1 (EHV-1) Glycoprotein M: Effect of deletions of transmembrane domains. Virology 278, 477-489.

Stokes, A., Alber, D. G., Greensill, J., Amellal, B., Carvalho, R., Taylor, L. A., Doel, T. R., Killington, R. A., Halliburton, I. W. and Meredith, D. M., 1996. The expression of the proteins of equine herpesvirus 1 which share homology with herpes simplex virus 1 glycoproteins H and L. Virus Res. 40, 91-107.

Telford, E. A. R., Watson, M. S., McBride, K. and Davison, A. J., 1992. The DNA sequence of equine herpesvirus-1. Virology 189, 304-316.

Telford, E. A. R., Watson, M. S., Perry, J., Cullinane, A. A. and Davison, A. J., 1998. The DNA sequence of equine herpesvirus-4. Journal of Gen. Virol. 79, 1197-1203.

Tewari, D., Whalley, J. M., Love, D. N. and Field, H. J., 1994. Characterisation of immune responses to baculovirus expressed equine herpesvirus type 1 glycoproteins D and H in a murine model. J. Gen. Virol. 75, 1735-1741.

What is claimed is:

1. A recombinant Equine Herpes Virus (EHV), wherein the EHV is:
   (i) an EHV-4 which is lacking the gM protein;
   (ii) free of heterologous elements;
   (iii) wherein said EHV-4 is based on MSV Lot 071398 and isolate E4ΔgM-w; and
   (iv) is the EHV-4 deposited at the ECACC/CAMR on Jan. 4, 2003 with accession number 03011401.

2. A recombinant Equine Herpes Virus (EHV), wherein the EHV is the EHV-4 deposited at the ECACC/CAMR on Jan. 4, 2003 with accession number 03011401.

* * * * *

SEQUENCE LISTING

```
<160> NUMBER OF SEQ ID NOS: 2

<210> SEQ ID NO 1
<211> LENGTH: 150223
<212> TYPE: DNA
<213> ORGANISM: Equine herpesvirus 1
<300> PUBLICATION INFORMATION:
<301> AUTHORS: Telford,E.A.
       Watson, M.S.
       McBride, K.
       Davison, A.J.
<302> TITLE: The DNA sequence of equine herpesvirus-1
<303> JOURNAL: Virology
<304> VOLUME: 189
<305> ISSUE: 1
<306> PAGES: 304-316
<307> DATE: JUL-1992
<308> DATABASE ACCESSION NUMBER: NC 001491, NCBI
<309> DATABASE ENTRY DATE: 2000-08-01

<400> SEQUENCE: 1
ggccaggctc tctctcgggc gcgggcccgt gaaaaaaatt tttcggcctc gcgacggcct      60
cgaagaaaac cgtagagggg agtgggggat gggattttt tattaggcca cgcccactgg     120
gaggccacgc ccactgggag gccacgccca ctgggaggcc acgcccactg ggaggccacg     180
cccactggga ggccacgccc actgggaggc cacgcccact gggaggccac gcccactggg     240
aggccacgcc cactgggagg ccacgcccac tgggaggcca cgcccactgg gaggccacgc     300
ccactgggag gccacgccca ctgggaggcc acgcccactc cggtgatgca gcggttatgc     360
gattgtcctc tcagcgctac agtggggctc actgctatgc tggggctcac tgctatgctg     420
gggctcactg ctatgctggg gctcactgct atgctggggc tcactgctat gctggggctc     480
actgctatgc tggggctcac tgctatgctg gggctcactg ctatgctggg gctcactgct     540
atgctggggc tcactgctat gctggggctc actgctatgc tggggctcac tgctatgctg     600
gggctcactg ctatgctggg gctcactgct atgctggggc tcactgctat gctggggctc     660
actgctatgc tggggctcac tgctatgctg gggctcactg ctatgctggg gctcactgct     720
atgctgggcc ccttgtttgt tcagcgccca ataccstacca accccggca agaagttttt     780
```

```
gtgcccttc gcgcgttcaa cccgctccgc gacattagtt gccacgcttc tgtccatcgt    840
tctgaaacac ccattgcctt gggcgttcgc acttgcattc cccggttttg ctccgcccct    900
ctagggaagt aatctaactt tactcaacca acaaccctgg gctctttaca cacagtctt    960
taacaccatg gcaggcctgt tgtccgccat tcctctgggg gtaattaatg gctgccactc   1020
aaatcgggta tccccactcc cctctacggt tttcttcgag gccgtcgcga ggccgaaaaa   1080
ttttttcac gggcccgcgc ccgagagaga gcctggcccc catctccccc cgcagccagc   1140
gtggggccca gcccactaga tttcccaact cgctgggttt cccaagcttt tttccattgg   1200
gctcctccct tttggctctg ggtatttagc ttccctccca cctctcattc cactttctcc   1260
acctgcacct tttccatctc ctctccaact cgccgccatg agacccgagg gagtttcgcg   1320
ggccgcgcc tcctctgtct ccatctccat gtgcccaccg ccgcccaatg gggcgcgccg   1380
cgcatcgctg ggctgtgcgc ccccgctgaa tagccggcct gtatgctgcg ccccgtcgag   1440
cgtctctctg agctcatcat cctcgcgaag gtccatgcct tcgctaggct cgtccagaag   1500
ctcgagcctg ccttctaccg gctccctgag atccatcacg cgggacccgg agcggcttcc   1560
gtcgaggccc ccgtcgtaca ccgccatcaa cccagagtgt ttactggaac gcggggcaga   1620
gcggccgcgg gcgtggacgg cgagcgtgat gaccgcccca ccgagttact cggaagccct   1680
gtgccaggcg ccacccgcgt acgagctcgt tcctgaactt tcttatcacc ccacccagga   1740
cccgcgcggc gtctactcgt cgcgctccga tccccaccag acctctcgaa ggagacagaa   1800
cccgatatgt atttttatta ttgttgttgc aaccatgttg ttgatactgg gactgttgct   1860
cactataacg ctcagttcgt taacaaacgg caagaaggag aaataaaacg actgtagtac   1920
cgcaaaggtt aatcgcattt attttttacat gcactccttt ccaaaccccc tgtacactat   1980
tccgatcagc accagaatct ggagcataag cagaatgatg tttattgcgg caaacttcct   2040
gcaaaaggtt ttactgtaga gccgcctttt gatgggtccc atacgaccgc tcgggtcctt   2100
gtgttgatcg cagaaaccgt cgaggtaaac ttccgatggt agtgcggccg ccccgcggtg   2160
atttctagta acgtcatcca gatgtagcac agctggactt tcagcgtatg catcggtaca   2220
gcggccagtg gggtcatctt gtgtagtagt gggtgagtcg gtaagcacat tgcttgaggt   2280
ggcggaactt atgcgggtgt actcctcgtt ctcggagtcg ctctcatacc cgtagggggct   2340
gacgcgggcc ggaccctgcc aggccgacgg ggggaatgcg actctgccgt accacacggt   2400
ggaggggcgc gtctggcgct tctttttaaa cagctgtgac attttcttga aaaacaactg   2460
ggagagcagc tgtcttctca gagactctcg tctgggacgt ggttcaacgt tgattgtggt   2520
agggtttgag acgtgtatgc gcctcctcca cgctggatcc atgcttaaac actttggagc   2580
gaggggggcgg ggtatggggg cgtatgcctg aaactcaatc tacagcgtta tgcccggggc   2640
taaaaagctg cgtcttcacg cccgaggcgc ttattgccca ctgggtacgg ggcgcgcttt   2700
tatatgtgta acgtcccacc ggtgtgacgc acgtactacg gttgttctaa atagctgtcc   2760
ccgtgattgc ctcggctgca cacatcgcct aggtttccgc cgtgcctggt gtcgagggcc   2820
cacccctgta accaacatcg atgggggcct gctgctcctc tagacgcaat cgctcgccgt   2880
cgctcgccgc cctggccgaa gaaacggagg ttgtccttcg ctgcctggcc ggaagggtag   2940
tagacctccc tggtggagat gaggtgcgaa tcgctccgga cgtcgggcgg cccgggcaga   3000
attttggcta ctttaagttt cccggccgt cgcgctttgc ctatgttaag tttataggca   3060
gggcgtacgc gctaggaagc gggcgcaagt ttctactgta cctatccaga aactttcagg   3120
```

```
tctttggata cgaggacggt accggcctac acatgctagc caagtccctc cacgattttt    3180
taaagttcaa aggactatct gacagggacc tggtggtagt cgactcggtt gcgctgacct    3240
cgcagctgcg accacttact cttcctatac gttcgacctc ggacgtggaa acgctagttg    3300
ccgaggaggc caccaccaac tacacttcta cggaaaacct actgggccag acccagagct    3360
ccacgcaccg tccgctgggt gtaccgcttt ccaacgtaaa aacaatgggt gtgccaccca    3420
cgaaaccgag tagccaaagg cccagggggca agggggggacg ccctccagcc cgcctcaagt    3480
ctatccgaga ggagaccgta tccggcatgg caagggcccg cgaagagtgc aactctccca    3540
gcgaacgaca ccgcctcacg tccgagatga cagactgcga cagcgactcg tcggtatcct    3600
ccgtcttttt ttaaataaaa agcaaaacac catatacggt ctgaatttat cgtttatttt    3660
ctcgctggcg ctctttggcc gaggttattc ccctagccac gcttaaaatt ttggcctggg    3720
cagagttggc tgcctgccaa cactctaggg aaaaggggggt tttgcagtgg cagtggaaac    3780
acagtccgtt gatggtggac tcctccccgt cctcgtcgca gtcgtactgg gtggcggcgc    3840
taaacggggc gctacacacg ctatgctcgg tggccaattc ctgcatgatt ctcgggttat    3900
tgaggatgca tttgaagttg gtcaggtcgg ggagcaagat ctgcttttcc gggtccctct    3960
tctcgaacac gccgatgaaa aaggcgtgta ggcgcgtttg cagatcgcag catgctctga    4020
tggtatacgt tctggtgttc aggtaagacc tgcttctggc cggctgggag gtggtctccc    4080
acgagctcca agtcaggtca agcggcagag gcgacacaac gttgctgatg tccaccaata    4140
gccccagctt gcagtcgctg ctgtaacacc cgccgtggtt cctcccgtgg gagcctatat    4200
cccgcggctc tgcatcagat gagtgttctg cgcggtttgc cggcagcata tttacgttta    4260
gttttccacc aggctgggaa tttgctcgac tgaaggtatc aagacgcagt gtacccaacc    4320
cgacagccac cactctttaa actcccaagc gccgccagt ttacatttta aaacacgaca    4380
aagcttgtgt gaataattaa actgtattta ttgatgagta acacaaaaca gtttcctgg    4440 gaaacacact ccacagtttt tttaaaagat ttggttacag taaaagtatt tgccgtgcag    4500
gtaaaccgga acgagggtgt aggccgatac aaggctgcag gtatctgcct tgcatcgccg    4560
cttgtgcgcg tctatcgcct cgagggttcc cgccagacag gctccaggta cgtagtcggc    4620
tagaacgcgc ccgtcgggtc ccagtgcgtc cctggacaca gtttcggcgc cgctccctac    4680
agcccgagct atgcgcgcca acatcacgaa catgaaggtg ggaacacacg cgacgtcaga    4740
cagccgctgg tggtcgcaca gctctgcgag ggtagggctt cccgacgatg agaggtagca    4800
ccgcataaag ggctcaagtt tcaggcgcag gttgtccagc agggccaccg aagaagagat    4860
gatagggtct ctggtgcgca ttggtaggtt tttggtgacg atcatcttgc accaagatag    4920
ggtttcatcc gccgacgcga gcgcctctag gaggttttcg cctcgcatca ccgcgtcgcg    4980
cagagaccgc gcagcctcgg ccgcgtggga ccgcacctca aaaagcttgt acaggttaac    5040
accgtgctcg accagcgtgt cccacgtgat tctcctcgcc tccggattaa actggtccga    5100
tccgaagccg agcaccggag cccacgggga cgagttttcg gctctaaatc caccgttttt    5160
caccggcgta gttagagtct cgcgcgcccc gtgaaacatc tcaccgatgc gtgagctggt    5220
tacgcgcctg cagacatccg ctatggagct ggcggccgcc gcgttgagtc tatccccgc    5280 ggatcgaccg ggtgtattag agccgtggtt agcgtttccc ctgcgtcggt tgcggtgaac    5340
tctggccacg ctttgcgttc tcgtcttaaa ccgccacctg tcagacggtc ctgcgccgcc    5400
atgtccagaa tctgctgagc tcgaatcgcc tccgcgttgg cccaggcgca tgtgtaccgg    5460
caggctcgac cgctttggcc agctacccgc tgactggcgc gccggcacgt tttccggctc    5520
```

```
cggcttttcc cagccacgct gttgctgctt ccagttgttg cgcctgaagg gtcgacggcg    5580
gtttctgcgc ccatggccaa acgccggccg ctcgctcttg gggtttgacg gttgcgcgcg    5640
ctgcggggac gccgagaagc tcacaacaac actctttggt gggtcgccga caacatttct    5700
aagcgctgac acggtgccaa ctgtttgcgt tggtacaaag gcgcttttgt tgaccaagcc    5760
gcgagttgcc tctgcgcatg tatcgccccc ggtgaagttg tcttcggtgt cagaccccat    5820
tatactcatt tcgtcctcca tgggctcaca gctgctcacg ctagaaagtg ccattgtctt    5880
gatacagcag agtatgtctt ccagggctct gtgtgtttag agcagcaggt gtaccaagaa    5940
aaggccaaga gtgcggacct tctcggtgac aggattttta tagagactta aagccgcgc    6000 ccacttgctc ttaggacgag aaggactcgc ccaataagcc aatttgaata cgctgttcgt    6060
agtgcagtag aatcgacaca cgcctatca caagtagcag atagactagt ttcccacaca    6120
ggttagccag caccgtggag cagcaactgg tacacaggcc tttcactccg tgggtggcgg    6180
gagtcggggg gtttgcgctc gagccagtct ttggggggctt ttcgtagata atagccacta    6240
tctccactat agttacagcc accacaaacc cccacgaggc gagtttaaga taaatggggt    6300
atatctgaga gcaggggtg tgaaccaagg ttacggttcc aactaccagg agtctagcca    6360
caaaatgcgt tcccacctcg agtccgatga gcgccaggc ggcgctgtgc tcgcagagaa    6420
atcctatggg gtcacgttta aaggtcctgc ttagagccac gcggcgcaga gacgcttcgc    6480
acagcagcag agcaaacttt gtgtagtgcg ttttgagcac ggtggtagca agcgtatagg    6540
tagcatagtt gaaggtgtag ccagtcggcg ataagaactc gttttggttt ctaaagggtc    6600
ccagcaagcg gcgctcttga cgcaaacaca aaaacgcaat gtagataagc cacgccccgg    6660
taatcatctg cagctgcacg ctccacaggt aagccctaca gttgcgagtg ccaaccacta    6720
ttcgcacttt gtcgtgcagc tccttcatgt tcttcaggac gtcgagcttg gactcgttta    6780
cccagttctc cctgcagacg tagtcaaatc cagacaggcc gtcgctgaat cgcttcgctc    6840
cattttctgg gtacgcatac actatagtgg agttgtatac ttcccacttg gcagcaatcc    6900
catccttaga gtctatggaa actgtagcgt acacgcaggg gttgtgcagc tgggcggtga    6960
gggtatacca gatggtaaac gcggcatagg cggtgataag gcccagtaca gataggtatg    7020
ccgttctacc accgagtaac atggcgctag ctggcctatt tggctctgtc cacctctagc    7080
gtaaaaatgg tgcacatctt attgttgccg cattttgtag caaagcactg ttgacttatg    7140
gacgcgcaga gtctgccgtg cacgtccgca cttatggaca gaaacgtacg agccagtcca    7200
cgtgccgatc gaaggtgctt ggcgcgcagg cagctgaatc cctgtgatct gtaagcgttg    7260
ccggatcggt tgatttgcat taaaatccag tcaggcttgg taacgacggt gtgtacccca    7320
accgtttgat attcgcccga ttggtcgggg aagtgagtgg cgaggtggga caccacctca    7380
ccgagtacca cgtcgacaac aaacgcttcc accgcctcgt gagatttat agacacgttg    7440 gcgctcgaca gaagagactc tagcgtggcg cgtttagtca tgatcgcttc tctgtttcga    7500
gctaccttgc gctcaaaaaa gctgacgtaa tctccaccca ggtcggtgat tacgtgagtt    7560
attgtaggat ggcgggggc cgcgtgaaag tgaaaattgg ccgggttcga atgctgcgct    7620
acaaactcat ctacatcgtt gcattttggg ggaatcacat aaaaaggata gagacctccg    7680
taaacttcac cagagtcgcc cactttgcaa aaaaatggaa gacgcaggct gcggccgtgc    7740
gagtaaacgc ccgtgtcgat aaacgaaaaa tccctcaaaa cggagcacat gctctctgta    7800
aacgtgcgct ccagaacaac agcctgctgt ataattcgcg ccagaccacg cagtgcttcc    7860
```

```
ggccctgcca ggaggtaagg gggtggcaca ggaaccgtta cacggaaccc catttttct    7920
gtacactcgc atgcgtctgt gtcatcgagt cgctgcagcg gcgttttttcc accctcttta    7980
tttgggggtg tattatcaca tgcggcctgt gggcattcat tgtctaccat catcatctca    8040
tagtcgtcca tcggcccatc agtgtattcc tccatggccg catagtcatc tataaagtct    8100
gattccatgt agcactcctc caccccgtca acgtagtctg ggaaagacga gggctcgccc    8160
ctatgaagcg ctctaacgag ttgagggggga cacgaggttt tgtaaaaata acacgggtaa    8220
gagtcccact gtacggtggc atcggaaaag attagtgata atgttgttat gatgccggct    8280
ctaaaaccgc gcattgcgag gtgaagcatg cccagcggaa cccgcctctt gatgccaaag    8340
tctacatcca agatgatatt actgaccgcg agcgatgagt tgaaaatttc attgcggttg    8400
atgtacatct gggcagacgc gttagaggac gccagggctg tacggcatac gccgctggtc    8460
gtgcgcgtta gctggaggtc gcgccatgcc agcgagcaat cgtcaatctc tccaaacccg    8520
gctaaagcaa agcctccctc gtacgcttgt ttactaccac ccggggcgcgc cagattttgc    8580
gttgtggttt cccagcggtc attagctatg acagcaaaag cctggcgctt ggaaggcagt    8640
gccactcgat agactggagc ggggccggga actccttttt ggccaaatag cacttctagc    8700
ggaagggctc taccgtttac tggtggtgat gatgcaatgt gtaatagccg ccgagatatt    8760
ccacactggg acgatacacc cggggagagc tcgtcaccac gcgactgatc cagcggtggc    8820
gtggaatgga cactctgggg tttgttgggt gaaactatgg tctgtatcca gccgcggcca    8880
gccagcgagg attccaccct gtctagtagc ttcaaaattg gtgtagaggt gtcacagaca    8940
ccaagcggag cgctcccagt agacatagtc gtggacgatg gggtgtaggt tttatcctgg    9000
gcatactggc tgcctataga cgccggcaaa caaaccactc tggggttcac gttgtgggcg    9060
atgtagtctc tgatattaag ctgaattctc acctgagcaa aaaatttctc aatcgttccc    9120
cttttcaggg acgaagtaga tgttatcgca tcaatgtctc cagggtcggc tatgctgaca    9180
gcaagcaggt ggtcatatag ctgtttgcgg ttgaagctct caaagtgggc aaggtaaatg    9240
taggtaataa actctcggtc agacacgcgt agtccctgtc tgtctgccgc gatgaacccc    9300
tcgagcgcgc ttacttcggc cacgtccgcc tgaattcgaa ggtcgacgta cctaggtagc    9360
gccagtgcgc acggccctct agaataccaa ctctgacagc aaaactttga caggagcgaa    9420
aatgatgtaa ggtgggtgag atccagccca gtggggttag gtgcggccgg aacgttatac    9480
gttctaataa agtcctttac tgcctgcagg tcgtaggtgc ccccggatct ggaacagcga    9540
atggcctgga ataggtaata tctggtgcc agcacaatct ccctctctcc ggggccaaac    9600
ttggaagcga accaaaacgg cgtggtgttg ttgttgcagt atagacgcct gaacgcggtc    9660
agcactttat tctcatggtg tatatacacg gaggtcaaac cggagcggcc ggtgctgtga    9720
ccgataacgg cggccttaac tgatcctcgt tgggggtcat acttggcggc tgctgcggtt    9780
cgtccgcttc tggcggtaac attctctgta gttatcgcca gagccaggat taagtcattg    9840
tggagcagaa aggtggcctc ttccgttaac gcctggagca gtgtattaga cgatagcggg    9900
tggccgtgtg atagagtcat tgccaacgcc cgggctccgg tccacgtgga aaacacacac    9960
acaaacattg ggcgtacgcg gtcttgtggc tcgtcactag cacctcccac cataccgctt   10020
aacaaacaaa agcttactga tggtttccgc tgtaaaagcg cggtcgccaa ctgatccgcg   10080
tctgactgct cagtggagct ccagccgtca ccagcatctg tgtttggcgc gcggggctgt   10140
ctcccaaaca gatcatcgag ctctgaactc cagtcgtagc ttatagcgta cacccctcc    10200
gagctctcct gtccggtcag aagcatcagc gaatacgtga taacgcagct gtcggtagca   10260
```

```
tagagaactc tgatagttgg ctctggttg cgttgcgcca tgtttaagtg gctgatgtca    10320
agtctatgtg gaattagaaa ctccacatcc ccagaagttt atgagccaat tattggtggg    10380
cagaacccag ctaccatgct ccgcctacag tccgctctgg ctgccgtcaa tgcgcttctg    10440
cccgcgaccc ttactataga ggacgtgatc tcctctgccg acaacacccg gcgcctggtc    10500
aaagcgcaga ccctggctcg cacatatcag gcgtgtcagc ataacataga gtgtctatcc    10560
agacatcggg ctagttccga caacccgaac ctgaacgccg tggtgacaac tcacatgata    10620
aacgccaagc gtctctcgga cacctgcctc gcggccctca tgcacctcta tctgtctgta    10680
ggggctgtgg atgccaccac ggacaccatg gtcgaccacg ccattcgcat gaccgcagag    10740
aatagcgtgg tgatggcaga cgttgctgtg ctggagaaga ccctcggcct ggatccccag    10800
gcaaccgtcc gggcacaaga cttgctggcc ctcaacagtg gtgttttaaa ttctgtgaat    10860
gccgtagccg agatgacaga cccgacagac gacgtcgagt ttacccagag tgtacacagt    10920
cctctcctcc cccggcagct tagcaccacg gaagtagttg gcgtgccatc tccagtaaaa    10980
tcaaacctca aatctaaaca caaacccaaa cgcaaagcca gtttggttgc ggtgtaaaca    11040
aaaaacaata aactattcag agttttttat aaacgagtct gtttttattt tatatctacc    11100
taacagtcat cgtaatataa tcacgggtag ttttttataa tccggttgag ccaaaccctc    11160
catccgcgcg taggctagag ggtgcctctc tatcgaagtc ggtcgtaaac ttccacagta    11220
cggggctttg gggcgccttt gtagactcag agggggagta cgtgggaaag gggttgtcgt    11280
agtttacggt cggcggtatc aacgcatcgt caatatcttc cgtcagcagt agctgcgcaa    11340
cgcgctgacc cttagtgatg gaaacaggat acttattgac gttaagtata aagaagcagc    11400
aggttctccc agctacccac ctagtcggta gcactattag ccccttcga ttcatagacg    11460
atcgcccaaa gatacacggc gtgacggcgg ggttggaatt agcgaagaca atcggcaagt    11520
ccacaaagtg gctctcgtcc gggtctatag tcgcgtcttc aggcgcgctg atgtcatatc    11580
cggcatcctc gacacgcttc ggagcaaagt aatcgtaaaa caggttagct tccgatgtac    11640
gcccatccct tgtagagccg atgctagtca cgtggatgct cttcctggcc agttttacca    11700
acacgagacc caagctcatc tgtccggggg gcacggacgt gttgatccca ggtgcgaatt    11760
gtaccgcttt cacgacgccg cgatatcccg agtcgactat accgtaggcg gtgtaatatt    11820
tggcagagtt ttcaggaaac gttacgttgc taaaattccc tggctcgggt tcaacaggca    11880
acaaccgct aatttgcgtg aggacaatgg catatccgct ggagcaggca acccgtacac    11940
ctacgtcagt gagcacacta taaaattcgc ccgcacttcc atgctcacca ctcagctcaa    12000
ctgtgtggtt gttgattaac accaacaatc tcccagcagc ttctgctcgc gctctccatc    12060
tctcaccaca ctcaaccacc acgatgctgt ccacgagatt cgtgacgctg gccattctcg    12120
cctgcctttt ggtggtgctt ggtctggcca gaggggctgg tggcgaccca ggtgtgaagc    12180
aacgaatcga cgttgctaga aagaggaga gacgcgactt ctggcatgca gcctgctccg    12240
gacacggatt cccaattacc accccaagca cggctgctat tctattttat gtgtctctgc    12300
ttgcagtggg agtggctgtt gcctgccagg cataccgcgc cgtcttgcga atcgtgacgc    12360
tggagatgtt gcaacacctg cattgagcaa ctgtgtatgt ataactcatc ccggatattg    12420
tttcaaccgt ttgactgtat aaaaaggcta gctctctacc tacaagaatc attagtgctg    12480
aaggttcctt tcggggttta cagcgctagt attagagttt tgtaagagtt tattattagc    12540
aagtgaatat gtccgatacg tggcgtagac gtcgcagtgg ctgtaacgat gctaacgcta    12600
```

```
cggaagagct tgtatactct accgttcgta gcgaccatag caacgacgg ccctctcgcg    12660 ggacttttgt tatgcgagaa acgacctct acgacaaaca gagtgtatct aaggaaaatg    12720
acttgtacga aagcgctagc ccaaacgacg acaaagttta taccaggcga ggtatgagca    12780
ctgccgcgca ctatcgtgac tctgaacaca tatacgaaac gtgtgagggt gatgaattct    12840
acgatgcatg cgaatattct ctgattggcg gtggtaaact atcgacctcc aatggccgcc    12900
aaagcccagc aaaagcgcaa ccacctccaa ggggagcagc tgctgctcca cccccacgtg    12960
ttccaacgcg accacctaca cgcgcggcgg ctacttccac gacgcccgg caacaggact     13020 gcgctcccaa acagcgcgcc tcgcctggtg taaactccat caagagcggt aagggcctcg    13080
cgtttagcgg caccccgaaa acgccaaaga gtcagtggta cggggccact cacctgttca    13140
acaaaaacgt gttttgcgcg gccgtgagtc gcgtggctgc cgcacacgcg agcgatgccg    13200
cgtccgcact gtgggacttg aacccgccaa agaccaacga ggacctggac aggtttctga    13260
aggccgcggc gattcgcata ttggtatgcg agggcgctca gctgctcgag gtggcgaact    13320
ctaccatgga aagtaccccc gatgggtatg cggcagctgg acccaacggt tacgatcgtc    13380
gacctcgtac agcctctaga cggcgatccc tgaaatgtaa accaccggcg gatgactttt    13440
tcgacgacac gaattccggt taacgcttat ttgcataaat tcataacact gtgccctcaa    13500
taaaatgtgc ctcttacata tttctttacc ttatttgtcg tgtgctctgt tacccggctg    13560
gtattttgac gcgcgcccgg cagcttcaat agttatgttt gctgccgcgg aagagaacga    13620
tgacccctat cccgggaaat ccggctataa tgacacctgc gagctcatgg atatggacgg    13680
tgctgtcgcc agcttcgatg agggtatgct cagtgccatc gagtccgttt attccattcc    13740
aactaaaaag cgtctggcgc tgccaccgcc caaggccgcc agccccggcg cgctatacca    13800
gcggctacaa ggcgagctgg gttttccgga gggccagacg cttctatccg ctatggagaa    13860
gtggaacgaa gacatgtttt ctgccctacc cggacatgta gatctataca cagaaatcgc    13920
cctgctgtcg acctcagtag acgaggtagt tagagcaggc ctcgatagcc tgcccactcc    13980
cagccactat agccccgagg tagacttgaa cgcgcatggc gacgagccct tcccagaggt    14040
tcccgccctg gaagacgacc tagaaatata cgtgatatcg gcacagcgct tttacctatc    14100
agagcttcgc acgcgcgaag agcactacgc gaggttgctt aggggctatt gcgtagcgct    14160
attgcactac ctatacggca gcgccaagcg gcagcttcgc ggaagcggct ctgacgcatc    14220
tttgatgcac aagtttaaac aggtggtgcg cgacaggtac taccgcgagg ccgctaactt    14280
ggccaggttg ctgtacctcc acttgtacgt atctgttact agggaggtat cctggcgcct    14340
tcacgccagc caggtaatca atcaaggtgt gttcgtctcg cttcactatt tttgggcgca    14400
gcgcagaaag tttgagtgcc tgttccaccc ggtgttgttc aaccacgggg tagtgatctt    14460
ggaaaacgac cccctagagt tccacgatct acagcggata aactatcgcc gacgcgagct    14520
tggcctaccg ttgattcgcg ctggtctcat cgaggaagaa aacagccccc tcgaggctga    14580
gcctctgttt tcgggaaagc tacccaggac tattggcttt ctgacgcacc agataagaac    14640
caaaatggag gcatactcgg acgcgcaccc ggcgaccccg ctctttcctc tggcggagca    14700
ctcctacagt aaacggatag ggggacgcct gtcatacggt acaacgaccg aggccatgat    14760
ggacccgccc tccccagcg cagtgctgcc aggcgaccca gtcccgcctc ttaccgtggg    14820
ggtgcgtcaa accgccgcaa cgcttgctat tccgtctaac ctcacgctgc agagcatgga    14880
aaccgacggc cttgactact catcaatgac gggcgatgag ctcaaccaga tgtttgacat    14940
ttaatacaat aaagtatgtt tccagactta acatgttggc cgtatttcc gtcgttgtgt      15000
```

```
tacgtgaata ggacgtagtg gtgggagtgg gcgtggtatg cggggggttct ttgtttaaat   15060
tgggcccagg cggatcagtg ccagttttgt ttgcattggg ggcctgtgcg gcatgcgaca   15120
ctcctcaatt gcgtatcttc agatatcgcc catttaacag tataaaacta gagagtatgg   15180
cggttttgaa gcttgtacca agcctataaa actagcgcgc cgtgcagtga gatgggtgtt   15240
gctatctaca ccagatagca ggcgcttctt tttcaaaact tggcggttgt acgccagcga   15300
tacggaatcg ggtaacatgg accagcatca cggcgcgcgc ggcggagctc cgatacgccg   15360
acctcgcaga tccatagaat ctcgctccca cccatttcga gctaccggaa atacacagcg   15420
cacatacagc acgccgagac tcagctatag agacggtctg tccgggcgca ccgcttcgag   15480
ggaccccccag gaacaagctt cgaaccagga tgagagttct aacccgagca cctctaatgc   15540
tcaacaaagc acatcattct ggggatatct tcgacgagtt ttctcagacg atgtccccgc   15600
acagccacaa gcacccagac ctcgcgcgga ctttgcaccg cccgccggcg aggaatcatc   15660
tagcgaggaa gaggaggaag agggtcccgc ccaagctccg ctggacgagg aagaccagct   15720
aatgtatgct gaccagtact ctgtagggga ctctagtgac gaaaacgacg aggaagaaga   15780
cccccgtcta ggatctgact atcccacgtc cgccgaatcc agtgaatacc atgaccatgg   15840
tgaaatggtg gccggtgcgg gagccgagag tgagtccgag acagatattg acgccgaaga   15900
agaagaagaa gacgacgaag acgatgagga tgatatggaa gtaatacgag acgaaagcta   15960
tagacttcct cgtacatggt tggacaagtc tatacgttta atggacgagg ccctcgctca   16020
atcttccgaa ttatcgaagg ctatcactaa atctacacgc agcttgtacg atagccagtt   16080
tgctcccggg ggtagaggct acacacagac ggcaacgccc tctcggcgcc tggtacagct   16140
atcgcgcgct ggaatgtacg attcggataa aatagttatg acgggggact acatggaggt   16200
tgacgacgat ccagacagcg cttaccagtc atgggtgcga gcaattcgcc acccactagc   16260
gatgaacccg tcatgggagg aaacaatttc caaccacacc aacccatcgt tttccaccga   16320
catcgactat gatatagacg agctaattga aaaaaacctg gcccgcacac cccctgtgtt   16380
tgagggatta ctagacagcg cagagttttt ttacaaacta cccatgctat acacatacgc   16440
caccattacg caggacgagg cctacgaaga gcggctagct tggtccaaca cacaggcgct   16500
acatggacac gaacaaagtt cctggcaggc actcctggtc tattactcca ggggggggaat   16560
gtacgtatcc ccgactcaag aacctcgagg gatttggcgg cgcgcgctaa acaggcgat   16620
ggcgcttcag ctaaagatgt gtgttctcgg cctatcggac gtcgtaacaa agcagaacgc   16680
tacgcaccac catgccgcgg taacatttct cgtggacgcg cttctcagaa ccgctaggaa   16740
ttgttacttg gcgagccggc ttctggtatt tgcctgggag aggcgcaggg aaactggggc   16800
aaaacgcccc gcagagcccc tcatagcact ctccggggtt acactcttgc agccccttcc   16860
cccagaggtg tctgaactgc ttgagcagcg tacatttgac attgggttgc gcaccccaa   16920
cagtgctgtg tttagggcgt ttttcggatc gctggtgtat tgggcagaac tgcgcctggc   16980
tcttcgagac cccgcgtcca taaactgtcg ctatgtcgga ttccatctac agacctccga   17040
aatctatttg ctggcgcggg cccactccgc gagtccaggc tacaccaaag aagaactggt   17100
ggcaatggag gctattctaa ccctcgctac actcatgcta gaggtggcgc tgcagtgggt   17160
tcacgtggct tgcgcacagc tgctcagcga aaacgatacc ataaaagcct ttaggcgggt   17220
cagcgcatct atcccgcacg ctctggcgcc ccttggtagc atacgcctac acgacgccga   17280
gtttgaagtg ctcagcaacc cagatgtgat ggtggctaga gacgaaaccg ccctgagcca   17340
```

```
ggcgctgttc ctcggttact tttccgtgag gaccgcgctg accgcgtgca tgcgtgatta    17400
ctcacacgag gccgacggtg gatccaaaga aaccgttaca ggggtgtttt tgggggtggg    17460
cctaatcctt cagcgcctgg cgggccacct caactttcta ctcaactgtt tggccggggc    17520
cgcgctgtac ggcggccaaa aaatcaacat acactcgcta actctgccgc gatacagcct    17580
attggcggat gtcatggccc ccatgctcca gcggcagtcc ctggtcgact tttggcgggc    17640
ccgcgataac atgttggagg atctagaaat aacacctcgc cccggccctc ctactcaggg    17700
caagcgcgtg gtggttgaaa tgccactccc atcagacgac ctcccagaca tgaccccgg    17760 cgcttccgtc aacaatggcg ccggcctggg acgcatggtg gacatggcca agcaactaca    17820
gcactacaga gaaacaatca taggggaaga agccacctcc tccgtgggaa aacgtggtct    17880
aatcagagct ggtgtgggcg tagccgccct gcgcggtagg cggagaaagt gagaagatta    17940
acactcggaa gcacttaatg ctgtttacgt ccggaatctc tctcacatcc cttaagcact    18000
tccccaaaac cgcctctcca gcttacacgg catccaacct gctatcggtc gtagcgccgc    18060
tccatatacc gactagctta caatggacgg aggggggtct tcttcgtgga ctcacgtttc    18120
caaaaaccta atagagcggc gcgctgtcaa gggggtgcctg ctgccaaccc ccagcgatgt    18180
tatggatgcc gctgtgatgg ccctgaaaga cgtgaccgag aacattgtgg ccaacaact     18240 attttcggta gatcgtacta acgctctgtc tgttattcac accaacgagg ttccggagtc    18300
aataattgcc acggccatcg cacgcgacac atccagagac tacttgaggg aatatgaagg    18360
tgcggctaag tgtaacttgg cagcaacgga tctatcgcat gatgaaatgt gggaagtggt    18420
tatcaaaaga tactggcgct acctccgcga gtccagcggc gcagaggttg tcgatcgcgg    18480
tgcggtgggt caggcgactc aatctgtatt atccgtgttg cttctccagt ccaccttcgg    18540
caaaaaacgc ttatctaaaa atcccttcaa acacaagggc cctaatgtcg gctacaaatc    18600
caacctggag gacctgcgct cagcgtttac aaaaattgaa aagtacatgt actacatgcg    18660
ccccaatgat cccatgacga agagcgaaga cacagagctg cgcttacacg agctactggc    18720
gtacgtgacc acatgttatc gatggctgtt gtggttcatg gacctgacag acgccaaggt    18780
gctgagaaac atagacaaag ggcccgttat cacacacggc cctcgcgagt ctcgccctcc    18840
ggacgaactc gtgcggcgcc acctcaagag cggtccggca atttccgccg gaacgggtgt    18900
ggctctgact ctgtcgacgg ccaccgccga cgccttgatc gttttgctga aatgagtgt     18960 ttcctggacg tcccactcgt ggaagagcaa tacccacggt gtcactggtg ctatcgtggc    19020
cgccgtggag ctggtcacgc tcatccacca ccacttacag tacattatta acaccgtatt    19080
tgcaggctac gtgtgttggc tcgatggtgg cgtggagaac tcatatctaa actctgccct    19140
ccgcagccag ggtaggttcg atcatttgt tggaaaacta gtgcccatca tggccaccct    19200
cagctgggcg aatatggaaa agggacagt catgtggttc aaatacgctc tggccaagag    19260
tatagtgtgt catggatcgc ctactcagca ctacttaaca gtgctagaat ctatcgcgtc    19320
taagcgcact ggcgcctgtc ctcccaggg atcaaccttt ggacgcaacc cctccggttt    19380
tcccggacag ttttgctgtc ctcccaagg gccgctaccg gcaccccca actctaaaac    19440 tcgcggcacg tttaggcgat gccggcccgg cagcttgcgc agctccaggc agctaccaac    19500
ctcccctccg tcgaacatag tttccccag gaccaaccccg gcaatagaag ggtctacggc    19560
tgctaaaaac gtccagggg gcggagacca tccaagtacgc tcttctggag aatttaacga    19620
ctgtatctgg tatataaacg gagcatatcc ccatcaacgc agcgacagca gctcctccga    19680
taacagcaca tgttccagca cggagactca gtatataact ctcccctcaa cgccatcgcc    19740
```

```
aaccggggac gttgtttaca ccaatccact ccttgggccc gacgaggaag tagacgcgag   19800 ccccaaccc gttgatccta tgagcgacta ctctgcgcca aaaaatcccg actatatgcg   19860
cccccgcagc actctggtcg aggaggtttg gcagctgcga gactccgatt acactcccta   19920
catgcgcccc agccgtgccg ggcgttcccg cgtgagagtg gaagaccaaa ctctggaacc   19980
atcgtccccc gccggttgta atccaccgc caattctcca gaaaacgatt cagacgatgc   20040
cgccgttgac tcacctccca ttagcccgga ggttgtgtat ggtacattta ggcccagggc   20100
caagtgcgtc tatgaccaat acggattgac cgcacttgct gccctaagcg cctcaagagc   20160
aaaggccagg cggacgcgcc ccggccccac ccaaccagat gtttgccgcg agcgtgacga   20220
ggaatctgca gagcccagac atgacggttt tatcaggcga accatgtcta cgactggacc   20280
ccctagaaaa cacccggacc agacggagcg tgttagctcg ctgtaacccc cacctactac   20340
ctaccctcta tgatgattat attaataaaa caattcaaat gataaaattg tgttactctt   20400
tatttaaagt acatatataa acaattttaa acaggttttt gcgcgacgtg tatagcgcta   20460
tttatttcag cgcatcggtt tctctattac cggggaaacg gtatgatgtg gtccagacga   20520
agcgcttggc gggccttgta gatcagctct ccaagcgggc tgagtgggcg ggctgcatag   20580
cacacaccaa accccttggt gtagcattct gcgaagctcg gtacgttgca gtaggccagc   20640
tgagtatcat cgaggttgag cttattcata acggattcgc tatctcccac gttgaggcag   20700
tccagcagac tcattattag gcctgcagtg ccattagaag ccgccatctc tgagtactct   20760
tcgcatactg cccccacccc gctgatgttg cgtgtgttgg atgatgcgtt cagcaacacc   20820
gggcgaacac actcgtcccc cagaccaaaa gtctctgcgg gacacggtgc cgtgcgtagc   20880
gcgccaatag gtactgttaa tatgaaggtg gacaccagaa tggcggttgt catcaaaacc   20940
cccagcgcaa acatgcccat cgtaaaaaaa aggcagcggc attttgcttt gcgctttgtt   21000
ctgcgtcgct ttgtataaac aagctcgttg ggttgagggg gggttgacag cggggcgca   21060 aacaccggaa cggttttcgt tggtaagggg ggagcctgag catcgacggt ggcggtttcc   21120
agctgtagta atttataatc ttccatcgca gctgttgggt ctcctgccat gttgctttac   21180
ttagacgtta cggccgcata gagatcagcg tataccgcag agtataatgg ctttataaat   21240
atcaccgggt cgcgattgta acacaaaccc aacggttttc acctagcgcg tataaccgca   21300 tattttagt gccatattct cgagagtgag tttgtgcgta cggttggcct atgcggacga   21360
cttgtgggag cccacctact gtttttacca gcgcttcaaa ctgtagtttt gacaaatagg   21420
ttgtttgggg gagagcggtc cagcctaaaa gtcagacttc ttgtacggcg cctgtgaggg   21480
cttggagcag taaaaacaga cggctgtgat gagaacgacc agcgccagtg ccgcggcccc   21540
gcaagtaact gcgatgatgc tcgtcaaaac cggcctgtcc tcaacaatcg gggaggcgtc   21600
atataccact gtgtccgaaa acataggcag gccgtcgggg taccccctcta ttatgcagct   21660 atactccctc tccccattct cttctgagag gggccggcgg ctttgcatgt taaccaatcc   21720
cgagtggcta gggcagactc cggttgtcat gtcttgcgac ggaacccctg gtaggtggtc   21780
gttcactgac cacgatacga acaccccggt gctcggtacg catttagccg tacagacggc   21840
gtctccgtct tctaccgaaa cggacacggt tggggcaaca aacacagagg gtgttccagc   21900
tttggctatg cgagcaaatg atacttcgtc cctgtaccag tctatgctac agcgaagact   21960
gggtgtgtat tcctcctccg gatcaaccgg gatagacacc gtagagattc gcgtgattag   22020
cccgtctacc cacacgcttg aggcgttcgt aacgtacttt gtaaagtcca cctcgcgggc   22080
```

-continued

```
atttttgtac caccgcagct tgacggagct gtgtggaaag tagcttgcga cgacgcacgt    22140
ggccctgtag ttttccccct tcaggctcgg gtgaacggaa aggtccagca acggtgcgtt    22200
gtaggttgag acggtaacgc tggtactgtt aacgagcgtg ccattttggg catacaagga    22260
ccacacgtaa atgccggccg tccgccaatc tacagatttg atggtcagtg gaaactttgt    22320
accaccttcc gtgtggaggg gaaggttaaa cagctggcgc tttggtagcc tgtctgggat    22380
aactcccagc tggccacccc ttcgagattt tttcctctct gccgttgaga ataacagcag    22440
agtctgatcc ttggtggcgt tatggttgat gtagttttct tcgtcgccgg ggggcgtacc    22500
cgaaaatggg gtgcgctggt tcaagtaaat ctcgaggcgg tactcgctat aatttacgcc    22560
taccgacgtt gtacagttca tatcgacaga tttgtagtag ggcacagata tgagactctt    22620
ggtgcaggtg attgtggttt catgggagtg tgtagattct gtaccgtttg cgttagttgt    22680
gttgtcagag cccgcgccgt gtgcggtagt tagattcgga gttgtgtgag ttggtgtagc    22740
gggcgtactc tggctggagc tagcactagc tccagaggca taagttaata tcgccccggc    22800
acagattaga tacgcgaccg ccacaaatct cacgagatta ggcaaccaca tctcgcgggg    22860
gccgggtgct tgctattccc cacgaaaaac gataataact ccactggtcg gagagttata    22920
aacataccat gcaccaaagg gtcagtttta aggggtttta ctttatgtga attcaccgac    22980
gttagaagca atatgctata cagtcgttgt tattactaat tggcatgttt aatgtgtgat    23040
tatagttgca taacacaaac cggcggcaac atatacacaa acaataagcc acctcgaaat    23100
gtgagttgcc gccaggcggc gcgcgcccgt tgcgcgcttg cgaaggtata gcgccccag    23160 tataccccg gatacagtaa atgcgagcga gaggggagcg gccacgccgt acccaaaggc    23220
ggcaagcacc atgcagacag cgtgggccgt ggagtggatg ccggaactcg cctctgccgt    23280
gtagtttact ctgatgacaa gctgctccag cagcatcgca gagacgtgtc caacagtcag    23340
acagaagaca acatacgccg gggtttgcca cacgttggaa attccgtaga ccaagcgtag    23400
gacgatccat attatggggg ttgcgtgagt tccgaccgct ggggagaaaa tcaccccgg    23460 catctccttg aaaaacttga acagcgaaac ctttcttcc gcgacttctt cgatcttggg    23520
gacggcttca acgtccgtca cccatctgta gttaataccc cggccaaggt ccgtaaaggt    23580
gcgcatgcac gcataccgtc cgattcgata gtggcatgtg tctcgaagag caagcccaaa    23640
gtcttgacag gaagctataa tagcgatagc tatccctatc cctatgggta catctttcag    23700
ctcaacgagc tttacggaaa cccctagcac acatccaccg ataatagcca ataggctcgc    23760
tctaaagtga gtccccgttc cattggctga gcatatgacg taaaataggg aaatttgagt    23820
tccggctata aacacaaaca aaatgcaaac ggtaacaact ataagtaaat gttccttttt    23880
gactgcagat cccgcgaccc agacactggc tgccactaga gtggccagcg cctgtatcga    23940
tcgacatacg gttactatag tttccatctt agatatgggt acgcggatca ggctcaacac    24000
atacatcgag atgatcatca gaatcagaca tgttgagttc cggttagca ggtcaatgtg    24060 taagatcgat gaagtgagga cgcaagcttg tagtccgatt ccaacgaaag ctttggaggc    24120
cgcccaggta catggcatgc agcccctctg ggagccggtg cagcgttgga ccgaagatga    24180
gcttagcacc agacacgagt cttcaccggg ctctctatct ggctggtaca tcatgattga    24240
taaccttgat gtagcaagcc aacctttgga gagtttgagg tacagggacc caagaggatg    24300
gttttatgca ccaggtatta gtcataaaac aaatacttag tgggcgtgtt tctacaagtg    24360
taaatagttt taaccaaata gtgaaactaa gcaataaaca tttccgcgtc tgtcgtttac    24420
aatatgcgtt tttatttca gtatagcaag catggtatac ttatactatt acaggtcact    24480
```

```
aaaaatgcat gggctgttcc ggacagggaa ttttcgctcc ggttttgtcc attaacaaaa   24540
caaaatttga cttaaacagc ttcccgtcag gaaatagttt tttgggggc tggtcgcttt    24600
cttcctcctc cgacgcgcgt cgctttactc cagcccccat tggggtcgat gaaaaggcag   24660
caggggaaaa cccaacctgg cacggctggg tcgggtacga acacataaaa aacatcatca   24720
cgctgaacgg ctgcttggtt gagagcccga tcatgggaat agagtctgga tccaggaaaa   24780
agttaagcac cgctcccgcg ttttttagtt taagcttctg aattagctgc ttaaagttag   24840
tgtcctcatc gagtaccagc gtaaacagac ggcgaccgct gatgcccctt atgggttccg   24900
gcgccgactt tttggtcttc atcggcatct tttccaatag gctggaactc gactctacgc   24960
cgcagttgtc tgcgtgctgg tagtccaccg aaaacacgac ttgccgatct ccggatctta   25020
cctggagagt gtcgtcgaaa aggcactgaa aggtgatggg gtcgccagct tgtttacaaa   25080
cccccaaaat tttgttcagc tgagccttcg atagagacat agaaacatcc ggctgacgag   25140
tgggtaacat gagtgcatag ttgttgaact cgtgtttcac caaccgcgac gaaacggtct   25200
gagttgctcc ctctgcatca gatcccatct ccgtatcttc ttccgtttga tcgcgcgcgg   25260
agaacaccgt ctgggtgagt attctactag gagaatagtt ttctatctcg aaaactacct   25320
tactcacgtt cgtctgggtc ttcgccttga aagcgtccag taaaccccctg cgcccgtcta   25380
cgttggccaa aaacacggcg ggggggcct ttttccacga gtacgactcc atgttgttag    25440
tctggatggg tatgtatacc tgctcaccgc cgacgctggt gtgaattagc aggccgtcct   25500
cgttgaagat cagaaaggcg ttcttgaggc tagggggcgat gggagtgagc atctcgaaag   25560
catctctcag agattctcgc tcgaaaaccg ccatggcgcg ctgtctctcc actgggttgt   25620
cgatgaccgg aagcgtgttg aataaaaagt tgttggggtg agacccgcct ggacgcatcg   25680
cgcgaggaag agccatcgtc gatgaggaga ttataggcta ggctgctcgc gtatctcgaa   25740
gcactctata ttagagcgaa acaagcagta ctttgaccta ccccgtagcg cttcttatag   25800
agtttcgcgc tagagataaa aggattaaca tgacgtaacc aggggagtgg tttgggggaa   25860
aatgggctt ggtttaccga aaagcgaaaa aatgggggtg gtatgtaggc gtgggtgtgt    25920
acatcggtta ggccacgtca gtgggcgcag gcgcaacagg cggtgtgggt ctgctttgga   25980
aatgcctata gacgacagta tcgtgttatt gtaaaagtga agtttaggg aggggttttg    26040
atggtgggca gagctaaact caacaccaat ggaaagcttg cctaatcgcg cacaccaatt   26100
tagattttcg actagagtag aactctgctt atattagctc gctttttggg agcaccggtc   26160
ggagttactg ctgggcaagt tttggaggtt ctacccggtg ctcatttact tccccactcc   26220
tctggtacgg gacatcgttt tggcgccagt cggccaagag aatgggactg tttgactcc    26280
taaaatacgc atactccaac cggcttgtga acacgatgc cattacaact ccaccgggaa    26340
ttatgacacc gatcgctatc gatctttgga atgtcatgta caccctgatg gaaaagtttg   26400
accaggagcg caattttccc ctggatggcg cagcggttac cgcacggtgc ttcttttccc   26460
tactaaggct tttgttaaag aggtcctact atcccatatt cgtgtccgac agaggcatat   26520
acggcgatgg gcgcgtaaag cagggagcca aggctattgt tagtcaaaca atgagcagct   26580
acggagggtc agggcgtctg tcgagcgcat gctttacagg cgacgaacac gataccgaat   26640
tccaggaaga tcccgaagaa aacgatgtct cagttccccc gcaagacacg tgtcccccaa   26700
cagaaatatc tgccggttac gtcgaaccgg agcgcaagtg cgagcatagc tccacgcgct   26760
ggagcgcgct tgatggagcc ccgcgccttt cctaccgtct ttgtgtcaat ctgattcggc   26820
```

```
acctcggata cccatacgtc aacgcgtgta acctagaggc agatgacgtt tgcgcaaact   26880
tgtaccacac caatacggtc gcgcagatct acactaccga tacggatctg atcctcatgg   26940
gctgcgacat tattttggac atcatgccgc tgtttccgcc aaccctccgc tgctgtgacg   27000
tgttaatgga cttgggagtc acatatgacg agttttttgac cgagtttgtg cgatgccaca   27060
cggatctcca cgagcccaa accctggctt cagtgcagag cgtaattagc tcgctccact   27120
cgccccccga cgaagatgaa ggcgccgata tgccgcagac tccctcagga cactcgtggc   27180
gctgccccaa cgagcgccga gtcatttctt ggcgcagaca ggacgaccat gactacgact   27240
cgtctacaga agatagcgac cagtcggata gcagcgaaga agaggaagaa tgtccagccg   27300
gtaaaggttt cggatacaga gaaaacccgg ccgtagaaac ttgtaaaaga cgtacgaggc   27360
ctcggcggtc tgcggaggcc tcaggtcgta ttctacacct caagtacacg tctagatatc   27420
ctccaatcat ggaatcggcc ccgcgcgctt tagtgagaat ggctcccccc aaaacccgcc   27480
acgaggttct ggagagaaag ttcgtaaagc atgtcgtttc catgctaact ccagaacgtc   27540
gaggctcgtt gtcgataatg cgacgcctac ccatcaccca ggagccgtca aacttttctc   27600
tggtccacga taccctcaaa aacctggttt cagaacacga gattgctcgg gagctagcca   27660
acatgttttg gaatcacatt cccaccccaa ctgattacaa cacggtgctg gtcaactact   27720
gggatgactg cggacaccgt agacagtggt cgtgaataaa gtttgttttg aatttcccac   27780
attacatctg tgttttttac tttccgcgcg taaagcttac acactacccg taaataagca   27840
cgctttaaat caaacaacaa caggttgtat ggctgtaaag ggtatgtttt tatttacaga   27900
tcgttaatta gagttccaga gtatgcggtg ctgcgccgct caaaaaagtt agtgtgtttc   27960
tcaactgtca tgaaggcgag aggaaagctc ggggatggtt tgggggcatt aaacaggggg   28020
gatagtccta tttcacccaa aaggcgatcc gcgctatagc gtacgtagct gatgatggcc   28080
ccgatgtcca acaggtgact atattgggga gcgtgggata gcagaaattc acactcgata   28140
ttcaccgcct cggagaacag ctcataaatc ctttgggct cgggcttctc aaatcccccc   28200
aggtagttgt tgtagatgca gcacgaggcg cgagtgtgga tcgcctcgtc gcggctgatc   28260
aaatcattgc tctggcacgt taccacaaat aggttgtggg tacggagata ggcgatagac   28320
gcaaaggacg atgcgaaaaa gagtccctcg atgaggatca tcagaatata cttctccgcc   28380
acagatccgc attcacgcac cttttgcctgt agccaggcaa ccttccgtcc gatggcagcg   28440
tctccgatga tggacgctac ataccctagcg cgcgcggctg cgtcgtttcc aaacaacatg   28500
agctgtatag cgctgtatac cctggagtgt gtaacctcaa tagactcttg ctctatgtag   28560
tagtggagaa tgtccttttg agtaaacaga gctgagagat cgcccaggtt caaattcacc   28620
aagtcgtcgg cggcagataa aaaggcgaac aggaaccggt aaaactcgcg ctcggccggc   28680
gtgagcttgg ccacgtcctt gaggtcatcg gaaatgggaa ggtcggtgtc cagccagcgg   28740
tttgcaacgc tgagcgagcg caggtgctcg atatcggggc attctggagt ataaaaaaac   28800
gcacctgcta atgataattc tgcggttagg gctgcttctt tagagttttc gatagacatt   28860
cttattcacc aggtgttttg tttgaagcgg caaggcgtcc ccactacagg ctgcagctag   28920
tacagacgag gtccccgccg acaaagactc cgttgtttgt tgctttctta attttgcagt   28980
agtacatacc ggttttgagg ccgcgcttat atgcgtggac cagaaggctc ataatttttgg   29040
aggcggggag ttttccgtca gcaggctcag ttataaacaa agacatggat tggctctggt   29100
ccacaaacgg agctctgtca gcacacatgt cgatcagcgt tctctgatcg tactcaaagg   29160
cagttttaaa cttgcttagg gggtggccca ccggcaaatc accaaacgcc ccgacaacag   29220
```

```
accactgcgc catctcgagg gtagacagcg cctgcaggcg cgcgcactcc cggggaaaaa    29280
tactccggat ggtgcgcatg agcaataaat tcggcctgag cacctcccca gtagccgtga    29340
ccttgctaaa taggtttgtg tagacgggcg aaaaccctc gctgctctct gtaacctgag    29400
acgatgacac ggtaggcatg tacgccacaa actgagagtt gtacagccca tgctgtttta    29460
tctcggtgcg gagtctgcgc caggcgttgc ggttggcgag ggtaacccg gggtacgaat     29520 cgaagggtag ttccccgaga ctgtacttgc tgtcctcaaa ccccttaaag ggtttcatgc    29580
cgagtctgca tagcgtcgcg ctcgctttca tggagttcag taaaagcctc tctgctatct    29640
gcttgtttaa ttggcgagcc tccggagaag ccatgtccag gtctagcatc aggaaggcgg    29700
tatgcagccc ctggatcccc agtcccagcg acctatttc gtcgactcca cgctgagact     29760
tgactgttgg gtacgtgccg gcgcgcatca tggagttgac aaagatggtg gcagtcgccg    29820
ccgcgcgacc cagagcggca aagtcaaaat aaggcacgcc cgcggtatgc ggcggggta    29880 tggcgaggca tttggggagg ttgatgctgg cgaggttgca caccccgttt tgggtctcgt    29940
ctgcgtgctg gataatttcc gtgcacagat tggaccccat gatagcacct tttctccgca    30000
gatcaaagtg gtagtgctta ttgcacgcgt ccttaaacat caaaaggggg cttccggtca    30060
ttacagcact cctgactatg atgaaggcca tgtcctggat gggaatggag tcgaccccaa    30120
atccacactg ctccaggcgc tcgtactcct cctcaaattc tttgccgtac atatggcata    30180
gatgtgacgc tgtgtcgtca aacagcgtcc acattacgcc gctctctccg tccaagtacc    30240
gttgatagcg gtcaaaaaac aggtctgggg tccacatgca ggcaaagatg ttgtcacacc    30300
gaacggtttc gtctctggcc agcatcccgc gcatgttcag aatcgcgcgt atgtctgcgt    30360 gccacgctc gaagtagacg cacacacctg taggccgctc gccgtcgctg ttaatggcca     30420
tggtcatgga gtctatcagc ttcagaagcg ccataacacc cctagagcac ccctctttgg    30480 gggggtgtt aaacctctgc agagacagcc cgattccacc tctgttgcat agaatgggcc     30540
cggcctcttc cattagagcc agcatagcag agttcatgtc cgtcaccctg gggttcagca    30600
gataacagct tgccagggac ccgcagtctc tcccgccgaa caacataatg ggcgtagcgg    30660
gtatgaggac ctgtccggcc agcgccgtaa agtaggcttt gaaaatatat gtccagccta    30720
cttccccgct gaccaacacg cgcgccatag ccggttcctc catcgtatag tgcgtggctg    30780
ttgtggcaag tcttagaaaa aattgcccca tagactctat acgcccacct cgcattttgg    30840
ccaaatacat ctcctcatac tttaacgcag actgcagccc cagggcgcac agctcgcggt    30900
actccgagga ctcaaacgcg tggagggtcc gctgaataaa gtctaggtgg tcgaggatgt    30960 cttctccac gatctcattc agagcgattt cggtagagtt tagccaatat tttaggtcct     31020
ccacgttccg cgttcgaatt cgcaggtgta ctagctcccc gcacacaacg tacagtcgct    31080
cgtctactcg acatctcggc tttagagtat ccaccaccct ggtgatgtac tccaagacct    31140
gggagcgaga cgggcgggga ggcagcgtgg ttgatagctc gttggcgtag ccataatcgc    31200
tgatagcatc cacgcgggag ataacatctt gaataattgc tagcggacag tcagattgca    31260
ggaaattcaa agccatggtc ccgtgtgatg tttgaaaaag tgcgctagaa acactaatac    31320
ccactaagcg ggagtattag gtgtgaaaac cttggggctc cgcttcgcct tatgtctggt    31380
cagatttcta cgtaacctac cacgtagact ggctttcatt ggccgctaaa atgacctccc    31440
attgtagcgc gcgtaatgta caacaaccaa caccaaagag tcaggtcgta aaatagaaca    31500
tgctttattg aaaagggttt agtaactgca ctcgacccaa tcctgtgggt cccaccgtac    31560
```

```
attttccagc caaaccacgg gcatatccac gctgccaaat ctctcgctac ggcgtgtggt   31620
tctgggggag tctgaggcta tggcccccag gcgaatatag gcggcataca tacacgaggt   31680
tctgtttggc cgaccccgca ggtctggtgc ccactggtac aacgcgttgg taaattctct   31740
gttgtttaga cgcgaaggcg ggcaccgcgg ctcacaccga ctgcttgaca gttcctggag   31800
cgggagggcg gcgtttgggt gcggctctgg cgcgtccgct ccctccgttc ctctgatggc   31860
gctctcggtg cgggctttgt gaaacagaaa gctgactgca tcctcgaagg ccacctcatc   31920
aaacttgctc accgccacgt acaccctcac tccctcccgg cgtaaccgct ggctgtacac   31980
aaatattagg taaacaaact ttgcgctcgc gtcgcccagt ttcagctcgt gatccacatc   32040
cagaaacgca cacgccggca cgtaaacgct agacctgggt accgccgagt tgttggtgcg   32100
ggcaccctct tgcacacccc cagcaacagc ggtgaggctg gcgagcttgt cctgaatcac   32160
gtgggagata aggcctccaa ataccgtcat gtgtttatga ggaaagacgt gggttcgcac   32220
catcgcctgc aaatattccc caaacctgtc taggcgctgt tccgttctac ggtcacggta   32280
gttggctagt acgtgcgccc taacggcttc cgcagcggcc ttgtcagagt actccccga   32340
gcgggatgcc accaaaaacg tcaaagaaag caacgagggt cgcagccccg tcgtatccga   32400
gcgaccggac actgacagtt ccgacagcgc ggcccaagcc tcgtccaact cctgcggatt   32460
gcgcccgggt ggggtgcttg atggtgacga tccaatggca tcgaggtggt ggcggaggcg   32520
gattatcgga agtccgggcc gctctgctgt ggggtcgcaa aagtcggtaa gcgttacctg   32580
acgtgtaagc ttcagcgatg ggttaaagct tgaaagcatc cacgagtttt gctctgagtt   32640
gatggccgcc gttatcacac ccgcagatga aatctggatg ccgcccatgt tgctgatcgt   32700
tatactattg ggggtggcct ggacaaatcc ggggagccag tccagcgtgt tggggagtcc   32760
aaacgctaca tgtccacgtc cacgtccgcg ctgttgctgg ggaaatccag ccggtgggga   32820
gatctgttcc cacctgacgg ctccatttgc gtccgtatac ataatgttgc tcatgccatt   32880
tccgatttgc acaaatctgt tgcccctag attcatcttg gtctttggcc cactcggtga   32940
gattcaagct accttctgt gctgctatat ctcgaaggtg agtacgtaaa cagcacgtaa   33000
gaaacaggga cgtccacgga cgtgctctgc ttggggcgcg cgagagcaat tgcaacaaac   33060
gcgcccaac aggctttatc tactatccgg ctcgcgaaaa tatcatgaat tgacatttaa   33120
aaataacaca actcgggttt aagcaatcag aggcgtgtct cattttggta cgccacacgc   33180
cgtacgtctg aaagatatca agccctatta aacgagcgcg gttgctgcct gacactcaca   33240
aacccacgcg cggcggtgcg tctcgctact acgttctcgt gccgaaaaat catggcgcgt   33300
gaacatgggt ccatgcgagc cctggtcaac tctctggccg ggctgctcgg agaaaccgac   33360
actgaggtcc ccagcctcga gcctgcaatg ttgatggtcc tcaaatcctc catatcagag   33420
tttttcctgt ccaccgacac tgtgtcggtg gacgaggccg cagaactatt ccccaggcta   33480
cagtttctag cctgccgggc ctacgcagca tcgcatacac ccgatgcggc catgctagca   33540
gaaaacctgg caggcctcgt tctgtggcgc atacaccaaa actggacgga cagggaaatg   33600
gaggcggtgg accagatgtt tgtgctgctg gaaattatga acggcgaatc gggtgtgtac   33660
atgctgtcta ataacaacct gagaatatcc gccaaatacg gaccctccaa catgcacctg   33720
atcgttagca cgtggctaga tacgtttcgc aatgttatgt cggttgccgc taaatcgact   33780
ccggactcac tcttcaactc aaaacgaatg gagtctatag aagagttttc taaacctta   33840
gtccacgcca gtttaattt gatatacgac atgccgttcg tacaagaggg cctgcgaata   33900
gtggctaaaa aaatcaactg gattctcccc ttcggcctaa tggtcaaggg ctacaaggac   33960
```

```
atgagcatgg ctcctctaac gcgggcgctg tttttgctgt ccttggtaga ctcctatttt   34020
cccaaaggaa ccgcgaccga aggtagcatg aaggcgttga cagcatactt ccgtgaactg   34080
gttagaacga tcgacaacag tgcttttgtg cctataacag aagttaacgc cacgccgcgg   34140
accgcgtacg aagttagagt ctcatcagct atagtacatc aaaacccata cgtaaccgac   34200
accaaggcgg gaatggtagc agagcgagtg cgaacgacg ctgaaatctt aacctcgggg    34260
gcgctattaa gctccggggc gctctctgcc catgcgacgg ccgtggctaa gctactctcg   34320
tccaacgaac ccgacgacgt gtcgtcccgg gccaggcgc gcgtggccga gcacgccagt    34380
aacacctggg agaccatcca ggccagcaca acacccacac aagtcgtgga agccctagtg   34440
actgcggggt ttacgtccac acactgtgga attttggagc gcgtggtggt ggactatttt   34500
acgcgcctgc gaagcaccgc caacagcggg ccggggagaa acgactccct agactacgcg   34560
caacaagtcg ttggttgcgt ggctatagta ggcggcgttg ttttcaggtt gctgttgtcc   34620
tacggctttg ggctagacta catccgggac tacacgacaa cgatatccac gctggagccc   34680
gtgtacaacg agctgctgtc tgccctgggg ctggcggaca agggagtgga acagaccctg   34740
aagcgcagca tggcaccgcg cccgtatatg aactacatct cagcggcacg cgccgcgcta   34800
gacgacgagc tgttaatagt cgaaaagcgc accactgggc ccggaaccca tagcgccgcg   34860
agggagtccc tactgacgtg gttcgacttt agggcccgag atcgatgggg tgtgcgtata   34920
ccagatagag atacgacatc gacacaggtt ttggccccaa tcacagcatc gctttattcg   34980
gacgacgacc taatagcggc ggcatctaaa ctgtcgtttg atgcactaga cgcaccccct   35040
acccaaatta tagacgaccc ctcttttgcc ccctacatgc tagccacggt ggtgctggac   35100
gcgtttaacg ccattttaac atcgcggttt ccgcagact ccgtgtctca ggcgctgcgc    35160
gtactctctt gggccaggga ctacggcgcc ggatccattg ccaacgtgga cgggtacaga   35220
actaaactaa cggcgataat agcctcggtg tccccctttt tgcaaaaaga tgcccctacc   35280
ccaaccatgg cccatgccaa caacctggag gcgcttttgg gagaactcca ctctgttgtt   35340
gtggccgcga tcgcactcat cccagaacgg gcgcgcatgc cagtgcccga acgaccctcc   35400
gttaaaacca gtacatttt ggcagggcta ttttaactg ctgtctacaa gaggctcgag     35460
acgctagttg gtcacaccgc ggagctcacc aacaacatcc taggaacggc gtcggggata   35520
gtatcatcca tagtcacgct caataggttt tttaactgtc gcatcatgcc cgttatggga   35580
cactacgccg tattgattta cccccaatcg gcccagtctg caccccttcgg taggtggcgt  35640 ctagtagacg tagtagacgc ggttggaagc atatacaacg aagtgagcga tctgcgcgcc   35700
gacctgcggg ccgacgttgt gacccttaag ggcgacataa cctcggcggc agaggcactg   35760
caagagtgcg aggccctggc tgtcaaaacg gagggtacgc gctttggtaa actattcaac   35820
tctctgctca cacgccacac gcagctggcc agggcccaga gggggttggc aataagggcc   35880
ggtaagctgc tcggggttc tgaggctccc ggcctgaaac acgttaatac gtttctacag    35940
cgatggggag ccattagcgt catgtaccag aaagctacat cgggatctac ccccgaggta   36000
aatattacct ccctcgccaa cactttgcgt cacgtgtggg acgaggtaca acaggagcgc   36060
aaagcaactc ccccaagtcg gaaattttcc aacagagacc tcgggctcgc cgtagaacgc   36120
ctgatgggag gctatccaga agtgttagac gacgacagta atagcacagc gctgacacca   36180
aaattcaacg tcgattcatg gaatagcgta aatatggacg ctctacgcaa gcagttacg    36240 atgcccgcta acatcgactc gattcgcggt aatgattctc tcgcgacgcg cgaatatttg   36300
```

-continued

```
aagaaagaag accttctcgc cgaaatagat gccattttta acaatacaaa gtaataaagc   36360
taattgtatg cacccagtaa tacagtgtcg cgtgtacata ttttccgcat gggggaggcg   36420
cacattcgca tgtgggtaaa aaaggtggg cattcagggt tactaacgtt aaaagaagtt    36480
gcagagcgga gcgcggctca ctgccctgcg cgaatcacta gcgtacggtg tggattaccc   36540
caacgctctg ggatatacag actacgcttt tgcaggagct gttgccgatg cgcaaaccc    36600 ttgttccggc gaataaggcg gggggcgctc aggccgatgt ggtagtgata ggctacagaa   36660
accaatacga ctcccaactc ggcgaggggt cccacgtatc gtgcctgaga tcttcgctgt   36720
cctttttgcg cctcattttt actcacgaaa tagactttgc cctaactgcc gacagtattg   36780
atggggtgct cgtcgaaggg cgggcctgga ctgtggccgg tagcaagtcc ggggaagcac   36840
cgtgtatggt ttctatcgtg gaacttccaa acaaaattac ctacgccaac tctgcgaacg   36900
cgctatgctg cgtgttttcg agactctacg gcgacagcgg attttacatg caccctggcg   36960
atgggtttca gagcacgcaa atacccgctc gtcagttttt cgatggtgtg tggaagtcga   37020
gatctgagtc atttgctctc attacgatag gggctattgg tctggcggtg tatcgccacg   37080
gtgatgtcgc gtatgttttc gatccgcacg gccatgggag tgttaccgag gcgttcgtgg   37140
ttcgcgtact ggcccgcgat gtttatgctt atctaacggg ttacgctgcc accgatccag   37200
agtcagactg ggccggcgcg cttgtatttt ttgttacgtg cggtcccacc gagagcgagc   37260
ccggcttttt gatttctgca acgtcgctgc tatacgggat aagcgaaacc tacctatccg   37320
acgagcaata tgtggagcgg tctgtcgcga caagccaccc aggaatctct actcccccac   37380
cgctaacaga tgtggctgtg ggtgcggttt cggaggcgtg gcagtaccag gaactcgaaa   37440
atggtgcagc tacgctagat gcggacatgg agggtgtggc acccgctgcc gcacaagtca   37500
gggccagtgt catcagacag ccgacggaaa agcgagtgtc cttgcccaag cggcgtcggc   37560
ccccgtggac gcctcccacc agcagcgaaa acctaactac ctcgggcaac acgcacacgg   37620
tagcaggaag gccgagtcag aaggttagaa acgccactgc gaatgttcag aatcctacca   37680
ccggtaacgg cagtgcttgg gcggaggcct tgaacgatgg aggagtggat aacgcgagca   37740
ggcccggaca agccgtgggt gccgctggaa cactccagaa ccccgctccc ggagatgcgc   37800
ttgccatgga aaccacacag gcgtcggaag aggctcttag aactcgcaga gttttccggc   37860 tctcgggga ggatgaagcc ccgtatgacc ttggcgacgc cgtgggtgtt ctgagcgcag    37920
agataaatga actggctaca cgagccgaag agctggatgt gctaagctct acctgcgtcg   37980
actcgacggt gtgggtcacc aggccccaca acagtcccga catggacatt ctggagcagt   38040
tcatcacaat gatattcaat agacttttgt cattcctggt ggaaaatggc gcgcggaccc   38100
gcacggactc gccttcggtc attgcgggtc ttttcccagg tgtgctagcg gccattccta   38160
ctcaatccgc agtagtaaac ctgttgcagg ccaccggtat ggcgcttagt gacgtggctt   38220
cctacaagtc tatcctaaac atggtttcga acgaagactc gcccgtggga gagcttgcgg   38280
ttatcaaact agagctcgtg gcctctgagg ttatcaaatc tacgcagaag ctcgtggcca   38340
gggttgaaga attggagcgt gacgttacta gcggtagcgt caacccgttg gggttgtaca   38400
catacctgac cgaaagactg gtggccgaaa tgaccaaaca cggcggtgac ctatttgccc   38460
gagaaccgaa accgggggca gtatcactga ccgagcgcat agggtcgctc ttcaggaaag   38520
cgcgcaccag ggaggcgcgc gcgacgcgca caaacgcctc attggcacga gacctcaacg   38580
ctatagaagc tgccgttcat gcggcccacg acaagtttga cgccatagaa atcaaacccg   38640
cagaccctag cgacaccacc aacatggacg agctagcaaa gtcattggac ctatcagccg   38700
```

```
tccctacccg cgtagccaag gtgatcaaga aagtggaaag tatggtgtcc gactctattc   38760
gcgagtactt tttgaggggg gttcaataca gtgcgagggc aatagcaatg acaaaacga   38820 gcggcgccag gtttcaagtc gcttccgctg ccgtatctaa cctagaacgc atgctagact   38880
ctttgcccaa ctttgagaag agtcttaact ccgtagtggc ctcggcgggt atccagggac   38940
ctccgccggc gcaaatatcc ggctcgcgca aggcgacgct actaggcaac ctgttgcgag   39000
ccggacagaa tctgaccacg gataatgctc tgggggcgtg ggcagcgctg ctatctgagg   39060
cgcacaccga ggggcacatc gaaaggcgtg agctcgaggc cgtcatcaaa gaaataacct   39120
ccattaacga ccatgctgcc aaaaaggcgt ccgtcgaggc cgacatggaa cgctttaggg   39180
ttttgagcgc cgcggtagac caggccacgt ccgacatgta taactctaac ccacacgcac   39240
tggacactat tatccgtggc gcggaagaaa tgattcgtca ggcaaaagtg gtcgaggcgc   39300
actttgactc gggaagaatt tctcgcgaag ccgcgtccag agttggcgtt agaaaacgcg   39360
aagtagagac gctggccaac tcggcgcgac agcgtgccgc cgaaattagc gccgcccgcg   39420
acgaaattta ctcgcgcctt cagagccttt tgcttcccct cgccgggttt gttggattgc   39480
gcgccgcacc gggggttttg gaacagctcg caaaagatgc tcagagatcg acctcagagg   39540
aattgagaaa tttaatgcac gaggcaccga agcaggtggt gtcaacagta cattctcatc   39600
tatggtccct gttcggccag tttagagaag ctctcgagca tccaaactcc accacctcat   39660
ccgccctagc gggagtgggc ccggcgtttg cgatcgtcgt cagaagtctt ctagacccaa   39720
acaaacagcg cgagagtgtg gagtttttta ttacacacgc ggacgcgcta gccgataccg   39780
tcggcgccgt cgaggcaaat ccaaactccg agctggccgt tgcgcatgcg gttaactcta   39840
tcgccgccgc aatacagaca gtcagcgtcg gtggccgcac aattacagag tttgcgtttt   39900
tggtgcctat gctggagcgt taccagtcga gactaaccat agtcagggaa acccaaagac   39960
tcgcgactgc gcagcgggca gtcgcagcgt ccgtgtctgc ggcggcagaa gtgactacaa   40020
aacttcgtgc ggtcgccgta ccgggggttc aggaggatgt gctcaaggcc gcgatagccg   40080
ccgccaaaca cgtgtcttcc gaggttactg ccgccgccac tgccgccgag cgggagctgg   40140
cgaggctgga ctctaaagca ttgagcgttg cccaggtggc ccgcgcgcat caggatctgc   40200
agaaacagac ggctgttgcc aaacagcgcg tcggcgaaat agaagaggta ttggccaacc   40260
tgaacaaaca gcagcgcgag cttcaagatc gtgctgtgca tgataggtgg aaatccgacc   40320
tactggcggc gttggacaag attgaaacaa aatcatcgtt tgacgtgtcc gaactttcta   40380
gactccggga cctcggtgct gcgcgcggct atgattctcg cgagtttgct aaacgcgcgg   40440
aacaggccct ggcggcaaac gcacgtgccg ttatcgctgt cttggataac gtgtttaaat   40500
ttaaccccta cgcgcctgtg aattcgaaaa aggaaactaa tcccaccatc tccatgctgt   40560
ataacatttc atggtgggac gactttacgc tcgcggcacc tatactcaat accctgtttg   40620
ctggtgttga cgtcgaagag ctcatgagtc tgatgcgcat ttcgactggc atgattacat   40680
ttgccagtac caacggcgga cgcccaaaat acaacgaagc cgtaaattcc ctgtctagcg   40740
acatgcttaa ggttccgcag ctagccaagt acgtagattt ctacggcaag tggtacacgg   40800
aattcaacgc cgagatggac gtgttgagca agctgcgggc agacgtgctt caagcagtgg   40860
gggttcgctc cggggaaata agcagggccc tagaagaggt cacgtacgtt cggaacgcag   40920
aagtcgctga aaaggttttg gccgacgggg taaagcttta cattccgagc gacgccctaa   40980
tagccaaagc cgtcaagtac ctggaggagt ttaatcagaa acggttcgcg ggctccgcct   41040
```

```
tcgaggaggc gatagccacg accatccggc aggacttgtc aacgcgcgc gaggctgcta    41100
ctcaagccga agccgctcgg agcgaggcca tgcacagggc tacccatatt ctgcgcgagg    41160
tggtggaagc cgcaaaggcc gcggatcgag atgccagcgc aaatcttgca aacctcaaga    41220
acctactaag actcacccca cccccacaaa gtgtggcagc cgcgctggac aaggccacct    41280
cgtcagacga cattgtgacc caagcggcgc tgttgctggg cacagtggaa tctacaccag    41340
agctggatat taaggccgtg gagtggctcc agcaggcgcg gtccattatt gattcccatc    41400
ccctaacaac taaatagac ggcaaaggac cgatggatcc gtatgccgag cgaatagaga    41460
agctacacac actacggggg gagctagacg agctgaggcg tcagctcacg gcgacagaag    41520
ttagctggga cgaggcatgg gggaatttct cccgcgccgt tccgcgagct gatgtttcca    41580
tggatgggtt cgtggatgcc catcagaggg cacgcaccct ccaggcgtcg atggggtca    41640
tttctgaaat gcgagcagat aacaaatatg ccgcttaccc ccaaagtt ataggagcca    41700
ttgaatcaaa gtttgcagag cgacacaaaa acttggaaac gtttaatgac acctcaaccg    41760
ttctgcagac ggccataaca cagtttgatt cgctcgtaca acagattcct ccggagatgg    41820
agtacgacgt gctacgctcc ctcttggcgt cgtttgacca attggcggct gtcctaccca    41880
agtgggttgg cgcagagtat gccgcgtaca ggagcttgct gctgatgaga ataggcctat    41940
acgacgaata ccagaaaatt gccggtatag ccgctgcggg aagccgccct cacctggaag    42000
ccgttgagta tcgcagcgcc gtggaggacg ccaatctaag acgcgccagt cgcgtgtcct    42060
ctctcatggg ggataaagat gtcatcctct cacttcgaga agcaaagtcc tctatcgaca    42120
ccgcgttccc tcaggtgttg ttggacgcca agggcgtacc cgtcgagtac agagtgtgct    42180
accgcgccgt tggggacaag cttgccgcca tgctatgtgg gaaactaggg gtcagcatgc    42240
gcccagcgat gcccagcgat cctatcgtgg agtcctcttc cgtgtctggt atcaatgtaa    42300
ctcatgacat tctccagctg cggtttgggc tggaaaaggc ctaccactcg ggattttcta    42360
cgttcgcccg atttgtgcgc cacaagaggg cagactggag ccctacagag cccgcccagg    42420
ctgcggccga gatatacgcg gcagtgctgg ctaccaccct aactcgggaa tatggcgcca    42480
cctggcaccg cataaggttc atggcgagtt cgggcctgtt tgtcgccagc ccagactcag    42540
tttgcgacac gcaaggaggc agaggaaaga aaagcaacaa catagtacac cttactttat    42600
ccgacgtggt tctgagcgcc atgttgcgga attccatgca tctagtaaac tttatgcggc    42660
tggacctgac acgccagcac gagtacatgg ccagaacaat aactccagtt ttgacaaaat    42720
cgcttctgtc tgatatttta attaacaccc tcgttcctac cgacacgtca acgcagtgga    42780
gatcgctgcc gctagctggc gacctagaag atttggctca aggcatgcta ttttccattc    42840
gcatgtccga ctggaagcaa aacagcttct ctaccaccag tctgctagat gtttggatgc    42900
gctctcccgg cgaaagcgga cgggcggcgg ccgcaaagat agcctccgcc attcccggaa    42960
accccctggc caccttttacc gtgctggcgc gtatgtgtat cccaccgaac gcattggcgt    43020
cgctgtggga agcgctgcag ccagaggcct ttagtcagca gaatctgtcc tatgatgacg    43080
tggttactag ccgcctggac atcgcctcta ccgtacagac ttccgtggcg gtggacccag    43140
aaatgaagtc tgttgacact aagtctagaa agcagctata caccactacc gggaccagca    43200
ctacgttcac gttggctggc tccgccccaa gcgccgtcaa ggaggttagc gctttggacg    43260
ttgccacgtg tgcactcatg tttggggctc ccgttgtgat tgccatggaa acgccggaaa    43320
tgttttccga agcgtctggg atgtcgttct gtctcaaaat cttcgactcc agacccgggg    43380
cgaccgacca cgaaataatt caggccgtgt cctcggacct gagctcgtgg gggacgtcgc    43440
```

```
ttttggcact agaccccaac gccatagaaa acgcctgcct gacaacgcag ctggagatac   43500
tctcaggctt ggtggcatca aagcttttag ctccagcgcc gccgtgtctt atagtgctcg   43560
accccagcat gagagtgata aaagtgttgt gggaatctga atcccccccg aatgatctag   43620
ttatcactct ggccgaagat gagattatag ctgagcttcc gtacttaaac gcggatgatg   43680
atctgctacc tccaatgaac ccggatgacc ctatctacac cagggttata agcggaacaa   43740
acattccgac ggcgaccacg gaaggcagct tatttgccga ccagcagctc gagtttttac   43800
gtccggagtc aaacccgttt ccgttcgcct cacacgacag ttcacagtct ttagatgtcc   43860
ccagttctcc gagtagcggc tccgacaaat atgaggagga cccaacgggg atagtgtatg   43920
acgcgcctgt ggacgatatg tcagacatgg caatgaacaa agcaaaggcg tggcaagagt   43980
ggttggagga tgggttcgcg gaagatgact accgagaact atccaacgcc atgccggcgc   44040
ctcccaaaac tactccggtc gttgagtcca acagaagtc tgattctgtc gacagagcac    44100
ccacactacc gcctaaggct gctcccctttc cgccatctga tgcatccgcc atcatgtccg   44160
gaaagcccgt gttcaagtat actccgggca acaagtctgc cgttccacct tccgtacctg   44220
ctcctcccac tcttccaccc gctccccctc tgccccaatc cacttcaaag gccgccagcg   44280
gccctcctcc cactcttcca cccgctcccc ctctgcccca atccacttca aaggccgcca   44340
gcggccctcc tcccactctt ccacccgctc cccctctgcc ccaatccact tcaaaggccg   44400
ccagcgcccc tcctcccact cttccacccg ctccccctct gccccaatcc acttcaaagg   44460
ccgccagcgg cgccacacaa tcggacagtg gcaaaactct caccctcgat gttccaaaaa   44520
cacagtcgaa agataaggtg gtaccagttc cacccaccga taagccgtca accaccactc   44580
ccgcggcact caaacaatca gatgcaagta aactcctac tgctgcaatt caacatcagc    44640
aaaaattagg tacacctgtc actccaaaag attctggaga taaaccaacc gataacgcaa   44700
gcgcgcctgt tggtgtatct ccagtaactc ccgatggaac acccggagcc aaaccacccc   44760
caaaagacgc accccctgtg gatgacacta acaacctgt gaggaaatcg cttccatcac    44820
aggtgcgcgg cgggcgtccg tacatacgcc cgtctctagg accatttaag tttacgggtc   44880
cgcctggtta tacgattcca gttcatggac ttccacctag tgactcaaac gtgacccaat   44940
caaccaagga gccccaaaag cctgccgtag agacccccgc cgcggccccg gccaaatctg   45000
cggcggcccc cgccgcggcc ccggccaaat ctgcggcggc cccgccgcg gccccggcca    45060
aatctgcggc ggcccccgcc gcggcccccgg ccaaatctgc ggcggcccc gccgcggccc   45120
cggccaaatc tgcggcggcc cccgccgcgg ccccggccaa agaccaaaca aaatcagctg   45180
ctgaagtccc aaagcggcc aaggaccagg ccaaggacca ggccaaggac caggccaagg    45240
accaggccaa ggaccaggcc aaggaccagg ccaagtcaac aacaggccaa aagctggcta   45300
aggaccctaa atctgatggg ctcacagacg atgttgcttt agagattgtg cccgaaaaaa   45360
cccctctgcc ggatgactcg cccattgggg cggttcccga aaacactccc ctaccagatg   45420
actctcccat tggaagtcca gatttgtcag catctaaaaa ctcgcatacc actgacgcag   45480
tcagcagtga ccgttttttct gttgcctgca agtaccgct cccagattcg ccggaagatg    45540
acttctactc gtatgccgtt gacgtcccat tgcccgattc tcccaccgac gaccctcaa    45600
gcggccgttc tgatgcacga gcaccaaccg tcggaggtgt tgccagcatt catcgtaaga   45660
gcgactccag aaacaaccga caatcagacg catggagacg tgcctttgct gacacgctac   45720
atgggcgtcc aagaaataga agcgctacta aaccatgtaa atcagcaccg tataaagttc   45780
```

```
ctcacgccat tcctatacg aaatacctt cggtacctaa cgatcaaagc ggtcttgcgg    45840 gaaaccctg cagcgaggaa ccgaaacgtc cgactggacg agacacccct gtcggttcat    45900
ggaatgtttc gccctcgcag gcgcccgcgg acattccgac cgccattccg caaaatcaga    45960
atacttcaga gagtccacgt acgacctcgc tgaagtctcc tactcgcacg gtgcaatcta    46020
gtatgccggc agatgatatt gatgaactcg ccgagtacga tcttcagatt gcccgtgccg    46080
ttcctgttac taaacatcct cagccgccac cggcaaacca gacgccaccg cctcaagaac    46140
ccccagcacc tattgacgat agaaagaaca tacgcccacc gctaagcgag gaggagatta    46200
tagccttcct aatcaatatg gacgacgacg acgccggtaa cgccgtctggc ccggttgact    46260 tacactcggt acaagcgccc aaacttccca aacaatcaaa acctacaacc aaccagtttg    46320
taccgctgga ttggtggact gaaacggaac ccgttgtgga cgccgacagt ctggacctgt    46380
cccccaaaca gcagcgtctg ttttcctggg agtctacgcg tgacctgtta acattaacg     46440 tgagggacag agtatacgaa gaggagtcgg acgatgagta taccgtttca tgggaccaac    46500
acttagtccc ggccgtttct cccacgtctg tatcatccta cagtagcgat accgtcactg    46560
atagctatac agacataaac gatcccagga gtgttgtgtg cccttagac ggaaacgccc     46620 aaaacaacgt ccgcgagttt ctagacacgc atagttctag agttcgcgtg gttcctgctg    46680
acgaattgct aagtcggcgg tactttcggt ccacgagtct gagtgccatg gcgttactca    46740
ttgctgcgtg tcgcaccatc gtccgacgac ttcgggcaac tagacgagtt cttacagaca    46800
tcaaccggag cttgctctta gacttaaaac aaatacgggt cctcttgggg tagtgtatct    46860 gttttttcaat aaacaccatt ggaacatgaa ctttgtctgt aaaccgttttt tattgttggg   46920 gaattacata gccggggggtg caagggaaag gtcagtcttc cgaaatgggc tgcatgaacc    46980
gaggtgggaa ggtgcgcttg agtcctatat ttgggcgcgc ccaggtagat gcgtcgttct    47040
gcgcgaacat atcagatcgt cgaacgaggg atttcaggtg gcgttgtcgt aggctaacca    47100
tggtcctggc ggttcccata aacagctgct ttagcccttc gctaatttca tcctcagtgt    47160
atttggtgta atccagttca tcgatgttct ggtttaggat agttatcaca tcaacgggca    47220
gcatgtcttt gaagttagcc gctttgatgt taggcgggtc cgctgggttg aacgccaccg    47280
gcgcctgctg ttgctgtttg tcggcagcca tggctaaatg tttgctgcga gcgcgcaacg    47340 caccctacg ctggccggtg tagcgacaaa tagcgcagtt tcgagtagtc gccggctttt     47400
tattagaaga ggcgcccctt tgtcgctatt gcgagtatta cagcaacaaa acaaacgct     47460 aagatcgcgg ccgcgatcct cacagggcgg cgtttcaccc gctccgaggc gaacgcgctg    47520
gagatgctgg cgaggctggc aaaaacctct gaagcgcacc gcttgggcgt gggacgccgc    47580
ttctgccgtt ccctacactc gcgatgctcc ctgggggaga ctataccgtt actgcgatcg    47640
cacgagtcta cggtgcgctt ttggtgcaac tccatcgcac caaaactagt cgcgcgctct    47700
agcagccgct gggttctaga cgcgtcttcc ggacccatga accgaaacga cagctgcacg    47760
acgggcattc tagtgaaaca gcttatttgc atcatcgcct gcaggggcct caggtctagg    47820 cctcccccctc gtttcactcg ttctatgcca gacagggcca gcccggtcgt gtgcgttgat    47880
ttgaggatca cgttgttatg ctcagacgtg attgaagcca tgggggcgtt ggggggtgcg    47940
aaaaaaaagc cctgaaatag cactgacact cccgtgtttt gaatgcgaat gtacggatcg    48000
cactgactac gagcccagtt cttcatcaac cggagcacat actctatagg aaatgttacg    48060
ctgttattat ccgcccgct aaattgaaac acgcacctgg ctggtaggtg tttgggatcg     48120
ttcagggttg catcgctctc tccgcagtgc agacttcccg agacaaccag acggatgcgc    48180
```

```
tgtaacaaac caccaccgac tgcaaaatct ctatagttgt acgagtccat ggttgtagcg    48240
aaatgtcccc aacagcggcc agtcaacccc cttaagcgac tgatgcgtgg ggcatgccgc    48300
cgctcaaact taaaccctcg ctgtatgtag ccactcccca cgacatgtct cgcactcggt    48360
gcagcagttt aggcgtcatg tagaatttgg tgtaaatcta gaaacttgtt aattattgtc    48420
gcaaatcttt ccttgcgggc gtctagggca gaggtgtgat cacaagcccc accgggcata    48480
cggttgtccg gggaatgaaa cactgaagag gccaggcgcc gcgtgaatga taaatagttt    48540
agtttggcgt ctgtcgtggg catcaacagt tccatctcag ggggcatcag gtcttcgaac    48600
cagacactaa agtcgtggtg tccgtaggca tcatctaggg cgtttaagct catcgattct    48660
acgtcgctgc tcggaatcaa gtctctgagc cttttcggag acgccggcg cgagcgtgct    48720 tgttgcatac cgcttaaggc agcatcagag gcgttttgct ccatggcggc cagctgcaat    48780
ctagacgtca taggcgaaga cggggatgt gcccttaccg gaggctggca gccgggtgcg    48840
ttcgagcgcc cgtacatggg atttgacgcc agacttctat caactaacag cagtctgtgc    48900
agcgagttaa tattttccgc gcacttaatg cagatttcac ctacgcccca gcctcgagag    48960
caagtcgatg tgtgcgaaga cccagacaac gatccgcccg aacctagctg cgcccagttt    49020
gtagatgcag tggccgactc cctggctctc gacaaactct gtttgatctg ccggacaatc    49080
gatttgtaca gacgccaatt tgggctttcc ccacagtgga tagcagatta tgcgatgctg    49140
tgtactaaga cgttggcggc cccgccatgt gcagtcgcca ctgtggttgc cgcattcgag    49200
ttcgtgtatc taatggataa acactacctt cggcgcggaa agactaccct agtgggcgcc    49260
ttcgcacgta gagttttaac gctcgtcgat atacagcgcc acttttttt acacgtctgc    49320 tttcgcacgg acggcgggt tccccgctgc gccgcgtccg ggacggcccc ggcggcaacg    49380
gccatggccg gcctcggtat ggcggacaaa gttcaatatt caaattactc gttttttagtg    49440 caatcgtcca cgagagccat gttactgact gtggccgacg ttccatctgg agacgacggc    49500
gcgttacagg ctgtgcccca cggcagacat ggagcgggca ggccggcgga tggggcggt    49560 ggggtgtttg gccccaaaca acaatctacc gtggccgcgc tgatgagttg gaaggagtgt    49620
gcaaaaatga tagactgttc tgggtctgag cggagacgcc ccggcgcgac tatgacatgc    49680
tgcgagcggc tcgggccga tgatgatgaa tacgaacgcc agctgttatc taccgagaac    49740
acatatctgg gctcggccga caatcaagca gagggggta acgacacaca tctcaagtgg    49800
ggctacgcag acctcaccct gctgctgttg agtcagtcca gcacctggga ggccagcgaa    49860
aaaacatccc tggcgagtca gtcgcgcagg gcctgcgtgg aggagtattg ggcctcccac    49920
aggaccgtgc tggcacgaga caccgctcct aggtttgcca gattcgtgga tgcagacgcc    49980
gttccggaca cggccacggg gccggtttta gcgactaccc tcaagcacgt acgcagccgc    50040
ggaagaacct cgcgccgaatg cgtgctatgt aacctgatac taacgcgcga acactggctc    50100
gcgctacgcc gctttaagcg agatgttata tcgtactcat ctaacaacgc aaacctgttt    50160
gattgtatct cccagtact gtcggccctt tctgacgcaa atagcgagcc gctcgccggc    50220
gactgcggcg tgggtggcgg cgggacctgc ccagaagact cgggcaggtt tctagagcta    50280
atgcatgccg ccggcacaga ggccatatac aagcacctgt tttgcgaccc catgtgcgcg    50340
ttggtggagc tgcagacaaa cccgagtgtc cttttttctc ccataggccc ccctccagaa    50400
ccagacgaga tagagcttca aaagcgcgc ctcgctagcg aaaattggtt tagtgggcgt    50460
gtatgtgctg ggttgtgggc gctggctttc acttttaaga cgtatcagat ctttacaccc    50520
```

-continued

```
aaaccgaccg cgtgcgcggc gtttattaag gacgcgggac tgctgcttag gcgccacaac    50580
ctcccgctca tatctctcga acacacgctc tgcaactatg tttgacggcc gcagcgatat    50640
ctacgactct acgagctttg ccgcagaatt agacgatcta tactcttgta ggtcaacggg    50700
ccgcgaaaat ggccgtagga gccgtgtcag cactcggggc gttcatcgcg atcgatgtgg    50760
atcggccgcc aagagacgaa gcaccaagcg acggtgcgag ttagtcgcca gggaaaggga    50820
ccgatacagc ctttacctag attacatggc cagccaccca tcggatgaaa tttcagccgt    50880
acgcgagctc gtggttcccc taattaaaac cacatcgatt acattaccgt ttgatttaaa    50940
tcaaaccgtt gctgacaact gtctctcgct atccggtatg ggctactatc ttggtatagg    51000
cggctgttgc ccaacctgca ccgtttccgg cgagcctcgc ctccatcgcg cagaccgcgc    51060
cgcgctaatt ttggcctatg tccagcagct caacaacatt tacgaatata gggggtttct    51120
ggcatccgtg ctggcggcag ccgcccaggg ggaccaggcc ggcgttgccg cctcagaggg    51180
cgttcaggcg gagcgcttgc tggaaaacgt tttggcccag ccagagctct ttttcgcgta    51240
ccacgttctc agggacgggg gcatccagaa cgtgcgagtg ctgttttacc gcgacctgag    51300
cgtatctgga tatatgatgt acgcggtatt tcctaccaaa tctgttcacc ttcactaccg    51360
tctcatcgat cgcctactgg ccgcctgccc tgggtacaaa atcatagcac acgtctggca    51420
gactgctttc gtgctggtag ttcggcgcga cgaggggcaa caaacagaca tggatatacc    51480
aacggttagt gctggagaca tttattgtaa aatgtgcgat ctcagctttg atggggagct    51540
gcttctagag tacaaaaaac tgtatgcagt attcgacgac tttcttcctc cggtgtaaag    51600
ggcgtcagct tttcaaagcc ggcgcgctca agcagtgcct gggttttcgt ggggtcttg     51660 tgggggttt ccggaataaa ccgctttaaa agattttctg ttgttctcac atcatttccg    51720
aatagagcct taaaggtcac gcttatggta cccaacaggt gggagaaata gtagtctgtg    51780
tttagcggta cgtcattctc ggaaacatag gtcgggtctt cggcgaggtc ggaaaccagc    51840
agtttgcgtt taggttgggg gcgtgcggtc ttggttacca cggggttttg ggcggtaccg    51900
cgcattgagt ttactacacc cgcttcgcgt tccgcggcct cggtctgcgc aactatcaca    51960
tacggaattc tctcttttac gctgggcagt tcttcattcc tcatggcgag cttaaagtag    52020
acggtgaggt gcggcaggcg cttgttggta tacgattcgg gtgagcggct cagctcagca    52080
gtcataacga actcgcgcac gtccaagttg ggggcagtga tacggttgta cgcctctacc    52140
agcactcgcc caaacttgtc aaagccgctc ggtagcgggc gccccaccca ttctgcggga    52200
ggcacgtctg tcacctctgc tgccgccgtg gccacatcct cgtcgtacaa caaaagatct    52260
accagatgtc gcgcgtacaa gtttatgaaa gagcagttat ttttgcggac caggtcgacc    52320
cccttcatga gcatcttccc cccgtttatg acacctatgt acttcttctt ggtgatcagc    52380
agcagtcgct gaaaggtctt ctcacactcc agtttgatgg gcgctctaaa gaggtccgct    52440
gaaatctgac gcgacatagc atcccccagc tccgataccc cctcgtacgt caggcccaca    52500
aacttgataa acacggagtc ggtgtctccg tagataaccc tgacggagta aggcttgtgg    52560
tttcggaaac ctatagcccc tggaaaattg tcctccagca gctcgcgcgt cgcccaacga    52620
gagtgaacgt aatctcgggt cttgaggagc atgtcgcgtc ctatcgtggt aacggtagcc    52680
gctatcctca gacacggcaa caggccgttt gccaccccg tgaatccgta aaccgagttg     52740
catatcacct taatcgcaga ctgctgctta tctagtaaaa ctgcctcctc gggggtgctg    52800
gtggggattc gcgccctcac cgcctttcgc atggccagcc agtcgcgcag caagatgcca    52860
agcaggcttt cgcgaatatg ggcgtggaca aaaaataact tttggtcacc cacctcgaac    52920
```

```
gtcgagtagt cgacggatgg ttgaagcccg gccagatcca cttcatcgag cgccagggtg    52980
gtgaaacaga ggttatgggc ctggataatg cttgggtata agctagcgaa gtcaaacaca    53040
accacggggg ccacatgaaa gccggatacg gggtctagaa cctttgctcc ctggtagccc    53100
acggccctcc cgacgccggg cttcccgcct ccgttttcag aagtagcgcc agatcctgcg    53160
gcgtccgggg taccgtccac accgtcgggt tcgtctgtac tgtcgaaggc gtggctttgg    53220
ctatccatag ccaactccga agtctctgac gcggcgtctg cctgactgtc aaaccggcgt    53280
ctgttgtctg gcaaaatgaa atttctctcg cgggcgagtt tcagcaagca cgtgtacacg    53340
cgaatttgct gaccgtcaaa aattacccgc gttagggtga tacgggcgag tttggccacc    53400
gccgatagtt ccagatgggg gaggtactta aaaaacagct tgcccaccag cctagagtcc    53460
tggatacaat actctcctat tacgcccctc cggtcaggcc ctcccgcgta ataggagggt    53520
atttctttat agggaaggtc tatcttatgc tcgccgagga cgtctcccac gaccgcgtcg    53580
agtttgtagc tgggtagctt tagctttttcc gtcgccacag aatacatgtc tagagatatc    53640
aggccattga ttttcacctt gctcttcttc tgaaaatggt tcgtggcgat gtcccacacc    53700
ttaaacagcc cccctttgtt gaacttgccg tacccgtcca gcttgatgtt atacaccgac    53760
gttaccttgt taactatgta cgcccagtca aaattaacga tgttgtagcc ggtggcgaac    53820
tcgggagagt actgcttgag aaaggtcagg aaggcaacca gcagctcgta ctcgctgtca    53880
aactccaaaa ccgtcggtct gggctcgccg cgctggacgc atgcaaacga gtattcctca    53940
gagatatcgc atgaccccgag ggaaaacagc agggtgtgtt cgtggttctg agtagcaagc    54000
gagtacagca gacaggagat ctggatgacc aggtcctctt ggttagttgc cactgggaac    54060
gccatttcgt tacccgttcc agctttacac tctatatcaa agcacatgag cttatagtcg    54120
ggccaggcag cctcgtctgg tatcggctcc aggttatcgg gagtacagtt aatctccacg    54180
tcgcttgagg tgacgtgtcg ctcaacgggg cgaagttgaa cacgctctcc gtgggtgccg    54240
ggtcgcaggc ggtaccaccc gaaactggta aaattttcat tgtccaacaa cagccgcgtg    54300
gtcacgtcca cgctccctc gaattttgta atctcccgggt gaaagttgtc gcagatgaac    54360
cctcccaggc ggctgctgga ggcagatact ctatagtaga gagctggctt agatccaaag    54420
tagtacagcg tcgtgtggca cacggtctcc actttgaagc agtccgcaga cacgtgcttt    54480
ccgccccacc atcccccgcc gctgccgccg ctctgtttgc cgccgttgcc atttcccagg    54540
gccgcgctca aagccgagct gtgcgcgcag tccaccattg cgcgcacgag ttctgcctcg    54600
gtggttattc cacaagcgct atccacctcc gcctttgcca tgtaaaaata atggcgcaca    54660
ccatagacgt gaaccgcgac tcgctttcca cactcgctca ttcccagcag tgttaccaca    54720
gacccgcttg ggcgggatag ctcagcaaac ctggatgggt catcgtgtga ggcgctctcc    54780
gaagtctcta ctatgtcgta cacgtgaaat ctctcaaatc tggggttgaa tccatcgccc    54840
cgaaaatcct ggccgttcca aacccgaatc ctgcgaggcc agcaacctcc ggaggcaaag    54900
ttcagcacgt cgtactctga gccatcgcag tacactttgg gtgggcgctc caaggtgccc    54960
acgtgtacac cgcgtcgctg gtcggcgggg gcttcttcat cgaggcatct tggagctata    55020
aacttaaagc tacccacctc tgtgcagtac gagtgttggg ggggccttgg gcgctctgtc    55080
tccgcggtct gcccgcttcc cggcctgaaa aatggcctct tgccaataaa cggattaaaa    55140
aacccgctcc tgcgaacgga gttggcctgt tcgcgcgccg ccatgtctgt gtaaatttaa    55200
agtgcgaatg gtttccttttt ttataatata tgggtcactc caccccctgg tctcgtgatg    55260
```

```
tgtggtttac tgggcgtgtt tagatttagc tttaaagtct gcccgccaac cttgcttaaa    55320
cgcttcgagt aaatctcgtt aggaagctcc tagctatctt tttaacaagg acccctacag    55380
cagcgctctc aaccatctac atctaaccat cttggtctta cctgagctcc cgggccgagt    55440
ttcgtaaaca ccatggagtc tgcgcccaag acagtgagcc taccggtgtc gcccctgggg    55500
tatgtctacg cccgccagaa agcgtctctg cagacgggca cggttagtct cacggccgcc    55560
cggagcgtcg attcggacct cgcggtactg cctgtgatcc gcggacttac cgtcgaacag    55620
accttcacaa ctaacgtcgc cgtggttgcc gggtcgaaaa ctaccggact gggtggtact    55680
gggattactc taaaactcac acccagtcac tttaaccccca acgcctttgt gttttatgga    55740
ggctcggtca tcggagccag ctctaatgcc cccaacctca cccgcgcttg cgaggctgcg    55800
agacggaggt ttggctttc tgcattctcc tcgccacccg ttgagaacgc cgtggaaacc    55860
tccggggaag aaatatgcgc ttctctcaac ctgtctccgg agaccaccgc gctgtacctg    55920
gtggtaaccg aaagtttcaa agagatggtg tacgtgtgca acaccttcct ccactacggc    55980
ggaaccagca cagttaccat cgatggacaa gatgccatga agattccaat ctatccggta    56040
cagctgtata tgccggatgt caacagactg gcgtcagagc cgtttaacgc taaacatcgg    56100
tccatcggcg acgagttcgt gtactctagg ccgttttttca actcggacct ctgtaggctg    56160
cttcatggct acgtactggg tccggcggct gtggcacttc gcgtcagaaa ccttgacggc    56220
gttgccagag gagcggccca cctggccttg gatgaaaacc acgagggctc tgtgttgcca    56280
caggatgtaa cctttacgct gtttgactcc acccagggaa acgccggcaa gggttcggga    56340
cgcgctcagc gccaagggga tggcagcgga tcgaaaaaca gcgcctctag cggtatagag    56400
cgacggctag cctcggtcat ggctgccgac acagccctct ctgttgactc cataatggga    56460
gcggggatat acgacacgga gctaccgtct gtagaagatt ggccagtgtt gtcttccgga    56520
gacgatacag agagtctcga ggccctcggc gcgtacgcgg ctagactgtc tggactggta    56580
ggagccatgg tgtttagcgc caactctgtg ttgtacatga cagaggttga cgacgggggc    56640
ccggcagacg gcaaggatgg atcaaatcct tcctaccacc gcttctacct aatagccgcc    56700
ccctacgtcg cggggaaccc acagacggac aaagatggac gcgttttacc gcacacggca    56760
gaccaacagg ctgcgcccat caatggctcc aaccaagagt tttccctgga ctatctagcc    56820
ctggcctgcg ggttttgccc ccagatactg gcgaggcttt tgttttacct ggagcgatgt    56880
gacgctggca cctttggggg tcgcaacgag acggacgcgc tgcgctacct ggctaacacg    56940
ctagaatctg atgttccttg cgggttgtgt aaccaggcca ctcggcctgc atgcgcccac    57000
accacgcttc atcgtttgcg tcagcgcctg ccacgttttg gggcaccggt tcgagctccg    57060
ataggaatat ttggtacgat gaacagcgcg tatagtgact gtgacgtgct gggtaactac    57120
gcttcctacg gagccctgaa gcggcccaat gacaacgagg caccaaagag catcatgcag    57180
gatacctatc gggccacgat ggagcgcctg gtcaacgaat ggaacaagc caaactcatt    57240
gacaaggaaa cgctcgcgca agccagcccc tgctcagccc ccaccagcgt agtgcatgat    57300
caagctagct tcataggact cctgtcaaac atcaaagaca ccatcgaggg tgcagcgaaa    57360
cagtttatgc gcactctggt tgaggcgcgt gatttcaaaa tccgcgaggg cctggccgac    57420
gcgaaccaca ccatgtctat ctccctggac ccgtactcta gcagcttttg tccggtcaca    57480
tcatttcttg cccgccgcac agttttgct gtcttacagg acctcgtgtt gagccagtgc    57540
cactgtctgt tctacggcca atctgtggag gggcgcaact ttcgcaacca gtttcagcca    57600
gtgctcagac gcagatttt ggatatgctc aacgggggct ttatcacagc caagaccgtc    57660
```

```
accgtgacgg tttctgactc tggagttttg gcaccagacc tcacacgtcc cgcctctgag   57720
ccgcccacca aggactacga cggggacatg gccagagtca gcatggaggt gctgcgagac   57780
cttcgagtta aaaacagggt gctgttttct aacggagggg ccaacatgtc tgaagcggcc   57840
agagccaggg tggccggcat ggccagcgcc tatcgcaggc cagataaggg ttctaacatc   57900
ttgaatggcg ccgtcgggtt tctcgtcaag cagtatcacg gagtcctctt tccccgggga   57960 caccccccg gcatcgacac tccaaacccc cagtggttct ggaccctgct ccagcgcaac   58020
cagatgccgc cgcgtctgtt gagcaaggag gacatagaaa cgatcactgc catcaagcgg   58080
ttttctgacg agtattccgc cataaacttt attaacctga caccaaacaa catcggggag   58140
ctggcccagt tctactttgc caacctggtg ctcaaatact gcgaccattc ccagtacttt   58200
atcaacggcc tcacggccat agtcgttggc tctagacggc ctcgcgaccc tgctgcggtg   58260
ctggcctgga tcgaccgtac aatcaacggc gcggcagatg tagagccggc tgcccaggag   58320
gtgctgcagc ggctcgggtc taacccggcc gcgtggacgg gcacgtttac gtccaccaac   58380
atggtccgct atgtcatgga ccagcgcccc atggtcgtta ttgggttgag catcagtaag   58440
tataacggga gcgcaggaaa caatcgcgtg tttcaggcag gcaactggaa cggtctcaac   58500
ggtggcaaaa acgtctgccc gcttatggcg tttgacagaa cccgccgttt tgtgttggcg   58560
tgcccgaggg tagggtttac ctgcgaggcc ggggatttg gcacggggt tagagagaac   58620 acgctaagcg agcaggtcag aggaatagtc tccgaaggag gaccgatggt tcagaccgcg   58680
gtgtttgcgg cagtcctgca cgctttggga gcccgcacgc agcacctggc cgtagatgat   58740
tggatcggtc tggtagacga cgagttttg gcggcgagtc tggatgccct gaatgccacc   58800
gtcgttgatc aatttggaga gtggagcgtg gaggctgccc aggagctggt gaaaaacatg   58860
gaggcgcaaa caaccgccgg agcggtagct gccggcgagg gagcgtttga cttcggggca   58920
tgcgtgggtg atactccaca acaatccact tcagcattta acgtggcct ggccatggca   58980 gctgcccctg ctggacaaaa acggtcccta ccggatgata tcctgtttga catgggtgcc   59040
cccccggaga aaagtcggg gctcaccttt gacatgctct aaggctacag atgattacta   59100 ctaccccct ccccgttgt gtttgtatct taactcatct ctattggtcc aatttggagt   59160
tcaataaacg ttttacattt tatattcggt tgactcgtgt tatatttcac tatttctgac   59220
acccaccacg cctctatcag ctatggagca agacgatgca cccgctgcca tgggtagcgc   59280
acaggcccgt cagcgtttac tcgcaatctt tggtcaggtg caggcctaca tatttcaggt   59340
ggaaatgtta aagcgatgcg acccatcggc gctgctacct ctggtagggt cgctaaaact   59400
aaacgcctta acgatacgca tgcttagacg caagctgggg ggagctctca tcgaacaggc   59460
gcagcatcag caaacaccac tcgcatgcgc cctgaccatg gccctagaat acgccgaggt   59520
tgaaggcgaa cgtgttctgc gtgcggtgga tgacgtgaat ctggctgggc cagaggggtt   59580
tttcagagcc acgatgcggc tagacgaacc gtgcgaatac cacgtgcggg tgcacctgga   59640
tacctacgga ggccccatag acgcggaagt tcagttttta cacgacgcgg aaaacttcct   59700
aaagcagtta aactattgcc acctgatcac ggggttcgag gccggcctcg atgcattgga   59760
aagcgtggct cgctttctta cccgcactgt gggcagcggc atagtggtac ccccggagct   59820
gtgtgacccc acccatccct gctccgtctg ttttgaggag ctttgcgtaa ccgctaacca   59880
gggggaagca gttcatcgca gactgctcga gtgtacgtgc gatcacatca ctcggcaaat   59940
ggctgtcagg gtcgcaaata ttgacattgc gcggcaccta ccgcacgcgc tcagtgtagc   60000
```

```
ctccgagcgg cgcgcggcgg cggaagcggc tctcagggcc ctcgaggcca ggcgcgtgca   60060
aggacacaac ggcaagagcg ccggcacgga ggacccgacg caacaagttg cgtcgcggct   60120
gctggagtcc caccacgtct tcaagcctgc ctcgcggtgc ctgtacgccg tgagcgagtt   60180
aaagttttgg ctcgcgtcta ccaaacacgg tgatatggga cagccaaggg ctatagacac   60240
gtttacagaa aacctggaga ctctggacaa gcaggaaaag ttttttcacc tgcaagccgc   60300
aaccgttgaa ttggcactat tcggacgcac cctagaccac tttgacagac tgtttgcaga   60360
ccagctgctc ggtctggacg tgatcgatgg aatgttggtg gggagctgtg cggtgtcacc   60420
ggacgatcac atagaagccc tgataaaagc gtgttatact catcacatgt ctgcgccgct   60480
cctgcagagg ctcacggacc cagacaccag caacagagag ccctcaagc agctgctggg   60540
tcgcataggg gtggataccg acgacggggc cggcgagttg ggggacgcct tagacgtgga   60600
tttggataat ctaggtgggg cccctcctgt caacagcacc ccctgtggtg aggacgccct   60660
ctgtcgaacc gtttccgagg aacgcccgtg ggacaaactt ttagagcggg cgactgcgga   60720
tgcttcgcag cgcaggcgca tgtacgcgga gcgtctgtca aagcgttcca tcgccagttt   60780
ggggcgctgc gtgcgcgaac agcgaagaga actagaaaaa accctgagag ttaacgtgta   60840
tggcgaagtg ctgctacata cgtacgtatc gtcctacaac gggttttgcg ccaggcgcgg   60900
gttttgcgcg gcggtgagtc gagcgggtac catcatagat aaccgctcta gcacgtccgc   60960
gttcgactcg catcagttca tgaaggcggc gctgcttcgc caccccattg accagtcgct   61020
catgccgtcc ataacacaca gttttttcga gctgatcaac gggcccgtgt ttgacaacgc   61080
tggccacaac tttgcgcagc cgccaaacac ggcattatat tacagcgttg aaaacgttgg   61140
gttgttaccg catctcaagg aggaactagc tcggtttatg attactgcgg ctaaaggtga   61200
ttggtcaatt agcgagtttc aaaggtttta ttgctttgag ggagtgacag gtgtgacggc   61260
cacgcagcgg ctggcgtgga atatatcgg ggagctcatc ctagccgccg cagtattctc   61320
ctcggttttc cactgtggag aggtgcgcct cctgcgcgca gatcgtacct acccggactc   61380
cagcggcgca cagcgctgcg tgagcggcat ttacataacc tacgaggcgt catgtcctct   61440
ggttgccgtt ctgtcggcgg ctccacatgg ggcaattggc gcggagacgg tggtgattta   61500
cgacagcgac gtgttctctc tcctgtatgc agtgctccag cagctggctc ctggatcggg   61560
agccaactag gcaatgttgg aaacttactc gccaccccc acccgctggg aaagccggca   61620
tcatcgaggg tgggcacaat agttctagcc tgtttgttgc tttttggaag ctgtgttgtt   61680
agagccgtac ccaccacgcc aagccccca actagtactc ccacttccat gtcaacgcac   61740
tcccatggga cagtagaccc tacgctgctc cccacagaaa cgcccgaccc actcagactg   61800
gctgtgcgcg agtccggtat actcgctgag gatggagact tttacacctg cccaccgcct   61860
accggatcca ccgtcgtacg catcgaacca cctagaactt gcccaagtt tgaccttggg   61920
agaaacttca cggaggggat tgctgttatt tttaaggaaa acatcgctcc ctacaaattc   61980
agggcaaacg tatactacaa ggacatcgtt gtaacacgtg tgtggaaagg atacagccat   62040
acgtccctgt ccgacagata caatgacagg gttccggttt cggtggagga gatcttcggt   62100
ctcatcgaca gtaagggaaa atgttcgtca aaggccgagt acctcagaga taacatcatg   62160
caccacgcgt accacgacga cgaggacgag gtggagcttg atttggtgcc gtccaagttt   62220
gcaactccgg gggccagagc ctggcagacc accaacgata ctacgtctta cgtggggtgg   62280
atgccatgga ggcactacac gtcaacgtct gtcaactgca tcgtcgagga ggtggaggcg   62340
cggtccgtct accccctacga ctccttcgcc ctgtccaccg gtgatattgt gtacgcgtct   62400
```

```
ccgttttacg gcctgagggc tgccgctcgc atagagcaca atagctacgc gcaggagcgt    62460
ttcaggcaag ttgaagggta caggccccgc gacttagaca gtaaactaca agccgaagag    62520
ccggttacca aaaattttat cactaccccg catgtcaccg tcagctggaa ctggaccgag    62580
aagaaagtcg aggcgtgtac gctgaccaaa tggaaagagg tcgacgaact cgtcagggac    62640
gagttccgcg gtcctacag atttactatt cgatccatct cgtctacgtt tatcagtaac     62700
actactcaat ttaagttgga aagtgccccc cttactgaat gtgtatccaa agaagcaaag    62760
gaagccatag actcgatata caaaaagcag tacgagtcta cgcacgtctt tagcggtgat    62820
gtggaatatt acctggcacg cgggggggttc ttaattgcat tcagacctat gctctccaac   62880
gaactcgcca ggctgtacct gaacgagctt gtgagatcta accgcaccta cgacctaaaa    62940
aatctattga accccaatgc aaacaataac aataacacca cgcgaagacg caggtctctc    63000
ctgtcagtac cagaacctca gccaacccaa gatggtgtgc atagaaaca aattctacat     63060 cgcttgcaca aacgagcagt ggaggcaacg gcaggtaccg attcttccaa cgtcaccgcc    63120
aaacagctgg agctcatcaa aaccacgtcg tctatcgagt ttgccatgct acagtttgca    63180
tacgatcaca tccaatccca cgtcaatgaa atgctaagta gaatagcaac tgcgtggtgt    63240
accctccaaa acaaagagcg gaccctatgg aacgaaatgg tgaagattaa cccgagcgcc    63300
atagtctccg caaccctga cgagcgagtt gcagcgaggg tcctggggga cgtgatagct     63360
ataacgcact cgccaaaat agagggcaac gtgtacttgc aaaactccat gcgctcgatg     63420
gacagtaaca cgtgctactc ccgccccccc gtaacattta caattactaa gaatgcaaac    63480
aacagagggt cgatagaagg ccagctggga gaggagaacg agattttcac ggagcgcaag    63540
ctgatcgagc cgtgcgccct caatcagaag cgctacttta gtttggcaa agagtacgtt     63600 tactacgaga actacacgtt cgtccgcaaa gtgccccca cggaaatcga ggttatcagc     63660
acgtacgttg aactaaactt gacccttttg gaagaccgcg agtttctgcc cctggaggtg    63720
tacacgcggg ctgagctgga ggacaccggc ctgctagact acagcgaaat acagcgccgc    63780
aaccagctcc acgctctcag gttttacgac atcgacagcg tggtcaacgt ggacaatacc    63840
gcagtgatta tgcaggggat cgccagcttt ttcaagggcc tgggtaaagt gggggaggcc    63900
gtgggaacgc tcgttctcgg cgccgccggc gctgttgttt caaccgtatc tggaatagct    63960 tcgttttaa acaacccatt tggggggcta gccatcggcc tgctggtaat cgccggcctg     64020
gtagctgcgt ttttgctta cagatatgta atgcagatcc gcagtaaccc catgaaagct     64080 ctataccca taacaacaaa ggccttgaaa acaaagcca aaacttccta cggccagaac      64140
gaggaggacg atgggagcga ctttgatgag gccaagcttg aagaggctcg cgaaatgatc    64200
aaatacatgt ctatggtttc ggccctggaa aagcaggaaa agaaagctat aagaaaaac    64260 agtgggtgg gcctgatcgc cagtaacgtc tcaaagctgg ccctgcgaag gcgcggtccc    64320
aaatataccc gactccaaca gaacgatacc atggaaatg aaaaaatggt ttaaacatgt    64380
ttaataaata ttatgacacg tactcaaagt gtgacctcat atttgcataa ccactttcta    64440
gttccggccc caaggatatt taagcctagt atctccgccg aggtttcatc ctcattcacc    64500
aactcacact tagagttgac gcttcctctt gcgcctttgc tctcgccgct cctgtgttag    64560
cgtatactgc ccaagaaatg gattctccac gcggtatctc cacagctacc ggtgatgccc    64620
acgccgaggc cgcggtttcc ccagccgcgg aaatccagat aaaaacggaa gccccgatg     64680 tagacggacc agaagccact actgagtgtt tagaccacac ctacacccaa cagacaagcg    64740
```

```
ggggtgatgg cctagatgct atcgatacgg acgatctgct ggagatggtg ctgacttccg    64800
aaaacacaga gagcgaaccc ggtattccgt ttgccctgcg gggaaacttc atctgctgtc    64860
gagacgacaa ctgtcgcgcc tgccgggagc tgccattccg tccatctgtg atcgggtttt    64920
cgagggaccc ccacgtttct atggcgcttg acatgaccag cggcaactgg gcttacgtcc    64980
cacgtgtttt tcccgacacg cccaccgccc cgtggatggc caactactgc atccctgacc    65040
tcgacgaaca cgcggattga taaaaaagca aaaataaac aatttttagt ttatatacgt      65100
gtatgtattt attgttagtt tacaaagtag ggggagggggg cctttatcca gtttaccgag   65160
cgctcatcat ctgagacacg aatatgtccg cgtcatcgcg cccaaactcc aggccggtgg    65220
acgcactggc gtcgaccgtc tgactgctag cctggggttg agtgacgggc aggaccgccg    65280
ctgacgtaac cgcctcaaac tgctggggtg cagctctagc ctgctcggcc tgctgcgggg    65340
cggtagaagc ggctacgacc ttggcactgc ccggggcttc cccggctggc acctgtggcg    65400
ccaacactgc ttgggttggc tgagagggga ttcccggtag ctgcggagcg acgatggcgg    65460
aaaccgcgtg ctgcggttgg atatactgat attggctgta ttgaggagga acggctggta    65520
tgggtttgta tagccccgcc ggtgcggctt gggctgcgc ggtcacggtt tgtatagctc     65580
tgagctgcga cacctcttgc tgcagagagg aaaccgcccc cattagatcc gcgatggtgg    65640
tggacgggcg cccggctctg cgctcgcctg ggcgcggtga gcgctctccg gggtaataga    65700
taccctctag gtcatcgcgt gtggttgcgt cccagtcatg gcggcgcttg cgtgcatatc    65760
gccgctcttg ctgcggagac agaggcggtg agcactgtga gccttgaata acatgggggt    65820
cgctacccct ggtagctttt cggtccgcgg ccagggctcc gactagcgct gtgatctgcg    65880
cctctaggtt agcactgtgt ggcacgctcc agtatggagg tgcctggtac atcgatggtg    65940
gcatcaggga attgtaagcc ggcggtatat actgagaagg caccgcgtga gtgacgggag    66000
ccgggccagc gtttattgga ggatgagaag tgtgttggcc aacaacgagc tggttatact    66060
gcgccgcggg gactaaaatg tagtcccctg aaaccagagg ggcgccagcc gccgacagtg    66120
tctgggggtt tgacgaggcc atcgcactta tatgttttg tgtgcgttcg cctatcccac     66180
ccttgtcgtt gtctgatgag ggtaacgcgt tggggcttga ggaagtgaaa gccttttgcgc   66240
cgagcgttac gcgtgaataa ggtgcgccgt gaacctttc tccgcttta taaccgcatg      66300
tgtctaccag ctccgccccg caaaagtcgg cttttgttgca gccgttggtg atcccgaagc   66360
tcgcgctggc ctgcaggtac gtgtgcccct ctatgccagc ctctctccgt cgtcgcgcca    66420
ccaggttcca gcggtttcgt aggagcatgt tgttaacggc ggttgacagt aagacccggg    66480
tcagggtgtc ctctgatagg tgccacgtgg ccgcgtcccc caagcgcgat tgtgcctcgc    66540
gtgccgttat taacaattcc tcgcgtgagg acggcgacag cctcttgaat ggcgccaccg    66600
cattttccgg ggtggcgtcg taagtgacga ttgttcccac tctacggccg attacgcaca    66660
gggagacgtg cgcaaatagg gtttcgtcag gctcctcgtc cggcccaagg cgccgggaag    66720
acagcgacgc tgacggcaaa tagttgctca cgaggtacag cagccgctcc tgctcagaca    66780
gcccttcgga tagctccccg aaaaagtcgg ggccgcagc cgtggctaaa accgcaccca     66840
gctgggggca gttaataatt cccagaaaaa acgggcctcg tgcgtcatcc actatggata    66900
acacctcccc aaccacacac ccgttgcggt ggtcgatgtt aatgggtaat ctagatgccg    66960
ggggaagcgc tgccgcgacg gtttccctgg taagcgttag ctccccccca tcacccatat    67020
catagagagc tatataccca gccacgtaga taggaaggct tactgcgtta ccgtccacgg    67080
tgtacgcgtc catagtaaga tatgcgtggg tttattccga gtaaaacaca ccagttcccc    67140
```

```
gcgcgcgcgg ctaataaaca atcttgttca cagtctaaga ctttattgta gtgactatgg   67200
gtaaggcgtt attacattgc ggatgtcaac gaaggaatgt atccaagaca aacaaagtat   67260
aacaggtcat aatcgctggc cacgttaaac tgacccaggc gtctggtctc ctcgagcgag   67320
gccctcaatc tgggcttttg catcagcagc cccaggccgc gctcgtactg gagggctacg   67380
gcgtcgtgcg cggcaagcac ctcgtttatt gggaccgggg ctgtccggcg tctattctcc   67440
agctctatgc ctattaacct ggtcaagttg gtctgattgc gcccggtaga cacgttaaca   67500
gcgcggtgct gcggctgatc gcgagctacc gtctgagcgc ctaagcatag ggctgccagg   67560
ccgggaaata gctgggtcaa ttccacctcc ctgttggcta tgtatatggg ggagacgtaa   67620
cgctcgcata aaaggtgaa gttgttgtta ccgctacgac taaccatagc ggcagcatct   67680
cccccgctcg ccccctggc gtcacgctgc gatactgcga ggttgggtac gattgccccg   67740
agctgaaaat tattgcgtaa tctgtccgta tagacgttgc cgttccacag cagacgacgc   67800
agcagcagca gcgcggtgat ggtgttgatc gtcgagcgta gtagggtttg gtcttccgtg   67860
agaaacaggt tttgggcgcg caccaaaaag gccgcagcgg cttttgtttac gtcgtctatg   67920 tacgcagtct ggtccgcgtc gagttcgggt ccgacggcgg tgctcgtggt tcccagacta   67980
cccggaatgg cgggcaaaac ctttaggcgt atcagcgtct ctagaacgcc atggccgttt   68040
agcgcgcccc gttcgtatct tccccctcct ccgggaacgt gaaactggtt ctttgggaga   68100
cgcgcgccgt tgaactcgta cccgaccttt ccgagcgttc cgtctccgag tgccgtggag   68160
aaagcctcga tgtacacggg cagctgttcg attagcccag aaaagctagt gggatacgtg   68220
tagttgctgt ttacggcgcg atgggctaaa tggaggcata gcacggctgc ctcgaatgcg   68280
gaatagggtc tgtttcctat gtaaagccta ccgcatgact gcagagatac gacagccgtt   68340
gtcataaacg ttttagacat gcgaccgtct ctatagtcga tgctgcgcgt ggccaccggc   68400
cgctccgtga ctagacggtc ctgaagcgct ctgtaccagg tgccgaatac caccccgttt   68460
gagccgcccg cggcgcggct cacaaacacc gtggctaata agtctacggc caggttcgtg   68520
tcgaactcca tgggaacgtc gttcttagcg atttgaattt cactgagcga ttgtccgatg   68580
ttgtcggggc gctgatccgc ttcactcgcg tttacctggg gcgtggcggc gtcggcgctc   68640
tccgctgcac gcgcggcatc ttcgagggcc gccagggcat cagctacttt ggcaacctgt   68700
cgctctaggg gtctaatcaa cgcatctacg tttgcaactc cgtactgact ctgcgcctcc   68760
aacgtgtcta tggccgctgc ggcggctcta tggcgggccg caaccagctt caggggatcc   68820
gccctggtgt tggagctgac ggtgaatgta ggtccgctcc aaaagttaag cggaaatggc   68880
ggggctataa agtttcgcac gtctgtcggt atagtggacg tggccgtatc gcttacgtaa   68940
agcgatccta acacataatt cacatactcc gccatctcca ccgcgactat aaggtcttta   69000
gcttcgatct tagtgtttat acttgcgtgt aggcgcgccg acaaaaaaag gggcactcgt   69060
ctttaattgc accggctttt attttgggga aaaagggac gccgcccagg cgagggggtt   69120
tacgtgcgat acagccaccg gctgatggac cgcggctgcg ttagtggtgt ttgccgggac   69180
cgcagctgga aataaactca cgacggcggc tgccgctgac ggctgggctg gcgttataga   69240
tggcactggc tccgctgccg cctttgtact aaaggctttg gccttggttc ctttggcgac   69300
gcaccgcctc cttgtcgatt tagctgaaac tggtggagcg tattccgcca aacgtgatat   69360
ggtgcaggat agcacggcag cgttgctata tacaacctgt ggcgataaac gcgttacccg   69420
caacacccgc attcctcgtt gagctacaaa cactagtacc ggagctagta cgatctcacc   69480
```

```
gcttcccggg ggtagcgttc tcgccagcaa cctgcacgag tcatgtagct gtcgcatgcc   69540
cccctteege tgtagatttt tactegeggt gttcatattt ttggaaaagc gacacgtttt   69600
tagctctatt aggatgcaca ctcccttggc gtcagaaccc tttccaaatt gcacggtaca   69660
gacacaatcc gggcgccgct gtccgaggtt aacctcaaag gccagagaca cgcccagtgc   69720
cgttttaaga gtttccgctg gcaccagttc actaaaaagg ggagcaagcc tctctccgta   69780
cacgccgttt cgcttggcgc ttgccaggtc ttgaaccatc gcgttataga agcggttgtg   69840
gcaccgtata ccagctctga gtctgcttct agctgtcaga cgctgtctac gtttcatttt   69900
cagaaatcaa tggcggctcg cgtaccttcc ggggaagctc gacggagcgc cagcggggcg   69960
ccggtcaggc ggcaagtaac aatagttaga atttacctcg atggggtcta cggcatcggc   70020
aagagcacga ctgacgagt tatggcatcg gctgcgagtg gaggaagtcc aactctatac   70080
tttcctgagc ctatggcgta ctggcggact ctctttgaag cggacgtaat tagtggtatt   70140
tacgacaccc agaaccggaa acagcaggga gatttggcgg ctgatgacgc ggcgtcaata   70200
acggcgcact accagagccg ctttaccacg ccctaccttta tcctacacga tcacacattt   70260
gggttgtttg ggggcgacag cctacagcgt gggacaagac cagacctaac cgtcgttttt   70320
gaccgccacc cagtcgcctc tgccgtgtgc tttcccgccg ctcgctacct catcggagac   70380
atgtccatgt gcgcgctgat tgccatggtt gccaccctac ccagggaacc gcaaggcgga   70440
aacatcgtgg ttaccaccct caatgtggac gagcacgtgc gaagactgcg cacccgcgcc   70500
agaatcgggg aacagattga catgaagcta atcgccacac tgcgaaacgt gtactctatg   70560
ctcgctaata ctagcaactt tttgcgctcc gggagagtat ggcgcgacgg ctgggggag   70620
ttgcccctt cgtgcgagac ctataaacat cgcgcaacgc agatgacgc cttccaggag   70680
cgcgaatctc ctgagctgag cgacacgttg tttgccatgt ttaagactcc cgagctgcta   70740
gacgatcgtg gagtgatatt ggaagttcac gcctgggcgc ttgacgcgct gatgctaaag   70800
ctgcgcaacc tgagtgtttt ttgcgctgat ctgagcggga ctccgcgcca gtgtgctgca   70860
accgtggagt ctctaatacc cctcatgagc agcacccctct ccgattcgga gtcggcctcc   70920
tccctggagc gggccgcgcg caccttcaac gccgagatgg gcgtctgaaa ctatatgtaa   70980
tgtttgttgt gccagtgtaa taattatgaa ataaagattc ctttgcctat atccctcata   71040
ccgcctcgtg tgtccagtgt gtaaacttcc aggttctagt tttggggata tataagtggc   71100
tgtgacctgg attcatttag tacagtgcgg ccgagccact caagatatac cgtggctgta   71160
cattaacttg ggaatcatta cttccgcgat catgttacaa ccgtatcgaa aaatgctgat   71220
cttttgcagtt gttactgttg cctttgcgat ggctgtctgg tcaacgcccg tcccagccac   71280
tccgtctggc gtgggtaacg ctacttggc aaacaatagc ttcaacataa ccaggtatga   71340
caagataacc atgggacagg tttatagtaa cacttcaaac tctcccatct tcttcgttgt   71400
tatatcggag cggaattttc gcatcgttaa cactccgctg ggcgcgtcgg tattttggat   71460
accaaagggc gctatgaatc ctccgcaaca ccaaccctgt gtcgccaacg ggccggaacc   71520
tggggaccca cgcgggccgt gtgtcaactc gaccgtcagt ttattgttta atgaaaacgt   71580
ggagccgttc ttaatgtcaa aaaatctttt agagtttgaa gtgttgcccg acacctacat   71640
aaccggttgg acgtttgagc ggtctaaaac agcgaccaca aaaagcaacc cggttggtgt   71700
ggttttatcg ccacccaggg gcagtccgtc agctaacaca acaatcaggg acgatggcgg   71760
acccaaaaag cccctgagca ttatagacga atacaccacg ctcgtggcgg acttgcaaaa   71820
tttcactatg acattgactt acataagccc ctttgccgcg gtgtggccta ttgaagcctt   71880
```

```
tcaaacgggc atcacggtca tggggtgcga cactacacag gttgttgcgt atctcggcca   71940
tgggtttatg ggcctgcaga taagctcggt taacaacccc ccgctggaaa tgatcgtcgt   72000
acccaatgac gtcagtgctc gtatacttaa ccgacgcccc tccagacttc gattggagcc   72060
cccgggacct cacgcgggac ctatctacaa ggtttacgta ctcagcgatg gaaatttta    72120 cctgggccac ggaatgagca ggatctccag ggaggtggcc gcctacccgg aagagagttt   72180
agactaccgc taccacctat ctctagccaa cctcgacact ctggcgatgt tggccgaact   72240
ctcctctggt aagagcacgg atgtaagcta ttacatgtac cgcattgttg cgcgtctggc   72300
cgtagccacg ttctctctgg ctgaagttat acgcctaagt gactatatgc tcctgcaaga   72360
agccattgat gtggatatga acctccgcct cattgtcccc ctcgtgatga agtacgccgc   72420
aggaggggcc gcggatagct cgtacacatc ttctgacgtg gccatggacc agtttgacgt   72480
tgcacaatcc cagattgaga aaatagtgtc agatatcaac gtggaggccg aattgcgcaa   72540
accgatgtac gagcaccgct cactgttgag aagcgtttac gcttattcca gaaagccgct   72600
gccaaacgcg gtggccttag cggaccggct aatattggct atgtataaag aagccattaa   72660
ggacagaatc acgtggaact ccacaatgcg cgaggtgcta ttttttgctg ttggcgcggc   72720
cgccggttcg catgttatcc tcactgacga acccgagcca ggcgcgcccg cccacaaaga   72780
cgcctcgcta tttctatccc tcaaccgcaa catcctcttg ctgtgcacgg ctatgtgcac   72840
ggcatcgcac gccgtatctg caggtctgaa actagaggaa gtcatggccg gcctcgttgc   72900
cggcggggtg caatttagcc tcctggaagt attcagcccg tgtatggcgt ctacccggtt   72960
tgacctggcg gaagaggagc acgtgttgga tttactttcc gtgatcccac cccgtctgta   73020
caccgacttg aacaccggct cgaggacga cggaactacc atccattctt acgggcgatc    73080
tgctaacggg attctaaact ctcgcatcgc gtacaacttc gatgctgtta gcgtgtttac   73140
cccagagttg gcctcgtgta gcactaaact gcccaaggta ctggtggtgt tgcccatatt   73200
taccaacaga agctacgtca tcactcgtac cgccccaagc atcggcctga cctactcact   73260
cgatggggtg aatatagcaa agcctatcgt tatcagttat atcacgtatg gaaactgtga   73320
agtctccaga gctaccatca gtctggtta  tttggataac cctggccaca cgcagacgtg   73380
cgtatactgc gggagcgtgt ttatgcggta catggtgtct ggagcaatca tggatttaat   73440
atacatagac gacaaagaag tggagctgca gctcgttgct ggagaaaact caactatccc   73500
cgcctttaat cccaaactgt atacgcctag catgaacgct ctttaatgt tcccaacgg    73560 aacggtgacg ctaatgtccg ccttcgcgtc ctattcgtcc ttcaaagttc caagcactta   73620
tctctgggct tctatcggtg gtctgctgct cgctatttta attttatata taatcatcaa   73680
aatgttatgc ggtggtgtaa ccaacgatgg ttataaattg ttattgagtt atgagtaaac   73740
aaatatcccg tgtgttgtta cccccatgt  tagacaatat ttgtgcgact gtggtatgta   73800
tgtgctaaac cagaaataaa cactattaaa atattacgcg taaaattgtt gaatttattt   73860
tcgctatatg cgggagcgag ggctgctgcg gcggcggcgc ggcgggagcg agggctgctg   73920
cggcggcggc gcggcgggag cgagggctgc tgcggcggcg gcgcggcggg agcgagggct   73980 gctgcgcgg  cggcgcggcg ggagcgaggg ctgctgcggc ggcgcggcgg gagcgag     74040 ggctgctgcg gcggcggcgc ggcgggagcg agggctgctg cggcggcggc gcggcgggag   74100
cgagggctgc tgcggcggcg gcgcggcggg agcgagggct gctgcggcgg cggcgcggc    74160 ggagcgaggg ctgctgcttg aatgaaaacg gctctggagc tcccagtgct taaataggaa   74220
```

```
attggggcgg cccaccggct agatgtgacg acataacgtt cgcactgagt tacaataatt    74280
attatatatt attagcaatt ggtgcgaacg gagctctggg ccaatcaacc agtctaaaac    74340
gaaccacgtg acatagaatc caatcaaaac atgcgtatcg attaggtatc gatacattat    74400
cgatacctaa tcgatactca atttcgccta atgcgggttg taagagcccc aaggtgttgg    74460
ccggtgagca aatagcctcc ccaagaaatg cgcatcccgg tattaccata gacgcggcgt    74520
atagtaccag cgtatctcac ctggtagcgg cgcgtagtgg attttgccca ccttaacatc    74580
atcagtctta gtaaaaggtg cggtgaaacg gtgttaaggt acagagtgtt tttatttttct   74640
gcttacatgc acagttacac ccccgcgctt cagcctctcg ctgagtaagt aatataagta    74700
gtatgccccc tttctgctta agtccaggcc atcgaatgct gttattgaag acacattgag    74760
cactattgcc actggtaggc cgctccccaa gatgcgacag gctacctgcg ccgctcctcc    74820
gattccgtct ttggcgtata gcttgttgag gacgctcgcg attctagctt ccatgttacg    74880
tacctcgtcg tacgaactga gcccaagctc aacccgggtg gcgtttgcag caaactccgc    74940
cagtagtcta gcctccagtt cgactacttc cgaaccgctg ccgttgacgg gatcggtggg    75000
ttgggtatag cgcacgatta tctcgcacag ctcacccaaa ataccacttt cgcgtattat    75060
ctcattgaca gcgtcggcca ccaggtgtgg gtctgggagg ggatcgcgag cctctggaac    75120
agctccgatg tagctctcgg ctagttgttc aagggccgcg tagcagttga taaggttcca    75180
cttgcccaag ataaactggc agagcacgaa ccgctgtagg gttgtgacac cctgctgagt    75240
cagctttccc ccgaaaaagc gcagtttccc ctcgttgccg tatactgcca aaatggcatc    75300
aacgattgtg cttcgcgcct ggttgaggtg ttcatccaac ccgggccacg gttcttctat    75360
cagaatgatt tcatcagcaa ttttaaatag tagttgtagt gattgtagcg atgcgccgct    75420
ggccacgcga ctcgccgaat cccagatgct gcagggcttt ggaatcaggc gcacctggac    75480
aaagtcgctt accacagttt ttctaagggg tcgtttggag caccgggttg tgccccctat    75540
tgccattgtt tttacagctc tgggggaggt aacgataata tcggtgcggc tatgtcctcc    75600
tgactcgtct cgtaggggg gtcttgctac tggaatacga tcaaatagtc cacttatcag    75660
tgtctctagt tctgggggca actcggttag gtacgcctga accaaagtga aacacgctat    75720
gtttggggtg tagataaacc ccgaggatgc gtttgtgata gtgggaacag tatagaggtg    75780
tagcattccg tcttgtggta tatctctccc cgtagatacg atgagtccag acgttacttt    75840
tagagatacc atacactcgg cgaggtaggg gtcgtatact tccagatcga agctcccgca    75900
gatgtctctg ccaaaggcct gggcgccctg ggccaatact tctaaacgat caacgaacac    75960
gtcctcttca gagctgggcg cactctcatg gcgtcccgtt cggttcaatt cgctgcgcac    76020
ataattggcc actactcggt cgttgtgtgt tagcccccgt aaggtcagcc caaactttgc    76080
gatttcaccg ctctcggccg tggcatgggg tctaggcaca gagagcagac acccaccgta    76140
tagaaaatac acgcgatggc caccgtcggt tatgtagaac acaacgccgt tgtggatgac    76200
tgtgtcgctg tacttgaagt ccatgattcc taccgcggcg ggtgtaagac acacagcgat    76260
aaaatcgtac ttggtggggt ctagcgaccc gtttggcttt taaacttatt ggctgggggtt   76320
tgcgagagac gctgcctctt tgcggtcgca gctgcaaatc cacaattgtt taaaagcaaa    76380
ttggttttat atcgaggagc cactttaaat atgagatacc tagaacggac ggtgagtggt    76440
ctacgcctgc ctaggaacgt ttatcacgtg ggtcaacgca tttatataaa ctttgcggtt    76500
tttagttttta ggggggaaatc actcgggaca aattagggg tgtccctaac ggtttatggc    76560
tacttttgcg atccctattt ggcgttttta ttcccggaaa tgccgcatta cgtgatagat    76620
```

-continued

```
atataaacgt taaactgtat gtcacgatat tgacttttaa ttatacacgc ttcaacgtgg    76680
gctatagcct cgcatataag gtttccatcc tggcgctggt tagactagtc catacactgc    76740
accgctcgca ggctgccaga aatatttctc tccgaatttt tgagggttgg agatgccaca    76800
ggtattaatg gggaataccc gtttacacgc accccctcgaa gatggcattc ccctgatcga   76860
aaacgatgaa aattcatccc aaaatgaagt tgatctctat gactatgtgt ctatgtcgtc    76920 ttacggggc gacaatgact ttttaataag ctcggccggg ggcaacataa cccccgaaaa     76980
tcgcccatca ttttctgccc acgtcgtcct gtttgccatt tctgccctag tgataaaacc    77040
cgtatgctgt tttatatttc tcaaccacta cgttataacc ggaagttatg actttgccgt    77100
ggctggagga gtttgtaccg tactatacta catgcggctc cgcgctcaccg cctggttcat   77160 gtttcgcaac atccaatcgg acatgctacc gctgaacgtc tggcaacaat tcgtcatcgg    77220
gtgtatggcg ctcggtagaa ctgtcgcgtt tatggttgta tcctacacta ccttatttat    77280
acgctcggaa ctgtttttca gcatgctggc ccccaacgcg gggcgcgagt atataactcc    77340
aataattgcc cacaaactga tgccacttat tagcgtccgc tctgccgtct gcttggtcat    77400
aatatctacc gctgtttacg ccgcagacgc gatctgcgac acaattggct ttacgctacc    77460
gcgcatgtgg atgtgtattt taatgagatc cagctccgtt aagcgtagct agtaggggtg    77520
cctccgtggg aggcaccact ggggtagcgg ccgactgaca gtataaaacg tgagaagaga    77580
gcagccccac gcgccattag cgctaggcca gttagcgcgg aggacctgag cgctacaccc    77640
agacggtgca atcggcgggg tacaggtttg tcaccaacga caggcatttt accactacga    77700
taatggaccg gcgctcagag gcgttcaaaa ttccggtacc agaagtaatc cccgccggac    77760
agattctatc aactatagaa gtgtcgtccc accgcactct atttgacttt ttcaagcaga    77820
ttcgctcgga cgataatggc ctttatgcag cgcagtttga cgtgctactc ggaacgtatt    77880
gtaacacgct aacgctggtg cgcttcttgg aactaggatt atccgtatcg tgcgtgtgca    77940
ccaagtttcc agagcttaac tacgttaatg atggcaccat ccaatttgaa gtgcagcagc    78000
cgatgatagc tcgggacgga ccccacccctg tggatcagcc cacccacacc tacatgatga   78060
agcacatcga gcagcgatct ctgagcgcgg cctttgctat cgcggcagag gccctgggcc    78120
ttatcggggg cacaacccta gacggtacgc agatctcatc ctcccctgcgg gtgagggcta   78180 tacagcagct ggccagaaac gtgcagacgg tgctagactc gtttgagcgc ggaaccgccg    78240
atcaactttt gcgtgttttg ctggagaagg cccccccgct gacccttttg gctcccctgc    78300
agatttaccg cgatgaggga cgccttgcgt ctcgagtcaa tcgcgccgtg ctggtctcag    78360
agctcaagcg gcgagtgata aagacacct tctttctcac caagcacgag cgtaacagaa     78420
aggagctggt ggtagcccgc ctggctgagc tggttaactg tacggccccc tccgtcgccg    78480
ttactagaat gactcattcg gacacaaagg gaagacccgt ggacggtgta gtcgttacaa    78540
ctgctggcgt gcgccagcgc ctcttacagg ggattctaac tctggaggat atggccgccg    78600
atgttccggt tacgtacggc gagatgatga ttaccggcac aaacctagtt actgctcttg    78660
taatgggcaa ggccgtgaga aacctggacg acgtagccca ccacttgttg gggatgcagc    78720
gtgatcaggt cagggcgaac gaaaaactta ttaaagacta cgaggatgtg cccagcacgg    78780
cgcgagtacg tgccgaccta gttctcgtgg gggaccgcct agtctttctg gaggccctgg    78840
aaaagcgcgt gtaccaggcg accaacgttc cgtacccgct tgttggaaat ttagatttga    78900
cgtttatcat tccctgggc atcttcaagc cggccaccga ccgtattcg cgccacgcag      78960
```

```
gaagctttac gccaaccccc ggacagccag accctcgcac ctacccaccc caaaccgttt    79020 acttttcaa  caaggacggt aatctcgtac agctatcctt tgacagcgcc gcggggaccg    79080
tgtgccacag ctcgttttg  gatgtggatt ctgtgctggt ggccatccga cgagaacccc    79140
acgagcttca ctgcgcgttt ggggcatacg tgaccctacc cccagccggc actctgcttg    79200
accagatgag aaggttttt  gagcgctggc atatgctcat gccagcgcga ccccgctgga    79260
ccgcggaggc gctaatgacc atcgaccaac ttctttcgcc aggcaacgca aacctgcgcc    79320
tggaacttca ccccgcattt gattttttcg ttgccccggc ggatgtcgtc attccaggtc    79380
cgtttgacat gccgaacgtc atgcccactg tgatggccat gccacgcctc atcaacggta    79440
acatccccct cccctatgt  cctgtggaat ttcgcgacag tcggggcttc gaactgagcg    79500
tggatagaca caggctcaac ccggcgacgg ttttggcagt gcgtggtgcg ttcagagacg    79560
ccaactaccc catggtgttt tacatcctcg aggcggtgat tcacggtagc gaacgcacgt    79620
tctgcgcgct agccagactt ataattcagt gtatcgtcag ttactggaga acacccacc    79680 aggtggcgtt tgtcaacaac ttttacatga tcatgtacat aaacgcctac ctaggaaacg    79740
gcgagctgcc agaggagtgc acggctatct accgcgacct tctggagcac gtccaggctc    79800
tcaggcggct agtagccgag tacaccgttc ccggagaagc cgtgggcggc cagggacacg    79860
acgcgctgaa caatgtgctg ctcgatccgg ccctgctacc gcctctcatc tgggactgcg    79920 acccgattt  gcacagggcc gacatgggca gggccagggc tcaggagcta tgggtggatg    79980
gggtggacta cgccgccatt ccttgggtgg agatggccga agttaacttt ggaaacaccg    80040
gcggccattt ggtgcacaac aggcccattc gaggagagaa caagagaaac ccgattgtac    80100
ctcaccacga cccagagtgg tcggtgctat ccaagatata ctactatgcg gtggtgcctg    80160
cattctcgcg cggtaactgc tgtaccatgg gagtacggta cgaccgcgta tacccgctcg    80220
ttcagacagt tgttatccca gacttggggg cggaggaaat tgcccaacc  agccccagcg    80280 acccgcgcca tccgctgaac ccacgccacc tagtgccaaa cactctaaac atcttgtttc    80340
acaacgccag agtggccgtc gacaccgacg ccctgctgct actccaggag gtagtcacca    80400
acatggcgga gcgcactact cccgtgctgg caaccgccgc gccggacgcg ggaaccgcca    80460
ccgccgtaac tcaggaaatg cgcacttcg  acggaaccct ccaccacggc attttgatga    80520
tggcctacca gcgtaacgac gaaactctt  tggagggcac cttcttttac cccgcccctg    80580
tcaacgctct ctttgcctgc cccgagcact tgggggctct tcccgggctt aacgcagaag    80640
tcttggaggc cgctagggat gtgcccccag ttccccactt ttcggtgga  aattactacg    80700 ctacagtcag acaacccgtg gcgcagcacg ccgtacagag ccgcgcggat gagaacacgc    80760 taacgtacg  gctgatggcg gggtacttca aactcgggcc aatagccctg tcccatcagt    80820
ttgccactgg gttccaccca gggttcgcct ttaccgttgt gcgccaggac aggtttctca    80880
cggagaacat cctctttgcc gagaaggcgt ctgaatcgta ctttatgggc cagctacagg    80940
tgaaccgcca cgaggcggtt gggggggtta actttgttct cacccagcca cgtgctaacg    81000
tggacttggg ggtgggcttc accgccgcct acgcagccgc cgcactacgc acgcccgtta    81060
cagacatggg aaatctgcca caaaacctgt atctgacacg cggtactata cccatgctgg    81120
acggagacgc ggatgcgtac ctgcggcgcg tggtcaacac cggaatcgc  cttgggcccc    81180 agggcccaag gccaatcttt gggcagctga tgccggccac gccggcgggc gttgcccacg    81240
gccaggccgc cgtgtgtgaa tttatcgtca cgccggtgtc tgcggactta aattatttta    81300
ggcggccatg caacccccaga ggaaggagcg ccgggcccgt gtacgcgtgc gatggagagg    81360
```

```
ccgacgcagt ggacgttatg tacgaccaca ctcaggagga tccggcctac ccgagccgcg   81420
ccaccgttaa cccgtgggca tcccagcgca actcttacgg cgatagattg tataacggca   81480
agtataacct gaacggggca tccccggtgt acagtccatg ctttaagttt ttcacaccca   81540
ccgaagtgga agccaagggg cgtaatatga cacagctcat agccgatgtc ggtgccagcg   81600
tcgcccccag cacgtctaac accgaaatcc agtttaaacg ccccacggc tcgacggacc    81660
tggtggaaga cccgtgttcg ctgtttcaag aagcgtatcc tctactcagc tctacggaca   81720
cggccctgct ccgcacgcct cacatcggtg aaatcggcgc tgatgaggga catttcgctc   81780
agtacctaat tcgcgacgaa tccccgctaa aaggctgttt tccgcgaatt taggttgggc   81840
ccgcctccaa gtttcacatg ctgccaaaac taaataaaac gcacagttta tatactcact   81900
tgtcagtttg ctctgcttga gcgctagcgc tccgtctcga cctcccagag tggttattgg   81960
tacggttggt gggtggtttt gactgccttt aatccctagc agactttaat cgatagaagg   82020
ggcataataa ggaagtcttt tggggggggc gtcgctcggg tttggggtgc ctccacgtag   82080
agatggcgag tgccgccttt gagattgaca tcctactgcc cagtgaccta tctcccgctg   82140
acctgtcagc tcttcaaaaa tgcgagggta agcttgtgtt tttgaccgct ctgcgtcgtc   82200
gcgtgatgct ctccagcgtc accctctcgt catactatgt caacggcgca cccccggaca   82260
cgctatccct gatggcggcg tttcgtaggc gttttcccgc tataatacag cgcgtgctgc   82320
ccaacaaaat gatagccgcc gccctgggag tcgcaccgct tcctcccggg gcgttcatac   82380
agaacacagg cccgtttgac ctgtgcaacg gggactctgt gtgcgcgctg cctcccattt   82440
tggacgtgga ggacaagctg cgcctaggat ctgtgggcga ggaaatacta tttccgctga   82500
ccgttccact cgcgcaagcg cgcgaactca tcgcgcggct ggtagcgcgc gcggtgcagg   82560
ctctcacccc aaacgcccag gcccagcgcg gagcggaggt gatgttttac aacggacgaa   82620
agtacaacgt gaccccggat ctcagacacc gagacgccgt taacggcgtg gcgcggtctc   82680
tggtgctaaa catgattttt gccatgaacg agggatcgct tgtgctgctc tcgctgatac   82740
caaacctgct caccctggga acccaggacg gatttgtgaa cgccataatc cagatgggaa   82800
gcgccacccg tgaggttggc cagctcgtcc accagcagcc cgtgccccaa ccgcaggacg   82860
gcgctcgccg cttttgtgtg tacgacgctc tgatgtcatg gatcagcgtt gcctcgcgtc   82920
ttggtgacgt ggtcggtggg aaacccttgg tgcggatctg tacgttcgag ggccaggcta   82980
cgatttcccg cggcgagaag gccctgtca ttcaaacgct tttgtaacct cacccctccc    83040
ccaacgccca ttttaacccc cttatgcaaa taaacttgac accatgttat atattacatg   83100
tagtatgagt ttttaatgat gtcggcaaac aaaactaaca cgtatcctca ctgcgcgggg   83160
agactggaaa acgcatcgct ggttggcggg aggctggaca aataaacggc catcaccagg   83220
gccaccaaca tatcgtccga cgcgccgttg cgtttaccgg taaacactct agtttcggag   83280
gttccggtaa ccacctcggt taagtttttc atttgcgtca gcaggtactc caccgggtct   83340
gtttgcaggc gcaccgtatt tgatactagc tcctgcgaag ctagcaccga gccggagttg   83400
aacgctttga taaagtggtc gaaggccccc gttttctgtt tctggagtag aaaaaacggg   83460
taggccactg agcttccatg gggcgtgcaa tgataaaaca gcaccgcccc gggcatgggc   83520
accacgtcgg cacggcgtag cgtgttgagc tccagctgaa tgtttgttgc gatggcgact   83580
gcagcgtctt ggctactgtt accctctacc gcaactcgaa ctgagtcaaa ggggcgtttg   83640
tgaatggcga aaacctgcgc caggcactgg gcaacacacc tagctatcag ctccgcggaa   83700
```

```
ctccccgtaa gggcgctcag gaaaaagtgc tccatgccga acacgaccca gtttgagcga    83760
tagcggccga ctacagccac accggttcct gaagccatag catttgtagt aaacgcagga    83820
tccacgtata cgtaaaggtc gctggacata atatcttgat tagcgacagt agaaggtctg    83880
tacaacaaga aacggtcttg agcagttttt gtaaaaacgg gctcatctcg atgtgctcca    83940
gacacgtttc ctccaccaat tatctcctgc ataaacgagt ccggtaaaaa tagctccgct    84000
gtgttacgca tggcccgtc cattgttatg aaaacgggct tgtttaaaat gtagcacgag    84060
cacgccgtgg cgtttgtgtg cgcctttacg cgctccatgt gctcgtcgca tatgtaagtg    84120
actacgttca gcaggtcgtc tgccgccccc tttaggttat ataaaaagct ggtactggcc    84180
ttgcccgtgt tggtggagga cacgaagatg atcttgcagt tggtctggtt cagaaagcct    84240
ataatcgttt gcaccgcttc ggggcgtata aagtttgcct cgtccacaaa tagcaggtta    84300
aagtcctggc cgcgaatccc ctgaaacata gagagaataa aaaagggat cgacgggtta    84360 ggcgtttcac ttaagctcgg ctctcgacgc gggccgcagc aatttcttgt aaaccggct    84420 accctgttcc atacctcccg gcgcaccaac ggcgcagcaa taatccgtct gacactacta    84480
tggacgcgca catcgctaac gaaaccaagc atctactggt acacgaaaac agtaaaactc    84540
gcgcgctggt gcacataatc gttcctgacg cgtgcttaaa gaaggctggc gtcgatccgg    84600
ttaagcttag cgaccgccat agagctagcc catccgcggc tcccgtattt cgggtgtttg    84660
cccagactcg atatcacgcc actggggaat gttcgttatg gcgcactgtt tttgctggat    84720
atgtgcccag cggggctatt gtgagcgcgc ttgtgccgac agttccagcg gaccacccac    84780
ggctatttca atcgactccc gactccggtg ggctattcgt atcactagaa attgagtgcg    84840
atgccgatgg ccgctttgac gcgtttactc tggttgcgct gagagtcgac attgccgacg    84900
acccacgtac cactgaagtt tgtttacct atgatgagct gttgccccca ggcactcgct    84960
acggggccga ttccaagcgc gtagcactcc tctgtcgaca attcgtggcg tatgtcaaca    85020
gccaccccac agtttcccag agcgccgtta ctgcggcatc gcacatagaa gccgcggtcg    85080
ccgaggatgt aaagtcggct agcggtcccc aggtatccta cggggctcgc atcgacccgg    85140
ccgagtactt attttcgggc ggggtttcg acaaccacca agccctggcg cggctcgaag    85200
atgacgataa agagataatg tctctgatcc gcagggcgtc tgaggtgatt gcaaaacgca    85260
acccggttag ggtgctcagc aatccagagg ttaacggcga cgcccatagg cggcaatgcg    85320
tggcgtccgg cctccgacag ggtgcccgcg gggcacacgc gtccgactct catgcgcgtg    85380
ttgggtttaa ttccagtatc cacgatgcga cggccttgct gttgggcctg gagccccag    85440 attctggcag atttgttaac agcggcccc agcggcatct gcccctcag ggacccagga    85500 gccccgcgag tcgggactgc cagtccggga tgctcgatga cgtgctgttg ctcactccgg    85560
aaaactccaa cccgctcacc cccctcgact ggctggacgt gggccacgcc gccgtggccg    85620
gaggagacac ccccagagac gtgtggcggc gcaggccgat ctccctagtg gcacgaaagc    85680
actacgggac ctgcgaaacc tttgtagtgg tgtcgtatga aaactccacc gcgtgggggg    85740
gtcggagggc gcgcgacgaa cacttggccg ggtccatcaa ccccccgtg atgcaggcgt    85800 gtgtggcggc cggtgtggac catcccagaa atttgccgcc tgagactcgc ggtgaactca    85860
tcgctaagtt tccgatgttg actgtgcccc tgggcgacac gccgccgccc gtggccgcgt    85920
ttgacgccgc tgccgagttg gctctgatag atcactttcg aggggcctgt gtttccgccc    85980
ttctaaaagc tatatcggaa cgcctgcgcg cggaacctag gatgtcgcag ctaatcgagt    86040
atgacattcc aaacaacaac cgcgactgca tcatcagcgt ggcgcagcgc gccccgagc    86100
```

-continued

```
tgctagaagc cgtggcactc gccattcaaa acgttactgt aacggagttt tgcaatagcg   86160
ccctgatgct atcggctctt tcgcatctaa acatcctctc cggaaacaaa cgtgggcgcc   86220
taccctacca cagatcttgg cttcccagcc tggcggggggg ggcggacgcc tttcttttcg   86280
actactacag ctccggtggc gaagttgtta aagtttcccc cgtcccactg gctatattag   86340
ttaccgcaac cagaacgggc caacattcgt gcaggtttgc ccgaggagcg ccggactcct   86400
cctctaagac gtatgagcgc tacctgccgg gggagtgcta cgcgtacata tgcgtcggcc   86460
taaacagatc gtttgaggct ttggtagttt taccaggagg ctttgcctgc cgagctagcg   86520
cggctcggaa actcgcgtgg cccgctcatc tcgtggagcc catcctagag cgctactgtt   86580
ggacaattcc ttctcactga gatcatctct acgtgccgca tgatggccgc cgcctcagac   86640
agctgtttga gtttatggga ggggtccgcg tcgtccccca accgccaact aaccccggaa   86700
gcggtgaact gtttaacgga ggcgctcacg gaagacgtcg ccgtgctacg cctcatacgc   86760
agcgatcccc gcgttaagat ttttatggcg gttagcgttt tgaccccag gctggctagg    86820
tttgcgcctc ccccgcccaa gctcacccac accgccaagt gcgccgtgat catgatctac   86880
ctgactcgcc ccaaggccct ggcgctacaa cccaaacagt ttcacatgct ggtaaccttc   86940
aacaaggcca gcgtatactc tctggtggtg cgggtgaaga caaagccctt tcccgtaggc   87000
acccagagat tccgcgccgt gtttcaagac cccgagttta ttgggctacc gtccgacatc   87060
cctgacccgg cagcagagaa catcccaacc gagattaacg accgcctgga cgtgagcaat   87120
tttgcaaccc cggcacaacc ccccaaagac aagtacgact gttgcgtcct ggctcctggc   87180
gtctggtggt ctaacgcaaa caaggctata tactttctac agatggacgt agctctgctg   87240
gctctttgcc cggctggatg gaaagccagg ggtctgggga tcattcttgg gcgtctgctt   87300
aaccaccaag agggttgtgc tacgtgccgc ttcaccgaac attcagatcc gctgaatgca   87360
acggcagact cggtggctac ccccgaatcg tgtctatgct gggcgccgtg tctgtggcga   87420
aaggcacacc agcgagagtt aaccgtggag ggggatcgat atctgtttcg agttctcttt   87480
atggatgcgt tggagcgagt gcgtttgact ggcctgaggc gcagcccaaa gataacagcc   87540
aatctcgccg acttggttgt ggggattggg ccgcacggac agcagattcc cgtcaacaac   87600
gccggatgga aactggtggc gctagacgct gatatcagca gactaatcgt ttgcggatgc   87660
tacgccctgc gatacatctg tccgcccaca aacagcaaac accaccgtc ttccccagac    87720
gagtacgcat aaaccccgtt cctagcctag tatatacgcc catcacccac tcgatactga   87780
cagccttgcc ccttttaaac cgccaataaa cagttaaaac ccaacaccgt ttaccctctc   87840
tctgttttta acccacaaaa cgcgtcgctt gggggtggta cttacgttgg tgttgtgact   87900
agatgcgaac acgattgtgc ttttcgatcc gtcgggaaag gagaatgata tattttcccc   87960
tttgacgtga tctactggag agttcccgaa ccactggcgg agcctcgcgc ctatctcatc   88020
aaaaaccggt tcggtggcct tgcgtatgtg ggccgtatat ccgatcttaa tccccttgaa   88080
ggtcgctagc gccagagcta tcaggggcac caaaaaccag gttttttccat gacgtcgcgg   88140
aaccaagaat acagtcgcgc gttgccgaaa atggcggatt gttgcgtcag aaaactccgg   88200
ggtgttaaac accatcttta gaaacgcccc tatacggtca gcatggtccc ccaggatgac   88260
tgcagctata aagtatgtag cgtgcatgag aatcatcttt tgaaatagct ccagagtccc   88320
gcgctgcttc ccgtaggtgg gaacgtccac cctggcccgc ttgcttgcct gttggccgtc   88380
cccgtctagg tcggctccgt taaaagaggt gtccaccagg cgactgaagc gcgccacaaa   88440
```

```
gctggctact tggtgaaagg cgtctgagga gcggagagcg tcgaaggtgt tcatgatact    88500
gtagtacgcg tttctacacg agcgcgcctc atcgtcgctg tactcgacaa aggagatagt    88560
cttaagagcc tgtcgcacct tggggtccac ataagcctcc acggaggccg ggtctaaccg    88620
ttctctcgcc tctccgctct gccattttga caggcttcta aacagcagcc tcctagccac    88680
agaagcaaat atttgcgcgg tctcgcagca gtcgtgtaac gtccctaccc caggaacgac    88740
ggtctggtgg cgctggggag taggaatcgc aaagttgaga aaggccgttt tcgcatcatc    88800
ctctccacca ttttgagctt ccgcggctct gttttttggcc cctcgacgcg cttggacctc    88860
tcgccgcagc gcttcaaaat actggacggt ctccctgccc agcaccctac caaacattgc    88920
agcccgaacc cccggtggtt aacggtatga gcttctcggc acggtctagg cgccagaggc    88980
tgcaattgga agaagcctac cagcgtgaaa tgatttttaa gatgcacacc ctggacttgg    89040
tacgcgaggg cgttaacaaa cgcagtcctg cctttgtccg tgcatttacg tcagcaaaag    89100
aagcaagttt ggacctggat agatacatgc aagcacattc cagggtgggg cgagtagaac    89160
aaaacgccag agcgctcgcg cagcgagtgg aggcccaagc tgcagtcggc gagatactag    89220
acaggcaccg caggtttctg cacccagatt ttattgataa ctttgattcg cgcgaggact    89280
ctatagtaga aagggaggag cgcctggggtg atgtgctatc agatataaac tgcgacggag    89340
gaggcggtga ggtcggagac ccacaggaat ggctaggtca cgaagacgaa gctctgttga    89400
tgagatggat gttggaggaa gcgccacgag tgagtacgag aattgcggcg gaccctcatt    89460
ctccccgctc aacctgtccc gccccaagaa aagcaccaga ggacgctcgc tgcggagcgc    89520
gcaagcctgg ggaggtaaac aattacaccc cgagcgctca accccgctcg caagaaacga    89580
ctgtggacca tctagcaagc ccagacgaag gcacgaggtt gggcgatcga acaagggact    89640
tggagcatca ctcgaccgca ccgatgagga cacatcccaa tgtcctcgca tcagagcgtc    89700
ggcgattagg tgtggtgcat caacgcgaaa aatcgtcaga atcacaggag agtgcgacgc    89760
gcagcaaggc gatagtcggc caggaagatc agaaatggct gggtggcatt cccccctaa    89820 gcgacgaaga actccaagtc gacatgggaa ttccgacaat gaacggtccc atttacccag    89880
attatcatcg cacggcgtag ttagggttgg gggtcgcccg ctcacacaga ctcccctcca    89940
gaaaacgata attttacaac caaagctcgt acgcaaagtg tttatgccta cctttacagt    90000
gaacccagag atgcactaca ggcgcgtggc tctgggtgag ataccaaaat ttggaggcgc    90060
cggtagctat ggagaggttc agattttcaa acagaccggc ctggctatca aaacggcctc    90120
gagtcgctcc tgttttgaac acgagcttgc cgtgagtctt ctgacggggg aatgctcgtt    90180
gcgcgcgcaa gctagcctcg gcatcggggg aatcatctgc ctcatggcct tttctctgcc    90240
gtccaagcag atggttttcc cggcctatga cgcggatcta aacgcgtacg gatacagact    90300
ttctcgcagc ggcccctccct ccgtcctggt tacagagtca atcgaacgag cgttcatcgg    90360
acttggtcgc gccctggtat acctcaacac cagctgcggc ctgactcact tggacgtcaa    90420
gggcggcaac atattcgtca accactctca ttttgtgata agcgactgtg taatcggaga    90480
cctgagcctg atgacattga atacaaattc tatggccatg cgggcggagt ttgaaattga    90540
taccggcgag gaggagatta aaacactccg cctacccaga agtgcgtcac agatgacatt    90600
cagctttgta attggccatg gacttaacca gcccataagc gtaattgctg actttattaa    90660
caatagcgga ctggcaaaga gtactggtcc gataaagcac gacgtcgggc tgacaattga    90720
cctgtacgcc cttgggcagg cactactaga gctactactt gtcggctgca tctctccttg    90780
cctgtcggtg ccaatccttc ggacggcaac ctactactac tactccaaca aactctccgt    90840
```

```
ggactacgcg ctagacctcc tggcgtatcg gtgttctctg taccctgccc tatttcccac    90900
cacccccttg acgactatct acggcatccc ctgggaccag gtagaaggcg tctttgagag    90960
tatcgccggg gctcaccacc gcgaggcgtt tagagctcac ctggagagat accgcttgac    91020
gcacaggcgg ttgtttgcgt ctatacgaat accgtccgcc tttaccggag tgcttgagct    91080
cgtctctcta ttgtgccacg ccaacgaaaa agcccgcctg tcgattcctc tgttatggac    91140
tcctcgcccg tgacttacag cggcgaaccc ccgtataagc tgcgtcgcct cagcccctcg    91200
tatccatacg tttcaaagtt acgcgagcgc tgtgcgtcaa agatcgaaac tctttccgag    91260
ggcagcgcac gagatagcct cgaagagagg acgtgtctga ggccatggca accggtgcgt    91320
ttctagctac ccgtctgtac ttaccatccg ttttacctca aagaataaca acgctgacgt    91380
ttttggacca ctttaagaag agccgtcctc tccccaatag cgataagcga ttgaatccca    91440
tcttttatcg cctggcctac atacgcgacc tggtaggaga gatggagcta gagggatcg    91500
tggaacgcgg aactgcctcg cgtttactcg gcgccagctc cccggctggc tttgtggccg    91560
gaacgtacac ccacgcgcgg gatctgtcca aaacaatgtc cctggccagc gtcaggacg    91620
ccgtgctagc gatagaggcg cagactcgcg accagagcga gagccagctg tgggctttgc    91680
ttcggcgtgg attggctacc gcgtctacca tgaaatgggg ggcactcggg ccgcagtacc    91740
acccgcagtg gtgcgaggtt agcaccaacg ccaagggaat cccaaacaac cccgctctcc    91800
agtttggaca aacaaacgaa cggacggcca ggtctctcat ctcggctctc tatgtcgccc    91860
gctctgaggc tgccaccca gacttactgg tggatcctgg atgcggtcaa tgctttgtgt    91920
ttgacgagtc cgcaagcgtc ccgggagacg cttatgcctg tggcctactg atggacgcca    91980
gaaccggcgt cgtgggcgcg tccttggata tgctggtgtg tgaccgggac cccagcgggg    92040
tgctgtctcc ccactcgact cagactacat tggatttttt cgaaattaaa tgcagggcaa    92100
agtatctatt cgacccccgat ctatttagcc ccgtggctac ggcgtacgcc aacttgctga    92160
aacaccgcac cgcggtatgc ctgcgaaaat ttctcaggtc tattaaaaac cccgcagtag    92220
agtatttcgc accgactagc gtgcccgggg caaccgaagc gctgattacg tgcaactctt    92280
cgtggaaacc acgtgaggta aatgagacca acaggcgttg cggtgacttt gatagggacc    92340
acattgcttt aaacctggac gcgtcatcag acgtttggct attagtgag ccggaccttg    92400
agtcggagac tattactcca gcccgctggg acacaggaga gttggcgctg tcggttccgg    92460
tgttcgcaaa ccccagacac ccgaacttta agcaaatact ggtgcaggcg tacgtgctat    92520
ccggccattt tccccgaccat caactcaggc cgttttttggt aacgtttatt ggccgtcatc    92580
gcaagaggtg tgaggaggga aaaacgttta ccatctgtga tcgccctgag gggagccgt    92640
acaatctgaa cgaggttgtc cactctagct gcgctatccc cattctgcta tttgtgaccc    92700
cggtgattgt ggaccgcgag ggttgctggg aagacattga gatcgagagt ctcaccgcgt    92760
tcaacaaaac cgccgacgcg atatgggaca gcgactctcc tgcggatgtt tcagaaccga    92820
ccagctcgta actcactctg gcgaagtggt atccctgaac gcggacacct ttgaggaatt    92880
tagcatggaa gagtttgata ttcccccacc cccacctctc ccgaaacccg tcttcaagca    92940
accaggccct tacaaaatcc cagccagatc tcaacgctgt ccttctaaac gacgagaccc    93000
ctattaaata aaatgactgt aaacgcatat aaacgtatca ggtgttttat tttttctata    93060
gtagtgcgtg gtagcgtaag cagattcatg gcctttgtat accactggca cgttgatgct    93120
atcggtactc ccggcgatgg cttcttttccg ggacgcgctg tgggtcgtca taatattcgg    93180
```

```
tttcaaattc ctcgctcacc acgtcgtaaa ttggctcttc tgcgtccgtt tccgagtctt  93240
cggctaagag catgcccctt gactctgcca cgttcaaggg ttgtgggttt ctgcgcgggc  93300
ccctcacctt gttggcgtat ctacgcgcct tggaagacac ggttttacg cgcccgtaaa  93360
attcggtatt ccgcttcttg tggaacatga tagctctgac cagtctcacg actagcatga  93420
tgatggagat gaccgccatg attccaacta tggctttgga tgcggtggcc agattcgggg  93480
cctggacgga aaccatggca tggaagtgaa cgaagtagct gtgggttgct acggccagcg  93540
tggagctcgc caccaaaact gcgagggccg gtcccactag aacgtgtacg tagtgggaca  93600
cgatgagttc gacgattatc aaaaacatta gtccgagggc cacaaacacg cccacggcaa  93660
cagtcaccgt ttgccacagg gtgatgtgaa agctgttggc gagtataatc cctagcatca  93720
gcgacagtat cggcagggaa attcctagca tccccatgcc gaggttggtc ataaccgcgc  93780
gtccgggtcc ggccatttta tgtagcgccg gtaggttggt ctttagtatc gaagattac   93840
tagagtattg agcgctcgcg gttcccaggc cgctgaagct catgcaaaaa aatactagcg  93900
atacaaagtg aaccacgtaa actgccgccc ccaggactgc ctgcttgtgc gagagtagca  93960
gtattacaac ttgcagaagc cacgtagcca gcgtcccgag tactagggtc acgtgggacg  94020
caataagcgt ggtcgttggc cgggtgcacc cggccaccgc ggtgcactct ttcccccggg  94080
catatctccg aactgaaacg gccgagatta tgaggtagaa ggatatcgcc accaggacga  94140
gtgtagtgta gtaaagaaac gcaaccaacg acgttgtctc caaaaataga gtcggggcta  94200
ctccaccagc tatctgccgc atccacactc catcgaccac gctgtggttt ttctgcgtgt  94260
agtcaaccaa tgacccataa aaacacggat atccggtctg aggaagagac gccgtcacta  94320
gagtgataaa aagcacggag gttgtaagtg cgaaacagaa cacttgcacc agccacgttc  94380
tccagttgat gccttcgatc ggacctatcc caacaatccc cgacgagggt agcagaggct  94440
cttctgcgac agctgctccc cgtcgtgcca tggcgagtta tcgagatact acgctgggcg  94500
gcagagcgga aggtgtagct ttctcggccg tggaagacag ctatacttcc agcgtttctt  94560
tggccaggat gttatatggg ggcgacctgg aagagtgggt gcgtcacacg cggcccggtg  94620
tgagtttgga aatccaatcg agggctccgg tacgctttcc tccgcccaac aaccccgtcca 94680
gcaggcgcgt aaccgtcgta agagctccta tgggttcggg caagacaacg gcgctgctaa  94740
aatggctcgg agaagcgctg gacgcgcctg atattagcgc tctcgtcgtt tcgtgccgga  94800
gaagcttcac tcgcaccta gctaaacgat ttaatgacgc tgaattgcct ggttttgcta   94860
cgtatttac gtccacggac tacaccatgg ctggggagcc ttttcgtcgc ctgttggttc    94920
agattgagag cctgcaccgc gttgacgata acctcctcaa caattacgac attttagtac  94980
tagacgaggt gatgtcaaca ataggggcagc tatactctcc tacgatggtt cacctcaaca  95040
aagttgacgc ccttttgact aggttgctaa agacatgccc ccgggttata gccatggacg  95100
caaccgcaaa cgcgcagctg gtggatttct tggcttcggc gcgcggcgag cgcagcgttc  95160
acgtgattat aaactcattt gccgcgcctg gattctcgca gcgcgacggg acactactgc  95220
gaactcttgg aactgacgta ttgcgggcag ccctaggatt tgttcttgtg gacgatgaaa  95280
acggaaccaa ggttatggag acggattcca gacccatttc agctagactg cgcgaggtca  95340
actccgcggg gttttttcggc cgcctgatgg acagactcgt ggcggggcgc aacgtttgtg  95400
tgttctcttc tacggtttca ttttcggaga tcgtggctag gttctgctcg cagtttacag  95460
actctatttt ggtgttgaac tctctacgac ccagcgagga tgtagccttt tggggggag   95520
taagggtgct gatatacacc actgtggtaa cggtgggcct tagttttgat acggctcatt  95580
```

```
tccacagcat gtttgcctac gtcaagccca tgagccacgg accggatatg gtttctgtat    95640
accagtctct ggggcgcgtc agagagctta ttcacaacga gctgttggtt tacgtggata    95700
gctcgggagc ccgtgcggag cccatcttta cccccatgtt actcaaccac gtggtgagcc    95760
gccagggtgg gtggccggct gagttctcgc aggttacgga cgccctctgc tgtcagttta    95820
aggctcgctg tggaccggct tatagaacgg cgtccacgcg cgggctcgct ttgtttgtta    95880
ggtttaaata taaacacttt tttgagaggt gcactctggc gagcgttggc gacagtataa    95940
atattttata cactctcctc gagtctaacc aaatgcgcgt cgctatcgag gggtgccaat    96000
tccctctaac ggccgcaggt ttttgtgact ttctgcaaga tctgagactc gacgcatacg    96060
ccgctaggaa agagataaag cagctgcgcg gacccggggg tattgccgcc accccgacgg    96120 aggttttga aaacgacgat gtggcggtgt ttattcaaaa gtacctgcgc cccggtgttg    96180
cgcacgatga gatattggca ctactggtag agctaaacag tcccatcgtt cgagagcagt    96240
tcgtcaatgt ggcggtcctg ggcgcctgcc tgcgcctccc agcggccctg gagagtcccg    96300
aagtatttgc cggagtttac aagcattacg cttccggggt cgtgccggtg attagtgacg    96360
ccggagcgct tgagagtgta tcaataacac cggacgttaa cgttctagcg cgctgggatc    96420
tgtataaaag ctgcacgcgc catgcccgcg atctagcctg ggacccgtcc cgcgggggt     96480 ccgggctgga catgtcggaa gattttatta caaacactct gagcgccgac tataacagat    96540
tccagagtct gctggtggag atagcaaagt gtaacgtaac acctttagag atgctagctg    96600
cgggtgccgt tcgaggcgtc actaccgcgc tctcgggtcg ccccaaaagc agggtcccgc    96660
tatcaaaagg agagcacgca gtctccctct ttaaggtgct gtgggaggac gtgttcgggg    96720
caaagcttgc caagagcacg caaacttttc cgggggtgt gcgggttaaa aacttgcgga     96780
aggacgaaat agtcgccctt ttagagtctg taaatgtaaa ccactcagag tgcaaaactc    96840
acagagagct gtacgccctg ttaatgtgca acaggaagct gtttgcggga cccagatata    96900
agctgagggc gccaaagtgg agcagaaacc tctgttttct agaattggac aatactggca    96960
cctgcaagac tccgcttgat gccgcgctgg cagacctagc ccctagcgcg tggccacagg    97020
tttacggagc ggttgacttc gacgcactgt aacatcaacc aacccacatg gagggcagcg    97080
tcgaatggtt taacgacat gttgtgcta ccagtattta ctctctatgg acagatccgc       97140
accacccagg gcatcttcag gcgctcgtct acatgctgtg tcggcgcggt agcgactaca    97200
ccgcagagtt ttgtcacgtt cccgtctcgg gcgaactctt gaaacgcgga gctcgcgacg    97260
catctctggt aacaccggcg cgcgttgcca gcgccgcgca gaccgcggct gtgcctgggt    97320
gctggcccct ggctcccctg ggaaacgcca tgttgtggaa atccgtctac ggtggcataa    97380
cggcggcgct taagcgcgcc gtgggaagct ttgctttcta tcaacccctg gtgttaggaa    97440
ttaacacgca aactggactt ttagttaccc tccgacccgc cgcgtctgcg ggtgaaggcg    97500
gtggcgacca cgtctctccg cgggcggcga tcgtaaatgt gtcggtggag gtagacttgg    97560
acccagcggg cattgaagcg agcgcggcta gctccacagg atcgtctctc gccagggcca    97620
gactctgcac gcttcgagat ggatattttc tctcaaagcg ggacattgcc ctagaagttg    97680
agatcgctac aaaggaggtt tcatttaca gaaagtatga ctctgtgcaa cagcctgcca     97740
acaagcgtcg cggcgacatg gcagatttgt tcgtcgtgca cgaacgaacc cttttgctag    97800
ggggatgtaa acgaatggga gttaaggttc tattgccgcg aacgtttgac tgtttagttg    97860
ccagctccca gtcagtgtcg ggtttagctg ccatggcgct gtacaaacag tggcacgcta    97920
```

```
ctctattctc tgtagagcta ccagatactg ttgtgcaaat ttttgcttac ctagggccag    97980
aattaaaccc gtgtggagag gaagtcgact attgttgctt tgttggattt cccggactcc    98040
cgaccctcaa ggctagttcg agcaccacgg aggctgtgcg cgatgcaatg gccgcctata    98100
gactgtccga cgggctgtgg ccggctctag gtatgagcgc gtttcacttt ttggctccat    98160
gggacccgga agacaggtgg cccgtgaat cggaggcaaa acgggtagag ggggcggtac     98220
acaggcttca gcttggtacc gaggatgatt gggggctgg gcgggtatca tgcattttag     98280
agtcggacgc tgtaatgcag gggccgtggt tcgcaaagtt tgacttttcg gcgttttcc     98340 ccacgctgta cctgttgctg tttcccgcca atgagcgctt ggctgaggtg gttagattga    98400
gggcacgtgg ccaacacccc acccttaagc tcgccttggt atccttttt gggggctgc      98460 agcacatcaa ccccgtagcc tataggtcca tcatagccct atccaacgga atcagtaagc    98520
ggctggagca cgaagtcaat cagaggggtt ttgccatctg tacatatgtc aaagatggct    98580 tttgggggc agccggaaat ctgccatcag actctgtatc ctacgccgac gcgctggttt     98640
acgcagagga gctaagaagc gccgctcaga aggcggccct cggacacgtg tccgagatgg    98700
ggttttcgct gccggagggt gtccacttga atttgcggct ggagggtttg tttacagacg    98760
ccatctcgtg gtccacccac tgttactggt tgtacaaccg cttcaccaag atggaagact    98820
ttgtaggctt ccccgccaag agcggggccg gcagagccgc gaaggcgagc ttgtctgcct    98880
tgctaccgct ggtagccgcg gtatgcgact ctagcgatat gagcaccctc catcagtctg    98940 tgcgggggc ctgcgaacag ctggtagccg gcgcttttgc cgagcgcaac aacccgcagt     99000
tttggagtac caggacgggg atcgagtcgt ctacgctact ccccccggca gtttacagga    99060
acggcagctt gctcgacaga gactgtgggc agagggaaat tgtgttgact cgcaaacacg    99120
actgtgaatc cccatcgccc gtaccctgga cgctcttccc accacccttg gttttgggc     99180 gcattgacta tatggtctat cttacgtcca ttttcaaaac ttatctaagc atgttaaaca    99240
gagcaatatc tgcctcgtgc gacgcggatg aatctatgaa tgtggacttt ccaatctctg    99300
attatgcatt tttatttacc taaaaataaa gaccataaac gttatttttt ttttcagttt    99360 attttgttg tttggggtac acacggtatg ggcatcataa aaccccctcca tctcaccagc     99420 tagtcgtata aaacatatat tgattccggc acaggctttt cgtccgtagc ggtccaccag    99480
ctatagagag tatcagccac tactttagta catagcggcg cattgaggtg ggctttatta    99540
caacgcaaga cgccagaggg gcaggggtg atgggtcttt tggataaagt ctgtctgtac     99600
cctgcgctgt aaatagcatc aagtatgcca ggggtgtttg attttggcc cagtagcatc      99660 ttggccatca tgtagttggg cagcacccgt gcctggtcaa aggggttgtg gttggtaacg    99720
cacatcagcg tgtttagcgt ccacgtggcg cctatataca tcaaccttcg catctttaga    99780
aggggggtga ttgtcttgga tatgttacgc agtatacact caatttgcac aaaaagcgat    99840
gatgtggcgc gctttgtgga gcagttctcc aggtacatct ggatgataca cagggtaaag    99900
tctataaggt cggtcgggcg atacagcacc agcctgtgcg acagtataac cggagccact    99960
ccgagcacgt ttaccggtc ttccagggga gtcaccacaa aaagagagaa cccccttaaag    100020 gcgggcagat ccaagcacga gcgcatgtag gtctcgcagg atatctccga gccctcctgt    100080
ccgtcgaggt tcaacatcag tttctccgac gacgcgtcta ctctcatgtc agtgaccgac    100140
gtggtcgtga aggagggggg taggcctgga acctctctga cttctgtcac gaatcgagga    100200
gtcgcgtgcc agaccagatc gtcgacgata gttgttactg aatcgtcgcc ttttgtgata    100260
gcctctacca tttcgtccac ggtcgcgctg tgggctagcg gatcgatctc ggccctcata    100320
```

```
gtagcgctca tcactaggtt tgcccagctg ctcctcgtca gactgggcct cgttgtcgtt   100380
aactggcagg tcccgctttg tggaattgag agccgcgatg gagtttctaa ctctcgccac   100440
aaagagagta gatagctctg taagataagc ctcgagccgg ttttttttga acaccgccac   100500
acacagctcc tcctccgagc ggtacgcctc ctggtgtgta atcaaaaatc caagatgacg   100560
tgccctgagg atggagaaaa agtatggcgc tagcagtagg gagattgagc tgttggagta   100620
ggaaacggac atctcctgac cttggttgtt ggttattctg ttcattttga aacagcgtag   100680
caactcctga tcccacagac gagataggcg ctccatatcg gccgtgtacg ccggtatgta   100740
cctagactga aagctattgg ccacgtatcc gtcgtctccc attaggtttc tgatgtcgat   100800
aacctcgtgc ccgagtcctc ccgcgccgga cttggcgcca ctcccgggaa gggccgctga   100860
gctcgcaccg ggctgggtac tcccgtctgc cgccgcctgg gagacgcgca gcagttgttc   100920
gcggaggtgg gtgatctcgc tctctcggtc ccggagctga tccaaaagcc cgctattccc   100980
ggttctcagg tcctctatgg tcttaaacaa gttgtttacg tatccctcca acatcccgtt   101040
aatgccgttg atcacagacg tgcgaaaggc ttcttgcacg ggcatgttgc cgccctgttt   101100
ggttttcccg ctctgcccaa atccgggcag ggaggtgtct acctgcgcgc cgctgagcaa   101160
attggtactc gtctcgttta gatacgatct aacggtctct gttatgtccc ctatgtgccg   101220
catgcttttc atgttgacga tgagtttaac cagccgcgac gcggcggagc tggaatgcag   101280
ctcctctccc tcgcccatga gcttgtccac ggccttggag gcccacccag ggccctgggc   101340
ctcgtccttt ttcctgccca ccaaaatctt gacgggtacc gtgttgagaa gctggcacag   101400
ttttgcgtgt tcccgcaggg cgtggcagtt acacacctcg ccgcagattc gctgtagcgg   101460
tgagtcgaac agcacgctgc cgtccttcca tattggctgc cacaacacca gacactctcc   101520
ccgcttgccc gtggtcgagt ctatcgccac cacctctctg cgggtgtagt ggtagaatat   101580
attcaccctg tcgtagtcca tgatggccac gctggcggtg cacctggcca gctccaccac   101640
ggcctccaac ccctctcgca ggaggctgtt ggccacatac agtttaccgg ccaggtcacg   101700
ctcgtccacg cagctctcca gcgagggaac gtccgtgggc agcttccgcc acagcttagg   101760
gtggacggtc gcgccggggg cgcgcttgag ccgctggagc ggaatcagac ccagacaggc   101820
tatccagtct atgtacttgg caaagctggc ggtgccgtcg ggttcgctgg cggagaaaca   101880
cgcggttata ctgcgaacaa agtccaagag cgacatctgt aacgtgcgat gccacgtggc   101940
aaaaatctgt tcggcgactc gcaccgcttc ccctcgctg tacattccat acgtggcggc   102000
tatttcctcc gcgctcacac cacggctgtc taggtgggtt tgccaatcct tggcgaggtc   102060
ctcgtagcgc gtagcgttga gcgtgttggt cagaatagtc gtctgtatct gtctaatagc   102120
cgcctcagtt gaccgaatgg cgttgtatac tccctgacct tctgtgtacc ctagctcccc   102180
catgaggatc tccttgaaga gcattgtttt gggggttggg tgaataagca cccaccccc   102240 atcagcggat atttgctcct cctcacccgg actctggagg ccagttgtag cctcaaagcg   102300
cggggtgttt ttccgctcta cctttcgccc tttgtttgca tcagcatagc gaaggcgttt   102360
ttgcttgggt tcgatggagt ccgccgacat tttaccgggg agtagaggga ccgtggatag   102420
acgctgcgag ggctccgagg agaaaataac gccgcctcgc ccgtcgaag atttaatcc   102480 gcagctttc ccaaacgagg tatatttgaa ctttacgtct atgcacggaa ttcagcccgt   102540
tgtagctcgt atacgagagc tgtcaagaaa aacggtttct gccgctatgg tgccgccgtt   102600
agaatggttt gaaaggctgc caagactgga aactcctcta gatatagagc cgttacatct   102660
```

```
acccttttcc gtatacctca ttagcgggaa cgccggctcc gggaaaagta cgtgtattca 102720
gacgctaaac gaaaccatgg actgcgtcat tacaggcgcc acccgcgtgg ccgcacaaaa 102780
cgtttacacg aaactttcct cggcattcgc aacccgccac atcaacacta tttttcagga 102840
gtttggattt cggggaaacc acgtccaggc gcagctcgga aagtaccaat actcgtgttc 102900
ctcgagcccg cctcctatcg aggagctgca aaagcgggat atcgtttact attgggaggt 102960
gctcgtagac atcacgcgcc gccttttcga atctacggcg tcccgcggtg agtttgaaaa 103020
catcagggct ctggagcgcc tgctggggcg tgcaccggga tccttgacta ggctcgcctt 103080
ctgcaccaac ggctcgctac cggcgtttac cagaaccaat atcgtcatca tagacgaagc 103140
tggactactt ggacgccatc ttctcaccgt ggttgtttac tgctggtgga tgttgaacgc 103200
ggcttacaaa tcgccgcaat acgccgaggg aaaggttccc gtgatcgtgt gtgtggggtc 103260
gccgacccag acagattcgc tggagtctcg ctttgagcat aaaaacttaa agtgtcacgt 103320
caggtcgagc gagaacgttc taactcatat tataaccaac agaacgattc gtgagtacgt 103380
ttctctatcc accaattggg caattttttat aaacaacaag cggtgccagg agtacgagtt 103440
tggcgagcta atgaaggtgc tagagtacgg gcttccgata acggaggagc acatgcgcct 103500
agtagacacc tttgtggtcc cagaggccta catcaacaac cccgcaaacc ttcccggctg 103560
gacgcgcctg tactcgtccc acaaggaggt gagcgcctac atggcaaaac tgcacgccca 103620
cctgaaagtg tcaggagaaa ggcaattcgt ggtgtttact ctaccagcgt acacgtttgt 103680
gaagacggcg gcattcgatg agtataaaaa gataacccag cagccatctt tgtcgctgga 103740
taagtggctc gcggccaacg cgagcagggt gagtaactac tcccagagca gggaccagga 103800
cgcgggaaag acgcagtgcg agtactactc ggaacacgga gtagtggtgg ccagaacgga 103860
cgtaacctat gtcctcaaca gtcaggtgtc ggttactacg cgcatgcgca agtttgtgtt 103920
tgggttcagc ggcacgtttg aaacgtttga tgccgtgctc aaggacgacg cgtttatcaa 103980
gactcagggg gagacgtccg tggagtacgc ctaccgcttt ttgtcgaccc tgctcttcag 104040
cggcatgata aacttttaca acttttttaaa gcgaccaggg ctggacgagg ggagggtccg 104100
ggaggcgtac aggcgcatgg ccgctctcac cgccaagctg attccaggcg cgtctgtgtt 104160
agagagcgcg tgcgataatc ccagcgggc gccgctaaac tttaggggtt tgaccgaccc 104220
accaggcttt acgggcggaa ctacaaacga ctgggatgac gacaacgacg tggtgttcgc 104280
ggccctgaac gaaggagcta tagacatgtt atactgcaac tacgagtttg tgagaccaga 104340
gaccacgcag gaggtttact cgcagtttct gatgctcaag actatgtttg tgggtagata 104400
ctccatattc atggacctgt ttggtgggga cttgaatct tccccctttg acacgtttgt 104460
agataatata agctataagg ggtgtgagat ttttgtgggc agtatgcgcg ggggcgtctc 104520
ttcgatcgcc ctccagacag acagctacac gcttatgggg tacacgagcg ccccggtcta 104580
cccgtttgtg gaggagctgg cgcgcagaaa gctacacgaa ggaatcgcgg aactctttgg 104640
ggccatgaac atgcctcgca tggttctgcg cgaccagcac gggttcatgt cggtgctgaa 104700
cgtaaacctg agcgagtttg tggagtcggt ggacgacgtg gagctggaca tggccaccgc 104760
ggtagactat gggctgagct ccaagctcgc catgactatt gccagatcgc aagggctgag 104820
cttagacaag gtgccatat gctttccccg caacaacctg agaattaaca gcgtgtatgt 104880
ggccatgtca cgcaccgtgt cgtcaaggtt tctacggatg aacctaaacc cgctgaggga 104940
acgtcacgag cgcgacactg tcataagcga gcatatatta gcagcccctga gggacagaga 105000
cgtccagatc gtgtattgag gtcaggcacg caagagtcga caaccgaccg cgtgcgtggt 105060
```

-continued

```
ttgcgccaat ggaaacgtgt agtcctcccg ttacgtttat tacctatgct ctgtatggaa    105120
taaaaacttc tcctgcttgg accctcccaa actttgaaca ggttatttgt agctgcgatt    105180
gggggtacag actgatcgcc gtgggggcag agtctaaatg cgatgtaaca ccgcagggca    105240
gcttcgtgat tcagcacggc gcctcaataa cggcgttagt gttggactgt ggcgtagagt    105300
tttgctcgta cgcgtttact cacgctgaga acactagggt cccctgacc accgaggacg     105360
ggtcggtact ggtggttccc ttctgcggct gggtctgcgt aggccgggac aggtgcttgc    105420
gtagcatgtc cggcggggtc cttactataa gctgggatac gagccagaca gcttacatta    105480
gcgttgccgt ctatcgcccg cctaccttac agtgtcacgc cctagactgt acccgtgcag    105540
aaactaccgt atgttccacc gctgccataa ccgacgcctc cgagtcagat cccttatacg    105600
ccgaccagga gggggaccag acgcaagatc aagatggagg tcacgatttt ttggaaacta    105660
ttctgatgga gtctgatctc tacggtacca acggagcctc ggcgttgctg agccgtgtt     105720
ttccctgcct ttccaacaac gactgacgac ggaccactcg acaagaaaac aattcctcta    105780
accccaccct accccattta aaaaatgaca ataaaaaaga gtttatgtaa acagataacg    105840
tttatttggt ttttattgat tgcttggcgg gttttttaca tgtgcctgag cgtgtttctt    105900
ctcggcctcg gtcgtccctg gtgcggctgt gtctgcctgg ctgctgtgga ttgggttaca    105960
gattgccgcc tctgagcgtg gttggcctcg ccgcggctgc cgccgcgctg ggtctgtcct    106020
tcgccgcggg gattgcgaac gtcaccacgc ggtcgttgag acgaccgcaa cgcacttccc    106080
atggccgcgt tcactggcgt gtctggccga ccgattgatt ttcttcgctg tgctgccatg    106140
gccagggccc cgagcgttcc agaaggcctc tccgagaggg ccagctgtcc gtcgccaccc    106200
gccccggcgt gtgggtcgta atgaggcaca gagttgcgcc tagacgacag agatctgtgc    106260
ctgggtcgcg ccgacacctc cggttgctgt ctggaggaag ccgtgtgcgt tggcgttgta    106320
gcggcggcaa gcttggcggc ggcccggctg ttcctttcta ggaacctgcg atagtcgtct    106380
gcggtcgcag cgcgtcctcg cccaaacacg tccatcctac gcaaggacgg tggttggttt    106440
gtatcggata gagagaagcg cgccgcctag acacactcac ttggcttgcg cgtcggcttc    106500
tataacgtta tccctgtgga ggtacacttt atccaccgca gaaaattcgt aaatgtacac    106560
gggaaccacc ggatgtgtac gtccgtccga cgatcgcgtg taatactttc ttggttttcg    106620
cgcttgaatt acagactgga gctggtctct aatctgcttg gcgtgagctc tgcgacacag    106680
gacgaacatc tgcaggcttt tattgcttcg catgacccgc tccgaggagg ggcagtgacg    106740
cttcctgcgg cgcgtcgagc ttgcgctgga gaacgaggag gttttggtgc acgcaatggt    106800
gaatttagcc agcgtcacgc gcaggtctt tctaatggtg tccgtcagct gacggcggcc     106860
gagttcgtca atggaggata ccataaacat ggtgtcaaag ccgacatagt tggcgttctc    106920
tccatccggg gcgagaccct tgatggattc cacggaaagg tcgggtacgc aaagcggggt    106980
tggggtggaa gtggtagtgc aagttgtgcc cgtgggggct ggtggccgca tttctgtaag    107040
gtggtcagct actggcccgg tgaccacctc tactggccac cccacccac taagcacggt     107100
caatgcggac tccatttact gtcgcggtta ggaaccggta ccaacctgtg caggtctagc    107160
ttatgtagcc accgggtatg ggtaggcgtt gttttcaccg taacttactc aatctgccag    107220
tctacgggct ttctacctgt cttcgtgagg tacgcattgg cctccaaaaa gtgcgggcag    107280
tctctgaaat tcacacgaga caggggcgaa gggtgtccgt aggtgagcac caggtggtgt    107340
tgtctgttcg gggagcagga cttctgggcg tgggcgcccc acagcatgaa gacgagccct    107400
```

```
tgggacgtgg tacacagcct gtcgataacc gccctgacca gcctgtgcca ccccagagtg 107460
gcgtgtgatc caggttttcc gcgtgcgacc gtcagcgtgg tgttgatgag aagcactccc 107520
tgttccgccc acctttccaa aaacccgtgc atgggatgcc gaaacgacgg gtacgatttc 107580
tgaacggccg agtagatgtt gcgtaagctg ggaggcacgg gtaccccctt ccggacgcta 107640
aaggctaacc cgtgcgcctg gcccggcgcg tggtacggat cctggcccac gataactaca 107700
cgcaccttct cgggggcga aaagcgcgtc caggcaaaaa tgtcttcttt tggggggaag 107760
acttcttcgc tagcgcaccg cagtttgtat tcgttgagaa aagtctcac gtacggctgt 107820 tgcatttccc tttctagaat gggacgccat gaggggcta tattaaattc ccgctcgacg 107880
tcttcccacg agctctggca gctggtcgta aagagtgggt gtgtggatac gctggtgttg 107940
atgagagcca cccctgcgg tagcccacag ggtctccttc gtttcggtgg gggagctcct 108000
gtctcacctg gcgccgggga gacgacacac gccgggccaa tttcgcttgt gggggtagaa 108060
ctatttgatc cgttttcctc tggtgttgtc tcgggtatgt ttacatgaga tgcctcggtc 108120
tcgtgatcac aggcgctact catctttagg tcttttgaag attggcgtag taggaagccg 108180
gtatacaact gtcctttaat ccttcggcta tgtccttaga cttggcggc gacaaaaaga 108240 aaggcccagt aaagcagccc aggggaggcg gaccgagaat ctcgtctgga gatgactgag 108300
attgagaaag ggaatcatct aaagcgaaaa gcagcttctc tttaaagtct tgaggcatgt 108360
ttccatttgt gacgtcttca gccaatccct gaacgactgc aaacggatta acccaaaccg 108420
gttttggagg tgtgtcaacc cacagaatag cttcagggggg gttgcagtgt gcctttacca 108480
taattccggt cgttcggttg agcaagtttt tgatgttggg agatgtaaac agttgacctt 108540
tcattatcgg accgctaccg cagctggcct ctaaaatacg cttgggctct cccggtcccc 108600
atgtgaaatc tagccttgtt gctttgacga gcttggtagt tactatccat gctagcatat 108660
agaccagttc gagcctagcc cagcagcgca taaaccgcct cattctttcg ggagtcacga 108720
aactaagtgg cggttggaat tctgtacatt ggtttatgta cgggcttttt tgccagacac 108780
acccaattag gatttgatac atcgggttgt ttgcgttaat ataaacacat acaagtttac 108840
gatcaggttt agtaccgact ctatatgtaa agcgtgtata aaactatgtt atgagggtca 108900
gaggttagat ccaagcaacc ctttgtttca caattcaata gaatcataaa tttaactttg 108960
gcgctagcgc taacgctagg gctagcgcta acgctagggc tagcgctaac gctagggcta 109020
gcaatgaggc tggccaccag caccggaagc ttgtcatatt tgtgagcctg gagcagccat 109080
tttccaaaat ctgtactgtc atgtttcttg acctttggat gtcatatctg tggactggag 109140
gcagccattt tccaacttgt gcatatgcaa cgcccaggaa gctgtaatat tccaccagg 109200 aagcggtcat atgcccagga cgagcaaggc tgcgggggc ttcgatctag aggaggaggt 109260
cttttggcag cggaccgcgg ataggtaaaa ggtaagacct ttcaatggta gatacaccat 109320
tagaccgcgc gggggggcagt cgtccaaggg gggcttgcag tatatttaag tgggctcata 109380
aaaaatgtat gcgatcgttc cgcaaagtca ctttgttttt ttgtttggta gaaagccatt 109440
gcattagtgc ggcgtgaaag tgtacccaat taacaagatt ggagaacaac aaactgtcga 109500
cgggacagga tatgccaaac atcaatagaa gcttggatcg gtgccaactg tgacgctagc 109560
caaaattcag ctaagttgca tttacagttg acttgggag ggggcgtagc atgaatgggg 109620
caacatttca tatttcttag tgcatgcata ttatatacc ccaattagcc cccaattggc 109680
acatggtaat ataccgccat ggcgccgtgc ttggtattgg tggtgatgtt cacataaaca 109740
gccagctggg ggtgttttgt ttaggtgggc ttttgtggta tataggtatg cacgcgctgg 109800
```

```
acattagggg gcgccttatt aatacgatgt ggaaagccca gctgcaatag catcagtaaa 109860
cagtttcca ttctaaaaat atctatggga ttatgctatg cactgtgggt ttaagattgg 109920
caaaagatct cccccatgca aatgttttag ggtaggctgt acatggaata ggtaaacgct 109980
tgggggtctt ctaactcggt tgcattaaag gggtcaaggc tttggtttgg ttttaaggcg 110040
attattacag catcgtgttt caaggcgctg tttgggaaaa ggagatttct gcaggtgcag 110100
tggttccccc gggccttata tcttgcagct ttagaaatct gctttctcaa acggaactgt 110160
gtaatcgtca taatgctgca gagcaattaa acccaaagat atctattttt aaagctcccc 110220
ctttcgcggt tgcccccacc cacacccctg cataggtttt tgtaataggt tccatatacc 110280
cagggcggcg actattaaca ctctctcaga ctgatagtaa acttttaaa aaaacagctt 110340
tatttaaaaa tgggggtaca aaactttaca ggtgtggtaa aaaagttatt ggtttctccg 110400
gtatctttgg cagttgtggg gacatcgcat ctcctctggt tcagcgggct gtgtctgaaa 110460
cgcccgttgc aggtcacgga cacgctgacc cccttgtcta atcaatgggc tggtggacgc 110520
tatgtctggg tagggcaccg ggggcacact ctgccgtctc ggtctcagaa gcacattgcc 110580
gcgccgccta gcggattcat cctcagttcg tctgcgcacg tgttgtgcga aacgcccacc 110640
aaatagccct gctccctcag agcttcggtc gactaaaaca accgcaacag agaagggctc 110700
tgttgcgcgg gggccagcac ccaggcgact ggggcccgcg gcttcgctcg tggagctgtc 110760
tcgcggtgcc agtgccataa acctgcgcgc aaactcccgc aggctgcatc taggccgcat 110820
gggccgctca cccgcagaac tgccagatgg tgcaacgggt tggtcccggg ggggttcttc 110880
agactcaggc gtgagttcag acaccaggca gattattgca gagtttgagc ttgtatgtgg 110940
ggatgcgggc gccgcctctt cctcgtcggg gataagcact ggctgatcgg tggtattcag 111000
gctgccgcta acatcggcag gttcggtgtc cccatcgctg tccagagtta agtctataat 111060
ttccccgttg tcccccccgt tggtgcggga gttggtctg gctggcgtc ttctcagcct 111120
ggcgctgcgc cgactagctg gtcctggggc agccggcctt ctccccgtc tgcgccctct 111180
ggtgggtggc cccggtcgtg cacgtgctgg tctggagtct tcttggcggg gtgcctgagc 111240
agaactattg tctgtgctgg tttcatcgct cgtatcttct gggtcggtta ggttgttggg 111300
gtcaacctct atgtcgctgt ctgtttcttc ctcagacgaa gagctcgatg aagaggagtc 111360
aatgtattct accccctcttc cgcgggctat tggcaagatc ggtctcgacg ctacgcacag 111420
ttctgcttgg acgatgagat ccgtgacaaa gggcacagtg tcttcgtgaa acatcggcca 111480
aaactggcga gtgagctctt cctcgttaca gccatgctcg cacagtgtat ccataacaat 111540
gttccgcatc accaacgcta gctctggggt ctcgaatagc tggtcgagcc tttcgaccag 111600
ccagtccacc agtggctgca gtcggggagc cccggcagtc ccattagcgt tgaggggcac 111660
aaatgccatg gtccgttcc acgcagagat attggcggga gcatcgccag aatccacggc 111720
caaaaattgc ccctcaaaac tgtcttcgtc ttcttcgctg tcatagtcaa agtccacgct 111780
cacctttgtt tctttaaact cgctgtcgct ctcgatggtg tgcaccacag attcgaccgg 111840
cactttgcaa agtggacagg tcgggttttg tcgtatccag cgcgtaatac acacgtagca 111900
gaacgcatgt aggcatggaa gcgccataga gtagttgctg gggtcctcca ggcagatcgg 111960
gcatcgctct gcaacagttg ccatggtggc agcgatttgg aagagtttcc aaatgaaaag 112020
gctgtatcag ctgttaaaac caggcttggt gccattcata tatctggctg caaaactcac 112080
gtggctgtgc acgccattc aacaccaccc atatgcttaa aattagcatc ttgaacgcat 112140
```

```
gccaaatttg cacgggatac ggttccaatt tatcgaacat ctgtatctca ggggtatagc  112200
atggggaccc gtttgaatgc gattggtggg cgggaaaccc ccgggtgagc acacggtggc  112260
gctctattct ctgcgtgtgt actacgctgc tttttggggt tgcatagtta agggtttggc  112320
catcggtgcc atttaacaca aaacggtttg ccctagcccc ctgccctagc cccctgccct  112380
agccccctgc cctagccccc tgccctagcc ccctgcccta gcccctgccc tagcccccct  112440
gccctagccc cctgccctag ccccctgccc tagcccctt  aaactccagt ttatctgctc  112500
taggggggat gccgctattt accaccacac ccccccccca attggcctat tagcacacct  112560
aacctcctga gtgtgagcgc ggtatagaca agctgagcat atagtgggga gaaactaatg  112620
gcagtagtgt tactaggggt cacagactat atatcacaca aatggacaca ttgagtcctt  112680
tctactctcc tcctcggacc agcttagaaa tgctataacc gtggaatagt accagtagta  112740
actagtttac tatatttccc ccattttccc cctccccaac catctccggc acggtgttg  112800
agccacttcc caccacccgc gtcccactcc cttgtcttta cagacccact ctggctcttc  112860
tgaacccagt ctctctctac ccgggccata tctggtcaag ggtcacgggc ccgcgcccga  112920
gagagagcct ggccccccca gcccgcgtct cacccccgca tttgaatagg ggggcgtggt  112980
ctaagggggg gggtcaaagt gacgtcactt cctgtgacgt caccggaagg ggcgtggccg  113040
gaagcggaag gggaggagtc cggtagtgac gtaggcggta gtgacgtagc ggaagggag  113100
gagcaggaag gggaggagca ggaaggggag gagcaggaag gggaggagca ggaaggggag  113160
gagcaggaag gggaggagca ggaaggggag gagcaggaag gggaggagca ggaaggggag  113220
gagcaggaag gggaggagca ggaaggggag gagcaggaag gggaggagca ggaaggggag  113280
gagcaggaag gggaggagca ggaaggggag gagcaggaag gggaggagca ggaaggggag  113340
gagcaggaac catcaacccg cccatcaacc cgcccatcaa cccgcccatc aacccgccca  113400
tcaacccgcc catcaacccg cccatcaacc cgcccatcaa cccgcccatc aacccgccca  113460
tcaacccgcc catcaacccg cccatcaacc cgcccatcaa cccgcccatc aacccgccca  113520
tcaacccgcc catcaacccg cccatcaacc cgcccatcaa cccgcccatc aacccgccca  113580
tcaacccgcc catcaacccg cccatcaacc cgcccatcaa cccgcccatc aacccgccca  113640
tcaacccgcc catcaacccg cccatcaacc cgcccatcaa cccgcccatc aacccgccca  113700
tcaacccgcc catcaacccg cccatcaacc cgcccatcaa cccgcccatc aacccgccca  113760
tcaacccgcc catcaacccg cccatcaacc cgcccagtaa acaaagacca cgcggtcaat  113820
caaaatttaa aaaaactttt attaaaaaca accactcagc gatagggaa  agcctggaag  113880
tgcccaccga ttgggcagac atgtgagcaa taaggaacgt gggctgctag atacaacgcc  113940
cccttcgttc ctcacatgtc gtccggggag ggccttgtct tcgcgtcagc agagggcggg  114000
gcggggttca gcgtcagcgg atggaggcgg gagtctaggc ggagtctgcg ttgtgctggg  114060
cggacacata gttgtggatg tactgatttt tcttgttttc ggccgcaggg aggcgctcca  114120
tcgtgttcag gagaggtacg gattgcacca gtctcctccg tcctcgtcgt ccgacaccac  114180
ctcgatcttg atgggagcgc ggcggagggc ctggccacg ccggggctcg gccggggtg   114240
ctcaaccacc agctccacat cgccggcccc gtcgatctcg agtcgtcgt cgggctccgg  114300
caggcacagc tccgtggccc ccatgtgcag gaccgaggtg gagcgagagc cgaacccggg  114360
ctcccagtcg acccgcgggg ctcggcggcg gggagcctcg gtgatgggca gcaccagggg  114420
ctcggcctcg gcgtcgggct ccagcagcgc caccccgcag aactcgctca gcagctcggg  114480
gatcagaagc tccgagggct ccacggcccc agcgccgcgc cggccgcagg cgaggtacac  114540
```

```
ggggcgcagc caggccccga gtccccatcg gttggccgcg cggtggctct gcgcggcgcc    114600
ctcctcaaag tccgggtcgt ggaacccgag gccctcggcc tgggcccgca tgtccttgca    114660
gccgtcgtag tcgggcagga cgcgctggcg gtactccctc ggagccaggg gaacgcgggt    114720
gcgctcgccg gcgcgagtgt ccaccgtgta ggccacgttg gaggagcggc acagcctcag    114780
gggcgcagag tccgggtaca ggcgcgcgaa cgcggcctcg ccctcgcga acagtccggg     114840
cccgaagagg gtgctggagg tgaggaccgc gcggctgagg tggcgctccc ggggccagcg    114900
cacgcgcag cgaccccgcg gagtcagggc ggcccgcatg tagatgtggt actggctgat     114960
cgcgggaccg tcctggggcc aatcctcggt ggagaccgcg tccagcacca ggagcttgcg    115020
cctggcggag cccaggcgca ggcagaggta ctcgacgcag ccggtgaagg ccaggtcccc    115080
ggtcgacagc agcaggaccc cctgggcgtt gagggccgag acgtccgggg ccccggtcca    115140
gttgccggcc caggcgtggg accgcttggt gaggatgcgg ttccccaggg ccgccagcag    115200
cgccgagagt ccccccttga ggtcggacca gaggggctcg cgccgagagc cgccggggcg    115260
ggaggccggg agtccgccca gcaggtcctc gtcctggagc ggggagtaga ggaccaccac    115320
cttcacgtcc tcgggtcgg ggatctggtg catccaggcg ccctccgtc tcagcgggcc      115380
gctggccgcc agctccccga agcgcgcgcc gtcccgggcc ggggggccgc tgcagcgggc    115440
cgcgatggtg gccagggcct ggggatcgaa ggtgagcgcc gggcgccagg cctcgggaa     115500
cagctggttg tcgatgagct ccgccaccag ctcgggggga cagtaggccg cgcaagccgc    115560
gtcgctgggc cgcggagtgt ggcagtctcc gcggggaacg cgcctgaatc cgccccgacg    115620
gtcgggccc tcggctggca tgggtcccag ggcccgggga gcctggtggc ccggggtggc    115680
caccctgcgc ttgggggccg gagggctgtc gaccggcccc gagggatcgt accccggcc    115740
ggacgaggag aaggaggccg aggctccggc ctgggccgcc ggctccaggg gctcggagcg    115800
ccgcttgccg ctcttgcccc tggggcgccc gtggatggca cggtcgtccg aggaggagcc    115860
gggcatcgcc tcctggctga ggtgggccgg ggaggcggcc gcctgagggg agcgggcctt    115920
ctgcggctgt tgctgctgcc cccggggagcg ggcgtttgtc tgggtggccc ggcagcaggt   115980
ggcggtcgta gccccggcgc ctccgccgct ctgggagtgc tgggggggact gggagtggga   116040
cgagggacc gtcgcggact gcttcccggg gacggtgggc cacaggggcg gcagggtctg    116100
aaggctcccc tccgcggccg cggagccgga gaagggctcg ccgccgggcg aggacgatga    116160
gggctgctgg gaccgagtcg gtggggccag caggacacg gcctccccca acatcccccc     116220
gaccaggctg ggtatgctga acacggcctg ggtgacggtc caggccgagg cccgggcccg    116280
ggcccctcg gcgttgtagc gcaccagcgg cgccacggtc cgggccacca ccagaacggc     116340
gcgcaccgcg aggcgcagct cgtcggagcc caggcggtgg gtagggtcag agtccccgag    116400
gagcctggcc cgctcgacca ggtccctgag ttcgtagagg gagagggccg ccgtctccag    116460
cccggccggg ttggagcaca gcgcctcggg agggcaggcg ggagagggga tctcgctggg    116520
gtccagtccg gggacggcgg acgccccgcc gcggaggcgc aggagggcct cgaagacggc    116580
ctggcaggcc agcacgcagg cgtccccgag ctccctgagt ctgaaggcgg acggcctggg    116640
cgccctggtc cccggagcgg ccgcggccgc ggcagccttg cgtcggggcc cgagggccgc    116700
gcagacccgg gtgtacgctt cgcggacgcg gaccgagggc gccggggcct cgggctgttg    116760
ctggctggcc gcggcagcgg cggcctgggc cgggtagccg gccacggcgg cgagtgagtc    116820
cggcctcccc gcctcgtctc tcgggtaggc catgtccgcg taggcgcgcc ggaggctctg    116880
```

```
gaggatgaag ctcttctgag tgcgatcgta gcggcggctc atggccaccg aggcggccgc   116940
gtgtggcagg gcccagagcg cgttcccggc cgccatggcg tccccgatgt ggggcagggg   117000
gttggccacg ctcccggtga tgaaggaccc gtgtccgcgc ggagcgtgga tgaacttctg   117060
gcagaactgc gccaggttct ggtcttgccc gctgagctta gagttctgca gccaggacat   117120
ggcttcgcgg ctctcgaaca ccatgcggac cagagcgttg tactgcttgg tggagtcccc   117180
catctccggc acgaagaccg gtactgggc ctgcgcctcg gcgtagcgcg aggcggccag    117240
gactatctcg gggtcgtccc acagcccgtc ccgcgagtcc ccggtccccc cgtatcgcac   117300
cctccccatc ggtggtggat ccgacccggg ccaggggtcc ccggacgggg tgagaagcgg   117360
ctcgcgctgg tagacgcccg gggcgcacga agccgccgcc ggggccgatg ctgctgctgc   117420
cgccgccccg gtagcctggg atgagttcat gtccagcaag tcccacacgg ccgtctgcgg   117480
ggcctcctcg gccggtgcct gggtctgggt ctggggtatg ggtctggggt tggcccgctt   117540
gcgcttcgac gctcccgcca gagccgattt cggacgctgg tccttgggga gccggtgagg   117600
gctccggccc ggcggagaag ccatccccgc gggcggttcg ggcctctcca gcgtcttggc   117660
cagattggcc tcgcgacgc cctccaggta ctctaaaatg cgagcccccg gagggaggag    117720
gcctcctccc gggcggctgg gagcgggcgc cgaagctgga gccggagcgg gtgcgccggg   117780
ggaagcggcg ccggagcggc agctcttcgg ggtggcggcc ccagcggccg ggcgatcccc   117840
tccggaggac ggcccgggag agccggcggc cgacggggtt ttcgcggcgt tctgcgagtg   117900 ccgcggggcga ggggtctcct cctcgccgcc ttcgtcgctg tcgctgtcgt cggaggacga   117960
cgaagaggag ctactcgccc cggcaccatc cgcctggtcg tcctcgtcca tcgaggacga   118020
ggacgaggac gacgatgaga tggagatgct ccggacccgg ggtgccgggg accctccgcc   118080
cggggaggcc gaggatggaa actcgggctg cggggacccc gggcaggtct cggtatcgct   118140
gtcgagggcg accgggtcgg ccgcgtcccc accgccgggt gatgaggagc ccgtggcccg   118200
gcgaccgttc cccggggcca cggaggagtg gaccatcttc agcatcgcgg cgagccccgg   118260
agccgggctg ggtgccgggg acgccggctg ggcggcagcc gccggggtag gaggaccgcc   118320
gctgccggcg gccgagggcg accgcttcgc cttccctccg cggggctcgg gagtcggaga   118380
cggcggaggg atgaccaccg ccggggtgga gagcggagcg tcgtccaccc cgaacatgtt   118440
ctggctgccg tacagcaggt cgggcgcggc gggctgggtg aacccctctt cggccgcgct   118500
ggctgcgcgg atgaggggt cctcgccgaa gtcgttgctc tcgatgaagt cgtagaggtc    118560
cggggcgaag tcgctgcgct ggctggccat ggcgtgctag ctccggcttc ggggtcgaga   118620
accaaccgca cgagaaggct cgctcggaag accgagaagg gaaggttggc gggtggccgg   118680
tggcggggtt ccgcggcggg cgctcggacg acgggcgccg cttctctacc ctggaaaagc   118740
agaggcggaa aagatgttga gttggagcgg agccgaatgg taaaagggaa cgcgggcggc   118800
ctgggcctct cccccgcttg ggtggtaacc acgcccgtc agatatccag gcttccgcgc    118860
cgagctccgc cgaggcagaa gccgcccggg tctgcccggg gaaggtatag ccttcgccgg   118920
cttcgaggta agtatcccca ccgcgcttcg accgctaggt cgaagcgggc ctcggagcca   118980 cccctcggg acatcgttgt tggagggtt ccatggcctt tttggcactc gccccgttct     119040
ctaacgctct ccccgggaga agaagcagat cgaagccggt cgtgtcccg gggagctctt    119100 acctccgcaa gccgaagaag gagtgccaag agcgggtaag cttttccaaga tgcgatcgat   119160 agtcctcgaa ggctggctgg tccagtgagc tgaaaggctc tctagtccgc gatgctacga   119220
tgggtaagca acaggtgctt tatactacta cgatggagtt ttgccttccc cctagtggga   119280
```

```
gtggccagcc cacactatcg attgtgattg gccgttgatg atgggcggtg ggcgtgtagc   119340
ggctctagcc tatggggccc ggtcccgcgc tttgcatttg catgcgcttt tcgcctcccc   119400
cccgctccaa ccaattagaa cccgtgtgtc gtttctaatt tgcgtatgtc tcctcccagg   119460
gaagcgcgtc gcgccaacgg gatgccgaat agcgcctctc atatgcataa aggtgaacgc   119520
ccctggacgc catgacacct cgatgcacat ctcatctgca tgcgtctcct ccccgggaag   119580
cgcgtcgcgc caacggggtt cgtgatcgcg ccgctcatat gcataaagac gaacgcccct   119640
ggacgccatg acacttcctg gtaaatctca tctgcatact gacgagcttg ggaggagccg   119700
agggagtggg cttcaaaagt aatttcaata aaaatggcga gtgcgatatt tccgaccgaa   119760
acggaaatga tgtaaaaaaa gtgggagggg gaggggaaa ggtgggcgtg aacgcgtctc   119820
tgtatttccc ggttgaatct cattaaagtt ataccaatta aaacatgtat cgctatcgcg   119880
tgtattttgg gcgggatgat atctacgtgt gctgatttac atattatctc acaaggagcc   119940
aggcggtggc gctgtttcaa aacacggttt tacatgcgcc ttcatacacg tccgcacgag   120000
ggcgccctcg tgtgttaacc ctcacagatg cggttactac atctaaccgc ttcgtggcgc   120060
catgtagtcc attaacatgt gacgccacga tgtgacgcta tacacacg cgccggcccc     120120 accccatcga cgtaacacgg cgcccctccc aatattcaaa tgacatgagg gggcgtggct   120180
tgagacagct gtgtgggggg agatgcccgg tacccaccct ccacccacgt ccacaccccc   120240
ccccatgccc cgcccacggt ttttttgag agccgaccgc acacacgcac aatcgttgta   120300
ccgtgtaaac ggtttcgatc cgttacattt tcccacgggt accgggtcat acataaaata   120360
cctaaagcgc ccccatccat acactccggg agatacacat cgatgtttca cttttatcg   120420 ttacacacta cccccccgtta tcgatttttt ttgccacgcg tgtacagagg tgcccctccc   120480
cccagtatgg ataagggggg ggtgtcaata aaattttgc gcgatgaaac ctaggggagg    120540
gtgcacggtt attgagggtg gggggggggc aaaaatttt gagcgcaaca gatagcatgg    120600
ctgggttacg gtgtgcggct atggggggg gcgctaaaat acggttaccc ggcacatact    120660
ctcgtcgagg tatgggccgg gtcacggtac ccactagttg gcacggtgcc atgcgcgctc   120720
ccgagacggg gggtgggggc gtggaacgga taagaagtcc gaacacgtag tgttcgcact   120780
ttgttgcaat aattattatt taacttatt ggtgattggt gcgaacgggc ctctgggcca    120840
atcagggtgc aggatttgtg ccacgggacg cgtttccaat tttcgtccga taatcgataa   120900
tctgtcgatt gcaaaggcgt ggtgatgtac cggtatccgc ctccctaagg gcggagaata   120960
tggaactcgt gtatatatta ccctgcggat caccaggtgt gggtacacac gcagcttgaa   121020
gcttagagcc ttttaacgtg catccacacc acggaaaaca gggcaaggta agtggtatcg   121080
cgagtgggtc tgcccatgag atcggtggtg gtcggtggtc ggtggtcggt ggtcggtggt   121140
cggtggtcgg tggtcggtgg tcggtggtcg gtggtcggtg gtcggtggtc ggtggtcggt   121200
ggtcggtggt cggtggtcgg cccatggggg agggcccact aattgatggg tgtggttata   121260 atgttttcc attcgttatc tccagcaacc ccagctccgg cgaccccggc ccagcccagc    121320
tccggcgacc ccggcccagc ccagctccgg cgaccccggc ccagccatgc cccacggaca   121380
gccgtgcggg gcgtgcgacg gatcctgccg catgggccag cggggacgc cgtccaccag    121440 cccctcatc ccgtccctga cccctcgcc cccggcgggg gaccccgtccc cacgctccag    121500 ccagcgcatc gacgccgtgc gcgtgccgc gaggctcccc ggcggctcgg accatccgga    121560
atacggaatg ccgctatccc cgcgggccct gcgcccgtac ctggcccggg ggccaggggc   121620
```

```
gttctgcgcc ccgccgtggc gccccgatgt gaaccgcctc gcgggggacg tcaaccgctt  121680
gttcaggggg atatccacct cctcgatcca cgtgaccgag gactcgcgca ccctgcgcag  121740
ggcgctgctg gattttacg ccatgggta cacgcacacg cgccccacac tcgagtgctg  121800
gcagtccctc ctgcagctgc tgcccgagca gagcttcccg ctgcgcgcca cgctgcgggc  121860
actgaactcc gaggaccggt acgagcagcg gttcctggag ccgccgagcg accccccgaa  121920
taccctcttt ggggaggagt gtgacgtgag cggcgacgag tcgccctccg aggaggaga  121980
agaagacgag gccagcgggg agagcagcgt ttcggagttt agccccgagg aggagactgc  122040
cagcagcgag tacgatagct tttcggacgt ggggaggac gactcgagct gcactggaaa  122100
gtggtctagc agcgaaagcg aaagcgatag cgagtccgat gcccccacca acaaccacca  122160
ccctacaacc cgcgctagcg ctgccaaaaa gcgccgcaag cgccaacccc caagggtga  122220
gcgtcccacc aaaagcgctc gccggtgagt cggataggtg tacgcatgca cgctttccaa  122280
aacacaccaa cgctacgttc taaccagtaa aaccaccact cgttgtcacc ccgatgaacc  122340
gcaaccccaa tacacacctt ttgacctctc cctccacacc tccaaaaccc actcgccaac  122400
ccacccatac cacccaaaac gagtaaccaa taaaaacatc gttgacggca ctctctgtag  122460
tttggcttcg tttatatggt tgtttttcc cctcttgctt ggctgggatg aatagttggg  122520
tgctccgagc cccggctggg ggagcggtag cgaaaaaacg gttgttgttt agcgttgctc  122580
atccacgcga ctcggggcga ggtcggggga aagcgtgaat gacagcgcca tcacacccaa  122640
tcccccgacgg ctattggaga gataacaaca cccacgcaga gggagggaga gctatgggaa  122700
gggtgggggtg gggggagga ggaacatcta tagctaccta aaccacgcca gcaggcgtgt  122760
gtgtgttccc gcgattccac gccccgccga ggaaatacag ctcgcggagg gccgcgcgca  122820
atcagtgcgc ccgatctccc ggccactgaa ccacaacggc atggacggcg cgtacggcca  122880
cgtccacaac ggctccccga tggccgtcga cggcgaggag tccggagcgg ggacggggac  122940
gggggcgggc gcggacgggc tatcccgac cagcacggac accgcggcgc acgcggtctc  123000
gctgccgcgc tccgtggggg actttgccgc ggtcgtgcgc gccgtgtcgg cggaggcagc  123060
ggacgcgctc cggagcggcg ccgggccgcc cgcggaggcc tggccgcgcg tgtaccgcat  123120
gttctgcgac atgtttggtc gctacgcggc cagccccatg cccgtcttcc actcggcgga  123180
cccgctgcgc cgcgccgtgg ggcggtacct cgtggatctc ggcgcggcgc cggtggagac  123240
ccacgccgag ctcagcggcc gcatgctctt ctgcgcgtac tggtgctgcc tgggacacgc  123300
gttcgcctgc tcgcgcccgc agatgtacga gcgcgcgtgt gcgcggtttt tcgagacccg  123360
gctcgggatc ggggagacgc cgccggcgga cgcagagcgc tactgggccg cgctactcaa  123420
catggcgggc gccgagcccg agctgttccc ccgccacgca gccgccgcgg cgtacctgcg  123480
cgcccgcggc cgcaagctcc ctctccagct gccctcggcc catcggaccg ccaaaacggt  123540
ggccgtgacc ggccaatcga taaacttttg aaaaatatac tcactatata ctaaacccca  123600
attccgcgag tctgcccctg tttgtgtttc cgtctctcta tccatttccc ccaccaatac  123660
ctcaactatc gagcgggcgt ggggaccccgg ggagagacca ccaggcctcg ccggtttct  123720
ctctctccgt tgggggggg atggtaggga ttggtgggtg aggtggttgt ggtagtcatt  123780
gtgagtaaac caacgcagac tgctactggg caaaaaaaca aagggggaagg ccgagcgggg  123840
gagagcggta ggggaggccg agcggggag agcggtaggg gaggccgagc ggggagagc  123900
ggtaggggag gccgagcggg ggagagcggt aggggaggcc gagcgggga gagcggtagg  123960
ggaggccgag cggggagag cggtagggga ggccgagcgg gggagagcgg taggggaggc  124020
```

```
cgagcggggg agagcggtag gggaggccga gcggggggaga gcggtagggg aggccgagcg   124080
ggggagagcg gtagggggagg ccgagcgggg gagagcggta ggggaggccg agcggggggag   124140 agcggtaggg gaggccgagc gggggagagc ggtaggggaa acgccgcctg ggatgagtgg   124200
gaccgagtag tgtgtgatag gcactagagg gcgccagcgt acagggagt gtacccacca   124260 aaactccaac accacggaaa atatggttta cgtttttta ttaaaaaagc tgaaacgctc   124320
aataccacag acttttcaga gatacagatt atttacaccg ttccaacttc ggcctcaaac   124380
ggccacgggg gtgtcttcgg ggttttctgc agacacgtgc gcgcggctgc ggggctgcct   124440
ggcccctctg gggtgggggt caggggagct ctggagatcc agccgcatga agctggtatt   124500
tacttcctgg aaggcgtctt cagtgacgtg caactggtac tcgaatccca gcttcatcac   124560
gtagcgctcc gatgggatag gaatcctctt cggcccctgc caatttgtga tcccctcggc   124620
gatggcgggg ggaaccttgg cgaatgcttc ttccgggaga gtgctggggt ccgcgctgct   124680
ggcatcggcg gcgtcggccc ttatgtaata gcgctcgtcc gcgggttcct cctcgccctc   124740
gtagtacacc tccgggtaga ggaacggcag gcggacgaag gttccgtcgt tcagctgctt   124800
gtagaacctc ttctcgatct tgggcagcgg cagggcggag tagctgagca cctctccggc   124860
caccaccccc tcgaccggca cgcggcacgg cacctcgctg ggtgcgacgg ggaagtagcc   124920 cgtgggggacc ttggcgaagt accccctcgtt catctcttcg cgacaccgcc tgaagtagga   124980
gcgcccgagc atgcacccga acgggttgaa caggtgctta cgctcgcctc tcggcgcctc   125040
ctcgccgctg gagttggcgg cccccccggc cgcggctgcg gcgaaggtgg gggccaagac   125100
gaggtggggc gggttggcat tgcggcggcg agcgagcgcg cagcggaaga cctcggtgcc   125160
ggcggtggcg gctgtcatca tgtcggagtt catcacgtct gttatcttca aggtgtctt   125220 ctctctttc tcccttcaaa atggaggga tgttgtgcag ggctaggcgg tggtgggtgt   125280
aaaggcgagg cttttgcaag gcaagaaacc actgctcaac ccacaaagcg aggtgaggta   125340
ctggcgagag tccctacct tttaacgtgt ggatgtccgg ccgaacactc cccagagtag   125400
gcgttccatc cacgtcacgt ctcccgcccg gcgggcggcg ggcgcccgcg ggtccccggg   125460
gcggggcggc gtcgcggcgg cggccgtgga ccgagcgggc gcgggagcgc gcgagcgccg   125520
cctcggggcg cgcatccccc ccctccgacg gccgccgccg cggcagcggc cgccccgggg   125580
cgggaatttc ccgaaggcgc gcggggtcga ccaccgcgta aatcacccgc ttaactgtgg   125640
gtggacgaac taatgaattc gagctatgtt tggaaaaccc acactcaccc actacggtgt   125700
cttctccacc cgccgctctt aatttgagcg gatgattatg ctcaacggtg gtccatggta   125760
ttgtctcaaa cagttttcca cacacgaagg gaggctgcca agatttatga aactcatctg   125820
ctatctctgc gtataccatt cgtttaggac cgggtatcag gtcaaacacc ggcttgcaca   125880
agtctgctgc ccccagcacc cagaggtgat agggctgatt aatgataagg ctggagttga   125940
gatggttata gccagagagt acagagagcc actctatgct cacacccatt ctatcttcgt   126000
ggtaaaccac cccgttttcta tctagagcta tagctgtagc ccccctggtt ctgactattg   126060
gcctacacgc cttttggtagg gtcaataaac tcgatgaaaa tctgtagaga tcggcggagc   126120
gtaccactat gggtattcca agcggttcag atgccaatac gaaacattgt cggctcaaaa   126180
actcccacag atgtccatcg acgtcgatgg aactgtttgg caatgctttg tgtctgtcga   126240
caactgtaac aactgtaatt aagaccacac ccatgttatt aacaaatggg tgggttgaac   126300
caactccata aatttcagca gagctgctct agatacacac tctgttgtga aaagactcg   126360
```

```
ccgtgcgcca agccctatag ctttataggc acacgcccac ggcatcggaa tggaaaataa  126420
acaatgcgac cacctaaccg actggttttc cactacgagc gacgcgtcag aatcgatgga  126480
caccacgcct ccgctaccac ctcccacacc ctcggtggat cccagctaca gcggtgcggc  126540
cgcggacgag gacctgtact ctgacataag cgagggcgat ctagaataca gcgactgcga  126600
tagcgcctct gaaagcgatg aggatgacga cgattgtctt ataccatcca agagaaagc  126660
tagggaagtg gctgcttcgt ttgggtacac ggtcatcaaa acgcttacgc ctggttcgga  126720
gggacgtgtg atggtggcaa ccaaagatgg ccagccggaa ccggtcgtgt tgaagattgg  126780
tcaaaaggga actactctca tcgaagccat gatgctgagg aatgtgaacc atccctccgt  126840
gatacaaatg aaggacacct tggtatcggg ggcgataacg tgcatggtcc tgcctcatta  126900
cagctcggat ctgtacacct ttctgactaa ggaatcaagg cgcattccca ttgatcaggc  126960
tttgattata gaaaaacaga ttctcgaggg gctgcggtac ctgcacgcac agaggatcat  127020
ccacagagac gtcaagactg aaaatatttt cataaacagc gttgatcaag tatgtatagc  127080
tgactttggg gccgcccaat ttcccgttgt ggaacccgcg gacctgggcc tggctggtac  127140
cgtcgagacc aacgccccgg aagttttggc cagagcaaaa tacaactcca aggcagacat  127200
atggagcgcc ggcatcgtct tgtttgagat gctcgcctat ccatcaactc tattcgaaga  127260
ccctccgagt accccagagg agtatgtgaa aagctgccac tcgcaactac tgaagataat  127320
ttcaacgctc aagataaatc cggaggagtt tcctcgagac cccgggtcga ggctcgtgcg  127380
cggatacatc gagtattcta gactcgagcg caagccctac acgcgctacc cctgctttca  127440
acgcgtcaac ctgcacattg acggggagtt tctggttcac aagatgctag cgttcaatgc  127500
cgcgatgcgc ccatcggccg aggagctgct gtcatacccca atgtttgcac aactttagga  127560
tgactaacct gtttctggga ggagacagcg tgggcgacgg tgtataaagt tggtctgctt  127620
tcaagccctg ccactgcgct acagtgccac caactgtaaa gcggtagtaa gctgcagtga  127680
tgttgactgt cttagcagcc ctgagtctgc tcagcttgct tacgagcgca accggacggc  127740
tcgccccaga tgaactctgt tatgccgaac cccgcagaac tggcagccca ccaaacaccc  127800
agcccgaacg cccacccgta atatttgagc ccccaacaat tgcgattaaa gctgaatcca  127860
agggttgtga gctaattta ttagatccac ccatagatgt aagctatcgc agagaagata  127920
aggtgaatgc gtccattgct ggtttttttg actttggcgc ttgccggatg cccatcgcat  127980
acagagagta ttacggttgt attggcaatg ctgttccctc cccagagact tgtgatgcgt  128040
actcatttac ccttattagg accgagggta tcgtggagtt taccatcgta aacatgagcc  128100
tcctgtttca gcctggaata tacgatagtg gcaattttat ctacagcgtt ctcctggact  128160
accacatatt tacaggacgt gtaacgttgg aagtggaaaa ggacacaaac tatccctgtg  128220
gcatgattca tggactcact gcttacggaa acatcaacgt agatgaaacc atggacaacg  128280
ccagcccaca cccgcgtgcc gtggggtgct ttcccgagcc catcgacaac gaagcgtggg  128340
caaacgttac atttactgaa ttggggatac cagacccaaa ctcatttctc gatgacgagg  128400
gtgattaccc gaatatatca gactgtcact cgtgggagtc atacacctac ccaaatacgc  128460
tgaggcaggc cacaggaccc cagaccctgt tggtgggtgc ggttggactc agaatcttgg  128520
cgcaggcatg gaagtttgtc ggtgacgaaa catacgacac catccgcgca gaagcaaaga  128580
atttagagac ccacgtaccc tcaagtgctg cagagtcgtc tctagaaaac caatcgacac  128640
aggaggagtc taacagcccc gaagttgccc acctgcgaag cgtcaacagc gatgacagta  128700
cacacacggg gggtgcgtcg aacggcatcc aggactgtga cagtcagctc aaaactgtgt  128760
```

```
atgcctgctt ggctctaatt ggactcggca catgtgccat gatagggttg atagtttaca  128820
tttgtgtatt aaggtcaaaa ctgtcctctc ggaattttc gcgcgcgcaa aatgtaaaac   128880
atagaaatta ccagcgactt gagtacgttg cttaacacct gtcaaataaa agtttcaaat  128940
caaaaacatt gttgtctgta ataactgagt gtggttttaa aaatactaaa tcgcggcaat  129000
tccggaaata gccccataca aaagggaggg ttgttggtgt ttagaaaata gtttccccgt  129060
tgatgagttt cgcgtagagg tctaactcat ccgcgatggg gttcatctat gcgcgcaaac  129120
tgttgctgtg catggctgtt agtatatacg ccatagggtc cactacaaca actgagacta  129180
ccacctctag ctcgtccacg tctgggagtg gccagtctac atccagtggg accactaata  129240
gtagcagttc tcccaccacg agtccaccta ccacatcttc atctcccccc acatcaaccc  129300
acacatcctc cccatcttca acctctaccc aatcgtcgtc aacggcggcg acaagctcgt  129360
ctgcaccctc tacagcgtcc agcacaacct ctattccaac atccacatca acagaaacca  129420
ccacaacaac cccaaccgca tctacaacga ccccaacaac aacgaccgcg gctcccacaa  129480
cggccgctac aaccacagct gttactacag ccgcgtctac atcagcggaa accaccacag  129540
ctactgcgac tgctacctca accccaacca caactacgcc tacgtccaca caactactta  129600
cagctaccac cactgttcca acaaccgctt ctacaacaac tgatacgacc acagcagcaa  129660
cgaccacagc agcaacgacc acagcagcaa cgaccacagc agcaacgacc acagcagcaa  129720
cgaccacagc agcaacgacc acagcagcaa cgaccaccgc ggctactact cctctgcaa   129780
ccaccgcggc taccaccacc gcggctacca ccaccgcggc taccaccacc gcggctacca  129840
ccaccgcggc taccaccacc gcggctacca caacggggtc tccaacctct ggttcaacat  129900
ctactacagg ggcttccacg tccaccccct cagcttccac tgccacatct gccactccca  129960
catcgacgtc aacatcagct gcggctacta catctacccc taccccaact tcagctgcaa  130020
catcagcaga gtctaccaca gaggctccaa catccacacc cactactgat acgaccaccc  130080
cttcggaggc aaccacagct actacatcac cggagtctac cacagtttca gcctcgacta  130140
cctctgctac gaccacggca ttcacaaccg agtcccacac atcgccggat tcgtctactg  130200
ggtctacatc cacagccgaa cccagctcaa cgtttacttt aacaccttct actgcgaccc  130260
cctccacgga tcagttcaca gggtcatctg cctcaacaga gtctgactcg accgactctt  130320
ccaccgtgcc cacgactggg actgaatcta taacagaaag ctcatcgacc accgaggcgt  130380
caactaactt gggatcgtca acctacgaga gtaccgaagc cttggaaact ccagacggga  130440
atacaacttc cggaaatacc accccatcac cttccccgcg taccccaagc tttgctgata  130500
cccaacagac cccagacaat ggtgtatcaa cccaacatac caccatcaat gaccacacca  130560
ccgccaacgc tcaaaaacac gcagggcacc acagaggtcg cgcaggggt cgtcggggta   130620
gccctcaggg ggggtcacac acaacaccac acccagaccg tttgactcct tctccagacg  130680
acacctatga cgatgataca aatcacccta acggtaggaa caattcaata gagatcgtgc  130740
ctcagctccc gccagaccga cccatcatag agctgggggt ggcgactctc agaaaaaact  130800
ttatggaggc gtcctgtact gtggagacta actcaggctt ggcgattttt tggaaaatcg  130860
gcaacgcaag cgtagacgcg tttaatcggg gaactactca cactcggctg atgcgcaatg  130920
gggtaccggt ttacgccctc gtatctacgc ttagagttcc gtggttaaat gttattccac  130980
taacaaaaat tacttgcgct gcttgcccca cgaatctagt cgccggcgat ggggtggacc  131040
tcaactcatg taccaccaaa tcaaccacaa taccgtgtcc gggccaacag cgcacccata  131100
```

```
tttttttctc tgcgaaaggg gacagggctg tgtgtatcac atcagaactg gtgtcccagc  131160
ccacaataac ttggtcagtt ggatcagata ggttgcgtaa cgatggattt tctcagacgt  131220
ggtatggaat acagcccggg gtgtgtggta tactgcgcag cgaggttcgc attcaccgca  131280
ccacctggcg ctttggatca acatcaaagg actatctctg tgaggtcagc gcatcggact  131340
caaagacgag cgattacaaa gtgctaccca acgcccactc aacttccaac ttcgctttag  131400
tggctgcgac cacgctaaca gtgacaattt tatgcctgct gtgctgcttg tactgtatgt  131460
taacccgccc ccgagcgtct gtatattaac tcaaaaatta tcccttggcc tttacaacca  131520
gtggtggcgt gtatgcagaa gcgtgccacc gccctggtac gtgtttttca ataaacgaag  131580
catgtctacc ttcaagctta tgatggatgg acgtttggtt tttgccatgg caatcgcgat  131640
cttgagcgtt gtgctctctt gtggaacatg cgagaaagcc aagcgtgcgg ttcgaggacg  131700
ccaggatagg ccaaaggagt ttccaccacc ccgctataac tatacaattt taacaagata  131760
caacgcgact cgcgctagcat caccgtttat taacgaccaa gtaaaaaatg ttgacttgcg  131820
gattgttact gctacgcgcc catgtgaaat gatagcgctg atcgctaaga caaacataga  131880
ctcaatcctg aaggagctgg ccgctgccca aaaaacttat tccgccagac tcacctggtt  131940
taaaattatg ccaacgtgtg caacgcctat acacgatgtt agttatatga aatgcaaccc  132000
gaagctatca tttgcaatgt gtgatgagag atcagacata ctatggcaag ctagtttaat  132060
tactatggct gctgaaactg acgatgaact tggacttgta ctggcagccc ctgcacattc  132120
tgcctcggga ctgtatcgcc gtgttataga aatcgacgga aggcgaattt acacggactt  132180
ttctgtaact attcccagtg aacggtgtcc gattgccttt gagcaaaact ttggcaatcc  132240
ggatcggtgt aaaactccag agcagtactc gcggggagaa gtttttacac gtcggtttct  132300
tggtgaattc aacttcccac aaggagagca tatgacatgg ttgaagttct ggttcgtcta  132360
cgatggtgga aacctaccag tgcagtttta tgaagcccag gcattcgcaa gacccgtgcc  132420
tccggataac caccctggat ttgattctgt tgagtcggag attacacaaa ataaaacaga  132480
cccgaaacca ggccaggcgg accccaaacc caatcagcct tttaagtggc ccagcatcaa  132540
acacttggcc ccaagactcg atgaggtgga tgaggtcata gagcccgtaa caaagccccc  132600
aaaaacgtct aagagcaact ctacgtttgt gggcatcagc gtcggtttgg gtatcgccgg  132660
cctagtattg gtgggcgtca ttctatacgt ctgcttgcgt cggaagaagg aactgaaaaa  132720
gtctgcacag aacggcttga ctcgcctacg ctcgaccttt aaggatgtta aatatcccca  132780
gcttccgtaa acagtgttgc gtaacctgct gggaggtgtc cacggcctta aagcttcgcg  132840
gtttggagat ataacgcaca acctacaaca aacgcgacac agcaagtagt agtcgctatg  132900
gccaaactca ctgggatgtt cagcgctgcg atattactgt ctatggctat atgctcaacc  132960
gcaatcatat atcgcggaga acatatgagc atgtacctaa acgccagctc tgagtttgcc  133020
gtgtacccca ctgatcagtc ccttgttttg gttggccact tgctctttct cgacggacaa  133080
cgcttaccca ccaccaacta tagtgggctg atcgaattga ttcattacaa ctactccagc  133140
gtttgctaca ctgttatcca aacgatatcg tatgaatcat gcccgcgtgt agccaacaat  133200
gctttcagat cgtgcctcca caaaacttct aagcactacc acgactattt ccgagtcaat  133260
gcctctgttg aaaccaacgt tctcttaaac atcacaaagc cacagcctac agattccggg  133320
gcgtatatcc ttcgcgtaaa acttgaccac gcgccaaccg cagatgtttt tggagtttcc  133380
gcctttgttt acgatctaaa atctaaaacg gtccccgatc caatgcccac cacacaaacg  133440
gtagaaccta caacgagcta tgtgtcgact cccacatacg actataccga tgacgtaacc  133500
```

```
accgaaactg aatccacatc aacatctacc caacaggcga tgacctccac tcaaacccct 133560
agcgctacat ggggaaccca gctaaccaca gagctgccga caaacgaaac tgtggttatt 133620
ggtcaggagg ccctgttatg ccattggttc cagccatcga caagggtgcc gaccctgtat 133680
ctgcatctgt tgggacgcac tggcaatctc ccggaagatg ttctactggt cgaagactct 133740
gagtttcttc gtaccacatc gcctgcacat aggccttctg catcacccgc tgacggtgat 133800
gattttaaac agacaaactc aacttccctt aaggcgcgca acaagatcgt cgcaatggtg 133860
gttatcccga ccgcgtgtgt actaatgctc ctgttggtgg ttgtcggtgc catcataaac 133920
ggtgccgtgc gcaaacattt attgagttgc gcaagccgca ggatctaccg ctccggacag 133980
gggggcgcat cggcggccga acggagacgg ctgacttgcg gtcctacttt agccgcgtca 134040
tcggagtcgc tggccgacga tacaacgtca tcacctccaa cccccaaacc ttcgaagaaa 134100
accaagttgg agaccgatcc gcttatggaa cagctgaacc ggaaactgga ggccatcaaa 134160
gaagaatcat agttgtgggg gtagatgggg ttggtattaa agtttgtgta ttatcgattt 134220
tatatttatt aaaatttgtg aaacataaac atcttgtgca atgtttacat tatttgtgat 134280
tgggacggtc cactgggagg tggtacaact cgggtttaaa gctctggatg tttggtagga 134340
aactcacagt tctccacttt ggcgtcaaag caatcagacg tctaattcga agtagaacgt 134400
cacaatggag ctgttggccg caagtcgcgc ttgtatattt tttgggctag taacagtact 134460
cgatgcgtgg ggagtccaac aagttgaact ttccgagggg gcttgggcta tgatcgacgg 134520
aagggacgtt ttaacccta ctaacacaac tactcgggtc acaaaggcct ggacgttttt 134580
ggaaacccct cccggttgcg ctggcgacat atcagttaag aaggtgtgcg tgagccatag 134640
tctgtgcgaa gataacatta aataggaaa gcactgtaac ctcttaactg gggaacatgg 134700
cattgcgttg gccgagtttta acgtagtaaa cggatcgctg cgcagaacag acgatgtgta 134760
ctttgtgaat ggtacagtct ttccaatcct tgccgaaacc cgcagcgtcc tacaaatcca 134820
tagggcaacc ccctctatcg caggggttta caccctccac gtttccatcg acggaatgat 134880
gaaacactcc gtcgtgctgc tcaccgtcaa gaagccgccc aaacaaccgc aaccacgctt 134940
gcgcgttaag accccgccac ccgtaaccgt tcctcaggtt cccgtaaaga cccacacgga 135000
ttttgtggtg cacggatacc actcgcgcgt gtacgctgat ggcgaatctt tcgagctgtc 135060
ggtgaacctg gagtcacata tcgtagagcc cagcttcagc gcggagattc agtggtacta 135120
tatgaataca tcatcgtcat catgcgatct atttcgagtt ttcgaaacct gcatctttca 135180
cccgacagcc atggcctgcc tgcacccgga acaacacacc tgcagcttca catcccccat 135240
cagagcgacc aagatcctac accgggtgta tggaaactgc agcgatcatg gaaattcgtg 135300
gccttctagg tgccatagca ctctgctggg caatcgtcta tactttattc aaccagcaca 135360
gaacagagtg gacctgttgt tcaaagacac tcccgcgtcg gctaccgggc tgtatgtgtt 135420
tgtattattg tacaacggac atccggaggc gtggacgtat acgctgctgt caaccgcaaa 135480
tcactttatg aatgtgctta ctgacgtgac ccgcccacgg ctaggagagc acttttatac 135540
ggacctcggg cacaaaatca tcactcctca tccatctgta gctaccactg aagagttggg 135600
agcttggact cgacactacc tcgccttttt gctggttatt atctgcacgt gcgcggcgct 135660
gctagttgca ttggtggtgt ggggctgtat tctctacatc cgaagcaacc gtaagccgta 135720
tgaagtgctg aacccctttg aaacggttta cacgagcgtt ccaagcaacg accctctcgga 135780
cgaggtcttg gtgtttgagc gcctagcttc ggactctgac gactccttcg actctgattc 135840
```

```
agacgaagag ttggaatacc caccacctcc caaaccagct ccacagctcc caccatacca   135900
gtttgtagac gggggagacg cccctagcgg caggtccgga ttcaaggttt ggttccgcga   135960
tacacccgag gcgtcccecgg ttcctcttca taaaccaacg ctacagggtc cagactacag   136020
ccgggtagcg tcgaagctaa agtcgatact aaaatgagca gcaacagcga taacacagag   136080
tgcttcgggg gagtcaacta tgccgaggga atgcgcaagc gtaaacgcaa ccctgtcaga   136140
aacagcacct ttcaagagta tctcgacgcg cgtaacgcgc gttatcccag atccggctca   136200
acctccgatt ccgacgagga ctacacaacc agatcaaagt acgagtcaga tgtcagcgag   136260
tttaaaaaaa tgatggatct ggaaactcta cctcccccaa aggctgagcc gcaagctcag   136320
aaggccgagc ctgatgctgc gaaggaggag ccagtcagca ccactagcta catcttaaac   136380
gaatgggtgg ctcctatgat tgggcatttt ctggcaatgt gtatgtatga gttgcttttc   136440
aaataaaaac aaacattaac ccctgtaaac atccgtttgt ctactgtgta tgatagagtt   136500
aaacccaacc ctagagagtt atgtatttaa tcccctggga ccccgcggaa gtcatatatc   136560
cctcggcccc ctcatttggg cgcacattgc ctgcccggcg gcagtcttac tcccttagct   136620
cgccctcttg cataagataa actattcccc tcccagctag tttcacccac cagattaagc   136680
gaggttttcc ctctcagcga tcacttttca ccaccgaaga acaggccctc atcggttttcc   136740
ctccgtgttt tccatccatt ctatccaacc actacatttt catggagaag gcggaggctg   136800
ccgcagttgt tatacccctg tcagtttcca accccagcta ccgtggaagc ggtatgtccg   136860
accaagaagt aagcgaagaa caatctgctg gagatgcctg ggtgtctgca gcaatggcag   136920
ccgcagaggc ggtggctgct gccgctacct ccaccggaat tgataacact aacgactaca   136980
cgtacaccgc tgcttctgag aatggggatc ctggtttcac actaggcgat aacacctacg   137040
gaccgaacgg tgctgcctca gggtgcccgt ctcccccatc accggaggta gtgggtctag   137100
agatggtggt tgtgtcgtcg ctcgctcctg agatcgcggc agccgtacca gcagacacga   137160
tttttgctag cgcagcagcc ccggcaaccc gcgtagacga cggtaacgct ccgctgctcg   137220
gaccggggca agcgcaggac tacgactcag agtcaggatg ttattacagc gagagcgaca   137280
atgaaacggc cagcatgttc atacggcgag tcggacgtcg acaggcccgc aggcacaggc   137340
ggcggcgcgt ggcgcttact gtcgcaggcg tgatcctggt tgttgtccta tgcgcgattt   137400
ccggcatcgt tggggcgttc ttggcacgcg tgtttccgta acaccacctt ttaccccaca   137460
acagcccctc gccccctgg tcgaccagct accggacgtc tcccaagcct cgtccaccca   137520
cagttaagcg ggtgatttac gcggtggtcg acccccgcgcg ccttcgggaa attcccgccc   137580
cggggcggcc gctgccgcgg cggcggccgt cggaggggggg ggatgcgcgc cccgaggcgg   137640
cgctcgcgcg ctcccgcgcc cgctcggtcc acggccgccg ccgcgacgcc gccccgcccc   137700
ggggacccgc gggcgcccgc cgcccgccgg gcgggagacg tgacgtggat ggaacgccta   137760
ctctggggag tgttcggccg gacatccaca cgttaaaagg taggggactc tcgccagtac   137820
ctcacctcgc tttgtgggtt gagcagtggt ttcttgcctt gcaaaagcct cgcctttaca   137880
cccaccaccg cctagccctg cacaacatcc cctccatttt gaagggagaa aagagagaag   137940
acacctttga agataacaga cgtgatgaac tccgacatga tgacagccgc caccgccggc   138000
accgaggtct tccgctgcgc gctcgctcgc cgccgcaatg ccaacccgcc ccacctcgtc   138060
ttggccccca ccttcgccgc agccgcggcc ggggggggccg ccaactccag cggcgaggag   138120
gcgccgagag gcgagcgtaa gcacctgttc aacccgttcg ggtgcatgct cgggcgctcg   138180
tacttcaggc ggtgtcgcga agagatgaac gaggggtact tcgccaaggt ccccacgggc   138240
```

```
tacttccccg tcgcacccag cgaggtgccg tgccgcgtgc cggtcgaggg ggtggtggcc   138300
ggagaggtgc tcagctactc cgccctgccg ctgcccaaga tcgagaagag gttctacaag   138360
cagctgaacg acggaacctt cgtccgcctg ccgttcctct acccggaggt gtactacgag   138420
ggcgaggagg aacccgcgga cgagcgctat tacataaggg ccgacgccgc cgatgccagc   138480
agcgcggacc ccagcactct cccggaagaa gcattcgcca aggttccccc cgccatcgcc   138540
gagggatca caaattggca ggggccgaag aggattccta tcccatcgga gcgctacgtg   138600
atgaagctgg gattcgagta ccagttgcac gtcactgaag acgccttcca ggaagtaaat   138660
accagcttca tgcggctgga tctccagagc tcccctgacc cccaccccag aggggccagg   138720
cagccccgca gccgcgcgca cgtgtctgca gaaaacccg aagacacccc cgtggccgtt   138780
tgaggccgaa gttggaacgg tgtaaataat ctgtatctct gaaaagtctg tggtattgag   138840
cgtttcagct tttttaataa aaaacgtaa accatatttt ccgtggtgtt ggagttttgg   138900
tgggtacact cccctgtacg ctggcgccct ctagtgccta tcacacacta ctcggtccca   138960
ctcatcccag gcgcgtttc ccctaccgct ctccccccgct cggcctcccc taccgctctc   139020
ccccgctcgg cctcccctac cgctctcccc cgctcggcct ccctaccgc tctccccgc   139080
tcggcctccc ctaccgctct ccccgctcg gcctccccta ccgctctccc ccgctcggcc   139140
tccctaccg ctctccccg ctcggcctcc ctaccgctc tccccgctc ggcctcccct   139200
accgctctcc ccgctcggc ctccctacc gctctccccc gctcggcctc cctaccgct   139260
ctccccgct cggcctcccc taccgctctc ccccgctcgg cctcccctac cgctctcccc   139320
cgctcggcct tcccctttgt tttttgccc agtagcagtc tgcgttggtt tactcacaat   139380
gactaccaca accacctcac ccaccaatcc ctaccatccc cccccaacg gagagagaga   139440
aaaccggcga ggcctggtgg tctctccccg ggtccccacg cccgctcgat agttgaggta   139500
ttggtggggg aaatggatag agagacggaa acacaaacag gggcagactc gcggaattgg   139560
ggtttagtat atagtgagta tattttcaa aagtttatcg attggccggt cacggccacc   139620
gttttggcgt tccgatgggc cgagggcagc tggagaggga gcttgcggcc gcgggcgcgc   139680
aggtacgccg cggcggctgc gtggcggggg aacagctcgg gctcggcgcc cgccatgttg   139740
agtagcgcgg cccagtagcg ctctgcgtcc gccggcggcg tctccccgat cccgagccgg   139800
gtctcgaaaa accgcgcaca cgcgcgctcg tacatctgcg ggcgcgagca ggcgaacgcg   139860
tgtcccaggc agcaccagta cgcgcagaag agcatgcggc cgctgagctc ggcgtgggtc   139920
tccaccggcg ccgcgccgag atccacgagg taccgcccca cggcgcggcg cagcgggtcc   139980
gccgagtgga agacgggcat ggggctggcc gcgtagcgac caaacatgtc gcagaacatg   140040
cggtacacgc gcggccaggc ctccgcgggc ggcccggcgc cgctccggag cgcgtccgct   140100
gcctccgccg acacgcgcg cacgaccgcg gcaaagtccc ccacggagcg cggcagcgag   140160
accgcgtgcg ccgcggtgtc cgtgctggtc gggtatagcc cgtccgcgcc cgcccccgtc   140220
cccgtccccg ctccggactc ctcgccgtcg acggccatcg gggagccgtt gtggacgtgg   140280
ccgtacgcgc cgtccatgcc gttgtggttc agtggccggg agatcgggcg cactgattgc   140340
gcgcggccct ccgcgagctg tatttcctcg gcggggcgtg gaatcgcggg aacacacaca   140400
cgcctgctgg cgtggtttag gtagctatag atgttcctcc tccccccac cccacccttc   140460
ccatagctct ccctccctct gcgtgggtgt tgttatctct ccaatagccg tcggggattg   140520
ggtgtgatgg cgctgtcatt cacgctttcc cccgacctcg ccccgagtcg cgtggatgag   140580
```

```
caacgctaaa caacaaccgt tttttcgcta ccgctccccc agccggggct cggagcaccc  140640
aactattcat cccagccaag caagagggga aaaacaacc atataaacga agccaaacta   140700
cagagagtgc cgtcaacgat gtttttattg gttactcgtt ttgggtggta tgggtgggtt  140760
ggcgagtggg ttttggaggt gtggagggag aggtcaaaag gtgtgtattg gggttgcggt  140820 tcatcgggt gacaacgagt ggtggtttta ctggttagaa cgtagcgttg gtgtgttttg   140880
gaaagcgtgc atgcgtacac ctatccgact caccggcgag cgcttttggt gggacgctca  140940
cccttggggg gttggcgctt gcggcgcttt ttggcagcgc tagcgcgggt tgtagggtgg  141000
tggttgttgg tgggggcatc ggactcgcta tcgctttcgc tttcgctgct agaccacttt  141060
ccagtgcagc tcgagtcgtc ctcccccacg tccgaaaagc tatcgtactc gctgctggca  141120
gtctcctcct cggggctaaa ctccgaaacg ctgctctccc cgctggcctc gtcttcttcc  141180
tcctcctcgg agggcgactc gtcgccgctc acgtcacact cctccccaaa gagggtattc  141240 gggggggtcgc tcggcggctc caggaaccgc tgctcgtacc ggtcctcgga gttcagtgcc  141300
cgcagcgtgg cgcgcagcgg gaagctctgc tcgggcagca gctgcaggag ggactgccag  141360
cactcgagtg tggggcgcgt gtgcgtgtac cccatggcgt aaaaatccag cagcgccctg  141420
cgcagggtgc gcgagtcctc ggtcacgtgg atcgaggagg tggatatccc cctgaacaag  141480
cggttgacgt cccccgcgag gcggttcaca tcggggcgcc acggcggggc gcagaacgcc  141540
cctggccccc gggccaggta cgggcgcagg gcccgcgggg atagcggcat tccgtattcc  141600
ggatggtccg agccgccggg gagcctcgcg ggcacgcgca cggcgtcgat gcgctggctg  141660
gagcgtgggg acgggtcccc cgccgggggc gagggggtca gggacgggat gaggggggctg 141720 gtggacggcg tccccgctg ggccatgcgg caggatccgt cgcacgcccc gcacggctgt   141780
ccgtggggca tggctgggcc ggggtcgccg gagctgggct gggccgggt cgccggagct   141840 gggctgggcc ggggtcgccg gagctgggt tgctggagat aacgaatgga aaaacattat   141900
aaccacaccc atcaattagt gggccctccc ccatgggccg accaccgacc accgaccacc  141960
gaccaccgac caccgaccac cgaccaccga ccaccgacca ccgaccaccg accaccgacc  142020
accgaccacc gaccaccgac caccgaccac caccgatctc atgggcagac ccactcgcga  142080
taccacttac cttgccctgt tttccgtggt gtggatgcac gttaaaaggc tctaagcttc   142140
aagctgcgtg tgtacccaca cctggtgatc cgcagggtaa tatatacacg agttccatat   142200
tctccgccct tagggaggcg gataccggta catcaccacg cctttgcaat cgacagatta   142260
tcgattatcg gacgaaaatt ggaaacgcgt cccgtggcac aaatcctgca ccctgattgg   142320
cccagaggcc cgttcgcacc aatcaccaat aagttataat aataattatt gcaacaaagt   142380
gcgaacacta cgtgttcgga cttcttatcc gttccacgcc cccacccccc gtctcgggag   142440
cgcgcatggc accgtgccaa ctagtgggta ccgtgacccg gcccatacct cgacgagagt   142500
atgtgccggg taaccgtatt ttagcgcccc cccccatagc cgcacaccgt aacccagcca   142560
tgctatctgt tgcgctcaaa aattttttgcc cccccccac cctcaataac cgtgcaccct    142620
cccctaggtt tcatcgcgca aaaatttttat tgacaccccc cccttatcca tactgggggg   142680
aggggcacct ctgtacacgc gtggcaaaaa aaatcgataa cgggggggtag tgtgtaacga   142740 taaaagtga acatcgatg tgtatctccc ggagtgtatg gatgggggcg ctttaggtat     142800
tttatgtatg acccggtacc cgtgggaaaa tgtaacggat cgaaaccgtt tacacggtac    142860
aacgattgtg cgtgtgtgcg gtcggctctc aaaaaaaaacc gtgggcgggg catggggggg    142920
ggtgtggacg tgggtggaag gtgggtaccg ggcatctccc cccacacagc tgtctcaagc    142980
```

```
cacgcccct  catgtcattt  gaatattggg  aggggcgccg  tgttacgtcg  atgggtggg   143040
gccggcgcgt  gtgtgtatag  cgtcacatcg  tggcgtcaca  tgttaatgga  ctacatggcg  143100
ccacgaagcg  gttagatgta  gtaaccgcat  ctgtgagggt  taacacacga  gggcgccctc  143160
gtgcggacgt  gtatgaaggc  gcatgtaaaa  ccgtgttttg  aaacagcgcc  accgcctggc  143220
tccttgtgag  ataatatgta  aatcagcaca  cgtagatatc  atcccgccca  aaatacacgc  143280
gatagcgata  catgttttaa  ttggtataac  tttaatgaga  ttcaaccggg  aaatacagag  143340
acgcgttcac  gcccaccttt  cccctcccc   ctcccacttt  ttttacatca  tttccgtttc  143400
ggtcggaaat  atcgcactcg  ccatttttat  tgaaattact  tttgaagccc  actccctcgg  143460
ctcctcccaa  gctcgtcagt  atgcagatga  gatttaccag  gaagtgtcat  ggcgtccagg  143520
ggcgttcgtc  tttatgcata  tgagcggcgc  gatcacgaac  cccgttggcg  cgacgcgctt  143580
cccggggagg  agacgcatgc  agatgagatg  tgcatcgagg  tgtcatggcg  tccaggggcg  143640
ttcacctta   tgcatatgag  aggcgctatt  cggcatcccg  ttggcgcgac  gcgcttccct  143700
gggaggagac  atacgcaaat  tagaaacgac  acacggggttc  taattggttg  gagcgggggg  143760
gaggcgaaaa  gcgcatgcaa  atgcaaagcg  cgggaccggg  ccccataggc  tagagccgct  143820
acacgcccac  cgcccatcat  caacggccaa  tcacaatcga  tagtgtgggc  tggccactcc  143880
cactaggggg  aaggcaaaac  tccatcgtag  tagtataaag  cacctgttgc  ttacccatcg  143940
tagcatcgcg  gactagagag  cctttcagct  cactggacca  gccagccttc  gaggactatc  144000
gatcgcatct  tggaaagctt  acccgctctt  ggcactcctt  cttcggcttg  cggaggtaag  144060
agctccccgg  ggacacgacc  ggcttcgatc  tgcttcttct  cccggggaga  gcgttagaga  144120
acggggcgag  tgccaaaaag  gccatggaac  ccctccaaca  acgatgtccc  gaggggggtgg  144180
ctccgaggcc  cgcttcgacc  tagcggtcga  agcgcggtgg  ggatacttac  ctcgaagccg  144240
gcgaaggcta  taccttcccc  gggcagaccc  gggcggcttc  tgcctcggcg  gagctcggcg  144300
cggaagcctg  gatatctgac  ggggcgtggt  taccacccaa  gcgggggaga  ggcccaggcc  144360
gcccgcgttc  ccttttacca  ttcggctccg  ctccaactca  acatcttttc  cgcctctgct  144420
tttccagggt  agagaagcgg  cgcccgtcgt  ccgagcgccc  gccgcggaac  cccgccaccg  144480
gccaccccgcc  aaccttccct  tctcggtctt  ccgagcgagc  cttctcgtgc  ggttggttct  144540
cgaccccgaa  gccggagcta  gcacgccatg  ccagccagc   gcagcgactt  cgccccggac  144600
ctctacgact  tcatcgagag  caacgacttc  ggcgaggacc  ccctcatccg  cgcagccagc  144660
gcggccgaag  aggggttcac  ccagcccgcc  gcgcccgacc  tgctgtacgg  cagccagaac  144720
atgttcgggg  tggacgacgc  tccgctctcc  acccccgcgg  tggtcatccc  tccgccgtct  144780
ccgactcccg  agcccgcgg   agggaaggcg  aagcggtcgc  cctcggccgc  cggcagcggc  144840
ggtcctccta  ccccggcggc  tgccgcccag  ccggcgtccc  cggcacccag  cccggctccg  144900
gggctcgccg  cgatgctgaa  gatggtccac  tcctccgtgg  ccccggggaa  cggtcgccgg  144960
gccacgggct  cctcatcacc  cggcggtggg  gacgcggccg  accgggtcgc  cctcgacagc  145020
gataccgaga  cctgcccggg  gtccccgcag  cccgagtttc  catcctcggc  ctcccggc    145080
ggagggtccc  cggcacccg   ggtcggagc   atctccatct  catcgtcgtc  ctcgtcctcg  145140
tcctcgatgg  acgaggacga  ccaggcggat  ggtgccgggg  cgagtagctc  ctcttcgtcg  145200
tcctccgacg  acagcgacag  cgacgaaggc  ggcgaggagg  agaccccctcg  cccgcggcac  145260
tcgcagaacg  ccgcgaaaac  cccgtcggcc  gccggctctc  ccgggccgtc  ctccggaggg  145320
```

```
gatcgcccgg ccgctggggc cgccaccccg aagagctgcc gctccggcgc cgcttccccc 145380
ggcgcacccg ctccggctcc agcttcggcg cccgctccca gccgcccggg aggaggcctc 145440
ctccctccgg gggctcgcat tttagagtac ctggagggcg tccgcgaggc caatctggcc 145500
aagacgctgg agaggcccga accgcccgcg ggatggctt ctccgccggg ccggagccct 145560
caccggctcc ccaaggacca gcgtccgaaa tcggctctgg cgggagcgtc gaagcgcaag 145620
cgggccaacc ccagacccat accccagacc cagacccagg caccggccga ggaggccccg 145680
cagacggccg tgtgggactt gctggacatg aactcatccc aggctaccgg ggcggcggca 145740
gcagcagcat cggccccggc ggcggcttcg tgcgccccgg gcgtctacca gcgcgagccg 145800
cttctcaccc cgtccgggga ccctggccc gggtcggatc caccaccgat ggggagggtg 145860
cgatacgggg ggaccgggga ctcgcggac gggctgtggg acgaccccga gatagtcctg 145920
gccgcctcgc gctacgccga ggcgcaggcc ccagtaccgg tcttcgtgcc ggagatgggg 145980
gactccacca agcagtacaa cgctctggtc cgcatggtgt tcgagagccg cgaagccatg 146040
tcctggctgc agaactctaa gctcagcggg caagaccaga acctggcgca gttctgccag 146100
aagttcatcc acgctccgcg cggacacggg tccttcatca ccgggagcgt ggccaacccc 146160
ctgccccaca tcggggacgc catggcggcc gggaacgcgc tctgggccct gccacacgcg 146220
gccgcctcgg tggccatgag ccgccgctac gatcgcactc agaagagctt catcctccag 146280
agcctccggc gcgcctacgc ggacatggcc tacccgagag acgaggcggg gaggccggac 146340
tcactcgccg ccgtggccgg ctaccggccc caggccgccg ctgccgcggc cagccagcaa 146400
cagcccgagg ccccggcgcc ctcggtccgc gtccgcgaag cgtacacccg ggtctgcgcg 146460
gccctcgggc cccgacgcaa ggctgccgcg ccgcggccg ctccggggac cagggcgccc 146520
aggccgtccg ccttcagact cagggagctc ggggacgcct gcgtgctggc ctgccaggcc 146580
gtcttcgagg ccctcctgcg cctccgcggc ggggcgtccg ccgtcccgg actgaccccc 146640 agcgagatcc cctctcccgc ctgccctccc gaggcgctgt gctccaaccc ggccgggctg 146700
gagacgcgcg ccctctccct ctacgaactc agggacctgg tcgagcgggc caggctcctc 146760
ggggactctg accctaccca ccgcctgggc tccgacgagc tgcgcctcgc ggtgcgcgcc 146820
gttctggtgg tggcccggac cgtggcgccg ctggtgcgct acaacgccga ggggcccgg 146880 gcccgggcct cggcctggac cgtcacccag gccgtgttca gcatacccag cctggtcggg 146940
gggatgttgg gggaggccgt gtccctgctg gccccaccga ctcggtccca gcagccctca 147000
tcgtcctcgc ccggcggcga gcccttctcc ggctccgcgg ccgcggaggg gagccttcag 147060
accctgccgc ccctgtggcc caccgtcccc gggaagcagt ccgcgacggt cccctcgtcc 147120
cactcccagt ccccccagca ctcccagagc ggcgaggcg ccggggctac gaccgccacc 147180
tgctgccggg ccaccagac aaacgcccgc tcccgggggc agcagcacca gccgcagaag 147240
gcccgctccc ctcaggcggc cgcctcccg gccaccctca gccaggaggc gatgcccggc 147300
tcctcctcgg acgaccgtgc catccacggg cgccccaggg gcaagagcgg caagcggcgc 147360
tccgagcccc tggagccggc ggcccaggcc ggagcctcgg cctccttctc ctcgtccgcc 147420
cgggggtacg atccctcggg gccggtcgac agccctccgg ccccaagcg cagggtggcc 147480 accccgggcc accaggctcc ccgggccctg ggacccatgc cagccgaggg ccccgaccgt 147540
cggggcggat tcaggcgcgt tcccgcggga gactgccaca ctccgcggcc cagcgacgcg 147600
gcttgcgcgg cctactgtcc ccccgagctg gtggcggagc tcatcgacaa ccagctgttc 147660
cccgaggcct ggcgcccggc gctcaccttc gatccccagg ccctggccac catcgcgcc 147720
```

```
cgctgcagcg gcccccgggc ccgggacggc gcgcgcttcg gggagctggc ggccagcggc    147780
ccgctgagac ggagggccgc ctggatgcac cagatccccg accccgagga cgtgaaggtg    147840
gtggtcctct actccccgct ccaggacgag gacctgctgg gcggactccc ggcctcccgc    147900
cccggcggct ctcggcgcga gcccctctgg tccgacctca aggggggact ctcggcgctg    147960
ctggcggccc tggggaaccg catcctcacc aagcggtccc acgcctgggc cggcaactgg    148020
accggggccc cggacgtctc ggccctcaac gcccaggggg tcctgctgct gtcgaccggg    148080
gacctggcct tcaccggctg cgtcgagtac ctctgcctgc gctgggctc cgccaggcgc    148140 aagctcctgg tgctggacgc ggtctccacc gaggattggc cccaggacgg tcccgcgatc    148200
agccagtacc acatctacat gcgggccgcc ctgactccgc gggtcgcctg cgccgtgcgc    148260
tgccccgggg agcgccacct cagccgcgcg gtcctcacct ccagcaccct cttcgggccc    148320
ggactgttcg cgagggccga ggccgcgttc gcgcgcctgt acccgactc tgcgccctg    148380 aggctgtgcc gctcctccaa cgtggcctac acggtggaca ctcgcgccgg cgagcgcacc    148440
cgcgttcccc tggctccgag ggagtaccgc cagcgcgtcc tgcccgacta cgacggctgc    148500
aaggacatgc gggcccaggc cgagggcctc gggttccacg accggacctt tgaggagggc    148560
gccgcgcaga gccaccgcgc ggccaaccga tggggactcg gggcctggct gcgcccgtg    148620 tacctcgcct gcggccggcg cggcgctggg gccgtggagc cctcggagct tctgatcccc    148680
gagctgctga gcgagttctg ccgggtggcg ctgctggagc ccgacgccga ggccgagccc    148740
ctggtgctgc ccatcaccga ggctcccgc cgccgagccc cgcgggtcga ctgggagccc    148800
gggttcggct ctcgctccac ctcggtcctg cacatggggg ccacggagct gtgcctgccg    148860
gagcccgacg acgagctcga gatcgacggg gccggcgatg tggagctggt ggttgagcac    148920
cccggcccga gccccggcgt ggcccaggcc ctccgccgcg ctcccatcaa gatcgaggtg    148980
gtgtcggacg acgaggacgg aggagactgg tgcaatccgt acctctcctg aacacgatgg    149040
agcgcctccc tgcggccgaa aacaagaaaa atcagtacat ccacaactat gtgtccgccc    149100
agcacaacgc agactccgcc tagactcccg cctccatccg ctgacgctga accccgcccc    149160
gccctctgct gacgcgaaga caaggccctc cccggacgac atgtgaggaa cgaaggggc    149220 gttgtatcta gcagcccacg ttccttattg ctcacatgtc tgcccaatcg gtgggcactt    149280
ccaggctttc ccctatcgct gagtggttgt ttttaataaa gttttttta aattttgatt    149340 gaccgcgtgg tctttgttta ctgggcgggt tgatgggcgg gttgatgggc gggttgatgg    149400
gcgggttgat gggcgggttg atgggcgggt tgatgggcgg gttgatgggc gggttgatgg    149460
gcgggttgat gggcgggttg atgggcgggt tgatgggcgg gttgatgggc gggttgatgg    149520
gcgggttgat gggcgggttg atgggcgggt tgatgggcgg gttgatgggc gggttgatgg    149580
gcgggttgat gggcgggttg atgggcgggt tgatgggcgg gttgatgggc gggttgatgg    149640
gcgggttgat gggcgggttg atgggcgggt tgatgggcgg gttgatgggc gggttgatgg    149700
gcgggttgat gggcgggttg atgggcgggt tgatgggcgg gttgatgggc gggttgatgg    149760
gcgggttgat gggcgggttg atgggcgggt tgatgggcgg gttgatggtt cctgctcctc    149820
cccttcctgc tcctcccctt cctgctcctc cccttcctgc tcctcccctt cctgctcctc    149880
cccttcctgc tcctcccctt cctgctcctc cccttcctgc tcctcccctt cctgctcctc    149940
cccttcctgc tcctcccctt cctgctcctc cccttcctgc tcctcccctt cctgctcctc    150000
cccttcctgc tcctcccctt cctgctcctc cccttcctgc tcctcccctt cctgctcctc    150060
```

-continued

```
ccccttccgct acgtcactac cgcctacgtc actaccggac tcctcccctt ccgcttccgg    150120
ccacgcccct tccggtgacg tcacaggaag tgacgtcact ttgaccccccc cccttagacc   150180 acgccccccct attcaaatgc gggggtgaga cgcgggctgg ggg                     150223
```

<210> SEQ ID NO 2
<211> LENGTH: 145597
<212> TYPE: DNA
<213> ORGANISM: Equine herpesvirus 4
<300> PUBLICATION INFORMATION:
<301> AUTHORS: Telford,E.A.
      Watson, M.S.
      Perry, J.
      Cullinane, A.A.
      Davison, A.J.
<302> TITLE: The DNA sequence of equine herpesvirus-4
<303> JOURNAL: J. Gen. Virol.
<304> VOLUME: 79
<305> ISSUE: 5
<306> PAGES: 1197-1203
<307> DATE: MAY-1998
<308> DATABASE ACCESSION NUMBER: NC 001844, NCBI
<309> DATABASE ENTRY DATE: 2000-08-01

<400> SEQUENCE: 2

```
ggccggcctc tctctcgggc gcgggcagtt gaaaaaaaaa atttgcctaa tcgccatcgt      60
gataagcaca cgttatgggc ggtgggggat gggatttcaa tggaggccac acccacatgg    120
aggccacacc cacatggagg ccacacccac atggaggcca cacccacatg gaggccacac    180
ccacatggag ccacacccca catggaggcc acacccacat ggaggccaca cccacatgga    240
ggccacaccc acatggaggc cacacccaca tggaggccac acccacatgg aggccacacc    300
cacatggagg ccacacccac atggaggcca cacccacatg gaggccacac ccacatggag    360
gccacaccca catggaggcc acacccacat ggaggccaca cccacatgga ggccacaccc    420
acatggaggc cacacccaca tggaggccac acccacatgg aggccacacc cacatggagg    480
ccacacccac atggaggcca cacccacatg gaggccacac ccacatggag gccacgcgat    540
cgaggcacgc ttgtagctgc catgccacat agtgcgggtt acacagtgcg tgttacacac    600
cgggtataca caattgttcc tgctcgttaa cttctattag ctcgcgccag ggtgtcaccg    660
tcgtgcttct ggtaaccacg acggctgcag ttatcccatt gttagtgtta tttctatccc    720
cgcaagtaac gttttcatat tgctattgct agtcccaccg cccataacgt gtgcttatca    780
cgatggcgat taggcaaatt ttttttttca actgcccgcg cccgagagag aggccggccc    840
cctaaacatt tcctaagctt ttcctttgga gctcctccct aaatgccttg gctatttagc    900
cttccgctcc tgtctgctta cactttacac ttttctgctc gtcatgaggc ccacggaagt    960
ttcacgtggt cgcgcctcct cggtatccat ctctgtgtgc ccacctcaac caagcgggaa    1020
acgacgtgca tcgctggggt gtgcacctcc acaacacagc cacgcggcat gctgtgcacc    1080
tccgcgtttg gattccagtt actcccagga acgctcgctg tcggcgctgc gcccgtcccg    1140
tgattcgcgt gtggattcca tacactcttt agggtcagtt acctacctat ccgagcaaca    1200
gcttccatca aggcctccat catacacggc tattaacccc gagggtttat tagagcgtgg    1260
agttgagaga cctcgagcgt ggaccgcgag cgtgattagc gccccaccaa gttactcgga    1320
agccatgttt caagctccgc ctgcatacga actggttcca gaactttctt gtcatcccac    1380
gcaagacccg cgcgtaattt actcacagcg ctcacgcccc caaccttctc gtagaagaga    1440
gaacccagta tgcatttttg tgattgttgt gataactatg cttttaatac tagcgttgct    1500
gctaactatt actcttagct cgctcacaaa atccaaaaat taaaacaagt ggttcaacac    1560
```

```
agttgtatta tgtttatttt cacaaacacc cctttccaaa tccacggtac actattccgg    1620
tcaacactag aatgttcaac atcagcaaga taatgtttat agcggcaaac tgtctgcaaa    1680 acttttgct gtaaagacgc ctctttactg gtcccatgtt ttcaaagctg ttactgcggc     1740
tgcgggtggt tacaaagcca tcgaggtaca cttcttctga atccagtgcg tctgtttcgc    1800
gtaaatctct tgggattcgc tctagatgta aaacagctgg actctcggag tatgtattgg    1860
aacaattgtt agcggtagcg ttctgggtgg gggttagaga ctcggtgaga acgttgttta    1920
ggctggcaga acttatgcaa gtgtattctt cgttctcgga gtcgctttca tacccatagg    1980
ggctaacgcg ggctggaccc tgccacgctg acggtggaaa tgcgactttg tcataccaca    2040
cggtagaggg tttcttttgg cgcttttttct taaatagctg agccattcgt ttgaagaata    2100
actgggacaa taactgtcgt ctgagcgact cgcgcctggg acgtacttcg gcgttaattg    2160
tggtaggtct taaagcgtgt atgcgccttc tccgcttttg gtccatgctt aaacactcca    2220
tgcctagtgg gcggagtggg ggagggcgta tgcttgtaat ttaagatcca cgttacaccc    2280
aaggagaaat tacaatctgg acagacgtcg ccctttata tgtagaacgt cacacttacg     2340
tgacgcatgt accgctgcag tactcaagaa cgccgttctt gattgaccca gcggcaaata    2400 tcgccttttgt tcctggcgtg ttgggtgtta agggcacacc cctgcagtta acatcgatgg   2460
gggtgtgctg ttctgtaaga cgcaagcact caccatcgct gacagccttg gctgaagaaa    2520
cagaaattgt actgcgttgc ttagcgggac gggttgtaga cctcccaggt ggggatgaag    2580
tgagaattgc accagatgtt ggacggtcgg gacaaaattt tggatatttt aaattttctg    2640
gaccgtctcg atttgcctat gtgaagttta taggcagagc atacgcactc ggcagcgggc    2700
gcaagtttct actgtatcta tccagaaact atcaggtgtt tggatacgaa gacggcaccg    2760
gcttgcatat gctcgccaag acactccacg attttttaaa gtttaaagga ctatccaaca    2820
gagatctggt ggtagttgac tccgttgcgc taacctcaca acttcggcct ctgacgcttc    2880
ctatacggtc tacctcggac gttgaaactt tattagcaga ggaagctacc accaaccacg    2940
cttccaccga aaaccttta ggtgagtcac aaaaacactca ccagcagcca ttaagtttct     3000
cgcttccaag cattagatct aaagcggcat cacaagtaca accaagtaac caacggttaa    3060
aaggccgcgt tgagcgagct acgtcccaca agtctactct ggaggaaact gtttcgcgta    3120
aatcaaatct atgtggagag ggtaacccac ccagcgagcc aaactgcctt acaccagaga    3180
tggcggactt tgacagcgac gcatctgtag cttctgtttt cttttaaata aaaaaaacat    3240
aacaccaaat actgtttaaa tttattgttt attgcatcgt tggcgctctt ttgcagaggt    3300 aattccccctt gcaacgctta aaattttagc ttgagcagca ttggctgctt gccaacattc    3360
tagagagaat ggagttttgc agtggcagtg aaaacacagt ccgtttatcg tagtctcctc    3420
cccgtcctgg tcacagtcgt attgtgttgc cgcactaaac ggtgcgccac acacgctgtg    3480
ttccatagcc agttcctgca ttattctggt attattgagg atgctccgaa agttgatcag    3540
gtctggaagc gagatttgtt tttcggggtc cctcttttca aacacaccta taaaaaggc     3600 atggaggcgc gcctgtatat cgcagcacgc tctaatggta taggtccgcg tgttaaggta    3660
ggacctgctt ttggcgggtt gggaggtggt ttcccacgaa ctccacgtta ggtccagagg    3720
cagcggcgac accacgttgc tgatgtccac cagtagcccc agcttgcagt cgctgctgta    3780
gcacccgcca tggtctctac agtgggtacc attatctcgt tgcttagatc cggatgcgtg    3840
ttccgcgcgg gctacgggta gcatttctaa tcggatggcc tgccgaccaa ctgggatct    3900
```

```
gcttagctct gggtaggaaa actcagtatt tccaacttta ctaaagacac cacctttaa    3960 attcaacccc caagcacctc cccgtttata ttttaaaact caacaaagct tttataaaat    4020
aatcaaaaca gtatttatta actggttaca caaacagaat ttgggttacg taacacaatt    4080
ttaaaagatt tggttacagt aaaagtattt gccgtgaagg taaacaggga ctagggtgta    4140
acttgaaacc aggctacatg tagattcttt gcaccgccgc ttgtgcaagt ctatagcctc    4200
tagggttcca gccaaacatg tccccggaac gtagttggct agagcatgcc cagcgggtcc    4260
aagtgcgtcc ggagacaccg cctcggcgcc actcccaacg cccgagcta tgcgcgccaa    4320 ggtcacaaac atgaaggtcg gaacgcacgc aacgtccgat aggcgctggt ggtcgcatag    4380
ctctgcgaga gttgggctgc ctgatgacga gaggtagcac cgcatgaatg gttctagttt    4440
taggcgcagg ttttccaaca aggctattga agagtggatg attggatctc tggtgcgcat    4500
cggaaggttt ttggtgataa tcatcttaca ccaagatatg gtttcgtcag cggaagccag    4560
tgcttcgagt aggttctccc ctcgcataac caagtcccgt agggaccgcg ccgcttctgc    4620
cgcgtgagat ctcacctcaa acagcttgta caagttttct ccatgggtaa ccagcgtgtc    4680
ccatgtaatt cttcgccctt ccggattaaa ttgttccaag ccaaagttga gcaccggaga    4740
ccacggcgat gagtgttcgg ctctaaatcc gccattttta acgggagacg taagcgtttc    4800
gcgtgcccca tggaacatgt cactgatgcg agagctcgtt acacgcttag agacgtcagc    4860
aatggcgttg gcggctgcgg cgttgagtct atcgcccgat gagcgactag acgcattacc    4920
gcttttgttg gtgttgcctc gttgcctgtt gtgatagact ctggatgcgc tgtgggttct    4980
ggtcttaaag cgccacccgc cagacggtcc ggcggtgcaa tgtccggcat cggcagattg    5040
gaaatcgcca ctcctatgac ctaggcgcat gtgtaccggc atgctcgatc tctttggcca    5100
gtttcgcgac ccctggttag cgggtgctgc ttcttggctc tgtttttccc aggcgcgctg    5160
tttccagttg tttcgccgaa agggtcgccg gcgattttg cgaccgtggg gaaatgctga    5220
tctctcgctg gtggtgtttt gcggtttggg gtttttaggc gacgctgcaa aactcaccac    5280
taggctcttc ggcacttcag agaccacatt tcgaatcgta gacattgtgc cggtagattc    5340
ggacatttca aaggcgcgct tgttaaccac ggcgctctga gcagcttcca cacacgaccc    5400
accgagagta tcatcggtgt cagatcccat tatgctcatt tcgtcatcca taggctcaca    5460
actgcttacg cttgaaagag ccatagtttt gatacagcag agtatgtctt ccagggttgt    5520 aagtttaat cagtaggtgt acccaaaaag gccaagagtg cggatctcct gggtgtcagg    5580
atttttatag agacttacaa gccgcgccca ctagttatta ttgtgacaag gactcgccca    5640
ataagccaat ttgaatacgc tgttcgtagt gaagcaaaat cgacacagcg ccaactacaa    5700
gcaacaggta cactattttt ccgcataggt tcgcaagcac agtggaacaa caactggtac    5760
acagtccttt cactccgtgc accatggggg ctgggggggct tacattagag ccgggtttgg    5820 ggggttttc gtatataatc gcaactatct ccacgattgt tacagcgatt acaaaccccc    5880
acgaagcaat tttaacataa atggggtata gctgggagca gggagtatgg actaaggtta    5940
cagttccaac aaccagaatt cttgcaaaaa gatgcgcacc cacctcgagg ccgataagcg    6000
ccagggcagc tgtgtgctca cagagaaatc ctatagggtc tcgcttaaag gttttgctga    6060
gagctaccct gcgcagagac gcttcacata gcagcaggga aaattttgta tagtgggttt    6120
ttaaaacggt agtagctaga gtgtaagcag catagttaaa ggtatagctt gtaggcgata    6180
gaaactcgtt ttggtttctg aagggtccca gcaagcggcg ctcctgccgc aaacacaaga    6240
acgcaatgta tatgatccac gctacaatga tcatctggag ctgtacgctc cataggtagg    6300
```

```
ctttacagtt tcgagttccc actactattc gcaccttatc atgtaattct ttcatgttct   6360
ttaaaacgtc cagcttggtt tcgttgaccc agttttctct gcagatatag tcaaatcctg   6420
ataggccatc accaaatcgc tttgctccat tttttgggta cgcatacact atagtggagt   6480
tgtagacttc ccacctggta gcgattccat cttttgagtc tatagaaact gtagcgtaga   6540
cgcatgggtt atgaagctta gctgtgaggg tataccaaac ggtgaacgcg cataggcag    6600
tgatcaatcc cagtacagat aggtatgccg ttctccccc gaataacatt gtgtatatta    6660
ttttgctctg ttcacctcta gcgtaaaaat ggtgcacatt ttattgttgc cgcatttttgt  6720
agcaaagcac tgttgactta tggatgcgca aagtctaccg tgagcgtcag cacttattga   6780
caaaaacgtg cgggccaatc cacgtgctga gcgaaggtgt ttagctcgca agcagctgaa   6840
cccctgtgat ctgtaggcgc ttccagatcg attaatttgc agtaaaatcc agtcaggctt   6900
ggtcactact gtgtgtactc caaccgtgtg atattcaccg gcgtggttag ggaaatgcgc   6960
actgaggtgt aacaccacct cacagagtac cacgtcgaca caaacgcct cgacagcttc    7020
gttagatttt atagacacgt tgtagctcga cagaagaaac tctagcgtgg cgcgtttagt   7080
catgatcgcc tctctatttc gagctacctt gcgctcaaaa aagctgacgt agtcaccacc   7140
gaggtttgtg attacatgag ttactgtaga actacggggg gatgcatgaa agtgaaaatt   7200
ggcagggttt gaatgctctg ctataaactc atttacattg ttgcagtttt ttggaacgac   7260
gtaaagggga tatagaccgc cataaaacctc cccagagtcg cccactttac aaaaaaatgg  7320
aaggcgaagg ctgcgaccat gcgagtaaac tccagtgtct aaaaatgaaa aatcccgtaa   7380
aacagagcac atactctccg taaacgtgcg ctctaaaaca acagcctgtt gtatgatgcg   7440
tgccacacct cgcaaagcct ccggtcccgc caagatgtac ggtggtggta ccggaacagt   7500
gatacgaaac cccatttttt ctgtacactg gcaagcgttg gtttcaagga gcagttgtag   7560
cggcgttttg tcggttgttt tattttgggg tttaaaatca cataccgctt gagcacattc   7620
attatcatca acaatcattt catagtcgtc tgtcagatca aagtgtatt cttccatggc    7680
ggcataatca tctagaaagt tagattccat gtaatattct tctacgcagt caacgtaatt   7740
tgagagcgac gagtgctcgt ttttggtacg cgctttaaaa agttgagggg gacactgagt   7800
tttgtaaaag taacacgggt aagagtccca ctgtactaca gcctcggtaa agatgagtga   7860
taatgttgtt atgatgccat ttctaaagcc tcgcattgct aggtgaagca tacccaacgg   7920
aatgggcttt tttatgtcaa aatctacatc caaaatgatg ttacttacgg caagggacga   7980
gttaaaaatc tcgtttcgat taatatacat ttgcagcgat gcgtttgaag aggccatagc   8040
ggcgcggcag acgccagtgt cgtcgcgcat aagctgcaaa tcgcgatgtg ccatcgcata   8100
atcgtccatt tgtgacaacc catcaaatga caaatcatgc tcagaagcca gccgataggt   8160
ctggtggtac atattttgtg ttacagtctc ccagcggtca tttgctataa ccgcaaatgc   8220
ctgccgtttt gagggtaaag ccactctata tacaggtgtt gggcccgaaa ttcctctttg   8280
gccaaacagc acttctagcg gcaaaactct accatcaatt ggttgtgatg atgcgatgtt   8340
taataaccgc ctagatattc cacattggga tggaacaccc ggagatagtt cttccaccacg  8400
tggctgatca gtggcggtg ttgtagtaat acactgaggt ttggtagatg gaattaaggt    8460
ttgtatccag ccatgtccag ccaaagatgt ttccaccccta tcaagcagct ttaacatttg  8520
cgtagaagtg tcacagatac tcagcgggtt gttacctgca aacatcatcg tggatgatgg   8580
ggtataagtt ttgtcactaa catactgttt gctgatagac acgggcaaac gaaccacctc   8640
```

```
agggcttaca ttatgggcaa tgtaatctat tatattgagc tgaattcgaa cctgagcaaa   8700
aaatttctca atagtgcccc gtttcagtga cgaggtagaa gttatgcgct caatgtccgc   8760
tgggtcagat atgctaaccg caagcaggtg attatagagc tgtctgcggt taaagctttc   8820
aaagtgtgcc aagtaaatgt aggtaataaa ctctctatcg gaaacacgca gtccctgtct   8880
gtctgcggca ataaactcct ccagcgcgct gacttcagac acgtctgcct gaattctaag   8940
atctacgtac ctgggaagtg ctagtgctga cggccctctg gcataccaac tttgacagca   9000
aaactgcgag aggcgggcaa acgatgtcaa gtgggtaaga tccaagttag ttgggtttgg   9060
caaacaggga acgttatacg ttttgataaa gtccttggtg gcttgtaggt cgtaggtacc   9120
accgcatcca gaatggcgaa ttgcttgaaa gaggtagtat ctggtggcca gtacaagttc   9180
cctttctcca ggaccaaatt ttgaagtaaa ccagaacggt gtggtgttgt tattgctgta   9240
tagacgtctg aacgcagtta gcaccttatt ctcatggtgt atatacacag aagttagccc   9300
gggacgacca gtactgtgac cgagaatagc agcctttacg gaacctcgct ggggtcgta   9360 ctttgcggcg gctgccgttc gtcctgttct cgctgtagcg ttgtccagag ttatagccag   9420
agccagtatc aagtcattgt ggagctggaa ggtatctccg tctacaagcg cctgaagcag   9480
tatcttagac gatattgggt gaccgtgtaa caaagtcttg gttaacgctc ttgctcctgt   9540
taaagttaaa aacgcacaca caaacattgg gcgtatgcgt tcttgcggct cgtcactagc   9600
acctcccaca ataccgctta acaaacaaaa gcttactgat ggttttcgct ctaaaagagc   9660
agccgccaac agctcctcgt ctgactgatc agttgtgtcc cagctgtcac caacatcagc   9720
gtccaatacg cgaggctggg agccaaaaag atcatcgagc tcagaactcc agtcgtagct   9780
tataacataa gcatcctcag agctctcctg gccagttaga agcatcagcg aataagtgat   9840
aacgcagcta tccgtagcat aaagaaccct aatagtggga tttggttgt ttaacgccat   9900 gtttaagtgg ctaatgtcca gtctatgtgg aactaaaaac cccgcatccc tagaagaagt   9960
ttatgagcca attatgggtg ggaagaaccc agccaccatg ctccgcctac agtccgccct  10020
ggctgcagtt aatgcacttt tgccagcaac cctcactata gaggatgtga tttcatcggc  10080
agacaacaca cggcgcttgg ttaaagccca gaccctggct cgtacctatc aagcgtgcca  10140
gcataacata gagtgtttat ccagacatag ggccagttcc gacaacccaa atttgaatgc  10200
cgtggtggct acgcacatgg ccaatgctaa gcgccttttcg gatacctgcc tcgctgctct  10260
aatgcacctc tacctgtcgg ttggggcagt ggatgccact acggacacta tggtagatca  10320
cgccattcgc atgactgctg aaaatagcgt ggtaatggcc gatgttgctg ttttggagaa  10380
gactcttgga ctggagcccc agccatcagt aatggcacat gacttactgg ccctcgaaag  10440
cagtgtgtat aattctggca attccgtgcc agtaaatgac tatccagcgg aagatgttga  10500
gtctacccag agtgtacaca gcccctttgct gtccaagcgg cctagcaaca ccgaggttgt  10560
ttgtagctcc atcccagtga atcaaacct caaatccaag cccagacgca aacccagttt  10620
ggtagcggcg taaaatttaa aaaccaataa acgatttaaa gcttttaaag gactatgttt  10680 atttatatc ttcataacac gtatagtgaa accaggggca gttatagtcc tgttgaacca  10740 aagccccct cagagcgggc actcgagggt gcgtcgtgat caaatgcttc tgtaaacttc  10800
caaaggatgg gcgtcgggtt atgtttgaca gctccggtgg gcgaataggt aggaaagggg  10860
gtgttatagt ttacgttggt gggtatcagc gcctcgtcaa tatcttccgt taacactagc  10920
tgagcaacac gctgaccctt ggtgatatat acgggatact tattgatatt aaggataaaa  10980
aagcaacacg ttctcccggt tacccaccta gttggtagca ctattaaacc ccttcgattc  11040
```

```
atagacgagc gtccaaatat acacggagta accgctgggt tagaggaata aaacacaatt    11100
ggcagttcca caaagtagct ctcatcaggt tctatagtgg cgtttgtttg tgcgctgatg    11160
tcatatcctg cgtcttcgtc gcgttttgga gcaaagtaat cgtaaaatat gttaactctt    11220
ggtgaccgcc cattttcagt taagttaatg ttagtcacgt ttatggtctc cgtgctgagt    11280
tttactagca cgagccccaa actcatacat ccagggggca ctaccgtatt tactccgttg    11340
gcaaattgta ccgctttcac gacgccgcga tatcccgagt ctactatacc gtaggcggtg    11400
tagtagttgg ctagattccc agtaaacgtt atgttgctaa aattccctgg ctcacgtcca    11460
acatgcggca aaccgctaat ttgcgcgaga acaatggcat atccgctgga gcaggcaacc    11520
cgtacaccta cgtcagtgag cacactataa aattcgcccg cacttccaag cccggcactc    11580
agctcgactg tgtggttgtt gattaacacc aacaatcttc catcagcttc tgctcgcgct    11640
tcccatccat tactacattc aaccaccacg atgttgtcag cgagattagt gacgctggcc    11700
attttaacct gccttttggt ggtgtttggt ttgaccagag gggctagcgg cgaccttgaa    11760
gcaaagcaac gactcgacgt tgcaagagaa gaagagaggc gcgacttttg gcatgcagcc    11820
tgctccggac acggatttcc aattaccacc ccgagcactg cagctattct attttatgtg    11880
tctttgcttg cagtaggcgt ggccgttgct tgccaggcat accgcgcctt cctacgaatt    11940
gtgacgctgg agatgttgcg acacctacac tgagcaacat tgtatgtata atcccggata    12000
tgttgcaacc gtttgactgt ataaaaggac tagcgctaaa cctactagaa tcattcgtgc    12060
tgaaagttcc tttctagtct acagcacttc cattagagtt tgtagaggtt tttactagtg    12120
agtaaatatg tccgatacgt ggcgtagacg tcgtagtggc ggtggtgatg ttaacgccac    12180
agaggagttc gtatactcta caattcgtaa cgaaaatagg caaagacgac cttctcgcgg    12240
aagctttgtt gtgcgagaaa acgaacttta cgataaacag cgtgtatcta gggaaaatga    12300
tttgtatgac agtgcatgcc gtaacgatga cgaagtttac accagacaaa gcagaggcgc    12360
tgccgctcac tacaacccccc aagaacacat atacgagacg tgtccaggag atgaattta    12420
cgatgcctgt gaatattctc tcgttggagg tggtaaatta tctacctccc atggccgttt    12480
gagccccaca aaaaccacac cccacccaaa gagcgcgggt gtaacccccac cccaacgtgt    12540
accagcgcga ccagctactc gtgcggcggc accgtctgca acaccaaccc agccggattg    12600
tgttgcaaaa caacgcactt cgccaggtgt aaactccata agagcggta aaagccttgc    12660
gtttagctgc accccccaaaa cgccaaagac gccatggtac ggtgcaactc acctgttcaa    12720
caaaaacgtg ttttgtgccg cagtgagtcg cgtagccgcc gcacatgcaa gcgacgcagc    12780
atcagcacta tgggacctag accctccaaa aacgaacgag gacttggaca ggtttttgaa    12840
ggctgcagca attcgcattt tggtttgcga gggatctaaa ctcctcgaaa tggcaaacgc    12900
aacaatggaa agatccccag atggggctgc agccggtcgcc cccatcggtt acgatcgccg    12960
tcctcggtta gcttctagga ggcgatcaat aaaatgtaaa cctccagcgg atgattttt    13020
cgacgacaca gattccagat aacgcatttg cataaattta tagcattaca atctcaataa    13080
aatgtaccac ttgcttattc ctttaccttta tttgtcgtgt gctctgttac tctgctggta    13140
ttcaacgcgc taccatggcg gctaacatag ccatgtttgc cgacatagaa gattacgatg    13200
acacccgctc ttgtgaatat ggctatggta cctgtgagct tatggatgtt gatggtgtgg    13260
ttgctagctt cgacgaggga atgttaagtg ccagcgagtc catttattct agcccagccc    13320
aaaagcgttt ggcgctacca ccacccaaag caactagccc caccgcatta taccagcggc    13380
```

```
tacaagccga gctgggcttt ccagagggcc aggcaatgct gtttgctatg gaaaagtgga   13440
acgaggacat gttctcggca ataccggtac atgtagattt gtacacagaa atcgccctgc   13500
tatcaacctc ggtaaacgag gtagttaaag cggggctcga tagcctgccc atacccacca   13560
actatattcc agaggtagac ttaaacgcac acggaagcga gcccttccg gaggtgcccg    13620 ctctggagga cgaactagaa acctacgtaa tatcggctca gcgattttac ctatcagagt   13680
tacgcgcacg cgaagagcac tattcgcggc tgcttagagg ctactgtgta gcgctattgc   13740
attacctgta cggcagcgct aagcggcaac tgcgcggagc cggatccgat tccgcattaa   13800
tgcataagtt taaacaggtg gtgcgtgata ggtactaccg cgagacagca aaccttgctc   13860
ggttgcttta cctacacctg tatatttctg ttaccaggga agtatcttgg cgcctccacg   13920
cgagccaggt agtgaatcag ggcatatttg tctctctcca ctatacgtgg ccgcagcgta   13980
gaaagttcga gtgcctgttt cacccagtgt tgtttaacca cggggtggta atcttggaaa   14040
acgatcccct cgagtttaat gatttacagc gtataaacta ccgccggcgt gagcttggac   14100
tgccgctgat tcgggccggg ctaattgaag aagaaaacct accccctggaa tcggagccga   14160 cattttctgg aaaactacca agaacgatcg gcttttttgac gcaccagata cgaactaaga   14220
tggaagctta ctcaaacgcg catccctcga ccccgctatt tccgctagct gagcactcgt   14280
acagtaaacg tatagatggg cgcttgtcat acggcacaac agcagaagcc atgatggacc   14340
caccatcccc cagcgccgtt ttaccagggg atccagttcc accgcttacc gtagggattc   14400
gtcagactgc tgaaacgctt gctcttccgt ctaacctcac cctacagagc atggaaactg   14460
acgttcttga ctactcatct atttcaggcg acgagctcaa ccagatgttt gacatttaat   14520
acaataaagc acgtttccaa acttaacata atggccgtat tttccgtcga tacgctgcgt   14580
gaatagaacg taatgggggg aggtgggcgt ggtctgcggg tggtgtatgt ttaaattggg   14640
cccggaggtc tataggcaag ttttgtttgc attcgtgatc tgctgcaaca aacgacaatt   14700
aactaccaat cttcaaatat cgcccattta acagtacaaa actaggggt atggcggttt     14760 tgaagctcgt agcttgccta taaaactcgc gcgccttgcc gcgagatggg tgttgctatc   14820
tagcgtagat agcgggcgtt tgccgtcaaa acctgacggt tgtactacag cgatacgaa    14880 gtagttagca tggaccaaca tcacggcgtt cgcggtgggg cgcctatacg caggcctcgc    14940
agatcaatag aaacgcgctc ccatccattt agagccgcag gaaatacaca gcgcacatac   15000
agcacgccaa gacttagtta tagagatgga ttgtctggca gagcctcttc acttgaaccc   15060
gggggccaag ctcacgatca aaatgagagc tctacacaaa gtacttcaaa taatcaacca   15120
agcacctcat tttggggata tctacgaaga gttttttcag atgatgcccc cgcgcagcca   15180
caagcaccaa ggtctcgcgc tgattttgct cctcccccg aggaggactc atccagcgag    15240
gaagaagacg aggaaggtcc ctcacaagct ccgttggatg aggaggacca gctcatgtat   15300
gctgaccaat actcagtagg taactctagt gatgataacg aagaagacta cctacagcca   15360
gaagttgaat atccaacttc cgcagaatct ggcgaatatc ataacagtgg gatgtttgca   15420
gaagaggagc cggaaagcga gtctgagtca gacatgaaaa actacgaaac gtacgaggaa   15480
aatgatacgg aagtcatatc agatgatagc catagactta ctcgtacgtg gttggatagg   15540
tctatacgct taatggacga cgcacttgca cagtcttctg aaatttctaa ggctatcact   15600
aaatctacgc gcaggttata cgatagccag tttactccag ggggtcgagg ctacaaacaa   15660
acggaaaccc cctcccagcg tttggttcat ctatcacgcg ctggtatgta cgattctgac   15720
gaaatcgtta tgacagggga ttacatggag gttgacgacg acccaaacag cgcttaccag   15780
```

```
tcatgggtgc gcgctattca ccacccggtt gccatgaacc catcatggga ggaaacaatt   15840
tccaatcaca ccaatacatc gttttctgcc gacatagact atgatataga cgagctaatc   15900
gaaatgaact tggcgcgaac accccccagtg tttgagggat tgctagacag cgcagacttt   15960
ttttacagac tacccatgct ctatacatat gctactatca ctcaagacga ggcctacgaa   16020
gagcggcagg catggtctaa tacacaggcg ctgcatggac acgaacaaag ttcttggcca   16080
gcgcttgtga gtgattactc taagggggg atgtacgtgt ccctactca ggaaccccgc    16140
gggatatggc gacgcgcgct aaaacaagca atggctcttc agctaaagct atgtgtgctt   16200
ggtttaacag aatttgtaac taagcgtgag ctcacacaac accattcagc tgtaactttt   16260
ttggtcgact cgctccttag aacagcaaaa aattgttact tggccagccg acttttagta   16320
tttgcctggg aaagacgcag ggaaactggt gtacgacgcc cagcagagcc cctcatagca   16380
ctctccgggg ttacgcttct ccaaccgctt cccccagaag tctcagaatt acttgagcag   16440
cgtacatttg atatagggtt gcgcacccccc caaagtggag tgtttagagc gttcttcgga   16500
ccgcttgtgt attgggcaga actacgcaga gccttgcgag acccagctgc cataaactgt   16560
cgctatgttg gatttcatct ccaaacatca gaaatttatt tattggcacg cgcccactct   16620
gccagcccag gctacaccaa agaagaactg gtggcaatgg aggcaacgct cacacttggg   16680
accctcatgt tagaggtagc gctacagtgg atacacgtgg ccagtgcaca gttacttagc   16740
gaaaacgatg cactgaaagc ttttaggcgt gtgagtgcgt ctattcccca cgccctggcg   16800
ccacttggta gcatacgcct acacgacgca gagtttgaag tgctaagcaa cccagatgtg   16860
atggtggcac gtgatgaaac cgccctgagc caggcgttgt ttcttggata ttttctgtt    16920
aggaccgcac taactgcgtg catgcgtgac tatgctaatg aggtggatgg gggatctaaa   16980
gagaccgtta ctggtgtgtt tttgggcgtg gggctaatta ttcagcgcct cgctggccat   17040
atgaactttt tactaaactg tatggccggc gcggcacttt atggcggtag caaaatcgcc   17100
atacactcat taactctgcc cagatacagc ctattggcgg atgttatggc ccctatgctt   17160
cagcagcagt ctttggtcga cttttggcgc gccagagacg acatgttgga ggaactagaa   17220
ataacaccac gccctggacc cccaacgcaa ggcaagcgcg tggtgctgga gatgcctttg   17280
ccctcggacg atcttccagc tatgactccc agtggccaag taaacaatgg cgccggtttg   17340
gggcgcatgg tggacatggc caaacactta cagcactata gagaaacaat tatcggagac   17400
gatgcctctt cctctgtagg taaacgtggc ttaatgaaat ctggtgtggg cgtagccgcc   17460
atgcgctgga ggcggagaaa gtaataagat actcacccaa aagcacttaa tgctgtttac   17520
gtccccggta tgctctcaca ttccgcaagc actttcatga aacctcttct acttacctag   17580
cacccaactt gtttgtacgt cttcgtaaca atctatacat taactgaata caatggaagc   17640
tagtgggtct gcctcatggg cccgcgtttc caaaaaccta atcgagcgcc gtgcagtcaa   17700
agggtgcctc ttgccgaccc caagcgatgt tatggacgct gctgttatgg ccttaaaaga   17760
cgcaaccgag aacgttgtga gcaaacacct attttctgta gatcgtacca acgcactgtc   17820
tgtgatccac accaatgctg ttccagaatc tataattaca accgccattt tacgcgatac   17880
aaacggagaa tatcgtagag aatacgaaga ttctgcaaag tgtaacttag ccgctacgga   17940
tttatcacag gatggaatgt gggaagttgt tatcaaaagc tattggcgct accttaggga   18000
atccagcggc gctgaggttg ttgatcgcgg aggcgtggga aacacaaccc agtctgtgtt   18060
atctgtactg attctccagt ctacctttgg caaaaaacgt ctatcaaaaa atccatttaa   18120
```

```
acacaaaggc ccaaatgtaa gctacaagtc taacttagaa aacctgcgcg ccgcctttac  18180
taaaatagaa aagtatatgt actatatgcg acccaatgat ccaatgacta aaagcgagga  18240
cacagaacta cggttgcacg agttactggc atacgtggca acatgttaca ggtggctatt  18300
gtggtttatg gacctgacag acgcaaaggt gttaaaaaac atagacaagg ggcccgtaat  18360
tacacacgga ccgcgcgaaa cgcgccctcc ggatgaactt gttcggcgcc acctcaaaag  18420
cggcccccgca atttccgccg gaacgggtga tgctttaacg ttatcaacag caacggccga  18480
cgctctgatc gttttactga ggatgagcgt ttcttggact tctcactcgt ggaagagcaa  18540
tacccacggg gttacgggtg ctatcgtggc cgcagttgag cttgtaacgc tcattcatca  18600
ccacttgcag tacataatta atactatatt tgctggatac gtatgttggt tggacggcgg  18660
cgtggaaaat tcatatttaa attctgcgct tcgcaaccag ggaaggtttg accattttgc  18720
gggaaaactt gttccaatca tggctacact cagctgggca acatggaaa agggaacggt  18780
tatgtggttt aaatacgcgc tagctaaaag tatagtgtgc cacggatcac ctactcagca  18840
ctacctaacc gtgcttgact caatcgcatc aaagcgcacc ggcgctggtt tacctcctgg  18900
ggcaaccttt ggtcgcacag ctaattttca aggacaattt ggctgcccgc cccagggacc  18960
tcttcctgcg ccaccaaact ctaaaactaa aagcatgttt aagcgacctg acgtggcag  19020
cgttcgcagc ttaaaacagt tacccgcatc cacaccaaac atggtttctt cagcgactac  19080
ctacaatgca gggggtaata cggccgctac aagcggtcaa ggtgaggaag ccatacaaat  19140
acacgcttcc ggtgaactta atgactgcat ttggtatta aatggtacct actcacatca  19200
gcgcagcgac agtagctcgt ctgataatag ctcgtgctct agcacagaaa ctgagtacat  19260
cactatatcc tccacgcctt cgccaaccag agaagttgtg tataccgatc cgcttttggg  19320
ttcggacgaa gaaaaagacg caagtccaca accagctaat acagtgagcg aatactcatc  19380
tcccgcaaat tccggctata tgcgcccccg gagcacgctt gcggaggaaa tttggcaatt  19440
gcgggactct gattacactc cctacatgcg ccctagtcgc gcgggtcgcc cacgtttaag  19500
attggaagac cagactttac aaacattacc gggttgcaag ccacccgcaa attctccaga  19560
agacaatttt gaggacacct tatttttcgtc gtcccagatt tactccgata acgcacacag  19620
taccttttaga ccaagagcca ggtgtgttga cgacgaatat gggttaactg cacttgcagc  19680
tctcagcgcc tcccaagcaa aagccaggcg ggtgcgtttg ggtactacca ctcccacttc  19740
tgctaacgaa gcaactgaga aatacaccac acccagcagt ggcggctgta tcaggcgaac  19800
cctttcaaca agcgagtctc ccgaaagcag cccggagcaa caagagcgtg taagctcgct  19860
gtaaccaccc catgtaccat ttaaaattat attaataaaa acatttaacg aataaaatct  19920
taaaatatta atactttatt taagcactca caaacacctt taaacagggt caaatgttgc  19980
gcctataact ctgtatattc cagcgtggag ttatctatta ctgcaaaaat ggaagaatgt  20040
ggtcaagccg aagcgcctgg cgggccttgt aaatcaactc tccaagtggg ctgagtgggc  20100
gggcggcgta gcacacacta acgcgttttc tggagcatac cgagttttgt gaaaagttac  20160
agtttgcaag tggtgtgtcc gtcagattta gttttctcc agccgattcg ttgatgccaa  20220
tgtttaggca gtccagaagg ttcattatca ggacagtagt gttgtccggg gccggcatct  20280
cagaatatgc tccacataca gcccctattt cgctagagtt gctgctgttg taagcgtcta  20340
gcgacacggg gcgtacacac tcgtcaccca gaccaaaggt ttgcgctgga catggtgctg  20400
tgcgtagcgc gaccatgggt actgttagga caaaggtaga caccaaaagt gtggtggtca  20460
ttagaacccc catcgcaaac atacccatcg taaaacagag gcagcggcat ctagatctgc  20520
```

```
gttttggtcg gcgccgtttt gtataaacga gttcggttgg ttggggtaga gtcggcagcg    20580
gtggtgtaaa ccccaaaaca gtctttgtag gtagttgggg agcttgatca ttaccggcag    20640
ctgtatcaag ctccagtaat tgataatctt ttagcgaagc tgttgggtct ccagacatat    20700
tttcgcttta cttagacgtt atggctgcat agagatgagc gtataatgca gagtaaaatg    20760
gctttataaa tccagccggg gcgcgattgt aacacaaaac taacggtttc cacctagagc    20820
atgaaaacgc atatgtttaa taccgtattt ataagagtgc gtttgtgaag acagccagcc    20880
agactgcggt ttgaactgta tttaaaaaaa ccagctgctg ttcaaactga cgacgagctt    20940
agaagtctgc tttcttgtac ggcacctgcg agggttttga gcagtaaaaa caaacggctg    21000
taatgagaac aaccagcgct agcgctgcgg ccccgcaagt aacggcgatg atgctagtta    21060
aaacgggcat gtcctcaaca ataggggatg catcatatac aacgctgtca gaaaacattg    21120
gaaggccgtc cggtaaccc tctatgatgc agttatactc tcgctctccg ttttcttccg     21180 acagggcct gctactccgc atgttgacta atcctgggtg gcttgagcaa actcccgttg     21240
ttacgtcttg tgatgggacc cccggtaaat ggtcgttaac gacccacgat acaaacactc    21300
cgttgctagg tacacattct gccgtacaaa ctgctgcacc atcttcaacg tttacggaca    21360
cggttggggc cacgaacaca gagggcgtgc ctgctttggc catgcgagaa aaggatacct    21420
cgtctctgta ccattctatg ctacagcgga ggctggggg atattcttcg tcgggtcag     21480 ctgggattga tacagtcgag atgcgagtga tgagaccatc cacccacaca ctagaagcat    21540
tggtaacata ctttgtaaaa tcaacctctt tggcgttttt ataccacctc agcttaacag    21600
agttgtgggg aaagtagcta gcaactacgc acacggctct gtggttttca cccttcaaac    21660
ttgggtgaac ggagaggtcc attaggggtg cgttgtacgt taacacggta acgctggtac    21720
tgttaatgag tgagccgttt ttggcaaaca agtaccacac ataaactccc gcggtacgcc    21780
agtctataga ttttatgttt agtggaaaat ttgtaccacc gttcgtgtgg gccgggaggt    21840
tgaacagttg acgcttaggt agcctgtctg gaataacgcc cagctggcca acccttcgag    21900
atttcgcgct agaatgtgcg gttgaaaata acagcagggt ttggtctttg gtagcgttgt    21960
ggttaacata gttttcttgg tcaccaggag gcgtgtctga aaatggggtg cgctggttta    22020
ggtgaatttc tagtctgtat tcactgtgat ttacacttac tgttgtagaa cagttaatgg    22080
taacagatgt gtagtaggga accgatatga gactatttgt gcatgtaatt gtattttcat    22140
gtgaatgtgg gtgactcggc gttggtgtag cttcggtgcc gtttacatcg gttgagttgt    22200
tcgtggctgt tgaattatta gagtccgtac tggttgtgta agttggtgtg actggagaac    22260
tggtgccttc gccagtattt gtggttggtg tggctggact ggcgctagca ctggtcccag    22320
acgtgcgtgt taatataaac cccccacaga ttatatacgc aaatgttatg aatcgcatta    22380
tatttaccaa acccattgct gtgggttata tgtttgcgat tttccacaaa gaacaataat    22440
aactcttctg gtcggagagt tataagcata ccgtgcccca aagtgtgtca tttaaaggcg    22500
gccttcttta tgtgaattcg accgatgttt aaatcaatac accttgtggt tgttgttaat    22560
actaattgac atgtttaatg tgtgattata gttgcgtaac ataaacccgc tgcaacatac    22620
acactaacaa tcagccacct tgaaatgtgg gttgcggcca acggctggc ccccgttgcg     22680 cgcttacgaa ggtacaaagc cccaagtacg cccccggacg tagtaaatgc aagcgaaatg    22740
ggagcggcca cccaataccc aaatgctgct aataccacgc aaactgcgtg ggccgtggcg    22800
tgaattccgg agctagcctc ggcggtgtag tttattctga cgataagctg ctccaaaaac    22860
```

```
atcgcagaaa cgtgtccaac ggttaaacaa aaaacaacat atgctggcgt ttgccacacg   22920
tttgaaagtc cgtaacccaa gcgcagtacg atccaaataa tcggggttgc gtgtgtccccc  22980 acggccggag aaaatatcac ccccggaagt tctttgaaaa acttgaacag ggaaaccttt   23040
tcttctgcaa cttcttcaat ttttggttcg gctccagcat ttgttatcca cgtgtagtta   23100
actccgcggc caaggtcagt aaaggtgcgc atacacgcat accgtccgat gcgatagtga   23160
caagtgtctc tgagattgag tccaaagttt gcgcaagaag tgattatagc tatggctatt   23220
cccagaccaa ctggtacatc tttgttgtta atttctacga gcttggcgga agcccctagc   23280
aaacacccac taataatagc aagcaggctg gctctgaagt gagttcctgt tccgtttgcg   23340
gcgcatatga cataaaataa agagatttga gcaccagata taaacacaaa caagatacaa   23400
actgtaacaa caataagcaa ctgttccttt ttgatgatgt gtccagcaac ccaaacaccg   23460
gcagctatta gtgttgagat cgcctgaaca aatcgacaca cagtcactag ggtttccatc   23520
ctagatatat gaacgcgaat taggcttaat acatacagcg atattagcat catgatcaga   23580
catgttgagt tcttggtgag taagtcaacg tgtattatcg atgaagttaa aacgcaggct   23640
tgaagtccaa ttccaatgaa agcttttgaa gctgcccatg tacatggcat gcagcccttc   23700
tgggatccgg tgcagcgctg cacagaaaac gagcttaaca caacacatga gtcttcccca   23760
agttctctcc ctggacggta aatcatgctt gccaaccttg atgtagcaag ccaccctctc   23820
ggagagtttg aggtacagga ctccaaaagg acggtttat gcccaaggta ttagtcataa   23880
aacaattagt gggcgttttc tacaattcta aataggttta ataaaaacaa aacacttgat   23940
tatacgttat ttaaaatatg cgttttatt tttcataaca caggtatggt aatagctcaa   24000
attaagaaaa gttaatggga gcttcgggac agggaatttt ggctccgttt ttgtccatca   24060
acaaaacaaa atttgtttta aacagctttt tgtctggaga tagtttcttt gggggactgt   24120
tgctgtcgtc ttcgtctgat gcgcgccgct ttaagccaac gccgagtgag tttggtgaaa   24180
aagcagaatg ggaaaacccc accttgcacg gctgctgagg ataggagcac ataaaaaaca   24240
tcatgacgct aaacggttgc ttggtcgaga gtccaatcat gggaatagat tctggctcca   24300
aaaaaaagtt gagcacggcc ccagcgtttt tgagcttaag cttttgaatt agctgcttga   24360
agttagtgtc ctcctctagt aacagcgtaa acagcttgcg accgctaatg ccccttattg   24420
gttctggcgc tgtctttttt gttttagcg gcattttttc caataaactg gaacttgact   24480
ccatgccaca ctttgtcgca ttctggtagt ccacagaaaa caccacctgc ctatctccag   24540
atcgtacctg gagagtgtcg tcaaaaaggc actggaatgt aatgggctcg ttggcttgtt   24600
tgcagacccc caaaatctta tttagctgct gtttagatag cgacattgaa acgtccggct   24660
tgcgcgtggg tagcatcaga gagtagttgt tgaactcatg tttaaccagt ttcgttgaaa   24720
ttgcttgggt tgtgttttct ggatccgatc ccatatccat atcgtcttcc atttgatcgc   24780
ttgtggaaaa cacagtttgc gtgagtatcc tggtaggtga agcgttttct atttcgaaaa   24840
ctactttact cacggttggc tgggccttgg tccggaatgc gtccaataaa cccctgcgtc   24900
cgtccacgtt ggctaaaaac accgcaggtg gggcttcttg ccaagagtac gaggccatgt   24960
tgttcgtttg gatggggatg tagacttgct cgcccccgac gctggtgtga attagcaatc   25020
cgtcctcgtt gaagatcaaa aaggcatttt tgagactagg agcaatagga gtgagctatct 25080 cgagggcatc tctcagagat tcgcgctcaa aaacagccat ggctctttgt ctctccacgg   25140
ggttgtcgat agctggtaat gcgttcaata ggaagttgtt ggggtgagat ccacctgagc   25200
gcatcgttcg aggaagagcc atcgctgtag ctgcaaagat tgggccaagc agctcgaagc   25260
```

```
actctatatt agagcgtaac aagcagtact ttaacccacc ccggagcact tcttatagag   25320
tttcacgcta gagataaaaa gggttaatat gacgtaacca tgggagtggt taatgaggga   25380
tgggacccaa ttcaccgtca gttaagatat cgaggcattg taggcgtgta gttttaagct   25440
gcgccagtta gagcaagcgc aatattgtgt tgtagtgccg actcgaaatg ccgttaagga   25500
taaataatcg tattattgta atagggaaat ttaggggagg ggtttcaatg gtgggcagag   25560
ctaaacttaa caccaatgga aagcttgcct aatcgctcac attaatttag attttcgact   25620
tgtgtccaac tctgcttata ttagcccgcc ttttggtagg gccagttgga gttactgcgg   25680
ggcaattttg gaggttttac ctggtgccca ttcaatttac tacttcagta ccatatatcg   25740
atttgttgcc cagtttttat caagatggga ctgtttggac tcttaaaata cgcgtactca   25800
aaccggcttg tgaaacacga tgccattact actccaccag gaattatgac accgatagct   25860
atagatcttt ggaatgttat gtacactctc atggaaaagt ttgagtatga ccgcagcttt   25920
cccatggacg gcgctgcagt tactgctaag tgttttttt ccctgcttag gcttttgttg   25980
aagaggtcat actatcccat cttcgtgtcg gacagaggta tatacggtga tgggagagta   26040
aagcaggggg ccaaggctat tgttagtcaa acaatgagca gctacggtgg atctgggcgc   26100
atctcgagct cgtgttttac cggcgatgaa catgatgttg aattgctgga agagtatggc   26160
gaaaccaacg gttccaccac ccagccagac atctgccaac ccaatgaaac ggccacggtt   26220
tgtgtagagc cagcgcgtaa atgcgaacac agctctacgc gctggagcgc acttgatggc   26280
gctccacgcc tttcgtaccg gctctgtgtt aacttgattc gacacttggg ataccctac   26340 gttaacgcat gtaatcttga ggctgatgac gtttgcgcca acttatacca caccaatacc   26400
gtcgcgcaaa tctacactac cgatacagat ctcattctaa tgggctgcga tattattttg   26460
gacattatgc cattgtttcc ccctacccct cgctgctgcg acgttttgat ggatttgggt   26520
gttacctatg atgagttttt gacggagttt gttcggtgcc acaccgatct ccacgagact   26580
caaaccctag cttctgtaca gagtgtcatt cgctctttat actcaccccc agatgaagac   26640
gaaagcaccg agacgcagca tgctatatca ggacatgcat ggcgttgccc taagagaaa   26700 cgaggaatct catggcgcag acaaaacgat gattattctg gctcatcaaa tgatgatagc   26760
gacaactcag atagcagcga tgaggatgta gcatgtttat ctgatagagg ttgtaggtac   26820
cgcgaacgcc cagcagcaga taccgtgaac aaacgtcagg ggcgtaggtc aatagaagcc   26880
tccagccgta ttgtacacct aaaatatacg tctagatatc cgcccattat ggaatcggct   26940
cctcgtgctt tagtgcgaat ggccccacca aaaactcgtc atgaagtttt ggagagaaag   27000
tttgtaaaac acgttgtttc tatgctaacg ccggaacgca gagggcatt gtctataata   27060 cgtcgcctac ccattactca agagccttca aactttctc tggtccacga tacctaaaa   27120 aacttagtat ccgaacacga aattgtcaga gagcttgcta atatgttttg gaaccacatt   27180 cccacccca ctgattacaa cactgtgttg gttaactact gggatgactg tggacaccga   27240
agacaatggt cttaaataaa gttaaatcgg gagtatcttt tctcagtatt ttttaaatc   27300 gcgtacatcc aacacgcaaa caagacaaat aagtgaatca aaattagttt ttattttac   27360 attacagatc gtttataaga gttcccgagt atgcggtgct tcgcctttca aaaaagttgg   27420 tatgttttc cacagtcatg aaagctaggg ggaagcttgg tgggggttg ggagcattaa   27480 acagcggaga tagtccaatt tcccccaaaa gcctgtccgc gctatagcgt acgtagcata   27540
tgatggcttc aatgtccaac aggtgggtgc ttttgggggc atgggaaagc aaaaattcac   27600
```

```
actcgatgtt tacggcctca gaaaacagcg cataaatcct cgttggagct ggcttttcaa   27660
aaccccaag  gtagttgttg tagatacagc acgaggcgtt ggtgtgaatt gcttcgtcgc   27720
ggctaattaa atcattactt tgacaggtta ccacaaagag attgtgggtg cgaagatatg   27780
cgatggacgc aaaggacgac gcgaagaaaa cgccctctat aatatcatc  aaaatatact   27840
tttccgccac agatttgcat tctcgcacct ttgcttgcaa ccaagatacc tttaggtcta   27900
tggccacgtc tttgacaaca gatgcgacat acctagcgcg cgctgttgcg tcgtttccaa   27960
acaacataag ctgtatagcg ctatatactc tggagtgcgt tacttcaata gactcttgct   28020
caatgtagta gtgaagaatg tccttttgag taaatagtgc ggataaatct cccaggttta   28080
aatttaccaa gtcgtcagca gcagataaaa aggcaaacaa aaaccggtaa aactctcgct   28140
cggctggcgc gagtttagca acgtccttga ggtcatcaga aattggaagg tccgtatcca   28200
gccagcggtt ggcaacgctc aacaagcgta ggtgttcaat atcgggacat tccggcgtat   28260
agaaatacgc atttatcaat aactcgtcag caaaatctgt ttttttagag ttttcgaggg   28320
ccataattat tttcccgccc tgggcaaaat ggcgaggctg ccctacaagc tgcagctggt   28380
gcagactagg tctccgccaa caaagactcc gttgtttgtt gccttcttga ttttgcagta   28440
gtacatgcct gttttaagtc cgcgtttata tgcgtggacc aaaagattca taattctgga   28500
ggcggggagt tttccgtcag caggctcagt tataaacaaa gacatggatt ggctctggtc   28560
cacaaacgca gccctgtcag cacacatgtt aattagcata gtctggtcgt actcaaatgc   28620
tgttttaaac ttactgaggg ggtgaccaac tggcaaatca ccaaacgctc ccacaactga   28680
ccatttcgca gcttctagcg tagatagcgc ttgtaagcgc gcgcattcct gtggaaaaat   28740
acttctgatg gtgcgcatta gcagtacatt gggcctgagt acttccccgg tagcagtaac   28800
tttgctaaac aggtttgtgt aaacaggaga aaaccctcg  ctgctctcgg taacctgtga   28860
cgaagatact gttggcatat aggctacaaa ctgagaattg tacaagccgt attgttttat   28920
gtcagtgcga agtctacgcc aggcgttgcg gtttgttagt gttacatttg ggtaggcatc   28980
aaagggtagt tcccccccgac tgtacttgct gtcttcaaac cctttaaagg gttgcatacc   29040
cagcttgcag agcgttgcgc tggccttcat agagttcaat aacagccttt ctgctatttg   29100
cttgtttagt tggtgcgcct ctggagatgc catatccagg tccagcatca aaaacgtggt   29160
atgtagcccc tgaattccaa gtcccagcga ccggttttct tcaacgcctt tctgggattt   29220
aacagttgga tatgtgctgg cacacatcat cgcattgaca aaaattgtgg cagttgcggc   29280
agcgcggccc agagcggcga agtcaaaata tggcacacct gcaatatttg gaggtggaag   29340
ggctagacat tttgggaggt tgatgctggc tagattacac accccgtttt gggtttcgtc   29400
ggcatgctgg ataatttctg tgcatagatt agacccatt  atcgcacctc tcttgcgcat   29460
gtcaaagtgg tagtgcctgt tgcacgcgtc tttaaacatc aaaaatgggc ttcctgtcat   29520
tacagcactt ctaactatga taaaggccat gtcctgtatg ggaatagcgt ctatcccaaa   29580
tccacaccgc tccaggcgct catattcccg tgtgaaatca tttccgtaca tatggcagag   29640
gtgcgatgca gtatcatcaa acagagtcca cattatgccg ctttctccat ccacgtaccc   29700
ttgatagcgg tcaaaaaaca ggtctggggt ccacatacaa gcaaagatgt tgtcgcagcg   29760
cacagtttcg tctctggcca gcattccgcg catatttaaa atggcgcgga tgtctgcgtg   29820
ccagggttcg aaataaacac acactcctgt tggtctttca ccgtcgctgt taatggccat   29880
ggtcatagag tctagtagct ttaggagagc catgacaccc cgtgaacaac cttctgtggg   29940
tggagtgtta aacctctgta aagacagtcc aattcctcct cggttgcaca aaatgggtcc   30000
```

```
aacctcttcc ataagagccg gaattgcaga gttcatatct gttaccctgg ggtttagcaa   30060
ataacagctg gccatagacc cacagtctct cccaccaaac agcataattg gcgtggccgg   30120
aatgacaacc tgtccggcta gcgcagtaaa aaaggctctg aaaatatatg tccagccaac   30180
ctcaccgcta accaacacgc gagccattgc tggttgttcc atagtatagt gcgtagcagt   30240
agttgcaagt ctaagaaaaa attgccccat ggactctaga cgtccgcctc gcattttggc   30300
taaatacatt tcttcatact ttagcgcaga ttgcaggcct aatgaacaca aatctcggta   30360
ttccgatgtt tcaaacgagt tgagggtttt ctgaacaaag tcaatgtgtt ccaatatggc   30420
ctgttccacg acatcgctaa gatcaatctc agacgatttt agccaatatt tcaggtctgt   30480
gttgcgtgct ttaattcgta ggtgtacaag ctccccgcac gcaatgtaaa ggcgttcgtc   30540
gactctgcac agcggcttga gtttatccac gactctggtg atatactcta acacctgttc   30600
tcgagacggg cgaggtgcca gcgttgttga taattcgctg gaatatccat actctttgat   30660
ggtattcacg ttggatataa tatcggaaac aatccccagt ggacagtcgg tgctcaaaaa   30720
atccaaagcc ataatttcgt ttagggtaaa agtgttccaa gacactatta ccaaaaacta   30780
gagcataaag tgtaaagaac agtggttttg caccgactta tgtatggtaa gctctatacg   30840
tagcttatta cgtatattag cttttattgg tcgctaagtt tatccctaat tgtcacgcgt   30900
ggtaaaaaca acaacatagt caagatcgtt aatttgcaaa gttatactgg ctttatttaa   30960
actggtttag tagctacact cgacccaatc ttgtgggtcc catcgtacat tttccaacca   31020
aaccactggc atatccacgc tgccaaatct ctcgctgcgg cgaatggttc tgggggagtc   31080
cgaggcaatc gccccaagtc gcatgtacgc tgcgtacata cacgaggttt tgtttggcct   31140
accccgcagg tcaggtgccc actgatataa cgcgttggta aattctctgt tatttagacg   31200
tgagggtggg catctaggct cgcacggccg gttggcaagt tcctgaagcg gtagagcagc   31260
gttagggtgt ggatctggtg cgtcggctcc ctcggttccc ctaattgcgg tttcggtgcg   31320
ggctttgtga aataggaaac taacagcatc ctcgaaggct acttcgtcaa acttactcac   31380
cgcaacatac accctcacac cttctctgcg taaacgctgg ttataaacaa aaattaggta   31440
aacaaacttt gcgctggcat cacctagttt tagctcgtgg tcaacatcca aaaacgcaca   31500
cgctgggacg taaacactag acctgggcat cgcagagttg ttggttcggg cgccctcttg   31560
aacaccacac gccacggcgg taatactggc aagcttgtcc tgaattacgt cggacagaag   31620
gccgccaaac acgctcatgt gtttatgtgg aaaaacgtgg gttctgacca ttgcctgtaa   31680
atattcccca aacctatcca ggcgctgttc cgtccttcgg tcacggtagt tagcaagcac   31740
gtgagcccta acggcatcgg ccgcagcctt gtctgagtac tcgatggatc tagaggctat   31800
caaaaacgta agagatagca acgatggtct gagtccagtt gtgtctgatc gacctgacac   31860
agatagttca gacagcgctg cccaggcttc gtctaaatcc tggggatttc gccctggtgg   31920
ggtgctagat ggcgacgacc cgatggcatc aaggtggttt cgtaggcgaa ttattggaag   31980
tccgggtttc tcagcggttg ggtcacaaaa gtctgtcagc gttacctggc gggtaagttt   32040
tagcgaaggt tgggagtttg acagcaccca cgagttatgg tctgagttga tggccgcagt   32100
tactacaccc gcagatgaga tttgaatgcc gcccatgttg ctgatcgtta tactatttgg   32160
agtagcatga acaaaacctg gcagccagtc cagcgtgttg ggtaacccaa aggctgcatt   32220
gctgcgtccg cgctgatgtg gaaatccagc gaagggggga acctgttccc atctgacacc   32280
cccattggcg tctgtataca taatgttgct cattccattt ccaatttgaa caaatctatt   32340
```

```
tcccccgaga ttcatttttgg ttttttcacc agcggcgtat aagatagctg ctatactact   32400
ttcttgaagg tggtaactta accaacttta ataacgaaaa cacacgctga cgtgctctgc   32460
tcggggcacg cgggagaaat tgcaacaaac gcgtgccaga gggctttatc taccactcag   32520
cgcgcgaaaa tatcattatt gggtatttaa aaataacaca acccttgtct gatcaatcag   32580
aggagtgtta gtacgcaatg cgtaatacgt ttaaaaatac cgggccatat taaacgcgta   32640
agcgctaacc tcaacactca cacaccgtcg agtggtggcg cgttcggcca caaagtcatt   32700
ctgcaaaaat catggcgcgc gaagactggt ccatgcgagc cctggttaac acactggctg   32760
ggctgctagg agaaaccgat acagatgtta ccagcatgga gcccgcgatg ttgatggttc   32820
tcaaatcttc aatatcagag tttttttgt ccaccgacac ggtatctgtg aagaggcag     32880 cggaattatt tccccgttta cagtttctag catgcagggc ttatgcagca tctcatacac   32940
ccgaagctgc catgttagca gaaaacctgt cgggtttggt cctatggcga ataccaaa     33000 attggaccga ccgggaaacg gaagccgtgg accagatgtt tgtgctgttg gaaattatga   33060
acggagaatc tggagtctat atgctctcca ataacaacct gaggatatcg gccaaatatg   33120
gcccatccaa catgcaccta atggtcagca cttggcttgg tacctttcgc aatgttatgt   33180
tgtcaattgc gaacacaacc ccagatgcaa tgtttaatgc aagacgaatt gaggccatag   33240
aggagttttc caagcctctc gttcataaaa ggtttgactt gatatacgat atgccttttg   33300
tacaagaagg tttgagaatt gttgctgcaa aaattaactg gctactacca tttggactta   33360
tagccaagag gtccaaggac acgagcatgg ctccactcac acgggcacta tttttgttgt   33420
cgctagtaga ttcatacttt cccaaaggaa ccgctactaa tagtagcatg aaagcattga   33480
cgatatattt tcgcgagata gtaagaaata ttgacaacag tgcgtttgtg ccagtaactg   33540
aagttaacgc taccccgcgt accgcctatg aagttagagt gtcatcagct atagtacatc   33600
aaaacccata cgttactgac acaaaggcgg gaatggtagc ggagcgcgtg cgcaccgacg   33660 ccgaaattt atcgtccggt gcgctgttga gttcgggagc gctttctgca catgtaactg    33720
cagttgctaa actactggcg tttaacgacc aaaacgacac gtcgtctgtg gctagagcgc   33780
gtgtagcaga acatgcgagt aacacctggg aagctattca agccagtaca acaccggccc   33840
aagtcgtgga agccctagtt actgcagggt ttacttcgac acactgtgga attttggaac   33900
gtgtagtagt ggactatttc acacgcctac gtagcacagc tgaaagtagg ccgggtcaag   33960
acaactccct ggattacgca caacaagtgg ttggatgtgt gtccatagtc ggaggagtcg   34020
ttttcagatt actgatgtct tatggatttg gccttgacta catacgtgac tacacaacaa   34080
cgatatctac actggagccg gtgtataacg agcttttact agcactcggt ttggcagaca   34140
agggcgtgga acaaacttta cggcgtagca tggcaccgcg cccgtacatg aactacatat   34200
cagcagcacg cgcagcacta gacaatgagc tactaatagt tgaaaagcgc actactggtc   34260
caggaaccca tagcgccgca cgagagtcac tcctaacatg gtttgacttt agggctagag   34320
atcgctgggg tgttaggata ccagatagag atacaacacc agcgcaagtt ttagcgccaa   34380
ttactgcatc aatttattca gacgacgact aatagcagc ggcagccaaa ctttccttcg    34440
atgcattgga tgccccacct gctcaaatta tagacgaccc ctcgtttgcg ccatacattc   34500
tatctacggt ggtattagac gcgttttacg ctatttaac agctcggttt tccgcagact    34560
ctatatccca agcgctgcgc gtactttcat gggcgagaga ctatggcgcg ggtcaattg    34620 ctaacgttga cgggtacaga actaaactaa cggctataat agcatcattg tccccatttt   34680
tacaaaagga cgcgcaaaca ccaacgatgg cacatgccaa caacgtagac gcgcttttag   34740
```

```
gtgaacttca cactgtagtg gctgctgcta tcgctttaat accagaacgt gcgcgcatgc    34800
ctttaccgga acggccaacc gttagaacca gtactttttt ggcaggcata tttttaacgg    34860
ctgttttcaa gaggctagaa actctagctg gacatactgc agagctcacc aatagcatct    34920
taggaaccgc gtctggaata gtttcatccg ttgttactct taatcgtttt tttaactgtc    34980
gcttgatgcc tgttatgggc caccacgctg tattaattta cccacaatcg tctcaggctg    35040
cgccatttgg tagatggcgt ttagttgatg ttgttgacgc cgttggaagc atatacaacg    35100
aagttagcga cttgcgcgcc gacctgcgcg ccgatgttgt tacccttaaa ggagacatgg    35160
cactggccac agaggcccta caagagtgtg aagccctggc ctccaaaaca gagggaactc    35220
gtttcggtaa actattcaac gctctgctta cgcgccacac acagctagcc agagcgcaga    35280
gtggtctcgc cataaaggct ggtaagctgc tgggggcctc cgaggcaccc ggcttaaaac    35340
acgtgaatac gttttttacag agatggggag ccattagcat catttaccaa aaagctactt    35400
ccggatctac cccagaggca aatattacgt ctctcgcaaa cactttacgt cgcgtatggg    35460
acgaggtaca gcaagagcgc aaattaactc cccccaaccg caaattttcc aacaaagatc    35520
ttggccttgc tgtagaacgt ctaatgggag gctatccaga agtgttagat gacgacagta    35580
acagcacggc gctgacacat agatttaacg tcgattcgtg gcaaagtgtt aacatggacg    35640 cttttgcgtaa gcgagttgaa cttccggcta acatcgactc tattcgcggg aacgatgggc    35700
tattaacgcg cgaatattta aagaaagaag accttctcgc agaaatagat gccatttta    35760 acaccacaaa gcaataaagt taattttttca gacccggtac ttgagtgttg tgtgtaccta    35820
ttttccactg agggaggcgc gtattcgcat gtgggaaaaa aaggtgggca tacaatttaa    35880
ataacgttaa aagaagttgc agcgcgcaac gctgctcact gctccgcgcg aatcactagc    35940
gtacggggtg gattacccaa acgctctggg ttatacaaac tacgctagtg ttggatttg    36000 taccgatggc acagacgctc ccacctgttc caacggccgg tggggcccag gctgatgtgg    36060
tggttatagg ctacagaaac caatacgact caaaacttgg ggtggggtcg catgtatcat    36120
gtttaagatc atcgctgtct ttttttgcgcc taattttttac gcatggcata gactttgcat    36180
taactgcaga tagcgtggat ggagcgcttg ttgagggacg agcatggaca gttgctggaa    36240
gcaagtcccg ggaagcgtgt atggtttcta ttgtggagct tccaaacaaa attacctacg    36300
caaactctac taactcgcta tgctgcgtat tttctcgact atatggtgac agtggatttt    36360
acatgcaccc cggtgaaggg tttcagagta cacaaatacc agctcgccag ttcttcgatg    36420
gagtgtggaa gtcacgatca gagtcttttg cactagttac tatagggct accggcttgg    36480 ctgtgtatcg ccacggggat gttgcgtatg ttttttgatcc gcatggccac ggtaatgtta    36540
ccgaggcatt tgtagttcgc gtaccatctc gcgacgttta cgcgtatctg actggatacg    36600
cgtccacaga tcctgagtct gactgggctg gcgcgcttgt attttttcgtg acatgcggtc    36660 caacggaaag tgaacccaac ttttttaatttt ctgcaacgtc actgctatat ggtataagcg    36720
aaacctacct atcggacgag aactatgtgg agcgtcaggt tgagactagt caccctgaaa    36780
tcactacacc cccaccaata acagatgtgg gcatgggatc ggtatccgaa gcgtggcagt    36840
accaggaact agacaatggt gcggctgcac aagatactga catggacgct tcaactccaa    36900
cggctacacc agttagagcc agtgttatta gacaaccaac agaaaagaga gtgtccttgc    36960
ccaagcggcg tcggccccg tggactcccc ccaccagtag cgaaaaccta actacggccg    37020
ataacacaca cacagctgcc ggcaggccta gtcaaaaaat taggacatcg acggcgaagg    37080
```

-continued

```
tttcagatgt aaccgcaagt aataacggcg acgtctgggc cgaggtattg gatgatgggg   37140
gagtaactaa cgcaggtatt tctgaccaaa cattgagtaa caatgtaccc gacaccccag   37200
cgcatggtga cgcgctagcc atggaaacca cacgagcggc cgacgacgta ctcaaaaccc   37260
ggaggatttt caggatttct ggcgaagacg aagcaccgta cgaccttggt gatgctgtgg   37320
gggtcctagg cgtggagata gaggacctaa ttacgcgagc cgatgagctg gatgtgctca   37380
gctctgcgtg tgttgactca acggtgtgga ttaccttacc aaataacaat ccagatatgg   37440
accttataga gcagtttatc accatgatat ttaatagact tttggcgttt ttggtggaaa   37500
atggcgcacg aacacgctca gactctccat ccgtcgtagc tactctcttt tcggatgtgc   37560
tagcggcagt accagaccaa tccgccgtgg taaacctgtt gagggttacg ggaatggctc   37620
ttagcgacgt tgcatcttac aagtctattc tgaatatggt cgctaacaac gattcgcatg   37680
tgggagagct agcagttatc aaactggagc tcgtggcctt ggaagttaca aaactaacac   37740
ggtcgctcgt ggcaaaggtt aaagaattgg agcgcgacgt tacaagctgt acagttaacc   37800
cgctggggtt gtacacatac ctaactgaaa aactggttga tgagatgact aaacacggcg   37860
gtgacctatt tgcacgcgaa ccaaaacctg gcgaagcaac gcttacagag caaatcggat   37920
cgctgttcag aaaagcgcgc accagagagg cgcgagccac gcgcactaac gcattttgg    37980 caagggacct caacgccata gaagctgccg ttcatgcggc acacgacaag tttgacgcaa   38040
ttgagattaa acccgcggac cccagcgaca cctcaaacat ggacgagttg gcaaggtcgt   38100
tagaccttgc ctcagtccct aaccgcatag ctaaagtggc gaagaaggta gaaagccttg   38160
tagctgactc tattcgcgag tactttctca ggggtgttca atacagcgtg cgggcaatat   38220
ctatggacaa aacaagtggt gccaggtttc aagttgcatc tgcggctgta tcgaatctag   38280
aacgcatgtt ggactctttg cctaacttttt ataaaagttt gagttccata gttacatcag   38340
cgggcataca gggtccccca ccgacgcaga tatctagctc gcgtaaggct gcacttcttg   38400
gcaacttatt gcgagctggg caaaatttaa ccactgataa tgcgcttggg gcttgggtgg   38460
cgctgttatc cgaagcgcac acagaaggac acatagagcg gcgtgagctc gaggcagtta   38520
ttaaagaaat aacctcaatt aacgactacg cggccaaaaa ggcgtcagta gaggcagaca   38580
tggaacgctt cagagttttg agtgcagcgg ttgaccaagc tacgtccgac atgtataact   38640
ccaacccgca tgcacttgac actatcatac acggtgccga tgaaatgatt cgccaggcaa   38700
aagtaatgga gtcacacttt gacgctggaa gaatttcaag agaggccgtg tctagagtga   38760
gcgttagaaa acgcgaagtt gaaacgttag ccaactcggc gcgacagcgt gctgcagaaa   38820
ttagcgccgc cagagatgaa atttactcgc gcctccaaac cctgttactt ccactcgctg   38880
ggtttgttgg attacgcgcg gctcctggag cgttggaaca gctggcgaag gatgctcaaa   38940
gctctacttc agaagaattg agaaatctta tgcatgatgc cccaaagcaa gtggtgtcaa   39000
ccgtacattc ccatttatgg tctttattta gccagtttag agaggcgctg gagcatccaa   39060
actctacaac tgcgtcttct ctggctggcg taggaccggc gtttgctata gttgtgcgaa   39120
gtcttttgga ccctaataag cagcgcgaga gtttggagtt ttttattaaa catgcagaca   39180
cacttgccga ggctattggg gccgtagagg caaattcaaa ctccgagctt gccgtgggac   39240
acgcagttaa cgcaatatca gcctcgatac aaacagttac cgttgggggc agtacaatta   39300
cagagtttgc gttttggtg cccatgttgg agcgttatag gtctagacta actatagtca   39360
gagaaaccca aagactggct acggctcagc gagccgtagc cgcgtctgtg tctgcagcgg   39420
cagaggtaac tgctaagctt cgcacagttg cagtttcggt catttcccag gatgtaatta   39480
```

```
cagcggcaat agcatctgcc aaacatgtat cttctgaggt taccgctgca gttactacag   39540
cggagcgaga gctggctggg ttagacgcca aggcattgag cgtggcccag gtagcccgcg   39600
cacatcaaga tctacaaaag cagacagctg cggcaaagca gagagttgta gaaattgaag   39660
aagttttggc caacctaaac aaacaacagc gcgagctgca agaccgtgcc atgtatgaca   39720
gatggaaggc tgacctgttg gccgctttgg acaaaatcga aactaaatca ttgtttgacg   39780
tgtctgagct ttccagactt cgcgacatgg gggccgcccg cagctataac tcacgcgagt   39840
ttgctaaacg cgcagaacaa gccctggctg caaacgcacg cgcagttatt aatgtattgg   39900
ataatgtgtt taaatttaac ccctacgctc cagaaaattc caaaaggaa actaatccca   39960 ccatttccat gctttataac atttcatggt gggacgactt tacgcttgcg gcacctatac   40020
ttaacactct atttgctgga gttgatgttg aggagctaat gagtttgatg cgcatttcta   40080
cgggaatgat tatgtttgcc agtaccaatg ggggcgccc aaaataccac gaggcggtaa   40140
actctctgtc tggtgatatg ctcaaaatac agcagttgaa taagtacgtt gacttttacg   40200
gcaagtggta ctcagagttt aatgccgaaa tggaagtgct aagcaagctg agggcggatg   40260
tgcttcaggc tgttggtgtt cgctctgggg aaataagtag ggctttggag gaggtaacgt   40320
acgttcgcaa tgcggaaata gctgaaaagg ttttagccga aggggtaaaa ctgtttattc   40380
caagcgacgc cctgatcacc aaagccgtta agtatttgga ggagtttaac cagaagcggt   40440
tcgccggatc tgcctttgag gaggctatag cagcaacaat acggcaagac ttgttagtcg   40500
cacgtgatgc agccacgcaa gctgcggcgg ctagaagcga gccctcaaca gaggcaaccc   40560
atattctacg cgaagtagtt gaagccgcaa agtcagccga tagagatgca agcgcaaatt   40620
tagcaaacct taaaaaccta ctaagactaa ctccaccccc acaaagcgtg gccgccgccc   40680
ttgacaaggc aacctcttcg gaggacattg taacccaggc ggctttgctg ttgggcacag   40740
tggaggcaac accagagctg gacgttaagg ccgtggagtg gttacagcag gcgcggtcca   40800
ttatcgactc ccacccacta acaactaaaa tagatggcaa aggacccatg gagccgtacg   40860
cacagcgcat agagcagcta cacacctcc gggggagct ggacgagcta aagcgccatc   40920
ttgctgctac tgaggttagc tgggatgagg catggggaaa tttttcccgc gctattccac   40980
gggctgatgt caccatggat gggttttgtaa cggcctacca tagagcgcgc acccttcaag   41040
cgtcaatggg ggttatttcc gagatgcgtt ccgatagcaa atatggtcgt ttgcccccaa   41100
aagttatcgg ctcgattgaa tcaaagtttg cagagagaaa caaaaccctt gaaacgttta   41160
atgacaccgc aacagttta caagcatcta ttgctcagtt tgattccctt gttaagaaaa   41220
ttccaccgga aatggagtat gacgtgttgc gctctctttt ggtatcattt gaccagctag   41280
cggccgtgct tccaaagtgg gtaggcgctg gattttctgc tttcagaaac ttgttgctaa   41340
tgagaatagg cctttacgac gaatatcaaa aaattgccgg aatagccgct gccggtagcc   41400 gccccacct ggaagccgtt gaatatcgca gcgcaacaga agaagataac ttacgacgcg   41460
ccagtcgcgt ggctgctctc atgggtgata gggacgtcat actctcgctg cgggaggcaa   41520
agtcaactat agacgttgcg ttcccgaaag tgttgttgga tgcaaagggt gtgcctgttg   41580
agtaccgcgt gtgttaccgc gctgtgggag ataaactcgc agcaatgata tgtgaaaac   41640 ttggggctac catgcgcccc gctatgaccc gcgagcctat agtggagtct tcgtcggttg   41700
cgggtattaa tgttactcat gacatactcc agttgcggtt tggccttgag aaggctcacc   41760
aatctggatt ttctacgttt gccagatttg tgcgccacaa gagggcagac tggagcccta   41820
```

```
ctgagcccgc atatgcagca gctgagatat actctgccgt gttggcaacc accctcacac   41880
gagaatatgg cgctacgtgg caccgaatac ggtttatgtc tagcgtaggc caatttacta   41940
ctgacagcca ctctggtagc gaatcacatg tagggaaggc aaagaaaaac cgcaacatag   42000
tgcatttaac cctatccgat gtggttatca gcgctatgct acgcaattca atgcatcttg   42060
taaactttat gcggcttgat ttgacacgcc aacatgagta tatggccaga actatgactc   42120
cagttttaac aaaggcgctt ttatcagaca ttttaattaa cacactagtc caaacagacg   42180
cgtctgtgaa ttggagacct ttaccactaa ctggtacccc agaagatttg gcacacggca   42240
tgctgttttt aattcgcatg tccgactgga agcaaaccag ttttttctaca acaagcctgt   42300 tagatctatg gatgcggtcc cctggtgaga acgggcgggc cgccgcagct aaggtagcct   42360
ctgctattcc aggcaacgcc cttactacct ttaccgtttt ggcgcgaatg tgtattccac   42420
cagacgcatt ggcgtcgctg tgggaagcgc tacaaccaga gtcactaagt cagcaaaatc   42480
tttcctatga tgacgtggtt actagcgac ttgacattgc gtctaccgtg caaacctctg   42540
tagctgtgga cccagaaatg ccgtctgttg acaatacagc accaaagcag ctatacattc   42600
caacgggggc cagcacaacg ttcacgcttg ccggctctgc ccagagcgcg gttaaagaag   42660
tgagcgcgct agacgtggcc acgtgtgcgc ttattttggg ggcgcccgtt gtaattgcca   42720
tggaaacgcc agagatattc tccgaagcct ctgagatgtt gttttgtctt aaaatcttcg   42780
actctagaag gggtgctaca gaccatgaaa taattcaggc cgtttcctcc gacctgagct   42840 cctgggggc gtcgcttttg gcactggatc ccaatgctat agaaaacgca tgcctaacta   42900
cacagctgga acggctgtct gggttggtgg cgtcaaaact tttatctgca tcaccgccat   42960
gtcttatatt actggatacc agcatggagg tgatgaaggt gttgtgggaa ccagaatccc   43020
aaccccaaga gctaatcatc actctagccg aggatgagat tatcgccgag cttccgtact   43080
taaatacgga tgatgacatg ttaccccac taaatactag tgaccctatt tacactaggg   43140
taataagcgg aacaaatatt ccaacagcaa tggtagaagg cagtttgtat gccggccagc   43200
agttagagtt cttacgtccg gattcaaatc cttttccatt tgcattactg aaccaacagc   43260
ctctagatgt accgagttct ccaagtagct gctctgataa atatgatgac gatcatactg   43320
gaattttgta tgatacaaat ggtgacgata tgtcaaacac agcaatgaac aaagcaaagg   43380
cgtggcaaga gtggctagag gatggatttg ccgaagatga ttaccaagaa ctatccaacg   43440
cagtaccaat tcccacaaaa actgctccag agtcaaaacg gagtttgggt ctacccgaca   43500
aaattcctcc tctattgcca cccaaaaagg cgccgcttcc accatcaaca gcctctgata   43560
ttttggctgg aaagccagtt tttagacagc cgcacaataa caaatcggtt gttaaacccc   43620
tagtaacgtc ttcatccaca gttcaccaa cacctccct cccagctgct acagaaaagc   43680
tttctagtat taacacacag tctccgagcg ataaaaacat accgcctagc aacacaaaga   43740
cacaaccacc cgataacagg ttaccagtcc catcggaaaa caatctccct cactttgttc   43800
cccaaacccc tgcaccccc acagatacta gtaaaccctg taccgtaatc caatctcagc   43860
aaaatttagg caccccagct ccccaaaaag agccggaaaa aaaaccaaca aacaacgcaa   43920
gcacggcggt tggtctacc aataaaaacca cagatgaacc ccaagtggtt caaccaccat   43980
ctaaaaacgc cagtgaagca aacaacataa aacagcttaa tgaaaaatcg ctttccaaac   44040
cttggcgtcc atcgatacgt ccatctttgg gaccatttaa atttacggcg ccacctgggt   44100
actctattcc catggatgga ctaccactc ctgatccaaa cgaggcgcta ttgaccgctc   44160
cgtccaaacc cgcagcggcc ccggctccgt ccaaacccgc agcggccccg gctccgtcca   44220
```

```
aacccgcagc ggccccggct ccgtccaaac ccgcagcggc cccggctccg tccaaacccg  44280
cagcggcccc ggctccgtcc aaacccgcag cggccccggc tccgtccaaa cccgcagcgg  44340
ccccggctcc gtccaaaccc gcagcggccc cggctccgtc caaacccgca gcggccccgg  44400
ctccgtccaa acccgcagcg ccccggctc cgtccaaacc cgcagcggcc ccggctccgt  44460
ccaaacccgc agcggccccg gctccgtcca acccgcagc ggccccggct ccgtccaaac  44520
ccgcagcggc cccggctccg tccaaacccg cagcggcccc ggctccgtcc aaacccgcag  44580
cggccccggc tccgtccaaa cccgcagcgg ccccggctcc gtccaaaccc gcagcggccc  44640
cggctccgtc caaacccgca gcggccccgg ctccgtccaa acccgcagcg ccccggctc  44700 cgtccaaacc cgcagcggcc ccggctccgt ccaaacccca aaacacactt gtggcaattg  44760
ttgccaagga tcaggccaag gatcaggcca aggatcaggc caaggatcag gccaaggatc  44820
aggccaagga tcaggccaag gatcaggcca aggatcaggc caaggatcag gccaaggatc  44880
aggccaagga tcaggccaag gatcaggcca aggatcagga tctcacaaaa caaaaaagca  44940
atcctgcgtt taaaactggt tttgaaacta caccttacc aaatacctct ccctctgggg  45000
ctgtaccaga aaacactccc ctcctggacg attttcccat cgatgcagtt ccagaaaaca  45060 ctccctacc agatgatgac tcgcctatag gagctgttcc agaaaacact cccctaccag  45120
atgatgactc gcctatagga gctgttccag aaaacactcc cctaccagat gatgactcgc  45180
cacttggaag ccctccacat cagccagtat ctaaaactct gcataacacc aacttagtca  45240
gcagtgaccg ttctgctgct gccgccaacg tacctctccc ggactcacca agcgatggct  45300
tctactcgta tgcagttaac ataccattgc ccgattcacc caccgatgat gaacctttca  45360
gcaaccagtc ccgtgcgcaa gcatcagccg ccggaagcgt ttccggcagt agttacaaga  45420
ttaacacagg aaccgggaga ataccaacag cctggcagcg tgccttgct cacacgtcgc  45480 atgggcgttc aagaaataga agcactagta accatctca atcagcgccc tacaaagttc  45540
ctcccgctct ttcctatacg aaaatacctg cggtgcctaa tgctcaaagc catcatgcgg  45600
gaaaacccag caacgaaaaa cctaaatgtg atactggacc aacggtgctg ttcggttcac  45660
ggaatatttc gccctcgcaa acgtctacga ccgcgaacat ttcgtccacc cttccacaaa  45720
atcagagtac tgctaagagt tcgcataagg tagctaaaaa aacccctctt cgggtcgtgc  45780
cgtctagcat gccggctgat gatatagatg aacttgaata tgatctacag ataaaccgcg  45840
cggtttcgaa caccaaaccg ctaccaaagt ctccactgca acaacccaa cctgaatact  45900 cctccgtaac tacagactat aaacaaaatg tccgacctcc gatgagcgaa gatgagatta  45960
tagcgttgtt gataaatatg aatgacaaca ctgaaaatga tgccgaacct attgacataa  46020
aatcgatacg agcacaaaac ctaccaaaac aaatcaaaca agctgcaaat aaatttgtgc  46080
ctctagattg gtggacggaa accgaatcgg ctgctgacgc cgacggcttg gaactgtctc  46140
ccaaacaacc aaagctgttc tcgtgggagt ctaagcgaga cttatcgaac attaaccta  46200 aggacaaaat ttacgaggct gaatcagacg atgaatatac catttcatgg gaccaacact  46260
tagtacctgc agtttccccc agatctgtat cgtcatctag tagcgatacg gctactgata  46320
gcgatacgga cacaaataat tcttcgagtg ttttaaactc gttagccgat aacacccaaa  46380
acgacgctag cgagcttgtt gacacacaca gctcaagggc ccgtgtagtt cctgcggaca  46440
atttgctaag cagacggtac ttcagaaaca cgagtttaag cgcaatggcg ttacttatct  46500
ctgcgtgtcg aacgattata cggcgacttc gggcaacaag acgggttctt acggacatta  46560
```

```
accgtagctt gatcatggac ctaaagcaaa tacgggtttt gttggggtag agtattttta  46620
ttttttaata aaacattaa catatgctgc gtttaactga tgtttattaa taatgaaccg   46680
caaagtcgcg aatgggggga ggtggtagtt aatcttcaga aatgggctgc ataaaccgcg   46740
gcgggaaggt gcgttttagt cctatatttg gccgggccca ggtagatgcg tcgttgtgcg   46800
caaacatggc agatcgtcga acaagggctt ttagatggcg ctgacgcaac acaaccatag   46860
ttttggcagt tcccataaac agctgcttta acccttcatt aatttcatcg tcgctgtatt   46920
tggtgtaatc gagctcatcg atgttttggt ttaaaatagt catcacgtca acaggtagca   46980
tgtccttaaa gtttgcagct ttgatattag tcgggtccca tggatcaaac gcaactggag   47040
cttgttgttg ttttttggtca gcagccatga taaatttctg cgagagcaca ccgcacccett  47100 acgctggctc ggatagctac gaatagcgca tggaattgtt gctggcagct ttttattaga   47160
aaaggcaacc ctttgttgct atcgcgagta ttacagcaac aaaagcacat gcaaaaatta   47220
cagccgcaat gcgaccggga cggcgcttaa ccctctctga agcaaacgcg ttagatatgc   47280
tagtaaggct ggcaaaaacc tctgatgcgc accgcttggg agtagggcgc cgcttttgcc   47340
tctctctaca ctctcgctgt tctctcgatg cagccaaact gttgtgatcg cataggtcta   47400
cggtacgttt tcgctgcatt tcaatcgcac caaaactggt ggcacgctcc agtaaacgct   47460
gggtcctgga cgcgtcttct ggtcccataa accggaacga tagctgcacg actggcattc   47520
tagtaaaaca gcttatttgc atcatcgcct gtagtggcct taagtctaac ccccccctc    47580 gtttaacgcg ttctatgcca gagagcgaga gaccagtcgt gtgcgttgac ttaagaatca   47640
cgttgttatg ctccgatgtt atagaggcca ttggggcgtt tggtggtgca aaaaaaaagc   47700
cttgaaatag caccgacact cccgtatttt gaattcgaat gtagggatca cactggcttc   47760
gagcccagtt tttcatcagc cgtaacacat actctatagg aaatgtaacg ctgttattgt   47820
ccggcccact gaattgaaac acgcacctcg cgggtaggtg ttttggatcg tttagtgttg   47880
catcgctttc tccacaatgc aagcttcccg atacaaccag acgaatacgc tgcagtaaac   47940
taccgccaac cgcaaaatct ctatagtcgt acgccttcat gggtgtaatg acaggtcctt   48000
aacagcggcc agtcaacacc caaaacaact gatgagaaga ggcatgccac agacagaact   48060
taaaccctct ttatatgtag ccactcccca ctacgagtac tacactttgc agatcaatgc   48120
aacttacgcg tcgtggagaa tttgatgtaa atctagaaac ttgttaatta tagtagcaaa   48180
tctttccttg cgggaattta gcgctgaggt gtggtcacat gcaccccctg gcgtacgatt   48240
atcgggggcg tgaaaaaccg aagatgccaa gcgccgcgta aatgataaat agtttagttt   48300
ggcgtctgtt gttggcatca acagttccat ctcgggggggc ataaggtctt caaaccaaat   48360
accaaagtcg tggtgtccat aggcatcgtc aagggcgtct aagctcatcg attccaggtc   48420
gttaggcgga attaagtgtc tcagcttttt ttgtaaagct tggcgcggct gagtggacat   48480
attgccagtg gccacactag agacattttg tgaaatggcg tttaattgcg atttagacgt   48540
catgggtgca aacgttgagt gtggtataac aggaggctgg cagccagaag cgtttgagcg   48600
cccgtacact ggatttgacg ccacgctttt agccaccaac tgtggtctgt gcagcgagtt   48660
aatattttct gcgcatttaa tgcaaatttt acccacgccc aaacctcaac accctggcga   48720
agtgtgcgat gagatggaca tggaccagcc cgagcctagc tgcgcccgt ttgtagaagc    48780 ggtggccgac tcgctagcta tagacaaacc ctgtttgatt tgcagaacaa tagatctgta   48840
taggcgcaaa tttgggcttt cgccccagtg gatagccgat tatgctatgc tgtgtactaa   48900
aacgttggca gcttcaccgt gtgcagtagc cacggtggtt accgcatttg agtttgtgta   48960
```

```
cctaatggat aaacactacc ttaggcgtgg aaaaactacc ctagtgggcg cctttgcgcg    49020
ccgagtttta actctggttg atattcagcg ccactttttt ttacacgttt gctttagaac    49080
agacggtggc gttccacgcg gagttggatc tgggacggca cccaaatcta cggcgttaac    49140
ggggcctggt atgatggata aagtgcagta ttcaaattac tcgtttttag tgcaatcgtc    49200
tactagagcc ttgctgttaa cggtatctga tacagcaccc gtagacaacg aggcgggaca    49260
acagccaact acatccatta gaccaggagc gccaaaatca ggcgatgggt ctggactgct    49320
atgccctaag caagaatcta ccacagcagc gctaatgagt tggaaggagt gtgccaaaat    49380
gatagactgt tccggatcag agagaagacg tcccggtact accataacat gttgcgagag    49440
agctcgtgca gatgacgatg aatacgagca ccagctgttg gccacggagc aaacatacgt    49500
tgacacaaat atcacagaaa tatgcgacgg tgcacctatt aagtgggggt atgccgacct    49560
ggcgctgttg ctactaagcg agtcaagcac atgggaaaat agtgaaaaaa catttctggc    49620
gagtcagtct cgcaaggcct gcgttgagga gtattgggct acacacaagg cggcgctgtc    49680
tagagataca gctcccaggt ttgctagatt tgtagaagct gacgctacac ccgacacagc    49740 tactggcect gtcttagcaa ctactctcaa acacctacgc ggtcgaggta gaacgtgcgc    49800
cgaatgtgtg ctctgtaact tgctattaac acgcgaacac tggctagcgc ttcgccgatt    49860
taagcgggat gtaatatctt actcatcaaa caacacaaac ttgtttgatt gtatctcccc    49920
ggtgctggcg gcacttcctg acgcgaatag tgaaccgcta gttagcgatt gtgatgaggg    49980
taaaacacgt gttggagacg cgggtaggtt tatggagctc atgcatgccg ctggtacgga    50040
ggccatatat aagcacctgt tttgcgaccc aatgtgcgcg ctctcggagc ttcaaacaaa    50100
ccccggtgtt ttatttttgc cactgggggcc tccccaggaa ccagacgaga tagagttgca    50160
aaaggcgcgc ctggccagcg aaaattggtt tagtgggcgt gtatgtgctg gactgtgggc    50220
attggcgttc acttttaaga cgtatcagat ttttacaccc aaaccaactg cgtgcgcagc    50280
gtttattaag gacgcgggac tgctactgag gcgtcacaac ctaccgctca tatctctaga    50340
acacacgctc tgtaactatg tttaacaacc acggcgatgt ctacaacccc atgagtctct    50400
cggccgaact aaacgatctg tattacgcta aaccatcagg ccgtgaaaat ggcaggcgga    50460
gtcgcaccag cacgcggggt gttcatcgtg atcgatgtgg atctgcagct aaaagacgta    50520
gcaccaaacg ccggtgtgag ctggccagca gggaaaggga tcgatacagc ctctaccttg    50580
attatatggc cagccaccct tcagatgaaa tttcggctgt gcgtgagcta gtagttcccc    50640
tcattaaaac aacatcgatt acactaccgt ttgatttgaa tcagacagtg gctgacaact    50700
gtctttcgct atctgggatg ggatactacc ttggcatagg cggttgttgt ccaacttgca    50760
ccgtgtccgg tgaaccgcga cttcatcgcg cagatagagc tgctctcatt ttggcctatg    50820
tccaacaact aaacaacatt tacgagtata gggggttttt ggcatctgtg ctggcggctg    50880
ctgcccaagg ggagaccgcc ggtggaattg aatctgatgg ggcccaggcc gagcgcttgc    50940
tagaaaatgt tctagcgcaa ccagagcttt tctttgcgta ccacgttttg agggacggtg    51000
gaattcaaaa cgttcgagtg ttattttatc gcgatttgag cgtgtctgga tacatgatgt    51060
atgcggtatt tccacaaaaa tctgttcacc tgcactaccg tctcatagat cgcctcctgg    51120
cagcttgccc gggctacaaa atcatagctc atgtctggca aacagcgttt gtgctagtag    51180
ttcggcgcga cgagggacaa caaacagaca tggatatacc aactgttagc gctgagaca    51240 tttattgcaa aatgtgtgat ctcagctttg atggggaact gcttctagag tacaaaaaac    51300
```

```
tgtatgcagt attcgacgac tttcttccgc cgatgtaaag ggagttagcc tttcaaatcc   51360
agcgcgctcc aacatctcct gggttttttgt ggaggtcttg tggggtcttt ctggaataaa   51420
tcgctttaaa aggttttctg tggtctttgc atcatttcca aataatgcct taaaggttac   51480
gcttatcgta cccaacaggt gggaaaaata gtagtctgtg ttaagtggaa cgtcattttc   51540
tgaaacatag gttggatcct cagccaggtc cgaaacgagc agtttgcgtt tggattgggg   51600
gcgttgtgtt ttgatggccg gggtttgtgt agtaccacgc atggagttta ctatacaagc   51660
ttcgcgttca gcggcttctg tttgcgcaac aatcacatac ggaattctct ccttcacact   51720
gggcagttct tcattccgca tagcgagctt aaagtaaaca gtgaggtgcg gtagccgctt   51780
gtttgtatat gattccggcg gtcggctaag ctcagacgtc atcacaaact cgcgcacatc   51840
caagttgggt gcggttatac ggttgtaagc ttctatcaac actcttccaa acttgtcaaa   51900
gccgctcgga agggggcgcc caacccactc tgagggaggc acgttagtta cctccgccgc   51960
cgcggtagct actgcctcgt cgtacaacag aagatctact agatgtcgcg cgtagaagtt   52020
tatgaaggca cagttatttt tacggactag gtctaccccc ttcatgagca ttataccccc   52080
gttgataaca cctatgtact tttctttgt aattagtagc agccgctgga aggttttttc   52140
acactctagt ttgataggtg cttaaaaag gtcagctgaa atctgtcgcg acattgaatc   52200
tccaagctct gaaaccccct cgtatgttag cccaacaaac ttgatgaata cagagtcggt   52260
gtctccgtaa ataactctga cagaataagg cttgttgttg cgaaaattta agcccctgg   52320 gaagtttgtt tccaacagct cacgcgtcgc ccaacgatag tgaacgtaat ctctcgtttt   52380
gagaagcatg ttgcggccta ttgtagtaac ggtggctgct attctcagac atggcaacag   52440
tccgtttgcc acaccggtga atccgtaaac tgagttgcat attactttaa ttgcagactg   52500
ttgcttatct agcaaaactg cctcctccgg ggtacttgtt ggaattcgtg ccctaacagc   52560
ctttcgcata gccagccagt cgcgcagcaa aataccaagc aagctttcgc gaatgtgcgc   52620
gtgcacaaaa aacaactttt ggtcgcccac ctcaaacgtt gagtagtcaa cacacggctg   52680
aagcccagcc aaatccactt cattaagggc taaggtggtg aaacaaaggt tgtgggcctg   52740
gatgatgctg ggatacaggc tcgcaaagtc aaacacaacg actgggtcaa catgaaagcc   52800
ggatatagga tctagcacct ttgctccttg gtatcccaca atcctacctg tgccgggttt   52860
tccgccccct gtttccaaac tggcagacga gctaatacca tcttggctcc cattaatact   52920
atctgagttg ttattgttgt caaaggcgtg gtcttcacta tttatggatg tctcggaact   52980
ttccaacaca gcgtccccat ggtagtcgaa tttgcgtcgg ttgtctggta aaataaaatt   53040
ccgctctctg gcgagtttta gcaagcatgt gtaaacgcga atttgctgac catcaaaaat   53100
tacccgcgtt agagttatgc gggctagctt tgcaacagca gagagttcca gatgtgggag   53160
gtacttaaaa aatagctttc caactaatct tgagtcctga atacaatact ctcctattac   53220
accccgctgg tttggtccac ttgcatagta agaaggtatg tctttgtatg gaaggtctat   53280
cttgtgctca cctagaacgt cttcaacaac tgcgtcaagt ttatagctag gtagttttag   53340
cttttctgtt gccaccgaat acatgtccag agatatcact ccattaattt ttaccttgct   53400
ttttttttgg aagtggtttg tagcaatgtc ccagaccta aacagccctc ctttgttaaa   53460
cttgccgtac ccatcaagtt ttatgttata acggacgtc aacttgttaa ctatgtacgc   53520
ccagtcaaag tttacaatgt tgtagccagt ggcaaactct ggagagtatt gcttgagaaa   53580
tgttaaaaat gctatcaaca gctcatattc gctatcaaac tccaagactg ttgggctagg   53640
ttccccgcgt tgtacacagc cagaagcgta ttcttcagaa atatcacacg accctagaga   53700
```

```
aaacagcagg gtgtgttcat gcttttgggt tgctaaagag taaagcaaac aggaaatttg   53760
aattaccaag tcttcttggt tagttgcaac tggaaacgcc agttcgtttc cggtaccggc   53820
tttacactct atatcaaaac acagtagctt atagtctggc caggacgcct cttccggaag   53880
aggctctaag ttatccgaag tacagttaat ttcaacgtca cttgaggtca ggtgtcgctc   53940
tacctggcgc agttgaacac gctctccgtt ggttccgggc cggaggcggt accacccaaa   54000
actggtaaaa ttttcattgt ccaacaagag ccgcgttgtt acatccacac tcccctcaaa   54060
ttttgtgatt tccgggtgga agttatcgca gataaacccg cccaggcgac tgctagagga   54120
tgaaacccta tagtagaggg ttggctttga tccaaagtag tacagcgtcg tgtggcatac   54180
tgtttcaact ttaaagcaat caggagatac gtgctttcct ccccaccagc cgccgctgtt   54240
tccaccgctt tgttttcctc cgttgctatt tcccagggcg gcgcttaaag ctgagttatg   54300
cgcgcaggca accatggcgc gaactaggtc ggattcgctg gttattccac acgtctgtc    54360 tacttctgac ttttcaatat aaaaataatg gcgcacaccg tacacgtgaa ccgctacgcg   54420
cttcccacat tcgctcattc ccagcaatgt taccactgat ccgcttgggc gagatagctc   54480
agcaaaccgc gacgggtcgt cgttcgaagc gcttcccaca aactctacta tgtcgtacac   54540
gtgaaacctc tcaaatcttg ggttaaactc atcaccgcga aaatctttgc cgttccaaac   54600
ccgaatcctg cgaggccagc aaccgtcagc ttcaaagtct aggacgtcgt actctgcgcc   54660
atcacagtac acttttgggg tgcgctcaag tgttcccaca tgcacagcgc gtcgctgatc   54720
ggttggagca tcttcatcaa gacacttggg tgctatgaac ttgaagttgc ccacctcggt   54780
gtagtatgag tggtgtgtaa cttttgggcg gtggtcatct gctttctgtg cgttttctgg   54840 atgacgacg aagggctttt ttccaagaaa tggattaaaa aacccacacc tgcgaacaaa    54900
tctgtcctgt tcgtgcgccg ccatgtctgt gtaaatttaa gaagtgcgat ttgtttcctt   54960
tttatgtttg ttgctccgcc ccatagatct cgtgatatgt ggtttgttgg gcgtgtttag   55020
atttaccttt aaatcctgcc caccaaggtt ggtcaaatgc tttgagtaac tctcgttaga   55080
aagcacttag ctattctacc ggagttccca acgctttgtt ggtgcgccat cagcctttgc   55140
gggtgtgatt tgaaatcttt ggagttttgg caacaacatg gagtctgcac cgaaaacggt   55200
gagccttccc gtgtcacccc tcgggtacgt ttatgccatc cagaatacat ttatggaaac   55260
agaagcgttg actctaatgg ctgccagaag cattgattct gacctcgctg ttctgcctgt   55320
gattcgcgga ctcacagtag aacaaacttt tacaaccaac gttgcggtgg ttgcaggctc   55380
gaaaactact ggccttggcg gcgctgggat tactctgaag ctaacgccta gccatttac    55440 acctaacgcc ttcgtgtttt atggaggctc tgttttggg gcaagctcta aggcccccaa    55500
ccttacacgc gcttgtgagt tggcaagacg gaggtttgga ttttctccat tttcctcccc   55560
accggtggat aatgccgtgg aaacctccgg ggaagaaatt tgcgcttcgc taaacctgtc   55620
tccagagacc actacgttgt acctggtggt aacagaaact tttaaggaga tggtgtacat   55680
gtgcaatacc tttctacatt acggtggaac cagcacggtt accatacacg gacaagaagc   55740
cgtaaagatt cccatttatc ctgtacagct ttacatgcca gatgtcaaca gacttgctgc   55800
tgaacccttt aactccaaac atcggtctat tggagacgag tttgtgtact caaagccttt   55860
ctttaactcg gatttatgca ggctgttaca cggctacgtt ttggggcccg cggcggtcgc   55920
gcttcgcgtg agaaacctag atggcgttgc cagaggagcc gcacacctgg ctttggatga   55980
aaaccacgaa ggatcagtgt tgccccagga tgttaccttt acgcttttg actcagccca     56040
```

```
gggaacttct ggtaaaggtt ctgggcgcac tcagcgccag ggggacggta gcgggctaaa    56100
aaatggatcc tccagtggca tcgagcggcg gttagcttca attatggcag ctgacacagc    56160
cctctccgtt gactccataa tgggagctgg cgtatatgac acggagttac cgtccgtaga    56220
agacctgcca attttgtctg tcggggacga ccgtgaaaga ctagaggccc ttggggcgta    56280
cgcgagtaga ctgtctggcc tggttggcgc catggtattt agcgcaaact ctgttttgta    56340
catgacagag gttgacgacg ggggacccgc agatggcaag gacgcatcca atccttctta    56400
ccaccgcttt tacctaatag ctgctcctta cgttgccgga aacccacaaa cagacaagga    56460
tggccgagtc ttgcaacaca ccgcagacca gccagctgct cccataaatg gatcaaatca    56520
agagttttcc ctggactatt tagcactggc ttgtggtttt tgtccccagc tattggcgcg    56580
gatcctattt tacctcgaaa gatgtgacgc tggaacattt gggggtcgca acgagacaga    56640
tgcactgcgt tacttggcaa acacgctaga gtctgaggta ccatgtgggt tgtgtacccc    56700
agctacgcgg ccggcatgcg ctcataccac gctccatcgt ctccggcagc gtctgccacg    56760 cttggaacg ccagttcgtg ctccaatagg aatatttggc acaatgaaca gcacgtatag    56820
cgactgtgat gtactgggta actatgcttc ctacggggcg ctaaagcgac ccaatgacaa    56880
cgaagccccc aaaagcatca tgcaggatac gtatcgtgct actatggagc gactggtaaa    56940
tgacctggaa caggctaagc ttattgacaa ggaagcgctg gctcatgccg gcacctgctc    57000
ggcctccaca ggcgtagtaa aggaccaggc cagctttata aatcttttgt ctacaatcaa    57060
agacataact gaggggcag cagagcagtt tatgcgcact ttggttgagg ttcgcgattt    57120
taaaatccgc gaaggcctgg cagatgcaaa ccataccatg tcaatttccc tggatccata    57180
ttccagcagt ttttgtccag ttacatcatt tctctcgcgc cgcaccattt ttgctgtttt    57240
gcaggaccta gtattgagcc agtgtcactg tcttttctac ggtcagtcgg tggaggggcg    57300
caactttcgc aaccagtttc agccagtttt aagacgtaga ttttagata tgctcaacgg    57360 gggctttatc actgctaaaa ccgtaacagt aactgtttca gactctgggg ttacggctcc    57420
caaccttacg cttccatcat cagagccccc aaccaaagac tacgacgggg acatggctag    57480
ggttagcatg gaggtgctgc gagatcttcg tatcaaaaac agagtgcttt tttctaatgg    57540
gggagctaac atgtcggaag cggctagagc tcgagtggcc ggcatggcca gtgcctatcg    57600
aaggcccgaa aaaggctcaa acattttaaa cggtgcggtt ggcttttttgg ttaagcaatt    57660 tcataaagtg ctctttccca ggggacaccc ccccggcatc gacacccca acccccaatg    57720 gttttggact ctgctccagc gcaaccaaat gcctgcgcgt cttttaagca agaagatat    57780 agaaactatc accgccatca aaaggttttc ccacgagtat tccgccataa actttattaa    57840
cctaactcct aacaacattg gtgagttggc ccagttttac tttgccaacc tggtgcttaa    57900
gtactgcgac cactctcagt actttattaa cggccttaca gcaatagttg tcggctccag    57960
acgacctcgt gatccggccg cggtattggc ctgataaac cgtactatca acggggcgtc    58020
agatgttgaa ccggcggccc aggaagtgtt gcagcaacta gggtccaatc ctgcagcgtg    58080
gacaggcacc tttgcgtcca caaacatggt tcgctatgta atggaccaac gcccaatggt    58140
agttatcgga ttgagcatta gtaagtataa cgggagcgcc ggcaacaacc gcgtgtttca    58200
ggcaggcaac tggaatggcc tcaacggcgg caaaaacgtc tgcccgctta tggcctttga    58260
tagaacacgc aggttcgtgt tggcttgtcc gagagttggg tttacctgtg aggctggcgg    58320 attggtatg ggggcaagag aaaacacact aagtgagcaa ataagaagta tagtctctga    58380
tggaggcccg atggttcaaa cagcagtgtt ttcagtggtt cttaccgctt taggcgcacg    58440
```

```
cacgcagcac ctggctgttg acgactggat tggcctcgtc gacgacgagt ttttggcagc   58500
tagcctggat gctttaaacg cagccgttgt tgatcaattt ggggagtgga gcgtggaggc   58560
cgcccaggat atgatcagga ccatggacgc tcaaacaaac atgggtgttg tgtctactgg   58620
cgacggggcg tttgactttg gggcgtgtgt gggggatgct aatcaatcct ccaccacatt   58680
taacatgggg ccggcctcga gttctgcgcc cgccggacaa aaacggtttc acccagatga   58740
tattttgttt gacatgggag cacccccaga aaaaagtct ggtctcacct ttgacatgct   58800
ctaggctgga tattatgtat cccctcccac ttctttttttt ctgtattttg tcaaatagtc   58860
attggtctga ttaaaaaggt ttaataaatg ttttacattt atatttggcc gactctgttc   58920
atattttact gtcgctgata tacgaaaact ttctgcatta gctatggagc aggacgatag   58980
ctccactgct atgggaaatg cgcaggcgcg tcagcgttta ctagcaattt ttggtcaagt   59040
tcaggcatac atatttcagg tggaaattct aaagcgatgc gacccatcgg cgcttcaacc   59100
tctgattggg gcgctaaaac tcaacgcttt aacaattaga aagcttaaac gaaagcttgg   59160
cggtgctctc atggaacaag cgagacatca gcaaacacca ctcgcgtgtg ccttggctat   59220
ggctctagag tatgcacacg tagaaggtga gcgtgttttg cgagcagcgg acaacgtaac   59280
tatagtaggc gcagagggtt tttttagagc tactatgaag ctagacgatc cgtgcgagta   59340
ccatgtgcga gtgcaccttg agacctacgg tggccctata gacgctgagg tgcagttttt   59400
gcacgacgct gaaaactttt taaaacagct aaactactgc cacctaataa ctgggtttgg   59460
ggctggcctc gcagcattgg aaaacgtggc cagctttcta acacgcaccg tgggaagcgg   59520
aatcgtagtg ccacctgagc tgtgtgaccc cacccatcca tgctcggtgt gtttcgagga   59580
gctttgtgta accgccaacc aggggaagc tgttcatcgt cggctactcg aatgtacgtg   59640
tgatcacatc acgcggcaaa tgtcagttag ggttgcaaat atagacatcg ccaggcacct   59700
accgcacgct cttagtgtat cggttgagcg acgggctgcc gcagaagctg ccctgaaagc   59760
actcgaagct aggcgcgttt ccgggcataa taaaaacgat aacacagaag accccacaca   59820
ccttgttgca tctaggctgc ttgaagccca caacgttttt aagcctgctt cgcgatgcct   59880
gtacgctgtg agcgagttaa agttttggct cgcgtcagct aaacattgtg atgagggccc   59940
ccctagagcc atagacacat tcacagaaaa tttggaaacg ctaaataaac aggaaaagtt   60000
ttttcacctt caagctgcta ccgtggagct ggcgctattc ggccgcacct tcgaccactt   60060
tgagaggata tttgcggata gtttgattgg tttggacgtt attgatgaa tgttagttgg   60120 aagttgtgcc gtttcccccg acgattacat agaagctctg ataaaggcgt gttacactca   60180
tcacatgtct acgccgttac tacagagact cactgacccc gacactagta accgtgaagc   60240
cctaaaacag ctattgggga gaattggagt tgaaaccaac agcggctccg ctgaacttgg   60300
gggtaactta gaaatagatc tggatactat gggctgtaac cctcaggtaa acaccccag   60360 tgacgagggc gctctaggga agcccgtttc agaagagcgc ccgtgggaca aacttttga   60420 gagagcttca gcggatgctt cgcaacgaag gcgtatgtac gccgagcgtt tatctaaacg   60480
ttctctcgcc agcttggggc gctgcgtgcg cgaacagcgc aaagaactag aaaaaacatt   60540
gagggttaac gtgtatggcg atgtgttgct acatacgtat gtgttatcct ataacgggtt   60600
ttgcgctaga cgcgggtttt gcgaggcggt gagtggcgcc ggtacaatca tagataaccg   60660
ctctagcaca tcatccttg actcacatca atttatgaag gcggcgctgc ttcgccaccc   60720
catagaccag tcgctaatgc cgtctataac ccacaaattt ttcgagctca tcaacggggcc   60780
```

```
agtgtttgac aatgcgggtc acaactttgc gcaggcgccc aatactgcat tatattacag   60840
cgttgaaaac gttgggttgt taccgcacct caaggaggaa ctagctcggt ttatggttac   60900
tgcggctaaa ggtgattggt caattagcga gtttcaaagg tttttattgct ttgagggtgt   60960
gacaggtgtg acgccacgc aacggctggc gtggaaatat atcggggagc tcattctagc   61020
tgccgcagta ttctcttcgg ttttccactg cggagaggtg cgccttctgc gcgcagatcg   61080
tacatatcca aacaccaacg gcgcacacg ctgcgctagc ggcatttaca taacatacga   61140
gacgtcatgt ccacttgttg ccgtgctatt tgtgccccc aacggtgtta ttggcgaaga   61200
gactgtggta atttacgaca gcgacgtgtt ctcgcttcta tacaccgtac tccagcagct   61260
ggctcctggc tctggagcca attaggaaat gtaaacttgc cagctacctc ccccatgtct   61320
aaagactcga catctctggg ggtgagaaca atagtcattg cgtgtttggt tctcttggga   61380
tgttgtattg tggaagctgt accaaccacg ccaagttctc agcccagtac tcccgcgtca   61440
acccagtccg ctaaaaccgt tgaccaaacg cttctaccaa ctgaaacacc agacccgctc   61500
agactggctg tacgcgagtc cggtatactc gcagaggatg gagactttta cacctgcccg   61560
ccgcctactg gatccacagt tgtacgcatt gaacccccac ggtcatgtcc caagtttgat   61620
ctggggagga acttcacgga gggcattgct gttatttca aggaaaacat agccccgtac   61680
aaatttagag caaacgtcta ctacaaagac attgtagtga caaaggtttg gaaggatac   61740
agccacacct ctttatccga tagatacaat gacagagtgc cagtttcagt ggaggagata   61800
ttcactctca tcgatagcaa aggaaaaatgt tcttctaagg cagagtacct ccgagataac   61860
attatgcatc acgcttacca cgacgacgaa gacgaggtgg agctcgacct ggttccgtct   61920
aagtttgcta ctcctggggc cagagcatgg caaaccacta acgacaccac gtcttatgtc   61980
ggatggatgc catggaggca ctacacatca acctctgtca actgcattgt cgaagaggta   62040
gaagcgcggt ctgtttaccc atacgactcc tttgccctat cgaccggtga tattgtgtac   62100
acctcaccgt tttacggcct tcggtcagct gctcagttag aacacaatag ctacgcacag   62160
gagcgcttta gacaagttga aggataccaa ccaagagact tggacagtaa attacaggcc   62220
ggagagccag ttaccaaaaa ctttattact acacctcatg ttacagtcag ctggaactgg   62280
actgaaaaaa agatagaggc gtgtacacta actaaatgga aggaggttga cgaacttgtc   62340
agagatgagt ttcgggggtc ctacaggttt actattcgat ccatttcgtc cacgtttatt   62400
agcaacacta ctcaatttaa gctagaagat gccccactca ccgactgtgt gtcaaaagaa   62460
gccaaagatg ccatagactc tatataccga aaacagtatg agtctacaca cgttttagt   62520
ggggatgtgg aattttactt ggcacgtgga gggttcttaa tcgcatttag accgatgatt   62580
tctaacgaac ttgccaggct gtacctaaac gagcttgtga gatctaaccg cacctatgac   62640
ctaaaaaatc tgttaaaccc caacgcaaac cataataccca atcgaacacg caggtcgcta   62700
ctatcaatac cagaacctac tccaacccaa gagagcctcc acagagaaca aatactacat   62760
cgcctacaca aacgagcagt ggaggctgcg aatagtacaa actcttccaa cgtcaccgcc   62820
aaacaactag agctaatcaa aacagcgtcc tctattgagt ttgctatgct acagtttgca   62880
tacgatcaca tccaatccca cgttaatgag atgctaagta ggatagcaac tgcgtggtgt   62940
acactacaaa acaaagagcg gaccctctgg aatgagatgt taaaggttaa cccaagcgct   63000
attgtttccg ccactcttga cgagcgagtt gcggcaaggg ttttgggaga cgttatagcc   63060
ataacacatt gtgtaaaaat agagggcaat gtgtacttac aaaactctat gcgctcctcg   63120
gacagcaaca cgtgctactc ccgcccacct gtaacgttta ccattactaa aaatgcaaac   63180
```

```
agcagaggga cgatagaggg ccagttggga gaagaaaacg aggtttatac ggagcgcaag    63240
cttatcgagc cgtgcgctat caatcaaaaa cgatacttta agtttggcaa agagtatgtt    63300
tactatgaga actacacgta cgttcgcaaa gtgcccccga ctgaaatcga agtgatcagc    63360
acctacgttg aactaaactt aactcttttg gaagaccgcg agtttctacc cctggaggtt    63420
tacacgcgag ctgagcttga agacacgggg ctattggatt acagcgagat acagcgccgt    63480
aaccagcttc acgccctccg attctacgat atagacagcg ttgtcaacgt ggacaacact    63540
gctgtcatta tgcagggaat tgccaccttt tttaaaggcc ttggtaaggt gggagaggca    63600
gttgggacgc ttgtacttgg agcggctggc gcggttgttt ctacagtatc gggtatagcc    63660
tcatttataa acaacccatt tgggggctc gcaataggcc tgttggtaat tgcgggctta    63720
gtggctgcgt ttttgccta ccggtatgta atgcaactgc gcagcaaccc catgaaagct    63780
ctatacccaa taacaaccag gagccttaaa aacaaagcca agcctcata cggccaaaac    63840 gacgatgatg acactagcga cttcgatgaa gccaagctgg aggaggcacg cgaaatgatc    63900
aaatatatgt ctatggtttc tgccctggaa aaacaggaaa aaaaggcaat gaagaaaaac    63960 aaggggggttg gacttattgc cagcaacgtt tcaaaactcg cactgcgcag gcgcggtccg    64020
aaatataccc gtcttcgaga agacgatccc atggaaagcg aaaaaatggt ttaaaaatgt    64080
taaataaata ttttgacacg tacttgtggg ttgactcata tttgcataac atctttctag    64140
ttccggctat aagcctattt aagcctagta tttttgccaa agtttatca tcctctacaa    64200 gcgcacatcc tctcaaaaga gttgaatttt gctgtttatt acgctatcct aaagctaaac    64260
gcctgtaatg aatctcaat gcaaaacttc tacatcagcc gctgatgaaa ctctgttggc    64320
tgcatcggct accgcggcgg aaatccaaat aaaaacagaa gcacccgatt cagacacgcc    64380
cgctgccacg gggtgtcaag accacaccta cgctcgccgg ctcaccgaga atggtgcaat    64440
cgaagagata aacacggctg atctactgga aatggtgctg gcttctgaaa cgctcaaag    64500 cgaacccgga attccgtttg ccctgcgagg aaacttcatc tgctgcagag acaataactg    64560
tcgcgcttgc caagaactgc catttcgccc gtcagaaatt gggttttcca gggaccccca    64620
tgtgtccatg gcgttagaca tgaccagcgg aacttgggct tacatcccac gagttttccc    64680
agacacaccc accgccccctt ggatggccaa cttttgcatt ccagacctcg acgagcacgc    64740
agattgttaa aaacaaata aactagtttc agcttatacg tgtatgtgtt tattgttaat    64800
ttttaaagta aagaccaaga aacgtttat ctagcactca tcatctgaga cacaaatatg    64860
tccgcgtcat cacgcccaaa atctaggccc gtagacgcgc tagcgtctac cgtttggctg    64920
ctagcttgag gctggttaac gggcaaaaca gctgctgaag taacagcctc aaactgaggc    64980
tgtacagcct tagagtgctc caccgcttga tgggtagctg ttgggctgc gcaaaccttt    65040 gcaccacctg gtgtttctac ggcgggcacc ggtgtggcaa taacagattg gggtggttga    65100
gcctgaattc ctgatagctg cggagagata attgcagaaa ccgcatgctg tgggtggata    65160
tactgatact ggctgtattg ctggggaacg cccggtggga cgggtttata tagtccagcg    65220
ggtgcaactt gctgctgcgc ggttacggtt tgtatagctc tgagctgcga cacttcctgc    65280
tgtaaagaag aaactgctcc cattaaatct gcaatggttg tggacgcgcg ccccgctcta    65340
cgctccactg ggcgcggtga tcgttcacct ggatagtaaa taccctctat gtcatcacgt    65400
gtgttggcgt cccagtcgtg acggcgcttc cgtgtgtatc gccgctcttg ttgtggagac    65460
agtggaggcg aacactgaga gttttggacg gcttgcgagt cgctacttt ggcagcttta    65520
```

-continued

```
cggtctgcag ctagggctcc aacaagcgcc gtgatttgcg cttccaagtt agtgctgggg   65580
ggcacactcc agtatggagg tgcctgatac atcgatgttg gcaccatgga attgtaagcc   65640
ggttggatgt actgtgtagg cactgcgtgt gttgcggaag cttggccagc gtttattgga   65700
ggatgcgaag tgtgctggcc tacaacgagc tggttatact gcgccgcggg tactaaaatg   65760
tagtcaccag acactagcgg ggctccagca gcagacagag tttgcgggtt tgatgaagcc   65820
atcgcaccag ggtgtttggc gcgttcgcct atctgaccag cactgttgtc cgaggacggt   65880
agtgcggaac tgcctgagga agtgaaagcc tttgcgccaa gcgttacacg tgaataagat   65940
atgtcgcgaa ccctttcgcc gcttttataa ccgcaggtgc caaccagctc cgccccgcaa   66000
aagtcagctt tgttacagcc gttggtgatc ccgaagctcg cgctggcctg aaggtacgtg   66060
tgtccctcta tgccggcctc gcgccgtctt ctagccacca ggttccagcg gtttcgtaaa   66120
agcatgttat taacggcggt tgatagtaag actcgggtta gtgtatcttc tgatacgtgc   66180
catgttgcca tgtcacccaa tcgtgattgt gcctcgcggg cagtgattaa caattcctct   66240
cgcactgacg gagacaaccg cttaaaaggt gctaccgtat tttctggtgt ggcgtcgtaa   66300
gtaacgattg ttcccactct acgcccaatc acacacagag aaacgtgcgc aaatagggtt   66360
tcgtccggct cttcgtctgg acccaagcgt cgtgacgata gcgacgcaga tggcagatag   66420
ttgctcacta ggtacagtag ccgctcttgt tctgacaatc cttcggacat ttctccgaaa   66480
aaatctgggc ctgccgcagt tgccaaaacc gcacccaact gggggcagtt aacaattccc   66540
aaaaaaaatg ggccgcgtac atcatctact atggacaata cctcccctac cacacaccca   66600
ttgcggtggt cgatattaat gggtaaccta gatgctggtg gtagcgccgc cgcaactgtt   66660
tctctggtga gcgttaactc cccaccatca cccatatcat agagagctat ataccccgct   66720
acgtaaatag gaaggctcac aacattgctg tctgtagcgt acgcgtccat agtaaaattt   66780
gcagaggttt attataggaa agtacactcg gcatcagcat ctgcggctaa taaacactct   66840
agttcacagt ttaagaattt attgtagtga ctatgggcaa ggcattacat ggcggatgta   66900
aacgaaggaa tatcccaag acaaacaaag tacaacaggt cataatcact ggcaacatta   66960
aactgtccca aacgtttagt ttcctcgagt gatgccctca atctaggctt ttgcattaac   67020
agtccaaggc cccgttcgta ctggagagct acagcgtcgt gtgcggctag cacttcgttt   67080
ataggcgctg gcgcagtttt gcgtcggttc tctagctcta tgcctattag cctagtcagg   67140
tttgtttgat tgcgcccggt agacacatta actgcacggt gatgtgggtg attacgagct   67200
ccagtttggg cgtccaaaca aagggctgcc aaaccgggaa aaagctgggt tatctccacc   67260
tctgtgttag cgaggtatat tggagaaacg tagtgagagc ataaaaacgt aaagttattg   67320
ttgccgctgc ggctaaccat ggctgatgcg tcaccccta tcgcccctct agcattcccc   67380
agtgccacgg aaaggttggg tactattgct ccgagctgga aattatttcg caatttgtca   67440
gtataaacat tgccgttcca caacagacgg cgtagcaaca acagcgcggt gatggtgtta   67500
atcgttgagc gcagtagggt ttggtcttcc gttagaaata agttttgggc gcgcactaaa   67560
aatgcagccg ctgctttgtt aacatcgtct atgtatgccg tttggttcac atcaagttct   67620
ggtccaatag ctgtgttggt tgttcccaaa ctacctggga tagcaggcag tacctttagg   67680
cgtattagcg tttccaggac gctatgaccg ttaagcgcgc ctcgttcgta tctacctcct   67740 cccctggaa cgtgaaactg gttttcgga agacgcgcac cattaaactc atacaccacc   67800
ttcccgatgg ctccatcctc aagggaggcc gatagagcct cgatgtatat gggcaactgt   67860
tcaattagtc ccgaaaagct cgtggggtac gagaagttgc tgtttaccgc acgatgagcc   67920
```

```
aaatggaggc ataacacggc agcctcaaag gcggaatatg gacggtttcc tatgtaaagc   67980
cgcccgcaag actggagagc taccactgct gtggacataa atgttttaga catgcgaccg   68040
tctctgtagt caatactgcg agtagccact ggccgttctg ttactaaacg gtcttgcagc   68100
gccctgtacc aggtgccaaa aaccactccg tttgaccctc ccgcggctcg ccccacaaac   68160
accgtagtta ataagtccac agctaggttt gtgtcaaact cataggaac atcgtttttg    68220 gctatttgaa tttcactcaa cgattgggca acgttgttgt cgcgctggtc tgagtcactc   68280
gcgtttactt ggggcgttgc cgcatctgca ctttctgcag cacgcgcggc gtcttccagg   68340
gctgccaggg cgtcggccac tttagccact tgccgctcca aaggtctaat taaggcgtct   68400
acgtttgcgg agctgtattg actctgtgct tctagcgtgt ctatggcagc ggctgccgct   68460
cgatgtctgg ctgccacaag cttagtgggg tctgcccggg ggtttgagct ggctgtaaaa   68520 gttgggggcgc tccagaagtt aagcggaaat ggtggggcaa taaattttcg cacatctgta   68580
ggtatagttg acctggcagt gtcgcataca tacagcgacc cgaagacata atccacatac   68640
tctgccatct cggctactac tataaggcct ttagcttcga tcttggtgta tacttgcgtg   68700
taggcgcgct aacaaaaaag gggcagcagt ctttaatgtc acgggctttt attttggggc   68760
aaatagggat gccacccagg caaggggtt tgcgagcgat atagtcgccg gttgatatcc     68820
cacagcggcg ttagtggtgt ttgcttgggc cgtcgccgaa aacaaactcg caacggcagc   68880
agtcgctgca ggtttagctt gcgttatagg ttgaatagac ccagtagtag ttttggctct   68940
aaaagctttg gaatttgttc ttcgcgtaac acatcgcctt ctagttgatc tctcagaaat   69000
gggaggggag tattccgcta ggcgtgatat agtgcaagat agcacagctg cgttgctata   69060
cactacctgt ggcgataaac gcgttaccct caacacccgc attcctcgtt gagctacaaa   69120
cactaacacc ggtgctagta aaatttcacc gcttcccgga ggcaaggttt tggctagcaa   69180
cctacatgag tcgtgaagct gtcgcatacc ccccttccgt tgtaaatttt tactagcggt   69240
gttcatattt tttgagaagc gacacgtttt tagttctatt aagatgcaga ccccttggc    69300 gtcagagcca tgcccaaatt gcactgtaca tacacaatct gggcgccgct gtccgaggtt   69360
gacctcaaag gctagagaca cgcccatagc cgttttaaga gtttccgctg gcaccaattc   69420
actaaaaagg ggagcaagcc gcgctccgta cactccattc ttcttggcgc ttgccaaatc   69480
ttgaaccatt gcgttataga agcggttgtg gcaccgtata cccgctctga gtctgcttct   69540
agcggtgaga cgctgtttac gtttcatctc cacaggcagt aatggctgct tgcgtaccca   69600
cgggagaagc tccacgaagc gccagcggaa cgcccacccg gcggcaagta acaatagtta   69660
gaatttacct cgatggagtt tatggcatcg gtaagagcac gacgggacga gttatggcat   69720
cggctgctag cggaggaagt ccaactctat actttccaga gcctatggcg tactggcgga   69780 ctcttttga aacggacgta attagtggta tttacgacac ccaaaaccgg aaacagcagg    69840
gaaatttggc cgttgatgac gcggcattaa taactgcgca ttaccaaagc cgctttacca   69900
cgccctacct gatactccac gatcacactt gtacgttgtt tggggaaac agcctacagc    69960 gtggaacaca accggacctg accccttgtgt ttgaccgcca cccggtcgcc tctaccgtat   70020
gctttccagc agcccgctac ctactcggta acatgtcaat gtgcgcgcta atggctatgg   70080
ttgctaccct accaagagaa ccccagggtg gtaacattgt ggttaccacc ctaaatgtag   70140
aggagcatat acggagactg cgtacgcggg ctagaatagg agaacaaatt gacattacgc   70200
tgattgctac attgcgaaat gtgtacttta tgctagttaa tacatgtcac ttttttgcgct 70260
```

```
ctgggcgagt tggcgcgac ggttggggtg agctacccac ttcctgtggg gcttataagc   70320
atcgcgccac acagatggac gccttccaag agcgcgtttc accggagctg ggcgacactc   70380
tgtttgccct gtttaaaact caagaactgc tagacgatcg cggtgtaata ttggaagttc   70440
acgcttgggc gttggacgcg cttatgctaa aactgcgtaa cctgaatgtt ttcagtgccg   70500
atttaagtgg tacaccgcga caatgtgcag ctgttgtaga gtctttgctg ccacttatga   70560
gcagcacctt atcagatttt gattccgcct ctgctttaga gcgggcggca cgcacccttta  70620
acgcggagat gggcgtctga agctatatgt aatgtttgtt gtgccaatgc caaaattgtg   70680
aaataaagat tcatttgcca atatccatca tagcgccttg tgtgtttcgt gtgtaaactt   70740
ccagtttcta gtttggggat atataagccg ttgtgctctt aaatcattta gtacagcgcg   70800
gccgagatac tcgaggtatc cagtggttgt atattgggaa taaatactgc tgcgattatg   70860
tcacaaccgt atctaaaaat agctatctta gtggccgcta ctattgtgtc tgcgattccc   70920
gtttggacaa caccggtttc aacttcacca ccccaacaaa caaaattgca ctatgtggga   70980
aatggtacct gggtacacaa caatacattc aacgtaacca ggtatgacag gataaccatg   71040
gaaccagttt ataataacaa tttatcctct actacctttt ttgttgctat atcggagaga   71100
aattttcgca cggttaacac tccacttgga gcgtccgtat tttggatttt aaaaagcgct   71160
cttaatcctc ccaaacacca accctgtata gctaatgtgc cagaacccgg tgacccacgc   71220
ggaccgtgcg tcaactcaac tgtgagtcta ttttttaatg acaatttgga gccgttttta   71280
atgacaaaaa atcttttgga gtttgaagta ttgcccgaca actacataac cggatggacg   71340
tttgagcggt ctaaaactgt ggctacgaaa ggcaacccgg ttggagtggt tctctcccct   71400
ccccgaacaa gtccggatgt aaataacacc ataagagatg atggcacccc taaacagcac   71460
ttgagcatta tagacgaaca tactacgttc gtgctcgacc tgcaaaattt tacaaaaact   71520
ttaacttata taagcccatt tgctgcggtg tggccaataa cagccttttca tgccggaatt   71580
acagtaatgg ggtgtgacac aactcaggcg attgcgtacc tcggcaatgg gtttatgggt   71640
ttgcaaataa gctcggtaaa caatccaccg ctggagatga ttgttgcacc aaatgacgtc   71700
cgtgctcgga tagttaaccg ccttccccca agacgtcgac ttgagccacc cgggccatat   71760
gcaggaccta tctacaaggt gtacgtactc agtgatggaa attttttactt gggtcatggc   71820
atgagcaaga tttctaggga ggttgccgcg tacccagaag agagtttgga ctaccgctac   71880
cacttatcgc ttgccaacct tgatactctg gctatgttgg cagaactttc ttccggtaag   71940
agcaaggatg tgagctatta cttgtatcgc ataattgcga ggctggccgt agcaacgttt   72000
tcccttgcag aagttatacg cctgagtgac tatatgctcc ttcaagaggc catcgacgtg   72060
gatataaacc tccgcctaat tgtacctcta gtgatgaagt acgccgctgg gggaacggca   72120
gatagctcgt acacatcctc ggacgtagct atggaccaat tcgaggtggc tcaagcccag   72180
attgagaaga tagtagccga tataaatatc gaaaatgaat tgcgcaaacc tatgtacgag   72240
caccgctcat tattgaaaag cgtgtacgct tattctagaa agccgctacc aaacgcggta   72300
agctttgcta accggctcat cacggctatg tataaagaag caattaagga cagaattacg   72360
tggaactcta cgatgcgaga ggtgttattt tttgcggttg gtgctgctgc aggttcgcat   72420
gttatcctca cggatgggcc agatctcggt ttacatgccc acaaagattc ttcgatgttt   72480
ctatctcttta accgcaacat actcttgttg tgtacggcca tgtgtacggc gtcgcatgcc   72540
gtgtccgcag gagtaaaact agaggaagtt atggctggcc ttattgccgg gggtgtacaa   72600
tttagcctcc tagaagtatt tagtccatgt atggcgtctg ctcgatttga cctggccgaa   72660
```

```
gaagagcatg tgctagatct actgtccgtt atcccacctc gcctgtacac cgacttaaac   72720
actggcttgg aggacgacgg aaccaccatc cattcatacg gacggtctgc taacggaatt   72780
ttaaactctc gaatcgcata taactttgat gctgttcgtg tatttactcc agagttggcc   72840
tcatgcagca ctaaactacc aaaagttttg gtagtgctac ccttagcatc aaaccgaagc   72900
tacgttataa ctcgtactgc gcccaatata ggtttaactt actctcttga tggggtaaat   72960
atagcaaagc ctatagtcat cagttacatc acttatggaa attgtcaagt ttcgagagct   73020
acaatcaggt cagtttactt ggatcatccg ggccacaccc agtcgtgcgt atattgcggg   73080
agtgtgttta tgcggtatat ggcatccgga gcaattatgg atttgatata catagatgac   73140
aaagatgtag agttgcaact ggtagcaggg gaaaactcaa ctattccagc ctttaaccca   73200
aagctgtata cgcccagcat gaatgctctt ttaatgtttc caaacggaac agtaaaccta   73260
atgtctgcat ttgcatccta ctcagctttt aaaattccca gtacttatct gtgggcttct   73320
attgggggtt tgttgctggc tattctgatt ttatatgtaa tcgttaaaat gttatgtggt   73380
ggtgtaatta ataatgacta tagttttgtta ttaaactctg agtaaacaca acaatgtct    73440 agtgtgttgt attgcgtgta aacagtatac gagtgaacat ttatacgtaa aatggttaaa   73500
ttttattttc gctataaacg ggaatgcggc ggcgagggct gctgcggcgg cgagggctgc   73560
tgcggcggcg agggctgctg ggcggcgagg gctgctgcgg cggcgagggc tgctgcggcg   73620
gcgagggctg ctgcggcggc gagggctgct gcggcggcga gggctgctgc ggcggcgagg   73680
gctgctgcgg cggcgagggc tgctgcgcg gcgagggctg ctgcggcggc gagggctgct   73740
gcggcggcga gggctgctgc ggcggcgagg gctgctgcgg cggcgagggc tgctgcggcg   73800
gcgtaaatgc agctattcca caggctcccc gcttaaatag gaaaggtggg cggcggtttt   73860
actggtaaat gtagttacgt agcgttcgca cttggttaca ataattatta tatattatta   73920
gcaattggtg cgaacgggga attggtccaa tcaaatggtt taaaaacggc catgtgacat   73980
acaaaccaat cacaacacct agtattgatt acttatcaat aggttccaaa tcataatttt   74040
cgcctaatgc gggtttgtac tacctccagc tatcttccgt tgaaaattac aacggcatgg   74100
ggcggtcggg acaccaccat atataaatat ctcgcgcttg cattgtagac cgcaaactca   74160
cctttaatgt agtaaatttt acaacattaa aatgttattc gccttaataa aattacaata   74220
cagcgatgta acttcggagt ttttatgctc tgttaacatg cacagttaca ccaccacgct   74280
ttaatctctc gctgagtaag taatataagt agtatgcccc ctttcggctt aagtccaaat   74340
tatcaaatgc tgttattaaa gacacgttga gaactatggc caccggcaag ccgcttccca   74400
gcatgcgaca ggctgactgt gccgcccccc cgataccttc tttggcgtat agcttgttta   74460
gtacgcttgc aattttagct ttaatttcat ttgattcgtt gaaggaacta gccccaact    74520 caactctggt ggagtttgca gcaaactcgg caagtaggtt agcctctagc tccacaactt   74580
cagaaaaact accgtttact ggagtgttgg agtgggtata gcgaacgatt atctcgcata   74640
ggtctcctaa cattgcactt tcgcgtatta tttcatttac ggcatcggcc accaggtggg   74700
ggtctggtaa cggatcgcat gcgtcatgca ccgctccgat gtagctctcg accagctgtt   74760
ctagggatgc gtagcagttg attaggttcc acttgtttag aataaactgg cagagtacaa   74820
atcgttgtag cgtggtaatg cccagttgag taagctttcc cccaaaaaat cgcagttttc   74880
cctcatggcc gtatactgct aaaacggcat caacaatggt acttcgcgct tggttgaggt   74940
ggtcatccaa gcccggccat ggttcctcaa ccaagataat ttcatcgacc agtttgaata   75000
```

```
gtaactgtag tgattgtaac gatgctccac ttgctgattt gcttgatgag ttccagatgc    75060
tacagggttt tggaataagt cgcacctgca caaagtcgct caccactgtt tttctaagtg    75120
tgcgtttgga tccatttgtg gtgcctatgg ccattgttct cacggctctg ggagaggtga    75180
ctattacatc tgtgcggcta tgcctttcta actcgtcccg tagtggggc ctggatacgg     75240 ggatgcgatc gaagagtcca gatacgagtg tatctagttc ttgtggcaac tcattcaaat    75300
atgcttgaac taaggtaaag catgccaggt tgggtgtgta gataaatcca gaagctgcgt    75360
ttgtaatagt tggaacggta aatagatgta gcgtcccatc ttgtggtata tctctccccg    75420
tagacacaat aagtccggat gtaacctta gagaaaccat gcactcggcg agatatgggt     75480
cgtacacctc cagatcaaag ctcccgcata tatctctacc aaaagcctgg gtaccctgga    75540
ccaatacttc caagcgatca acaaatacgt cttcttccga gctaggcgcg ctctcatggc    75600
ggcccgttct gtgtaattcg ctgcgaacat aattggcgac aactctgtcg tttagcttta    75660 gacccttag agttaaacca aactttgcaa tttctccact ttctggagct gcgtgcgatc     75720
ttggcactga gagtaaacat ccaccgtaaa taaaatacgc ccgatgacca caatcagtaa    75780
tgtagaaaac tactccgttg tgaattactg tgtcgctgta cttaaagtcc atagtttata    75840
ctacactgca ggcgtatgca cagcgataaa ggtgtatgtt gtgaacttaa aagcagctga    75900
gtataaacct tgtgaatggg cgttgctaga gacgctgcct ctatgcggtc gtggctgcaa    75960
atccacaatt cttttacagc aaactggttt tatattgggg atccgcttta aatatgagat    76020
acctagaaca ctaacagtaa gtggtctaag acggggacaa cccgtttatc acgcgggtca    76080
gcgcgtattt atataaactt tgcggttttt agttttaagg ggaccggttt gggacaaact    76140
aggggatgtc cctagctgtt tatgacattt tgtgattact gtttagtgtt tgggttcccg    76200
gaaatggcgc agttcgtggt aaatatataa acgttaaacg gcgtgtcacg atattgactt    76260
tttgaattat tcacgcttta tcatgggccg ttgccccgca tataaaattt acaaccccta    76320
gcttgttata ctagtcctgg ctgtaccata tcctgctcac agactaccaa aatctctctg    76380
cattctttag ggctaaaaat gccacaaatg ggaaataccc gtttacataa accactcgag    76440
gacagcattc cactgattga aaacgatgaa aattcatccc aaactgaagt tgacctatat    76500
gactatgtgt ctatgtcatc ttacggggc gatagtgact ttttaataag ctcggctggt     76560
ggcaacatag ccccagatag tcgcccgtca ttttcagtat gcgtgttcct gttttccatt    76620
tctgcacttg tggtaaaacc tgtttgctgt tttatatttc tcaaccacta cgttataacc    76680
ggaagttatg actttgcggt agctggggga gtttgtacta tagtgtatta catgcggctt    76740
gcaataactg cctggtttat gtttcgcaac attcaagcag acatgctacc gctaaacact    76800
ttgcaacaat ttttattgg gtgtttggcc tttggtagaa ctgtcgcgtt tttggtggta    76860
gcatatacta ccttatttat acgctccgag ctgttttttca gcatgctagc acccaacgcc    76920
gagcgagagt atataactcc catcattgcc cacaagctta tgccacttat tagcgtccgc    76980
tctgccgttt gcttagtcat aatatctacc gccgtttacg cagcagacgc tatctgcgac    77040
acaattggat ttgcgatacc gcgcatgtgg atgtgtattt taatgagatc aacctccatg    77100
aagcgtaact aggggcctc ccactgaggc actaccggct tagcagctga ctaacacagt     77160
ataaaacgtg agaagaaatc agtctcatgc gccattagcg ctaggctagt tagcgtggag    77220
gaccggagcg ctaccgccag cagtttcatc cgcctggtta cgggtttgtt aacacctacc    77280
ggtgttttac cgctaccata atggaccggc gctctgaagc gtttaaaatt ccggttccag    77340
aagtaatcca tgccgggcaa attttatcaa ctatagaggt gtcatcacac cgcacgctgt    77400
```

```
ttgactttt  taagcagatt  cgctctgacg  acaatggctt  atacgcagcg  cagtttgacg   77460
tgctacttgg  aacatattgc  aacacgttaa  cactggtgcg  gttttggag   ctcggattat   77520
ccgtatcgtg  tgtgtgtact  aagttcccag  agcttaatta  cgttaacgat  ggcacaattc   77580
aatttgaagt  acaacagcca  atgatagctc  gggatggtcc  ccacccagtg  gatcagccta   77640
cccacaccta  catgatgaag  cacatagagc  agcgatcctt  gagcgcggct  tttgctattg   77700
cagctgaggc  tttgggtctg  ataggaggca  cttccctcga  tggaactcag  atctcgtcgt   77760
cgctgcgggt  gagagctata  caacagcttg  ctagaaatgt  gcaaacagtg  ttggactctt   77820
ttgaacgagg  cactgccgac  cagcttttgc  gcgttttgct  ggagaaggct  ccaccgctta   77880
cacttttggc  tcctctgcaa  atttaccgag  acgagggccg  cctggcgtct  cgggtaaatc   77940
gcgccgttct  cgtttcggag  ctcaaacggc  gggtaataga  agatactttt  tttttaacta   78000
agcacgagcg  taacagaaag  gagctggtgg  tatcccgcct  ggctgagctg  gtaaattgta   78060
cagctccttc  tgttgcggtt  acgcgaatga  cccactcaga  cacaaaggga  agaccagtgg   78120
atggtgtaat  tgtcactact  gctggtgtgc  gccagcgctt  attacagggc  atcctaaccc   78180
tggaggatat  ggccgcggac  gttccggtaa  cgtatggcga  gatgatgatc  agcggcacga   78240
acctggttac  agcgctagtg  atgggaaagg  ccgtgagaaa  cttagacgac  gtggcccatc   78300
acttgttggg  aatgcagcgc  gatcaggtta  ggtctaatga  gcgcatgatt  aaagactacg   78360
aagacgtacc  cagcatggca  cgggtgcgtg  ccgacctagt  tagtgtggga  gaccgtttag   78420
ttttttttgga  gtccttggaa  aagcgcgtgt  atcaggcgaa  aaacgttccg  tacccttttgg  78480
ttggaaattt  agacttgaca  tttatcatgc  cacttggaat  cttcaaacct  gccacagaca   78540
ggtactcgcg  ccacgcagga  agcttcacgc  caacccagg   acagccagat  ccccgaacct   78600
acccaccca   gaccgtgtac  ttctttaaca  aagatggaaa  tttggtacag  atttcttttg   78660
atagcgccgc  tggaacggtg  tgccacagct  cgttttttgga  cgtagatgct  gtgctggtgg   78720
ccatcaggag  ggaccctcac  gagctccact  gtgcatttgg  ggcttacgta  accctacccc   78780
ccgcaggcag  cttgctcgac  cagatgagac  ggttttttga  gcgatggcat  ctgctgatgc   78840
cagcgcgccc  gcgttggacc  gccgaggcgc  taatgtcaat  agatcagctt  ctctccccct   78900
gcaacgcaaa  cttacgccta  gagcttcacc  cagcatttga  ttttttttgtg  gccccgcag   78960
atgtggcact  tccaggccca  tttgacatgc  caaacgtcat  gcccacagtg  gtggcaatgc   79020
ctcgtcttat  caacggaaac  attccacttc  ccctctgccc  cgtggaattt  cgtgacagtc   79080
gcggctttga  gcttagcgta  gacagacaca  ggctaaaccc  ggctacggtt  ttggcggtac   79140
gtggcacatt  cagagacgcc  aattacccta  tggtgtttta  cattctcgag  gccgttattc   79200
atggcagcga  acgcacattt  tgtgcttttgg  ccagactcat  aatgcagtgc  atcgtcagct   79260
attggcgcaa  cacccaccag  gtggcgtttg  ttaacaactt  ttacatgctc  atgtacatta   79320
acgcttacct  cggaaatggc  gaactgccag  aagagtgtac  ggctatttac  cgcgacctcc   79380
tggagcatgt  gcaggctctc  agaagacttg  tagttgagta  tacagttcca  ggggaagcag   79440
tgggtggaca  gggacacgac  gcgctaaaca  acgtcctgct  cgatccagct  ttacttccac   79500
ccctgatttg  ggactgtgac  cctatcttgc  acagggctga  tatgggccga  gctcgggcac   79560
aggatctatg  ggtggatggg  gtagactatg  cagcaattcc  ttgggtggag  atggccgaag   79620
tagactttag  aaaacaggc   gggcgcttgg  tccacaaccg  acccatacgc  ggggaaaaca   79680
agagaaaccc  aatcgttcct  catcacgacc  cagaatggtc  agtattatcg  aagatatact   79740
```

```
actacgcagt ggtgcctgca tttcacgcg gaaactgctg taccatggga atccgatatg    79800
accgcgtata cccgcttgtt cagaccgttg ttattcctga ccttggggca gaagaaattg    79860
cccccaccag ccccagcgac ccgcgccacc cgctcaatcc gcgccactta gttccaaaca    79920
cgctaaacat attatttcac aacgccagag tagcagtgga cgccgacgcc ctgcttcttc    79980
ttcaggaggt ggtcactaac atggcagagc gcacaactcc catattggct acaaccgctc    80040
cggacgcagg aacgtctacc gcagtaacac aagagatgcg cacttttgat ggaaccctcc    80100
atcacggcat ttaatgatg gcttaccagc gcaacgacga aacgctttta gagggtacct    80160
tcttttaccc cgccccagtc aatgctcttt ttgcctgccc agatcaccta ggggcattac    80220
cgggtcttaa tgcagaagta ttggaagccg ccagagacgt gcctccagtt cctcactttt    80280
ttggagggaa ttactacgcg acggttagac aacctgtggc gcagcacgcc atacagagcc    80340
gcgtggatga gaacacgcta acatattcgc ttatggctgg gtacttcaaa ctgggtccca    80400
tagccctatc ccatcaattt gccactgggt ttcacccagg gattgcattt accgttgtac    80460
ggcaagacag gttccttacg gaaaacatcc tctttgcgga gaaggcgtca gagtcatact    80520
ttatgggcca gctacaggtt aaccgccacg aggctgttgg gggggttaac tttgtactaa    80580
ctcaaccgcg agccaacgtt gacctgggag tggggtttac agctgcttac gagccgcgcg    80640
ctgccactcc cgtaacagac atgggaaatt gcctcagaa tctgtatcta accagaggta    80700
cgatcccaat gcttgacgga gacgcagacg cgtatttgcg gcgggttgtt aacaccggaa    80760
accgcctagg acccccaaggt ccccgcccta tctttggtca gctgatgcca gctacacctg    80820
cgggcgtagc tcacggtcaa gcggcggtat gtgaatttat cgttacaccg gtgtcggcag    80880
accttaatta ttttaggcga ccctgcaacc ccagagggag gagcgctgga cctgtatatg    80940
cctgtgacgg tgaggccgat gccgtggatg ttatgtacga ccacacacag ggtgatcccg    81000
cttaccccaa ccgtgctacc gttaacccctt gggcttctca gcgaaactca tatggtgaca    81060
gattgtataa cggcaagtat aacatgaacg gggcatctcc tgtgtacagt ccctgtttca    81120
agttttcac gcctacagaa gtagacgcca aggggcgtaa tatgacacag ctaatagccg    81180
acgtgggtgc tagtgtggcc ccgagtacgt ccaacacaga aatccagttt aaacgcccc    81240
atggatcgtc agacttggtg gaagacccat gttcgttgtt tcaagaagcg tatcctctac    81300
tcagctccac tgatacagca ttgctacgca cgcctcacgt tggcgaaatt ggcgcagatg    81360
aaggacattt tgcccagtac ctaattcgcg acgaatcccc cctgaaaggc tgttttccac    81420
gaatttaggt tgtgcccgcc tacaactttt cacttgcaaa ctcaataaaa cgcacagttt    81480
gtatattcag ttgtcagttt gctctactcg agcgtcggcg ctttgtctag ccctcttagt    81540
gggtattgtt accggctggg gttttattgg cgttgttatt ggggagattt tagttgatag    81600
aaagcatacc gaggtttttgg gggtgtcgct taatttcggt gtctgtaaac gtaaaaagag    81660
atggctagcg ctgcatttga gatcgacata ttgcttccag gagacctgtc tccttccgat    81720
ttgtcggcgc tgcaaaaatg cgagggtaag attgtttttt taactgccct gcgtcgtcgc    81780
gtcatgcttt ccagtgttac cctcgcgtcg tactacgtta acggcgcacc cccagacacg    81840
ctatccctga tggcggcgtt tcgtaggcgt tttccagcta taatacagcg cgtgttaccc    81900
aacaaaatga tagcagtggc cctgggcgtt tctgttcttc ctcctggaac gttcatacaa    81960
aacacaggcc cgtttgactt aaccaacggc gactctgtgt gtgcgcttcc cccaatatta    82020
gacgtggagg acaaactgcg tctcggatct gtgggcgagg aaatactatt cccgctaact    82080
gttccgctcg cccaggctcg agaactcatc gcgcggctgg tagctcgtgc ggtgcaggcc    82140
```

```
ctcactccaa acgcccaggg tcatcgcgga gcggatgtaa tgttttacaa cggaaggaaa    82200
tacaacgtaa ccccagattt cagacaccga gacgcggtca acggagtggc gaggtcgctg    82260
gtcctcaaca tgattttgtc aatgaacgag ggctccctag tgctcctttc gctgatcccc    82320
aatctgctca cattgggtac ccaagacgga tttgtaaacg ccatcattca gattggtagc    82380
gccacacgcg aggttggcca gcttatccac cagcagcccg tacccagcc gcaagatggg     82440
gctcgccgct tttgtgtata cgacgcttta atgtcgtgga tcggagttgc atctcgtctg    82500
ggtgacgttg tcgggggaaa acctctggtg aggatctgta cgtttgaagg cccggctact    82560
atttccagag gagaaaaggc cccggttatt caaacgctgc tgtaacttaa taccccaaaa    82620
ctatctaata aataaaaact gagactgtta tattcattc agtgtgttta ataagaattg     82680
tgaacataac ttattctata tctcattgcg tggaaagact ggaaaacgca ttggtggtag    82740
gtggaaggct cgccatataa acagccatca ctagggcaac caacatgtca tcagacgcgc    82800
cgtttcgctt accggtaaac actctggttt ctgaggtacc ggtaatcacc tcggttaagt    82860
ttttcatctg ggtcagcaaa tactccaccg ggtctgtttg aaggcgcacc gtatttgata   82920
tgagctcctg cgaggcaagt accaatcctg agttgaatgc tttaataaaa tggtcaaacg    82980
cccccgtttt ttgttttgt agtaaaaaaa acggataggc aacggaactt cccggggtg     83040
tacagtgata aaataacaca gtcccggca tatgcaccac gtccgcctgt cgtagcgtgt     83100
tgagttccag ttgaatgttt gttgctattg ctaccgcagc gtcttggcta ctgttacccc   83160
cgacagctat tctaacagag tcaaaggggc ggctgtgaat agcaaaaacc tttgctaggc    83220
attgagcaac acacctagct atgagctcag ccgagctacc cgttagggcg cttagaaaaa    83280
agtgctccaa gccaaacaca atccagttg agcgatagcg gccaactaca gccacgccgg    83340
ttcctgaagc catagcattt gtagtaaacg caggatcaac gtagacgtaa aggttgttgg    83400
acataatatc ttgattagcg acagtagaag gtcgatacaa caaaaaacgg tcctgagcag    83460
tttttgtaaa aactggttca tctctatgtg ctcccgaaat gttttccacca cctattattt   83520
cttgcataaa tgaatccggt aaaaatagct ctgccgtgtt acgcatggct ccatccattg    83580
ttataaaaac cggtttgttt aaaatgtaac atgagcacga agtagcgttt gtgtgcgcct    83640
ttacgcgctc catatgttcg tcgcagatat aggttaccac gttcaaaagc tcgtctgccg    83700
ctccttttgag gttatataaa aagctggtac tggcctttcc cgtgttggtg gaggacacga   83760
aaatgatctt gcagttggtt tgattaagga atcctataat cgtttgtaca gcctcggggc    83820
gtataaaatt ggcctcatca acaaacagta ggttaaagtc ttggccgcga ataccctgga    83880
acagagggaa taaaaagag aacagattgt tagaggtttc acttaagcct ggccctcgac     83940
gcgagttgca gcaattttgt tttttaacca gctatatacc tagttctata tacaatccga    84000
gggcattgac ggcgcaacaa taaaacacta aaaactatgg atgcgcatat agccaacgaa    84060
actaagcatc tgatgacaca cggtaatcgc aacacactag cgatggtaca cgtaattatt    84120
ccagatgagt gtctaaaaaa ggctgggatt gagccggcga ggcttcaga tcgacataga    84180
gctagtccgt ctacgactcc cgcgtttaga gtgtttaccc agactcgata tcatgccact    84240
ggaaaatgtt cgttatggcg caccatttt gccggtatg tgcaacgagg ggccattaca     84300
agcgcgctgg tgcctactat tccttcagac caccccggc tatttcaatc aaccccggat    84360
tcgggtggat tattcgtatc tctagaaatc gaatgtgacg cagatggccg ctttgatgcc    84420
tttactatag ttgcactgag aattgacatt accgacgact cgcgtactac agaaattttg    84480
```

```
tttacctatg atgagctgtt accccccaggc accagatacg gggcagattc cgcgcgtata   84540
gcactcttgt gccgccaatt tgtggcttat gttaacagtc attctaatgt ttcagatagc   84600
gctattaaag cggcttcgca catagaagct acgtttgctg aagatttaaa gtctactggc   84660
tgtcatcaat tatcgcaggg atcacgcata aatcctaccg agtacctatt ttcgggcggg   84720
ggctttgaca acaaccaagt tttggcgcgg cttgaggagg acgataaaga aataatgtcc   84780
cttattcgca gggcgtctga ggtaattgca aagcgtaacc cggttcgggt gctaaacacc   84840
caggatcgta acggtgcctc tttaaggcga aaatgcatag catctggcct caaacaaggg   84900
gctattggag cacatgcacc ggtatcttcc acgcgcgacg gagctagtca tagtagccaa   84960
gagggaactg ctttactctt gggccttgaa cccctgact ctggaaggtt tgttaacagc   85020
ggctctcggc gccatctacc tcagcaaggg ccaaaaagcc ccgtgggtaa agactgttcg   85080 tcggggggcaa tagacgacgt tttattgctc accccgaaa actcaacccc cctcacccca   85140
ctagactggc tggatgtggg ccacgcagca gttgccgggg gagatacacc cgtagacgtg   85200
tggcgccgaa ggcctatatc tctggtggct cgaaagcact acggaacctg cgaaacattt   85260
gttgttgtgt cgtatgaaaa ttctaccgca tgggggggta ggagggctag agatggacac   85320
ctgactgggt ccatcaaccc cgctgtgcta caggcgtgtg ttgccgtagg cgtagaccac   85380
cctagaaatt tgccacccga aacgcgtgct gcgcttatag cacagtttcc aatgcttcgt   85440
atcccccttg gtgacactcc accgcctgtg gccgcgtttg atgcggctgc ggaattggct   85500
ctaatagaac atttccgcaa agcgtgtgtt tctgccctttt tggccgcaat ctcagaacgc   85560
ctgcgcgtag aacctcgaat gtcacagcta attgagtatg acattccaaa caataaccgc   85620
gactgcatca taagcgttgc acagcgagct cctgagttgc tggaagcggt ggcccttgct   85680
attcaaaatg tttccatagc tgagttttgt aatagcgctt taatgcttgc ggctctttcg   85740
catttaaaca ttttatcaaa aaacaatcac ggacgaatac cctatcacaa atcctggctt   85800
ccaagcttgg ctgggggacc agatgcgttt attttcgact attatagctc gggtggggaa   85860
gtaattaaag tttcccacgt tccactggct atattagttt ctgcaactcg gaccggccaa   85920
cattcgtgta agtttgctcg gggtgcgccg ggagtatctg ccaaaacgta cgagcgatat   85980
cttcctgggg agtgttacgc gtacatatgt gtgggcctaa acagatcgtt tgacgctata   86040
gtagttttac ccggtggatt cgcttgtagg gcaaatgcct cgagaaaact cgcgtggcca   86100
gctcatctca tagagccgat attagagcgc tactgctgga caattccgtc ctactgagat   86160
taaacgctaa aaattatggc tgccgactta aatagctact cgagtatatg ggaggggtcc   86220
tcgttgtccc ccaaccgaca actcaccata gaagccgcta attgtttaac agaggcgctc   86280
acagaagata ttgcagtgct acgccttatt cgcagcgacc cacgcgtcaa aatttttatg   86340
gcggtgagtg ttcttactcc caggctggcg cggtttgccc caccccaatc taaactaaca   86400
cacactgcca agtgtgccgt gataatgata tacctaactc gcccgaaggc cctggctcta   86460
caacccaagc agtttcacgt gctagtaacc tttagcaaga gcagcgtata ctctctggta   86520
atgagagtga aaacaaagcc gtttcctata agcccacaga gattttgtgg ggtgttttcaa   86580 gaccctgaac caatcgggct accgtccgac gtgcccaacc ctgccacaga aaatattccc   86640
actgaaatta cgaccgtttt ggacgtaagt aattttgcaa ctcagacgca gccccccaaag   86700 gacaagtacg actgttgcgt tctggcaccg ggtgtttggt ggtataaggc gcaaaaagct   86760
atatactttt tgcagatgga cgaagctctg ttggctctgt gcccagctgg gtggaaggcc   86820
agaggtttgg gaattattct cgggcgtttg cttaaccacc aggaaggctg ttctacatgt   86880
```

```
cgctttactg aacactcgga tccgctcaac gcaaccgcgg actctgtggc tacacccgaa    86940
tcgtgtttat gctgggctcc atgtttgtgg cgtaagtcac gccagcgaga gttaaaggtg    87000
gaggggatc  gctatttatt tcgcgttctc tttatggacg ccgtggagcg agtgcgtcta    87060
acgggattgc gacgcagccc aaaaatcaca gctgatctcg cagaccttgt cgtgggtata    87120
gggtcacatg gacaacaaat tccagttaat agcgctggat ggaaactggt ggcgctcgat    87180
gctaacatta gtaaacttat cgtttgtgga tgctactctc tacgctacct ctgtccttcg    87240
actgactgca aacccaaca  gttatcaacg agcgaggacg cataacaagc tacgaccaa     87300
gtaaacccg  gccggtgttt ctcccattga aactgctatt tttaccatcg caaataaaca    87360
tttcaaaaac cccttgtctc cctgcggttt gttataacca ataatacgcg ctaccggagt    87420
tttataaaac cacttacgtt ggtgttgtgg ctcgaggcga atacgatagt gcttttgat    87480
ccatccggaa atgagaagga tatattttca cctttaacgt ggtcgacagg agagttgcca    87540
aaccattggc gaagcctggc gcctatctcg tcaaaaccg  gttctgtagc tttgcgtatg    87600
tgggccgtgt atcctatttt gattcccttg aaagtagcta gagctagcgc tataaggggc    87660
accaaaaacc aggttttccc atgtcttcgc ggaaccaaaa agacggtcgc gcgctgccga    87720
aagtggcgga tggtggcgtc cgaaaactcg ggagtattaa acaccatttt tagaaacgcc    87780
cctattcggt ctgcgtggtc ccccaagata acggcagcta taaagtaagt agcgtgcatg    87840
agaatcattt tttggaaaag ctctagtgtt ccacgctgct ttccgtaggt ggggacatcc    87900
acctttatgc gcttgcttgt ttgttggccg tccccgtcta ggtcagctcc gttaaaagag    87960
gtgtcaacca ggcgactgaa gcgcgccaca aagttggcga cttggtgaaa ggcgtccgaa    88020
gaacgaagag agtcaaaggt gttcataata ctgtagtagg cgtttcggca cgagcgagct    88080
tcagcgtcat tatattcaac aaaagaaata gttttttagtg cctgttttac ttttgggtct    88140
acataagctt ccactgagga gggatccaat cgttctttgc tttctccacc acgccatttt    88200
gacaggctcc taaatagtaa tctcctagcc accgaagcaa atatttgcgc tgtttcgcag    88260
cagtcgtgca acgttccgac cccaggtaca acagtttggt gacgctgggg agttggaatc    88320
gcaaagttaa gaaaggccgt ctttacgtca tcttctcctc cggtttgagc ttccgctgcc    88380
ctatttttag caccactgcg agattgaacc tcttttcgga gagtttcaaa atactgtata    88440
gtctccctgc tcaacgcttt gccaaacatt tttgcgtaca cctcccccag ccgccggtat    88500
gagcttctca acacagtcta ggcgcaggag gctgcagttg gaagaagcct accaacgtga    88560
aatgatttt  aaaatgcgta ccctagattt ggtgcgcgag ggcgttgaca acgcaaccc     88620
tgcctttgtc cgtgcattta cgtcagcaaa ggaggcaagt ttggacttga atagatacat    88680
gcaggctcat tctagggtgg ggcgagtgga acaaaacgcc agggcgctcg cgcagcgcgt    88740
ggaggcacaa gccgctgttg gtgaaatact tgacagacat cgcaggtttt tgcataaaga    88800
ttttatagat aagtttgact cactagagga ctctctagta gaaagagaag agcgcttggg    88860
tgatgttcta tcagatataa actgtgacgg tggcagcggt gaagcaggcg agtcggagga    88920
atggctcggt cacgaggacg aagctctgtt gatgagatgg atgttggagg aagcaccacg    88980
agtgagtacg aaaattgcga tggaccctca ttctccccgc ttaacatgtc ctgtgccaaa    89040
aaaagcacca aaaacgctc  gctgcgaagc tcgcggattt ggggtggaaa atcatccgac    89100
tcagagcaca ctccattgct caccagaaac agttgcggac caacgggtaa cactagacga    89160
aaacatgcgg gaatatcaaa ccacaaacgt ggagcatcac ttaaccacga aatgggggac    89220
```

```
aaatcgttcc aatcaggaca caactgcccc cgcattagag cgtcagcggt tagatgtggt    89280
gcagcaacgc gaaaaatcgt caggattacc gaagaaggcg cctcacggca agacaatatc    89340
tggcccggcc agtcaggaat ggctgggtgg cattccccccc ctaagcgacg aagaactcca   89400
agtcgacatg gggattccaa ccatgaacgg tcccatctat ccggacaacc ttcacagagc    89460
gtagttagag ttggaggtcg cttgctcacg caaactccac tccgaaaaac tataatttta    89520
caaccaaagc ttgtacgcaa agtgtttatg cctacattta ctgtaaaccc cggtatgcac    89580
tataggcgcg tatctttagg ggaaacacca aaatttggag gtgccggaag ttatggcgaa    89640
gttcaaattt ttaaacaaaa tgggctagcc atcaagacgt cttctagccg ctcttgtttt    89700
gaacatgagc tggcagtgag tcttttaacc ggagagtgct cgctacgtgc gcaatctacc    89760
ctaggtatag ggggaattat ttgccttatg gccttttctc ttccgtctaa acaaatggtt    89820
tttccggcct atgatgcaga cttaaacgca tacgggtata gactatcacg caatggtcca    89880
ccctccgtgc tggttaccga gtcaatagaa cgggcgttca tcggtctcgg gcgcgcgctg    89940
gtatatctta acactagctg cggcctaacc catttggacg ttaaaggtgg taacatattt    90000
gttaaccatt ctcattttgt tataagcgac tgtgtaatag agacttaag tttgatgaca     90060
ctgaatacta actctatggc gatgcgtgca gagtttgaaa ttgatactgg agaagaggaa    90120
attaaaacac tccgcctacc caaaagtgcg tcacagatga catttagctt tgtggttggc    90180
catggacata accagcccct gagcgtgatt gcggacttta ttaacaacag cggactcgcc    90240
aaaaatactg gcccaataaa acacgacgtt gggctagcag ttgacctgta tgcacttggg    90300
caggcgctac ttgatctcct acttgttggt tgcatctcgc cctgcctgtc ggttcctata    90360
cttagaaccg caacctacta ctactattca aaccggcttt ctgtggacta cgcactagac    90420
cttctggcat accgctgctc tttataccccg gcgattttcc caaccacccc tctaacaacg    90480
atatacggca ttccctggga ccaggtcgag ggtgtttttg aaagtattgc aggagcacat    90540
caccgcgagg cttttagagc tcacctggat aggtaccgcc taacacacag gcggcttttc    90600
gcgtcaataa gaataccatc cgcatttacc agcgtactcg agctcgtttc tctcctgtgt    90660
cattccaacg aaaaggctcg cctgtcgatc cctctgttat ggactcctca cccgtaacat    90720
acagcggagc acctccgtat aagctgcgtc gcctcaacac atcgtaccca tacgcctcta    90780
agctacgcga gcgcgacagt ttaacagttg aaacattttc cggatacata aaccaggaga    90840
gtatttccga ggaagaagtt tacgagacta tggctactac cgctgtcttg tctacccgga    90900
tgtacctacc atcagtttta cccaacggga tagccaccat gacgttttg gatcatttga     90960
agaaaagcct cccacttccc catagcgata agcgattaaa cccaatctttt tatcgtcttg   91020
cctacatacg cgacctggtg ggacaaatgg agattgaggg catagtcgag cgtggaaccg    91080
cttcacgcct actaggtgcc cgtaagccag caggatttgt ggcgggaact tacacacacg    91140
ctcgagattt gtccaagaca atgtctatag caaacattcg ggatgccgtg ctagctatag    91200
aggcgcaaac ccgcgaccag agcgaaagcc aactgtgggc actacttcgg cgtggcttag    91260
ctacagcgtc taccatgaaa tgggggggcgc tcggaccaca gtatcacccg cagtggtgtg    91320
agcttagtac caattctcgc ggaatcccaa acaatccggc gctccagttt ggtcaaacca    91380
acgaacgaac ggcgaggtct ttaatctctg ctctttatgt agctcgttcc gaagccgcca    91440
ccccagatct gctgatggac ccaggatgtg gacaatgctt catgtttgac gagtctgcta    91500
gtgttccccgg cgacgcctat gcatgtggct tactcataga cgccagaaca ggtgttgtgg   91560
gggcatcttt ggatatgctt gtgtgtgacc gggactccaa cggggtactc tctccacact    91620
```

```
ctacccaaac tacattggat ttttttgaaa ttaagtgcag agctaagtat ctatttgacc   91680
ccgatttatt tagccccgta gctacggcct atgccaactt gttaaaacat cgtaccgcag   91740
tatgcttgcg caaatttctg cggtctatta aaaccccgc agtagagtac tttgcttcca    91800
atcgtgtgcc gggtgcaaca gaagcgctga ttacatgtaa ctcctcgtgg aaaccacgtg   91860
aggtaaatga gactaacagg cgctgtggtg actttgataa agatcatctt gctttaaacc   91920
tggacgcgtc atcagacgtt tggctattta gtgagccgga ccttgagcta caaactatta   91980
ctccagctcg ctgggatact ggagagttgg ctctgtcagt tccggtattc gccaacccga   92040
gacacccaaa ctttaaacaa atacttgttc aggcatacgt gttgtctggt cattttccaa   92100
accataaact tcggccgttt ttggtaacgt ttattggccg ccatcgcaag aaatgtgaag   92160
aaggaaaaac gttcacaatt tgtgatcgcc cggaggggag cccatacaac ttgaacgagg   92220
ttgttcactc cagctgcgct attcccattc tcctgatcgt gactccggtg attgtggacc   92280
gcgagggttg ctgggaagac attgaaattg agagtctcac cgcgtttaac aaaacttcgg   92340
acgcaatatg ggacaacgac tctcgtgtgg atgttttaga accaaccagc ttgtaaccca   92400
cagcggtgag atagtgtctc taaacgctga cacatttgag gagtttagca tggatgagtt   92460
cgacattccc cccgccccc cgaggccagt cttcaagcaa cccagccctt acaaacaacc    92520
aaaccccgcc aaagttcagc gaaacctttc ttcaaaacga cgagaccat attaaataaa    92580
aaagaattgt acggcatata aacgtgtaac gtgtttatt gtttaatagt atagcactgt    92640
ttaattacag acagttctgt aaaaaactag tacgtttgtg ttaacggtaa tctctgcgcg   92700
agtttctatt caaatcgtgg tggggtcgt catagtattc tgtctcaaat tcattgctaa    92760
caacgtcgta aattggctct tctgagtccg tctctgagtc ttcattcaag agcatgcccc   92820
tggactcggc aacgttcaaa ggttttgtag ttctgcgggg tcctctcacc ctgttgacat   92880
attttcgcgc ctttgacgac accgttttta cgcgcccgta gaattctgta ttacgctttt   92940
tgtgaaacat aattgctctt actagtcgca cgactagcat gattatggaa attacggcca   93000
taattcccac cactgcttta gaagcagtgg ccagatttgg agcctggaca gaaaccatcg   93060
tatgaaagtg aacaaagtaa ctgtgggtag ccactgccag cgtagagcta gccaccaaaa   93120
cagcgagcgc tggtcctatt aggacatgca catagtggga caccacaagt tcgacgatta   93180
tcaaaaacaa tagcccgagg gccacaaaca cacccacggc tactgttacc gtttgccaca   93240
aagtgatgtg aaagctgttg gcgagtatta cccctagcat tagggacagt ataggcaggg   93300
aaattccaag catgcccagg cttaggttgg tcataaccgc gcgtccgtgg cccgccattc   93360
gatgtagcac tggcatgttg gtcttttaaga tgcgaaggtt gctagagtac tggtcgcttg   93420
aggttccgag tccgctaaaa ctcaggcaaa aaaatacaag cgcaacaaaa tggactatgt   93480
aagctgccgc tgccaaaacc acttgcttgt gtgaaagtag caaaattaca acctgtaaga   93540
gccacgtagt cagcgttccc aacacgagag tcacatggga cgcaatgagt gtggtagtgg   93600
gccgggagca tccagcaacc gctgtgcact ctttaccccg agcgaatttg cgtaatagaa   93660
ctgccgagat tatgaggtat aatgatatgg ccatcagtac gattgtagag tagtaaagaa   93720
atgcaaccag cgacgtggtc tctaaaaaca gggttggtgc cacccccacca actatttttt   93780
gcatccacac cccgttaacc acgctgtggt tctcctgtgt gtagtctacc agagacccat   93840
aaaaacacgg atatccggtt ttttgaagag acgccgtcac aagagttata aaaagcactg   93900
aggttgtaag tgcgaaacag aacacttgca caagccacat cttccagtta atgccttcaa   93960
```

```
ttggaccggt ccccatagtt cccgacaacg gcagcaaagg ctcctcgatg acagcagcgc    94020
cacgtcgtgc catggctggc tttagtgatg caacgcttgg tggtccgaaa gaaagtttag    94080
cgttctcagc ggtggaaaac agctatactt ccagtgtttc tctggccaag atgttatatg    94140
ggggagactt ggaagagtgg gtgcgtcaca agcgtccagg tgtgagtctg gaaatccaat    94200
cgcgagctcc cgtttgcttt ccacgcccc acaatccgtc tagcaggcgc gtaactgttg     94260
taagagctcc tatgggttcg ggcaagacaa cggcgctact aaaatggctc agcgaggcgc    94320
tggacgcgcc tgatattagc gctctcgtcg tttcgtgccg gagaagcttc actcgcacct    94380
tatctaaacg atttaatgac gctaaattgc ctgggtttgc tacgtatttt acgtccacaa    94440
actataccat ggccggggag ccttttcgtc gcctactggt tcagattgaa agcttgcacc    94500
gcgtcgatga taaccttctc aacaattacg acatttagt actagacgaa gtaatgtcca     94560
caatagggca gctctactca ccaacaatgg ttcaccttaa caaggttgat gctcttttaa    94620
ccaggttact aaaaacttgc ccccgtgtaa tagccatgga cgctacagca aacgcgcagc    94680
tagtggactt cctagcatct gcgcgcggtg agcgcagcgt tcacgtaatt ataaactcat    94740
ttgccgcgcc tggatttccg cagcgccatg gaatcctgct acggacccta gggacggacg    94800
tattgcgggc agccctagga tttgtttgtg ttgaagatga aaacggagct aaagttatgg    94860
aggcagactc cagaccaatt tcggccagac ttcgcgaagt tagctctaca ggttttttttg   94920 gtcgcttaat gcataggctc atcgaggggc acaacgtgtg tgttttttct tctacagttt    94980 cctttttcaga aattgtcgcc aggttttgct cacattttac agactctata ttagtgttaa    95040
actctttacg acccagcgaa gatgttgcgt tttggggggg agtaagagta ctcatataca    95100
ccacggtggt tacagtgggc ttgagttttg atactgcaca ttttcacagc atgtttgctt    95160
atgttaagcc aatgagtcac ggaccagaca tggtgtctgt atatcagtct ctcgggcgag    95220
ttagagagct catcgacaac gaactgtttg tttacgtgga tagctccggg gcccgcgctg    95280
agccaatttt tactcctatg ctacttaacc acgtggtaag ccgagagggt ggatggcctg    95340
cagagttttc tcaagttaca aacgcactct gttctcagtt taaggctcgc tgtgaccctg    95400
cctatagaac tgaatctaca cgtggactca ctctgttgt tcggtttaag tataagcatt     95460
ttttcgagcg atgcacactg gcaagtgttg gagacagcat aaacatttta tataccttat    95520
tggagtccaa ccgcatgctg gtatctatag aagggtgcca atttcccctg accgccgctt    95580 gttttttgcag cttttacaa gatctgcgac ttgacgcata cgccgccaga aaggagttaa    95640
agcagttaag gatatccgcc agtcctgcga caacaccgac tgaagttttt gaaaacgacg    95700
atgttgctat gtttattcaa aagtacttgc gccacggtgt tactcacaat gacatattag    95760
accttttggt agaccttaac agtcccatag ttagggagca gtttgttaat gtggccgttt    95820
tgggtgcctg cttgcgccta ccagcagcac tagaaagccc cgaagttttt gcggggttt     95880 acaaacatta cgcttccgga gttgtgccgg tgattagtga cgctggagca cttgagagtg    95940
tatcaataac accagacgtt aacgttctag cgcgctggga tttatataaa agctgcacgc    96000
gtcatgcccg cgatatagct tgggacccgt cccgcggggg gtccgggctg atatgtctg     96060 aagatttcat tacaaacact ttgagcgctg actctaaccg atttcaaagt tgctggtgg     96120 aaatagcaaa gtgtaacgtg acaccgttag agatgctagc tgcgggggct gtgcgtggtc    96180
ttaccaccgc gctatcaggc aaacctaaaa ctagagtgcc gctatcacaa gcagagcatg    96240
ctgtttccct gtttaaggtg ttatgggagg atgtgtttgg ggctagactc accaagagca    96300
cacaaacctt tcctggaggt gtgcgcgtca aaaacttacg taaaaacgag atagtggctc    96360
```

```
ttttagagtc agtaaaggta aaccactcag aatacaaaac gcacagagag ttatatgcac   96420
tgctaatgtg caacaggaag ttgtttgctg gacccagata taagctaagg gcgccaaagt   96480
ggagcagaaa catctgtttc ttagaattgg acactactgg tacctgcaaa accccacttg   96540
acgccgcgct agcagatata gcccctagcg cctggccaca ggtctgcggt gctgttgact   96600
ttggcgccct gtgagactaa accccatggg ggaaaacgtg gaatggttta atggatatgt   96660
atgtgccaca agtatctact ctttatggac agatccacac cagcctggga atctccaagc   96720
gcttgtctac ttgctatgtc ggcgcgtgga caactataca gcagagtttt gtcacgttgt   96780
agtctctgga gaacttctaa ggcatggagc ccgcaaccca tctttggtaa cacctgcacg   96840
tgtagccagt gccgcaaaaa ccgcagcggt acctgggtgt tggccgttgg ccctctggg    96900 agatgctatg ttgtggaaat cggtgtacgg tagcgtagct tcagcgctta aactaactct   96960
gggaagtttt gcttttata aacccatgat gtttggagtt aatacgcaaa ctggactttt    97020
ggttaccatc aaacccgccg catctgaggg tgttcgtggt ggagacccg tctctccgcg    97080 ggcagcactc gtaaacgcat ctgtggaagt agacttagac cccactggta tcgaagcgag   97140
tgctgctagc gtcacaggat catccctcgc tagagccaga ctctgcgcgc ttaaagatgg   97200
atattttctc acaaagcaag acatcgccct agaagttgag atcaccacga aggaggtttc   97260
attttataga aaatatgact ctgtgcagca gccagcaaac aaacgccgtg gggacatggt   97320
agatctattt attgtacatg aaagaactct taggctaatg ggatctaagc acatgagcgt   97380
taaagtttta gtaccacgga cgtttgactg ttttgtggct agctcccagg cgttgtcggg   97440
tctagcagct atggctttgt acaagcagtg gcacgctact ctattttctt tagagcgctc   97500
agaaactgta gtgcaaattt ttgcttatct tggcccagaa ttaaacccgt gtggagagga   97560
cgcagactac tgttgctttg ttggatttcc cgggcttcca accctcaagg ctggtcttaa   97620
caccgcggat gcagtgcgcg aagctctcga cgcatataaa ctgtctgacg gtttatggcc   97680
tgctctgggt atgagcgcgt ttcactttt acaccctgg gaaccagaag acaaatggcc    97740
aggtgaaacc gccgcaaaac ggttggagag tgtagcccc atactacaaa ttgaaagcgc   97800
agatgtttgg ggagcaggcc gggtaacgtg cattttagag tctgacgctg taatgcaggg   97860
accatggttt gcaaaatttg attttttcagc attttttccc acgctttatc tgttgctgtt   97920
tccaactaat gagcgcttag cccaggtagt tataaaaaga gctcgcggtc aaaaccccgc   97980
cctaaagccc gctctggtat cattttttgg tgggttgcag cacattaacc ccatggccta   98040
taggctaatt atagctatat ctaacgaaat cagtaggcgg ttagagcacg aagttaacca   98100
gatgggtttt gccatatgta cgtatgttaa agatggcttt tgggggggcag ctggaaatat   98160 gctagtagac tcggtatcct actccgatgc tctggtttac gctgaagcgc ttagaagcgc   98220
tgctcaaggc gcagcgctta gttacgtgtc agagctgggg ctttcgttac cagatggagt   98280
tgacctgcgt ttgcggttgg agggtttgtt tactgatgcc atttcgtggt ctacccactg   98340
ttactggcta tacaaccgca taacaaatat tgaagacttt gtaggctttc ccaccaaaag   98400
tgaagctagc agagcagcaa aggctagctt atcggctctg ctcccgcgtg ttgcggcggt   98460
tgcagactct ggagacttgg atatgctcca tcagctcgtg aaagagtcgt gtgagcagct   98520
tgttgcagaa gcgtttgcca agcggaacga cccaaagttt tggagtacta agacagagat   98580
agattcgtct acgcaactcc ccacagcagt ttacaggagt ggatgcttgc tcgaccaaga   98640
ccgtgggcag agggacattg tactgacgcg tcgaagtgat tgcgaatccg cattgcctgt   98700
```

```
accctggatg cttttttccac caccgctggt attggggcgc atagactgta tggtatatct   98760
cacgtccatt tttaaaactt acctgggcat gctaaaccga gcgatatcag ctttatgtga   98820
cgcggataaa cccgtaaatg tagagttcca aattacagat tatgcgtttt tatttactta   98880
aataaaaacc aaaaacgttt cattttttttt cagtttattt gcgtataata caccacccag   98940
gctagtcgta taacacgtat attgattcgg gaaccggctt ttcgttggtt gaggtccacc   99000
aactatagat agtatccgct attgtttttg tacacagcgg agagttcaga atagcctttt   99060
tacagcgcat tactcccagg gggcagggtt tatcgggttg gttgacaaac gcagccctgt   99120
aaccggcgct gtaaatagcg tctaatacag ccggagtgtt tgatttatgt ccagtaaca    99180 tcttagccat catgtagttg gggagcactc gggtctggtc aaacgggttg tggttagtcg   99240
ctgacatcag cgtgttaagc acccacgttg cgcctatata catcaatctt cgcatcttta   99300
aaagcggggt gatggttttg gagatgttgc gcagtatgcc ctcaacttgt acaaaaagcg   99360
atgaagtagc tcgttttgga gagcagtttt ccagatacat ttggattata catagggtga   99420
agtctataag gttggttggg agatacagta caagtctgtg agataatatt acaggtgcca   99480
ctcccagcac gtttactcgg tcttcgagag gagttactat aaaaagagaa aatcccttaa   99540
aggcggacag gttcaagcat gagttcatgt acgtttcaca cgaaacctcg gcgtcttctt   99600
ggccgtccag ggttagcatt agtttgccag acgggtccac tcttatgtta gtgattgacg   99660
tggtcgtgaa ggaagggggc agcccgggaa cctctctgac ttctgtcacg aatcgaggag   99720
ttgcgtgcca aaccagatcg tcgactatag ctgttgctaa atcgtctccg tttgtaatag   99780
cctccaccat ttcgtccacg gtagcgctgt gggctaaggg atctatctcg tcccgcataa   99840
tagcgctcat tgtcaggttg ctcttcttca gatggggtat cgtctccggg aacagacgtc   99900
ttccaattag cagaatttag agccgcaatt gagttcctaa ctttcgccac aaaaagcgta   99960
gataactctg tcagataagc ttcgagcctg gtttttttga acactgccac acacagctcc  100020
tcctccgagc ggtacgcctc ttggtgtgta attaaaaatc ccaggtgacg cgcacgaaga  100080
atagaaaaaa agtatggcgc aagcaaaagg gatattgagc tgttagagta cgaaactgac  100140
atttcttgac cttggttgtt agtgattcgg ttcattttga agcagcgtag taactcttga  100200
tcccacaaac gcgataggcg ctccacgtca gcagcataag ctggaatata cctagactga  100260
aagctattgg caacatagcc gtcatccccc attaaatttc ttatgtcgat aacttcatgc  100320
ccgagttctc cggctttggc gcccccatga gcggtgcagg atcccacact aggtggtggg  100380
gtgttcccgt ctgcggccgc ttgtgttaca cgcagtaatt gttcgcggag gtgggttaat  100440
tcgctttctc tgtcctgtag ctgatttagc agcccgccgt ttccagcccg taaatcttct  100500 atagtttttga acaggttgtt aacgtatccc tctagcattc catttatgcc attaatcaca  100560
gaggtgcgaa aggcttcctg cacgggcata ttacccccct ggcgggtctt tccgctctgc  100620
ccaaatccgg gcatagacgt gtctatctga gcgctgctga ggatattggt actcgtttcg  100680
tctaaatacg atctgactgt ttcagttatg tcacctatat gtcgcatgct tttcatgtta  100740
actatgagtt taaccagcct agaggcgcg gagctagaat gcatttcttc cccctctccc  100800
atgagcttgt ccacggcttt ggacgcccat cccggtccct gggattcttc cttttttcctg  100860 ccaactagaa tcttaacggg cacagtgttc agcagttggc atagtttagc gtgctcgcgt  100920
agggcgtggc agttacacac ttcgccgcaa atccgctgaa gtggagagtc aaacagtacg  100980
gtgccatctt tccatatagg ctgccataac accaaacact ctccccgcct accggtggtt  101040
gagtctatag ccacgaccctc tctgcgtttg tagtggtaaa atattttcac cctgtcgtag  101100
```

```
tccataatgg ccacgctggc ggtacacctc gccagttcaa ccacagcctc caacccctcg   101160
cgcaagagac tgttggccac atacagttta cctgccaggt ctcgctcgtc tacacagctc   101220
tccagagagg gtacgtcagt tggcagctta cgccacaact tgggtgtac ggttgcgccc    101280
ggagcgcgct taagcctctg tagggtatt agccccaaac acgctatcca gtctatgtac    101340
tttgcaaagc tggcggtgcc atccggctcg ctggcagaaa acacgcggt tatactgcga    101400
acaaagtcta atagcgacat ttgtagcgtg cgatgccagg ttgcaaaaat ttgttctgct   101460
acgcgtaccg cttcccccctc gctaaacatt ccgtaggtcg ctgctatttc ttccgcgctt  101520
accccacgac tgtctaggtg ggtttgccaa tcctttgcga ggtcctcgta tcgcgtagct   101580
ctaagcgtat tggtgagaat agttgtttgt atctgtctga ttgctgcctc tgttgaccta   101640
attgcgttgt acactccttg gccttctgtg tatccgagct cccccatgag gatttccttg   101700
aatagcattg ttttgggggt tggatgaata agaacccaac cccttcagt agatatttgc    101760
tcctcttctg cttgattctg aaggccagtt gcagactcaa agcgcactgg gttttttcgc   101820
tctctttttg gggcttttagc ttcagcataa cggaggcgtt tttgcttggg ttcgatggag   101880
gcccccgaca tttttttaga acaccgcgaa actgggaacg aacgccgcga gggctcagag    101940
gagaaaataa cgccgtctac ctcctccgaa gattttaacc cacagctctt cccaaacgag   102000
gtatattga actttacgtc tatgcacgga atccagcccg tggtgactcg tatcagagag    102060
ctgtctagaa aaactgtttc tccagctatg gtgccgccgc tggaatggtt tgaaaagatg   102120
ccaaaactgg aaacgcccct agatatagag ccgttacatc taccctttc cgtttacctc    102180
attagcggga acgccggctc cgggaaaagc acgtgtattc aaacgctaaa cgaaaccatg   102240
gattgcgtca ttactggcgc tactcgcgtg gctgcacaaa atgtgtacac gaagctgtct   102300
tctgcttttg ctactcgcca catcaacacg attttttcaag agtttggatt tcggggaaac   102360
cacgtgcagg cgcagctggg caaataccaa tacgcgtgct cttctagccc gcctcctata   102420
gaagagctgc agaagcgcga catagtttac tattgggagg tgctagttga cataacacgc   102480
cgccttttg agtctactac atcacgcggt gagtttgaaa atatcagagc actggagcgc    102540
ttgctgggac gcaccccgg atctttaaca aggctcgcct tttgcataaa cggctcgctg    102600
ccagcattta ctagaactaa tattattatt atagacgaag ttggactatt gggtcgccat   102660
ctactaacgg ttgttgtgta ctgctggtgg atgttaaacg ctgcctataa gtcgccgcag   102720
tacgctgagg gaaggattcc tgtggttgtg tgtgtggggt ctccaaccca aacggattcg   102780
ctagagtctc gctttgagca taaaaactta aagtgtcacg ttaggtctag tgagaacgta   102840
ctaactcata ttatcaccaa caaaacaatt agggaatacg tttctctgtc aactaattgg   102900
gcaattttta taaataacaa gcgatgccag gagtacgaat ttggtgaact aatgaaagtt   102960
ctcgaatatg gactcccaat aacagacgag cacatgcgcc tagtagacaa ctttgttgta   103020
ccagaggcct tcattaacaa cccggctaac cttcccggtt ggactcgact ttactcatcg   103080
cacaaggagg taagcgcgta catggccaag ttgcacgcgc acctaaaagt ttcgggagaa   103140
aaacaatttg tagtgttcac gctgccagca tatacgtttg taaaaaccgc cgcctttgac   103200
gaatataaga agataactaa acaaccatct ttagcgttgg ataagtggct aactgctaac   103260
gctagccggg ttagcaacta ctctcagagc agagaccagg acgctggaag aactcagtgc   103320
gagtattact cagatcacgg cgtcgtggtt gctcgaacgg acgtgacgta cgtgttaaac   103380
agccaggttt cggtaactac gcgcatgcgc aagtttgttt ttgggtttag tgggacgttt   103440
```

```
gagtcgtttg acgccgtgct caaggatgac gcgtttatta aaacccaagg agaaacgtcc    103500
atagagtatg catatcgctt tttgtccaca ttgcttttca gcggcatgat aaacttttac    103560
aacttttaa agcgcccggg tctaaacgaa gggaagatta ccgaagcata taggcgcatg     103620
gcagctttaa ccgcaaagct agttcctggc acgtctgttt tagaaagcgc atgcgataat    103680
ccaagcggtg caccgctaaa ctttagaggg ttaacagccc ccccgggcca gactgtggat    103740
agcgctaaca gctgggatga cgacgacgtg gtgtttgcag cccttaacga aggcgccata    103800
gacatgctgt attgtaatta tgagtttgtc aggcccgaaa ctacacaaga ggtatactcg    103860
cagtttctaa tgctaaagac catgtttatg gggagatacg ccattttcac ggacctgttt    103920
ggtgatgaat ttaaatcttc cccatttgac gcgtttgtag acaatataag ctataagggg    103980
tgtgaaattt ttgtggggag catgcgcggg ggcgtttctt ctatagctct tcagacagac    104040
agctacacgc ttatggggta tacgagcgcc ccggtttacc cgtttgttga ggaactggct    104100
cgcagaaaac ttcatgaggg catcgcgagg cttttttggtg caatgaacat gcctcgcatg    104160
gtgctgcgag accaacacgg gtttatgtcg gttctaaacg ttaaccttag cgagtttgta    104220
gagtcagtgg acgacaccga gttgaacatg gccaccgctg tggactacgg ccttagctct    104280
aagctcgcca tgactattgc cagatcacag gggctgagtt tggataaagt ggcgatatgc    104340
tttccccgca acaacctgag gattaacagc gtctatgttg ccatgtcacg cactgtgtca    104400
tcaaagtttt tacggatgaa cctaaacccg ctaagagaac gtcacgagcg cgacactgtc    104460
ataagccagc atatattagc agccctgagg gacagagacg tccagattgt gtattgaaag    104520
ctgccacgca atagtcggag atttaacgcg cgcaggtttt acgccaatgg agtcttgtag    104580
cccccggtt acgtttatta cttatgcgct gtatggaata aaaacttctc ctgcttggac     104640
tcttcccaac tttgaacagg ttatttctag ctgcggctgg ggatacagac tgatcgccgt    104700
tgggtcagag tctagatgcg atgttatgcc aaaaggcagc tttgtgatac aacatggcgc    104760
ctctataaca gcgctggtgc tggattgtgg cgtggagttc tgctcgtacg cgtttacgca    104820
tgccgatagc accagagttc cactaaccac cgaagacggg tctgtgttgg tggttccatt    104880
ttgtggctgg gtatgtgttg gtagggatag atgtttgcga agcctgtccg gtggggtact    104940
cacaatcagc tgggatgtga gccagacggc gtacatcagc gttgccgttt atcgtccatc    105000
caccgtacag tgccatgccc tgacctgtac caacgtggaa actaccggaa gttcaaacgc    105060
ggccattact gacggctctg actcagagcc gtcagtattt gcaaaccagg aagctgacaa    105120
tacccaagat caggatggcg gtccagattt tctggaaact attctaatgg aatcagatct    105180
atatggtgcc aacggaccag ccctaatgga gccgtgcttt accggcctct ctgacgactc    105240
gctgccttaa caaacaaacc tgtttctatg ttttaaaccc ccccatatgt ttaaatgaaa    105300
accaaaataa aagtttatat aaacaaataa acgtttattt gttttttata atgttttta    105360
catatgcctc agcgtgtttc ttcttggcct tgggtgtcct tgctgctgtg ggagccttgc    105420
tgatgtagac tgtgttatag attttcgcct gtggtattga ctttcgctgc ggtgaccgtg    105480
gctattgctg cgctgagtat agctcgagct gctggaactg tgcccctcac tgcgcgaatt    105540
gcgcccctcg ccgcgcgacc gttgagacga gcgtagcgta ttagacgctg aagcgttaac    105600
tagcggttct tgcctgctga tagattttct tcgctgagcg gccatggcaa gtgctactag    105660
cgttccagaa ggcctatcgg ggcgatctcg atgcttgtcg cccccggcca caacgtgtgt    105720
gtctttgcta gaaacagagt ttcgcctaga caaagatctg tgtcggggtc tctcttctgc    105780
ctccggttga gatataacag aatccgtccg tactggtgtt gttgcggcgg caagcttagc    105840
```

-continued

```
ggcagctcgg ctgttccttt cgagaaacct gcgatagtcg tccgcggtag cagcgcgtcc   105900
tcgcccaaac acgtccatgc ttctcacggc tggtcgggct atgcagagta aagagctgc    105960 gccgaaacac tcacttggct tgcgcgttag cttctataac gttatccctg tggaggtaca   106020
ctttatccac agcggaaaat tcgtaaatgt acacgggaac caccggatgt gtacgtccgt   106080
ccgacgatcg cgtgtaatac tttctgggtt ttcgcgcttg gattaccgac tggagctggt   106140
ctctaatctg cttggcgtga gctctgcgac acagaacaaa catttgcaag cttttattgc   106200
tgcgcaccac gcgctcagac gggcattggc gccttttgcg acgcgtggcg ctcgcgctag   106260
aaaacgaaga ggttttttgta catgcaatgg taaactttgc cagagtcacg cgcaggtcct  106320
ttctgatagt gtccgtgagc tggcggcggc cgagttcatc aattgaagat accataaaca   106380
tggtgtcaaa tccaacgtag ttagagtttt ccccgtcggg ggtggggccc ccgaaggatt   106440
ctaaggataa gtcaggtacg caaagcgggg ttgtgggagc ggtggtggtg catgtcgagc   106500
tggtcagcgc cggtggccta agttcggtaa gcgagtcgcc tactgttccg ttgacaacct   106560
cgaccggcca tccccaccca ctcagcacgg ttaatgcgga ctccatttgc ggtagcggtt   106620
aggaaccggt ctggacctgc ggagggcttg cttatgtagc cacgggatat gggtgggcgt   106680
tgttttcacc gtaaattact caatcagcca gtttatggga ctttttcctg ctttagcgag   106740
atacgcatta gcctccaaaa agtgtgggca atccctgaaa tttacacgcg agagaggcga   106800
ggggtgtccg tatgtgagca ctaggtggtg ttgtctgctt ggagagcaaa acttttgggc   106860
atgagcaccc cacagcatga acacgaggcc ctgtgacgtt gcacatagcc ggtcgataac   106920
agcacgaact aacctgtgcc atccaagagt agcgtgggat cctggctgtc cgcgcgtaac   106980
cgtcagtgtg gtgttgatga gaagcacacc ctgactggcc catttatcca aaaatccatg   107040
tgtcggaggc ctaaatgccg ggtacgattt ctggacggcg gagtatatgt tgcgcaagtt   107100
tgggggtaca ggtactccct tttgaacgct aaatgctagc ccatgcgcct gaccgggtgc   107160
atggtacgga tcctggccca cgataaccac acgaaccttt tctgggggcg caaaccgagt   107220
ccaggcaaaa atgtcttcct tttttgggaaa cacctcttcc ctggcacatc gcagcttata   107280
ctcacccaga agaagtttga cgtactgttg ttgcatttct ttttctagaa taggcctcca   107340
agagggcgct atgttaaatt ctagctcaat ctcttcccat gagctttgga ggttgttggt   107400
caaaagtggg tgtgtagaaa caccggtgtt aataagagag actccaggtg gaagtccaca   107460
tggccgcttt cgcttttgtg ggggagcccc agattcacat tccttggtg attccttaca    107520 caccgtttgg ctggctttgc tggtgggtat tggcagtctt tgttgttttt cgaccggctt   107580
agtctcgatt atgtctgcgg tggtagatag ttttgtttta agatcacaag cgctgctcat   107640
tctgaagttt cttgaatttc tgcgtagtat gaagctggta tgcagctatc ttttactcct   107700
tcagctattt ctttagactc tggcgttgat aaaaaaaaag gccccgcaaa acagcccagc   107760
ggaggagggc ccaatatctc gtctggagag gcctgagatt gagtaagaga ctcatctaag   107820
gcaagaagga gcatctcttt aaagtcttgg ggaatgtttc cgtttgtgac gtcttcagcc   107880
aaaccctgaa tgacggcaaa tggattaacc caaacaggtt tgggtggtat gtcaacccac   107940
aaaatggctt ctggaggtgt gcagtgagcc ttcaccataa tccctagcgt tttgtttagt   108000
aagtttttaa cattgggggg tgtaaatagt tggcctttca ttataggccc actaccgcag   108060
ctagcttcta aaatacgctt gggttcaccc gatgaccacg taaactccag cttatttgac   108120
ttcgctagct tggtagctac aagccatgtt atcatataga ttagttcaag cttaatccaa   108180
```

```
cagaacatcg gccgcccat tcttttaaaa gactctaaac taagtggctg tttagctttc 108240
gtacatcggt ttatgtacag attttttgcga gacacaccca attgggagtg atacatttgt 108300
ttacgttaat ataaacacat attaacatac tatagtttat tctcgcctca gagtgagatg 108360
agggttaaaa aacgatctgt gtggcacacc tatagggata aaaatcatac ccgcaaacta 108420
tttggtggaa caactgatgt gaactttaa cgctagggct aacgctaacg ctagggctaa 108480
cgctaacgct agggctaacg ctaacgctag ggctaacgct aacgctaggg ctaacgctaa 108540
cgctagggct aacgctaacg ctagggctaa cgctaacgct agggctaacg ctaacgctag 108600
ggctaacgct aacgctaggg ctaacgctaa cgctagggct aacgctaacg ctagggctaa 108660
cgctaacgct agggctaacg ctaacgctag ggctaacgct aacgctaggg ctaacgctaa 108720
cgctagggct aacgctaacg ctagggctaa cgctaacgct agggctaacg acaggaagtt 108780
gtcataattg cgcgctatag ctgccatttt gaaaaatttg tactgtcatt gttttttgaca 108840
ttatgatgtc atctttgtgg gacacaatca gccatttta aaccacgcct tttgacaacg 108900
cccataaagc tgttagatgt acccattgaa agtggtaata cccgcccatg gtggtctagg 108960
ttgggggtt tttatattag aaaaaacaag gcggtatttt ggcagcgggt agcatattgg 109020
taaaaggtaa gtgattttta atattaaaca caccattaac ctatgcggaa gtcagttaaa 109080
aagggggccg attggtgtat atttggaatg gttcataaaa aatgtatggg ggcatagtca 109140
gcagagtcgc tttatttta atggaaagcc accacatcgg gttggcgtga acgtgtaccc 109200
aattaagaaa attggatgtt gccaaactgt aaaaaaaaac aatatattcc aaatatccaa 109260
gcattaatag aggagattgg actagcacca aatgtggtgt acatttttta atttaagttt 109320
aatgtaaaca tttactttgc tagggtcat aaaattggga agtgttacat tttatatctt 109380
tagtgaatgt atattagcgt ttcatttatt aattttaaat gggtgggaat cccgtgtgtt 109440
tggtattggg gagttgggaa tgcgttaata acccaataag gggtgtttgc taagggtggc 109500
cttttgtatga taagagtaaa acattctcta gctagccact agggggataca tattaataacc 109560
gcaggaagcc tcatattgta atagcttaac aattcatttt tccttccaaa atatttagg 109620
atatcctgcg tgctatccac gatggattta aatgtgccag gtaaactaag caaatatttt 109680
actaaatggt atagttgcag tattcgggtg tatatatgtt ttatgaaggt tacctaaaat 109740
cattagcgct attttttaact attgcatcat cgtgttaaaa ggcgctgttt gggaaaagga 109800
gatttctgca ggtgcagtgg cttgctaaag cttaaaatct tgcagcttta ggaatcttct 109860
ttttcaaacg gaactataat cgacattata atttatacta atgttatgaa cctcttatat 109920
ttccccttt gcttgtttgt attaattatt tacaccaccc ccctcctttg ctagggttaa 109980
catttttgtg ttaaatatt ataattgctg gtattaactt ttaaaaaca ttataaaact 110040
ttttattta aaatagattt atttacaaga tgtaggttat cttttacaca ggtcatataa 110100
ggtcattggt ttcttcgata tctgtaacag ttgtggggac atgtcctctc ttcgtgtgtg 110160
gaaggccgcg actgaaatat gcgctgaaga ctgcgaactc gttggctccc ctgtctaagt 110220
aatgagttag gggacaacgg gtctgggtat ggcacaggtg gtacactctg tcgtcgtggt 110280
ctcagcaaaa cattaccacg tctcctggta atgctacctt ctgttggtct ttgcacagtg 110340
tgtatgttgc atccactaaa gctttcagag tctgcagatc cgtgttctgc atgtatagct 110400
gcagtggtag gttccataaa cagacgatta gtattttgtg agccagattc tgaggcttcg 110460
ccgctagagc gtcttcgtgg ggcaagggct ctaaaccttt gtacaaactc ccgcaggttg 110520
tatccggacg gcgctagctg gtctccgctt gataacacaa caggttgttg ctgtgtctga 110580
```

```
acgggtaacg aggcttgcca atgcaaacag cgtcttcctg ggattgaacg gttttgctgt  110640
tgggtagcag gtacttcgtc ttcagcatta tgctctggtt ggggagtgca atccaatgtg  110700
ttagtatgct cagaagttag gtccactgtg ggtatttcac cctcgctgtc caaagttagg  110760
tctataatag cccccacggc ttcccgaccg gaaaggttaa cctccgacgg attttcttgt  110820
ctggccgggc caccagtggc ggctggcaca gctgctggcc ttctaccccg tcccccccgt  110880
cttccccgtc ttccacgtct accccttcta gtgggtgcgt taggccttgg gtgcacgggt  110940
ctggggtttt ctgggcgaaa tgttgtattt ggcatgtttt ctgagtcaga gtcgttgctg  111000
gtgtctcctg ggtcagttag gttgtttgga tcaacctctg tgtcgctgtc tgtttcgttt  111060
tcagaggaag agctcgacga ggaatcgatg tattcaacac ctcttccgtg agaaagtgta  111120
gagataggcc tcgatgcaac gcacaactct gcctggataa taagttcagt aacaaaggaa  111180
gctgtgtcgt ccaaaaacat cggccaaaac tggcgagtga gctcttcctc gttgcagccg  111240
tgatcgcaca gtgtatccat aacaatgttt cgcattacca gcgccagctc cggggtatca  111300
aacagttggt ctagttttc acaaagccag tccaccaaag gctgtaatcg aggggatcca  111360
gcagtaccat tagcgttaag gggtacaaat gccattggtc cattccatgc agatatattt  111420
tccggagcat cgcctctatc agcatcccaa aattggccct caaagctatc ctcgtcttcg  111480
tcgctgtcat agtcaaactc aacgctcacc ttagtttctt taaactcgct gtcactctcg  111540
atagtatgta ccacggagtt gacaggtacc ttgcagagag gacaggttgg gttttgtcga  111600
atccagcgcg taatacacac gtagcagaaa gcatgcaagc atggaagcgc catagagtag  111660
ttgctggggt cttctaggca gattggacat cgctcagcat caacagccgc catggttgca  111720
agaagtttga agtttccaaa tgaaaaggct gtatcagcta ttaactcaag ctttgggccg  111780
ttcatatatc tagattaaga accacgtgat attgcacgcc catctatggc atttatccaa  111840
tcccacccct ccgaaaaaac atttttttaat gcatgccaca ccggccttga aaacggttta  111900
accttatcga acatttgtaa aatagttagc atgtgtaata atgggggcgt gtttgttaag  111960
agcttgtagc taatttagag ctattttca tagcgtgtgt actacgctgc tatttaaaat  112020
taatgttgtg tgtattgggc cggcttagta ttccataccc caatattgct tggtatctaa  112080
ttttactcac cgtatttag gtgggctaca agttttggca gaaacgatag aatgcttat  112140
tacaacaata tacacgtggg tggtactgtg ctataccaat gttctgggta tagtgtaaat  112200
aaaaagatcg tagtgggggt aggactcaaa aacagaattt ccaatttagg ccaatataaa  112260
ccaaaggtgg gtgggtttat tactgcgtat agtttcctca ttttgtcaag gtccccaaaa  112320
ccacaccgat accacttaaa atatcacatt atagtgttta tagttcactt agccacttag  112380
tttccaaagt ataattattg ccgtttgggt cacgggcgtt taccttgccc gcgcccgaga  112440
gagaggccgg cccccaccgc ccataacgcg ggccctcatt caaatagggg gcgtggcttt  112500
ttgggggggg cttaaagtgg gtgtgaccgg aagcggaagt gacgcaagcg gaaggggagg  112560
agcaggaagg ggaggagcag gacccactaa cccgcccact aacccgccca ctaacccgcc  112620
cactaacccg cccactaacc cgcccactaa cccgcccact aacccgccca ctaacccgcc  112680
cactaacccg cccactaacc cgcccactaa cccgcccact aacccgccca ctaacccgcc  112740
cactaacccg cccactaacc cgcccactaa cccgcccact aacccgccca ctaacccgcc  112800
cactaacccg cccactaacc cgcccactaa cccgcccact aacccgccca ctaacccgcc  112860
cactaacccg cccactaacc cgcccactaa cccgcccact aacccgccca ctaacacaaa  112920
```

```
ccacaccgga attaataatt aaaaacatgt tttattaatg taattttgtg aagcaagcaa  112980
caggggggcgc gtttggggat ggattggggt ggagtttgcg ttgtgacggg cgaacacata  113040
gttgtggatg tgctgatttt tgttttggtg tgtccatagg gtggagctgt tgtttaggtg  113100
agataggggt tgcaccagtc ttctccgtcc tcctcgtccg ataccacctc tatcttgatg  113160
ggggcgcgtc ggatcaactg cgctgccggg ctcaccccag ggtgatctgc aaccagctcc  113220
acgtcccccg gtccgtcgat ctcaagctca tcgtcggact cggaaggca cagctccagc   113280
gcgcccatgt ggaggaccga ggtcgagcgc tgaccgaacc ccggctccca ctcaacccga  113340
ggggctcggc ggcgaggagc ctccgtgatg ggcatcacca ggggttcagc ctcggcgtcg  113400
ggctccagca gcgcgaccct gcagaactcg ctcagcagtt ctgggatcag cagctcggcg  113460
ggctccacgg ccccggctcc gcgccgtccg caggcgaggg acaccgggcg cagccatgcc  113520
ccaaggcccc atcggttggc cgcgcggtgg ctctgggctg cgcctcctc aaagtctggg   113580
tcgtggaacc cgagcccctc ggcctgggct ctcatgtcct tgcagccgtc gtagtctggc  113640
agaacccgct ggcggtactc cctaggtggc agtggaacgc gggtgcgctc tccggcccgg  113700
gtgtccaccg tgtaggccac gttggccgcc cgacacagct tcaggggctc cgagttcggg  113760
tagaggcgcg caaacgcggc ctcggccctc gcgaacagtc cgggcccgaa gagggtgctg  113820
gaagtgagga ccgcgcggct gaggtggcgc tcccggggcc agcgaacggc gcaggcgacc  113880
cgaggggtga gggtggcccg catgtagatg tggtactggc tgatggcggg accgtcctgg  113940
ggccagtcct ctagggagac cgcgtccagc actaggagct tgcgtctggc ggagcccagg  114000
cgaaggcaca agtactcgat gcagcctgta aaggccaagt cccccgtgga gaggagcagg  114060
actccctggg cgtttagggc agacacgtcg ggggcccag tccagttgcc agcccaggcc   114120
tgggaccgct ttgtgagtac ccggttcccc agggccgcca gcagcgccga gagcccccc   114180
ttgatgtcgg accagagggg ctcccggcgc gagccgccgg gtcgggtggt tgggagtcca  114240
cccagcaggt cctcgtccgg tagcggggag tagagcacca ccaccttcac gtcttcgggg  114300
tcggggatct ggttcatcca ggcagcccgg cggcggagcg gtccgctggc agccagctct  114360
ccaaagcgcg cgccctccct ggccggaggc ccgttgcagc gggctgcgat ggtagccagg  114420
gcctgggggt cgaaggtaag cgcggggcgc caggcctcgg ggaacagcgg gtggtctatc  114480
agctcagcca cgagctctgg gggacagtaa gcagcgcggg cagagtcccc gggggtggc   114540
gtgtggcagt ctccatgggg aacgcgtctg aagcctcccc ggcggtgtgg ccctcgggc   114600
ggcatgggcc ccaaagctcg aggggcctga gtacccaccc tgcgctttgg ggcaggaggg  114660
ctctctaccg gagcgaccgg gtcgtatcct ccgcggggacc ccgggagctc ccccgccgcc  114720
ggctccaggg gctcggagcg ccgcttcccg ctcttgcccc tggggcgccc gttgacggga  114780
cggtcgttcg gggaggcgta gggtgccggt ccgccccctc cctgcgagga ccggcatc    114840
tcctggccga ggatagcctg ggaggcagcc ggtggggagc gagccttctg ccccgagggg  114900
cgagcctggg tctgggtggc ccgggagcag gttgtcggcc cccgctgct ctggtgctgc   114960
ggggaagaag actgagagtg agacgtgcc ggcaccacga gaggcttccc gggaacagtg    115020
ggccacaagg cggggatgcg ggaggtctgg cttccctcgg aggaggagag ggactgctgc  115080
tgcccaacgt cgccgccgac agacgatgaa gactgtgacc gaggaggcgc aagcaggccc  115140
acggcttccc ccaacatgcc cccggccaga ctgggtatgc taaacacggc ctgggtgatg  115200
gtccaggccg aggcccgggc ccgggctccc tccgcgttgt agcgcaccag gggtgcgacg  115260
gttctggcca caaccagaac cgcgcggacc gcgaggcgca gctcgtcggg gcccaggcgg  115320
```

```
tggatagggt cagagtcccc gagtagcctg gcacgctcga ccaggtccct gagttcgtag   115380
agggcgcagg cagcagtctc gagcccagcg gggttggagc acagcgcttc gggagggcag   115440
gcgggagagg ggatctcgct tgggtcaagc ccggggacag cggacgctcc gccgcggagg   115500
cgaagtaggg cttcgaaaac ggcctggcag gccagtacgc agacgtctcc gagttccctg   115560
agcctgaagg cggtaggctt gggggttctg gtaccaggac ccgcggccgc cgtcttgcgc   115620
cgtggcccga gggccgcgca cccctggtg tactcctcgc ggaccctagc agatgtggcc    115680
gggggatccg gctgttgaga ggcagcctgt gcttgggccg ggtagctagc cgtgaccccg   115740
gccgccgagt gggagtcctg ccgcccggcg tcgtcgcgcg ggtaggccat gtccgcgtac   115800
gcccgtctga ggctctggag tatgaagctc ttttgcgtgc ggtcgtagcg gcggctcatg   115860
gccaccgagg ctgccgcgtg cggaagggcc catagagcat tcccggccgc catggcgtcc   115920
ccgatgtggg gcagggggtt agcaacgctc cccgtgatga aggacccatg tccgcgggga   115980
gcgtgtatga acttctggca gaactgggcc aggttctggt cggccccgcc gagcttggag   116040
ttttgcagcc aagacatggc ctcgcggttc tcaaacacca tgcgcaccag agcgttgtac   116100
tgcttggtgg agtccccat ctcgggcaca aatacaggta cggcggtctg ggcttcggcg    116160
tagcgcgagg cggccagaac tatttcgggg tcatcccaga gccgtcccg cgagtccccg    116220
gttcccccat agcgcaccct ccccggtggt ggggcgtccg acccgggcca tgggtctccg   116280
gatggtgtga gcagcggctc gcgctggcag gttccgagcc ctggggcctg agaggagcag   116340
ttcatgtcca acaggtccca cgcgcatccc gggagggcct cttcggcccc ggttgtggcg   116400
gcggtctggg gtatgggtct tgggtggcag cgcttgcgct tagaggcccc ggccaacgca   116460
gacttgggcc gctggtcctt gggagctctg tgtgggctct gccctggagg agacattctc   116520
gggtcgggct tctccagcgt cttggccaga ttggcgtccc taaccccctc caggtactct   116580
aaaatgcgag ctcccggggc gaggggcccg cccgggttac tcggggtggg agcgccggtt   116640
gaagccgcaa aagcgccgac ggggctttgg tgccccttct ctgagcgtcc gctctttggg   116700
gtgtacgatc caggggctat acgatccccg ctaatctgcc caggggaccc ggtggccggt   116760
tgggttttg cggcgctcgg cgagggatgg gggcgaggag ttttctcttc gcccccatca    116820
tcgctgtcac tgtcttcgga ggaagacgaa gacgagctgc tcgccccggc accatcggct   116880
tggtcttccg tcgatgagga ggacgaggac gacgatgata tggagatgct ccggcccctt   116940
ggcgccggcc tccctcggg ggaggccgag ggtggaaact cggccccggg agaccccggg    117000
caggtctcgg tgtcgctccc ggtgccctgg ttataggcac ctccgcccga tgatccggtg   117060
tccctgcgac cggcccctgt agccgcggac gagtgaacca tcttcagcat ctcggcgagc   117120
cccggagcgg ggttatgagc gggcgatgcc ggcactgctg ctctggccgg agaccgcttt   117180
gccttcccgc cgcggggctc ggggccggg aaggcggcg ggatgactac cgccggggtg     117240
gccaagggcg cgtcgtccac cccaaacatc ccctggcttc cgtacagcag atccggggcg   117300
gccggggtat ggaacccctc ttcggccgcg ctggctgcgc ggatgaggtt gtcctcgtcc   117360
aggttgttgc tctcgatgaa gtcgtagagg tccggagcaa aatcgctgcg ctggctggcc   117420
atggctcgct ctctcccggg ttttagagga aacgggtga ggtgcgcgct cgaaccgagg    117480
ttagacgctg ctggagctct ctaccctgaa aaggcaaggg cggacaaaat gcttggttgg   117540
agcggcgcct aatggtaaaa gggaacgcgg gccatggcct ctcccagctg ggtggtagc    117600
tccgcccac tagaaaccca aaagccagca ccctaagctc ggccgggcag acgcaggccg    117660
```

```
agtatgcccg cagagtgatg cctcaagcgg cagagccgga gtagcgccgt agttttggct   117720
cgagaacagc gaaggagaag agagcagata agtatgaagc caagttggta agccgtcccc   117780
cgggagctct tacctccaca agccgagaag ggagcaccaa aagcgggcaa gcctgccaag   117840
agtaaatcga tgtcctttga ggagatggtt ggtctagttg agctgagagg ctctctagtc   117900
tgcgatgcta cgatgagtga gcaacaggtg ctatatacta caacgatggg gtttgtacct   117960
cccccaatgg gagggggccaa cccacaaagg ccgtttggat tggctggctg cgatgggcgg   118020
tgggcgtgta tccgttccaa ccaatgatac actagtgtac aattttcatt tacatgcgcc   118080
taacgccttc ccctagctct acccaatggc aattggtatg tcattttttaa tttgcatgtg   118140
tttcctccca gggaagcgcg tcgcaccaac aggaggtagc cgagcacatc tcatatgcat   118200
aaagatggac gccaactgcc gccatgacac ttccgtgcat atatcatttg catgcatctc   118260
ctccccggta gagcgtcgca ccaactaggg tccgtatctc acatctcata tgcataaaga   118320
ggaaggcgct gtggtgccac gacacttcct ggtaaatatc atctgcatac aaatgagcct   118380
gggaggagca cggggagttg tatgcgaaat taatttttaat aaaaatggcg cgtgcgttat   118440
ttcccaagga agcggaaatg gcgcacctgc aaagggaggg ggcaatgggc ggtgggcggt   118500
aactcatttg ttttgtaatt tcctgtgaat ctcattaaag tttaaccaat taaaacacgt   118560
atcgttttttt gtgtatgaaa tgggcgggat actatctacg tggaccaatt tgcatattat   118620
atgaaaacta accgcatgat ggcgctattt tttaaacact cgatttacat gcactttttat   118680
atacgccctt gtggtggcgc agttacacgt taacaggtgc agtttataca gataaccacc   118740
atgtggtgct ctagatcgca gtccatcgta acgacattct atgacgctat acactcagta   118800
caacccacgc cccctctacg taacacattt cccaccctat attcaaataa gtatgtgggt   118860
tgggtctatt aagatcaatg ggagggggta ccggggggaa atatacacgc ccattttcac   118920
ctcccgcccc cacccccatcc aatttgattt ctgtttatcg gccaactaaa agtaaaaacc   118980
gtagaaccgt gtaagcggtt aagcgcttta cgttttacta caggtgtgag aatgtagtag   119040
aaaaataaga ttcaaccacc catcagtaac tccacgacat acatcttgcg ggtctgccat   119100
ttataattaa acgacccccc cttagttttt ttttattgct aatgcgtaaa cctgccccat   119160
gcccccagta caaacaaggg gggggggggca ctaaaaattt ttgcgcgaaa aaaaaaacgt   119220
gggtgatata cggcgggtat ggatatgggg gggggcaata aaagttttta cgatataaac   119280
ggcaacgtac ggtttacggt gtgcgtgtgg ggggggcgca ctaaaatacg gttactaacg   119340
cacccccagcg tatggcgaga gtggttgggt aggttgctag ctggcacagt gccatgcgcg   119400
ctcccgagat attacgtaac ccggataaga agtgcgaaca tgtagtgttc gcactttgtt   119460
acaataagta ttataactta ttagtgattg gtgcgaacgg cacctatacc caatcaggat   119520
tgagtataaa aaccacgtgc catgtttcca attttgtccg ataatcgata acctattatt   119580
aaagaaggcg tggtgaagta catgtatacg ccttctggaa ggcgtggaac atgggactag   119640
tgtatatatt agccagcgcc tcaccatgtg aagggacaca cgcagctcca aaactcaagc   119700
cgtttgatac gcatccactg caaaacctat cgaggtaggt gtggcgtacc gtcgtggggg   119760
tggtcgtggg ggtggtcgtg gggtggtcg tgggggtggt cgtgggggtg gtcgtggggg   119820
tggtcgtggg ggtggtcgtg gggtggtcg tgggggtggt cgtgggggtg gtcgtggggg   119880
tggtcgtggg ggtggtcgtg gggtggtcg tgggggtggt cgtgggggtg gtcgtggggg   119940
tggtcgtgac cattttctc attcgcttat aggctcgagc gccaatcgcg accccgcct    120000
cgttttggcc gaacaaaacg ccccgtgtct actcgatttg cgccaagcga gcccagaccg   120060
```

```
cagcaaccat gccacacggc cagccatgtg gggcgtgcga cggatcctgc cgcatgtcac   120120
agcgggggc gccgtccacc agccccatca taccctccct gtcccctca tctggtggga    120180
acccatcccc acgctccagc cagcgcatag actccgtgcg cgtgcccgcc aggcttcccg   120240
gcggctctga ccatccggaa tacggcctgc cgctctcgcc gaggtcgctg cgcccgtacc   120300
tgtctcgggg gccgggagcg ttctgcgctc cgccgtggcg cccagacgta aaccgcctcg   120360
ccggggacgt caatcgcttg tttaggggta tatctacttc atctattcac gtaacagaag   120420
actcgcgcgt cctgcgcagg gtgctgttgg acttttacgc tatggggtac acgcatgcac   120480
gccctaccct agaatgttgg caggccctt tgcagctgat gccggagcag agccttccgc    120540
tgcgggccac gctgcgtgcc ataaactcgg aagacaagta cgagcagagg tttcttgatc   120600
cgcccagcaa gccacccaaa accctctttg gggaagagtg cgaagttagc ggcgacgagt   120660
ctccgtcaga ggaggaagag gctagcggaa atagcaccat ttcagagttt agtcccgagg   120720
aagagagcgc cagcagcgac tttgaaagct ttcggacga ggaagacgac tcttgttgca    120780
cgggaaagtg gtctagcagc gaaagcgata gcgaggcaga tgtccccacc aaccctccca   120840
ccacacgtgc ccgcgctgct caaaagcgcc gcgggcgccc tgtccccaaa ggcgggcgcc   120900
cggccaaaag cgctcgccgg tgattaaaag cacacgcaac caaaaccgca taggtagtta   120960
ccgtttttag tagccctatt agttcccacc ataaccccca acacgccgca gttaattcat   121020
atgtagcatc aatgcgcgtc tatcccgct tataaccaaa taaatcgttg actaaccttc    121080
atcgagcaca atctcgtgtt tgtcgcgtgc atgcagcaaa cggtgggtgg tattgggtt    121140
gggcgagcgc tatacagaag atctccccg ccgtcgtaac acgcgttccc cgttaaacgt    121200
gcaagccgtg tgcgtacgcc caacggtgcc cctttatcgc cgtatgaata tgtgaagagc   121260
gataacagca cccacgcaaa cgggccggcc ggggtgagat gtgtgccgga aggcatgatg   121320
gaagaacaat aggatagagg cacgggcggg gctatgcac atgcgattcc ccgccccgcc    121380
gaggaaatac ccctggtacc cggccgcgcc cggtcagtgc gcctaggctc cacgctcccg   121440
agagttatgg actgcgcgta cggttccccc atggcgtag acgggggtgt gagaaccggg    121500
ggagactgcg gaggcggtga ggggctgtac cccaccagca cggacacggc cgcgcacgcg   121560
gtgtcgcttc cccgctcagt gggcgaattc gcgtcagcgg tgcgcgctat gtccgcggat   121620
gccgctgacg cgctcaggag aggagcgggg cctccccccg aaatctggcc gcgcgcgtac   121680
cgcatgttct gcgaactatt cggccgatat gcggtcagcc ccatgcccgt tttccactcg   121740
gcggacccgc tacgccgcgc ggtggggagg tacctggtag acctaggcgc cgcgccggtg   121800
gagacccacg ctgagctcag cacccgcctc cttttttgcg cccactggtg ctgcctgggg   121860
cacgcgttcg gctgttcccg ccaggccatg tacgagcgcg agtgcgcacg ttttttcgaa   121920
gcgagactcg ggatcgggga gacccccccca gccgactcgg agcgctactg ggtggcgctg   121980
ctggacatgg cggggccga tccggagcta tttccccgac acgccgccgc cgccgcgtac    122040
ctgcgtaccc gaggccgaaa gctcccgctc ccctgcccc acaggcgggg ttccgcgacg    122100
gtatcggtgg ccagtcaatc aataaacttt taaactttct atattgcata aaccaaagcg   122160
ttcaagtacc tccccacctc cccacctccc cacctcccca cctccccacc tcccacctc    122220
cccacctccc cacctcccca cctcccacc tccccacctc cccacctccc cacctcccca    122280
cctccccacc tccccacctc cccacctccc cacctcccca cctccgatag ggggtgggaa   122340
acaagctacc cgggccatcg aacaaacgcg cagaggctgg ggttctctac tatgaggttt   122400
```

```
tattgactgg cgggtgcggg acagcagggt gggaaatcgt ggcggtagag gcgatggccg 122460
cgtccgcggg ttcgcgtcac tgaaatacgc gcgcgaggaa cgccccgacg atcccggata 122520
tcgcgcacag gacagcgacg agcacgacgc cggcgaccgt gagggccacg cgtcgccgcc 122580
tgtgtcgccg cgcctgccgc cggccgaccc tctggatgaa caggctggcg ttaaacagca 122640
acgaccaggt tgtctgagtt tttatcaacc gaatttccat tttttggctg ttgggcatct 122700
ctgggatgtg catctaaaac ttgatcaccg atgcttgatt gttgagcatt tctggtatgc 122760
tgttttggtt caccctgaag atctaggcgt aaaaaggttg tgtttatttc ctgaaacgca 122820
tcttctgtaa cgtttgactg gaactccat ccatgtttta gtacatagcg cctagatggt 122880
atgggcaatt tctttggacc agtccagttt gacatttcct cttctagcca ttttggaacc 122940
tcagcaaatg cttcttcaag cagatcactc ggatcgacgc tgtaagcatc ttttgtgtct 123000
gctctgatgt agtaaagtgt ttctgatggt tgattttctc cctcgtagta ctcttctgga 123060
tataaaatg gcaatcggac aaatgttcca tcgtccagct gcttgtaaaa tcgcttttca 123120
aactttggag gtggtagggc cttaaagctg agcacttcgc catcaacttt actttcaact 123180
ggaacacggc caggcatctc actcggtcca actggaaagt agccttcggg tacctttgca 123240
aagtacccct cgttcatttc ttcgcgacaa cgtctgaagt atggccgccc aagcatatac 123300
ttatatgggt taaagagata tttgcgcggt tcttgagaag cgccgtcctt ggcgttggac 123360
tcgctcacag ttgcagatga aaaggtgggt gccaaaacta gatgcggtgg attagcgttg 123420
cggcggcgag caagattaca gcgaaaaact tcggtgcctg cagtggcggc tgtaagcatg 123480
tcggagctca tgtctaaaga tagacgtgaa gtttgtaagt aaaaatctca caggaaacca 123540
cacttggcaa agcgcagtga ctagcaaaga gcttccccaa ccttttaacg tctggctgtt 123600
ctatcaaaca cacccctag taggcgtgat ttccacgtca tttctgtggg tttccgggca 123660
gctgcacgag gagataggt gctaggtggt attgtagagt tggcttgcat cgacgtgcta 123720
acgcgctgca agtttttgcc ttttgatggc tgtggagtaa acacatctt atcgtttagg 123780
ctggctgtag actcttggca aaacaggcca ttataagttt ttttagaacg tcttttagtt 123840
tttgttctgt tagttatttg tggacataaa ttctcttgta aacgcatagg gtctacaacc 123900
gcataaatta accgcttaaa atttggcggg ggagatacaa aagatgattt atgttgtaat 123960
aaactgcgcg cgctctcagg gtggtcttgt ccgggtaaaa ccttttgttt tagtagatgc 124020
ttataatcca cggttgtcaa cggtattgtt tcgaatagtt ttccgcacac gaagctgggc 124080
tgccaagatt tattaaactc atcttcgatc tccacataca caattcgctt ggggcccggt 124140
atgaggttga acacaggcct gcataaatct gcagctccca aaacccatag gtggtatggc 124200
ctattgatga taatgctgga gttgaggtag ttgtagccgg atagtacaga aagccactct 124260
atactaatgc caattctatc ctcttgataa atcacgccat ttcttttctag gctatagca 124320
gtagccccc tagttctcac tataggcctg catgcttttg gcagggctaa gagactcgaa 124380
gaaaatttgt acaggtcagc agaacgcacc actattggta ttcctagagg ttctgaggct 124440
aatacaaaac atagtcgtcc caaaaactcc cacagttttc catctacgtc gatagaactg 124500
tcgggcaaag ctttatgcct gtcaaccacc atgacaactg taattaaaac cacacccatg 124560
ttattagcaa atgggtgtgt taaaccaacc caataaattt cagcagagct gctctagcta 124620
cacactttgt tgtgaaaaag acttgctgtg ttacgggatt cgtagcttta taagcacacg 124680
cccacagcat cggcatggaa aataaacaat acgaccacct attgtccgac tggctatccg 124740
gtaatattag cgaggcatct gaatcgatgg atacgacacc cccactacag ctttctgtac 124800
```

```
atcctcaaaa tccaagctgt ggggggcag  ccgctaatga ggacctgtac tcagacataa  124860
gcgatggcga ccttgaatgt agtgactgcg atagtgcatc tgagagcgat gaagacgatg  124920
acgatgggct aatgccccca aaagaaaagg cgaaggaagt ggctgcttca tttgggttca  124980
aggtcattaa aacgctaact cctggctcag agggcgtgt  tatggttgca acaaaggagg  125040
gccagccaga ccaggtcgta ttgaagattg gccaaaaggg aactacgctc atcgaagcca  125100
tgatgctaag aaacgtaaac cacccatgcg tgattaaaat gaaggacacc ctagtgtctg  125160
gtggaataac ttgcatggta ctacctcact acaattcgga tctgtacaca tttttgactc  125220
ggcgatcaac gcgtatacct attgatcagg cattgattat agaacgacag attctagagg  125280
ggctgcggta ccttcacgca cagcggatca tacacagaga tgttaagact gaaaatattt  125340
ttataaacag cgtcgatcaa gtgtgcatag cagactttgg agcagcacaa tttccggttg  125400
tggaccccat ggaccttggt ttggctggta ccgtggaaac taacgctccg gaagttttgg  125460
ccagagcaaa atacaattcg aaggtagaca tatggagcgc cggaatagtt ctgtttgaaa  125520
tgctcgcata tccatcaact ctatttgagg acccgccgag taccccacaa gagtatgtaa  125580
aaagctgtca ttctcaacta ctgagaataa tatcaaagct aaagataaac cctgaggagt  125640
ttccacggga accagagtct aggctcgtgc gcggatacat cgaatacgcc agcctagagc  125700
gtaagccaca tacgcgctat ccttgcttcc agcgcgtgaa cctacacatt gacggggaat  125760
ttttgatcca taaaatgcta gcgttcaatg ctgcgatgcg cccatccgca gaagagttgt  125820
tgtcctaccc aatgtttatg aatctgtagg atgactaaca gatttggggt ggagacggcg  125880
tgggcgatac tgtataaagt tgtactactt accagcccag tcagtgtgct gtagtgccac  125940
cacctgtaaa gctgtgataa gctgcagtta tgttggctgt gggagcaact ctgtgtttac  126000
tgagtttcct aactggcgct actggacggc tagctcctga cgacctctgc tatgcagaac  126060
cccgcaaaac cggtcccatg ccccgctcaa aacctaaaca ccaacccta  ctatttgaag  126120
ccccaaaggt tgctcttacg gcagagtcaa agggttgtca actaatattg ttagaccctc  126180
caatagacat gggctatcgc ttagaggaca agataaacgc ttccattgct tggttttttg  126240
actttggtaa ttgtcgaatg cccatcgcat acagagagta ctatgattgc gttggcaacg  126300
caatcccatc tccagaaaca tgtgatggtt actcatttac acttgttaaa acagagggtg  126360
tagttgagtt taccatcgta aacatgagct tactgttgca gcctggaata tacgacagtg  126420
gaagttttat atacagcgcc cttctagata tggatgtatt gactgacgc  gtaatttga   126480
acgtggagaa cgacactaac tatccatgcg gaatgactca cggcctcact gcttatggca  126540
acatcaacgt agatgaaacc acgcacacaa ccccacatcc acgtgctgtc gggtgttttc  126600
cagaactcat taacttcgat gcatgggaaa acgttacatt cgaagaaatg gggataccag  126660
acccaaactc atttcttgat gatgagagtg attacccgaa tacaatggac tgttactcgt  126720
gggatttata cacatatccc aaaagcctga agcaggcaga ggggccccaa accttgttaa  126780
taggtgcagt tggactcaga atactcgcgc aagcatggaa gtttgttgaa aatgaaacct  126840
acagcagcat acgcgcagat gctaaggagt tgatgttaca cagccagtcc tgtacagctg  126900
attcgtcgca agaaagcaca tctatgaaga ataaccctat ttattcagag gggagcctca  126960
tgctaaacgt tcagcacgat gacagcatcc acacggaagg gatgaagaat aaccctgttt  127020
attcagagag cctcatgcta aacgtccagc acgatgacag catccacacc gggggtgtgt  127080
tgcatggcct ccaagactgc gacaaccagc tcaaaactgt gtatatttgc ctagctctta  127140
```

```
ttggactcgg cacatgtgcc atgataggac taatagttta cattttttgtg ctaaggtcaa 127200
aaatatcttc ccacaattta tcgcgctcac aaaatgtaaa acatagaaac tatcatcgac 127260
ttgagtacgt tgcataatac atgtcaaata aaagttaaaa attaaacatt gttgtctgta 127320
ataactgagt gtggttttaa aaatactaaa tcgcggcaat gttgcaaacg gtcctctaca 127380
aaagagaggg ttgatggtat atatgaaata gtcccccctt catgagtttc gcgtagaggt 127440
ctaacttaac agcgatgggg ttcatctatg ttagcagaat actgctatgc ctggcagttg 127500
gtatttatgc catagggca acaaccgcgg aaactactac cgctagctcg tcaacttctg 127560
gaagtaccca gtccgcgtct agcgaaacta atagtagtag ttcccccacc acgggcccca 127620
ctaccacatc ttcccaaaca tcctcttcta actctaccca aacaccttca acgtctcaaa 127680
cacccactac tagctcgtct accgtttcca caactactac ttcaaactca acaaacgaaa 127740
gttctactgc gacggctaca tcaactgcaa ctccaacatc cacagaagct tctacgtcaa 127800
caactacatc aacctcggtg tccgaatcac caacatcaac cacagctacc acagctgcta 127860
ctaccacaac tgaatccacc acaactgaat ccaccacagc tgctactacc acagctgcta 127920
ctaccacagc tgctactacc acagctgcta ctaccacagc tgctactacc acagctgcta 127980
ctaccacagc tgctactacc acagctgcta ctaccacagc tgctactacc acagctgcta 128040
ctaccacagc tgctactacc acagctgcta ctaccacagc tgctactacc acagctgcta 128100
ctaccacagc tgctactacc acagctgcta ctaccacagc tgctactacc acagctgcta 128160
ctaccacagc tgctactacc acagctgcta ctaccacagc tgctactacc acagctgcta 128220
cgccaacaga gtcaagcgag gcatcttcca cattagcggc caccacagct gacaccacag 128280
ctgacaccac agctgacacc acagctgaca ccacagctga caccacagct gacaccacag 128340
ctgacaccac agctgacacc acaactactt cagggtccac cgcagctaac acaacctcta 128400
ccacatcggc cactgtaaca atagctccaa caacatttac gactaagtat accacaaatt 128460
cttcgtctac cgggaaaata aacacctcca aaaatacacc aaaaccccca caatatacta 128520
cagcttccac ggagaaacca actaaggcga attcttaac agcggcgaac gcaacgggct 128580
tatccaccaa accccaact ttattcacgc ccacacaaac aagcccaaca cctagcgaaa 128640
cgtctgtggg taccagagag tacttggcaa tcacctatgg aaaaactaca tatcaaactc 128700
ccactaatgc cctaagttca actaatgttt ggcctgccag agataatagt tcaactcaac 128760
aaacaaccca acatgactac atagtaacta cccaaaaact tacgggacat ttacaccagc 128820
acaagggccg cgcaaatggt aaaaacgtca ataataagtc tcacccatca gtgcgaccag 128880
ataggttaac gccacacacg gattaccact attactacga tgataccgat tacccacagg 128940
acggttcatt tgagcgtgta accccacccc cacaaggcca accaaacata gagctgggtg 129000
tggctacgct tagaaaaaac ttttttggtgg caacgtgtac cgtggaggct actatgggct 129060
tgtcattttt ttggaaaatt ggcaacgcca gcgttgacgc gtttagcagg ggaacaacgc 129120
atacgcgagt gatgcgcaat gggtcacctg tttatgcgct aatatctacg ctaaaaattc 129180
cgtgggttaa tgtgattcca ttaaccgaga ttacttgcgc tgcgtgtaaa gacaattta 129240
ttggcaatga agctgatctc acctcgtgca ccgttaaatc aaccacaata ccatgtccag 129300
gccaacaacg cacccatatt ttcttttcta tgaaggggga cagagctgtt tgtattacat 129360
cagaacttgc gtccccacca actataacat ggtcggttgg atcaaacagg ttgcacaaca 129420
atggatttac gcaaacgtgg tatgaaatac aacctggagt gtgtggaata ttgcgtagcg 129480
aggtccacat tagccgcccg tcttggcgcg ttggtgcccc aacgcgcgat tatctttgcg 129540
```

```
aagccacagt atcagatgca aagacgagtg attacaaggt tttacctaac gcttactcga  129600
cttccaactt cgctttagtg gctgcgacca cgctaacagt aacaattta tgtttgctgt  129660 gctgcttgta ctgtatgtta acacgccccc gggcgtccgt atattaactc aaaaattatc  129720
tctttggctt tacaacccgt ggtagcgtgt gtagaagcgc gccgctactt tagtgggttt  129780
tttttaataa acgcggtatg tctaccttca agcctatgat gaacggatgt ttggtgtttg  129840
cggctattat aacgctcttg agttttatgc tatctctggg aacatgcgaa aattacaggc  129900
gtgtggttcg ggggaaccaa aatcagcgac ccgagtttcc accacccga tacaacttta  129960 caattgtgac aacatacaat gaaacgtcgc taccatcacc gtttattaac gaccaagtaa  130020
aaattgttga cgttcgaacc gtggctgcta cacgcccatg tgaaatgata gcgctgattg  130080
caaaaacaaa cgtagactca attataaaag agctagatgc tgcccacaaa acatattccg  130140
caagactgac ttggtttaaa attacgccaa catgcgcaac gccaatccat gatgttgttt  130200
atatgaaatg caatccaaag ttattatttg gaatgtgtga tgagcgatca aatatattat  130260
ggctcaatag tttgattaca actgctgcgg agacagacga cgaacttgga cttgtattgg  130320
cctcccctgc ccatagctac tctggactgt ataggcgcgt tatacaaatt gatggaaggc  130380
gaatttatac agacttttcc gtaacaattc cgagcagcca ttgtccgctt tcttttgagc  130440
agaactttgg taatcctgat cgctgtaaaa ctcctgagca atactcgcgg ggtgaagtat  130500
atacaagtcg ttttctcagt gaattcaact acagacaagg tgtacattta gcatgggtaa  130560
aacactggtt tgtgcaagat ggtggaaacc ttccagtaca gttttacgaa gcccaggcgt  130620
ttgcaagacc agtaccaccg gataatcacc caggatttga ttcggtcgaa tcggaaataa  130680
cacaaaataa aacaaaccca aagcaagaac aggcaagtcc aaaacccaat ccaccattta  130740
agtggcccag tataaaacaa ttggccccaa gaatcgatga ggtggataat gccaagaaa  130800 tcaccacaaa aaaaccacca gcgtctaata gcaactctac gtttattgga gttgttattg  130860
gtttgggtgt tgttggcttg atatcagttg gagcaatttt atacgtttgt tggcgtcgaa  130920
gaaagtcaca gaacaagtct ggaaaaaatg gctcacctag cctacgctct acctttaagg  130980
atgtcaaata tactcagctt ccgtaaacag tgttgcgtaa catgctggga ggtacccacg  131040
gccttaaagc tacgctgttt ggagataaaa cgcacaactt acatcaaacg cgacacagca  131100
agtagtcgct atggccaaac atactgtatt gtttactgct tcgatattac tagctatatc  131160
tatgtgtgca accgcaatta tatcgcgg agaacatatg agcatgtacc tcaacgccag  131220
ttcagagttt gcagtgtacc caaaagacaa gtctctagta gttgttggac acatgctgtt  131280
tctagatgga caacgactcc caactaccaa ctatagtgga cttatcgagt tgattcatca  131340
caactactct aggggctgct actctgtcat tcaaacaata tcgtatgaat catgcccgcg  131400
tgtggccaat aatgctttca gatcttgcct tcacaaaact tctaatcaca accaggacta  131460 cttttcatgtg aacacctctg tagaaactaa cgttctctta aacattaccc ggccacagcc  131520
cgcagattcc ggggcgtata tcctccgcgt aaaactcaac cacgctccca cggcagatgt  131580
ttttggtgtt tcggccttcg tttatgattt acaatctaac acagttccag agccagttcc  131640
aaccgctaaa gaaaccagta atgtgtttac acggacacct gccctgcac ctgctaacac  131700 ctctaccaaa actggctcca acacaacatc gtctcaatcg acgtggttgt atactccgac  131760
tcctcgccca gccttggaaa cacacctcac tacagcaccg gctaacgaaa ctgtagttag  131820
tggtgatacc gccatgctct gtcatgggtt tcggccatca accgcagtac caacaatata  131880
```

```
catgcatcta ttaggactta ctggcaacct acccgaagat gttttgctaa tagaggactc   131940
ggagattctt cgtacaccac cccccaaacc gcaaaccact tcttccagaa ctgagggtga   132000
tgactttaag caaacaaact caacttcccc aaaatcgcgc aataagattg ttgcgatggt   132060
ggttattcca accgcgtgtg tgttaatgtt gttgctggtg gttgttggtg caatcatcaa   132120
cggtgccgtg cgcaaacatt ttctgagctg cgcaagccgc agaatctacc gctcaagaca   132180
aggtggagtt tcatcgtcag agtggagccg gttggcgtgt gggcccacct tagcagcctc   132240
atcagaatcg ctggctgatg atacaacggc ctcgccacca tcccacaagc ctacagaaaa   132300
acctacaccg gaaagcgatc ctcttctaga acagttgaac cgtaaactgg aggccataaa   132360
agaggaagac taataatggg gggttttaaa gtttatgtat tattgtttct atatattaaa   132420
aattgttgaa atataaatat cttatgtaat gtttacatta ttcgtgattg ggacggtctt   132480
aggggaggtg gtgcaactag ggtttaaagc cctgaatgtt ctggagtgaa cccacagttc   132540
tcctctttgg cgtcaaagca atcagacgtc caatctaaag tagaacgtca caatggagct   132600
gttagactcc cgccgtgctt ttttcttttt tgtactaata acagtactcg atgcgtgggg   132660
agttcaacgg gttgaactca ccgagggggc atgggccatg atcgacggaa gagacgtttt   132720
aaccccaact aacacgacca ctagggttac aaaggcctgg acatttttgg aaaccccacc   132780
gggatgtgct ggtgatataa cagtcaagac tgtgtgcgta agcgctagtc tgtgcgaaga   132840
taacattata ataggaaatc actgtaacct actaaccggg gagcatggca ttgcgcttgc   132900
agagtttaac gtagttaacg gatcgctaca aaggaccaaa gatgtgtact tgttaatgg   132960 aacagttttt cctattctgg cagaaacccg cagcgtgtta caaattcaga gggcaacccc   133020
atccatagct ggagtttata ctcttcatgt ttccatgaac ggacaaataa aacactctgt   133080
tgtattgctc accgtaaaga aaccaccaac actaccacgc gtacatgtca agacgcctcc   133140
acccatacta gttcccaggt tacaccagaa ggcacataca gatttcatag tgcgcggata   133200
ccactcgcgc gtatatgctg tgggtgagtc ctttgacctg tctgtgcacc tagaatccca   133260
catacaggag tctagcttta acgctgaaat ccaatggtac tatatgaata cgtcatcgtc   133320
atcatgcgat ttgtttcgag tttttgaaac atgcattttt cacccaaccg ctatggcctg   133380
cctgcacccc gaacaacacg cctgctgctt tacatctccc gtcagggcta cgaagattct   133440
tcatcgagta tatggtaact gcagcaatcg tggatccaca tggccttctc ggtgccatag   133500
tactttgttg ggcgataggc cacattttat ccaaccggca ccaaacaggg tagacttgtt   133560
attcaaagat atacccgaat cagcgaccgg gttgtatgtg tttgtgttat tgtacaacgg   133620
acatccggag gcgtggacgt atacgttgct ttctacagca aatcacttta tgaacgtgct   133680 tacgaccga acacgcccac ggctaggaga gcacttttat acggaccacg ggcaccagct   133740
tttcactcct catccatctg aggcaacaac tcaagagttg ggagcttgga ccagacacta   133800
cctcgctttt ttgttgatca taatctgcac ctgtgccgcg ctgctaattg ccttggtggt   133860
gtggggctgc attctataca tccgaagcaa ccgcaagccg tatgaagtac taaacccgtt   133920
tgaaacggtt tacacaagcg ttcccagcaa cgatccaacc gacgaagtct tggtatttga   133980
gcgtctggct tcagactccg acgactcctt cgactcaagt tcagacgaag aattggaact   134040
accacaacct ccaccagccg cacaacttca gccgtatagt tcactagaaa gtgcagacgc   134100
gtcgagaggc cggtcgggtt tcaaggtctg gttccgcgat acaccagagg cgtctccgga   134160
gccgcttcat agaccaaccc cacccgtcgg accggactac agcaaggtcg cgtcaaagct   134220
caggtctatc ctaaaatgaa tttcaacaac aaagataccg cttgcgcagg aaatgtgtgc   134280
```

-continued

```
tatgctgaag gactacgcaa tcgtaagtag tccggttcga aacagcacct tcgaagagta   134340
tctcgactca cttaataatt acgaccgccg tttgagagct gactcaactt cagattcgga   134400
ctctgagtgt aaaaccccct ctgaagacga ttcaaatatc aaagagttta caaaaattat   134460
ggatctaaaa ccaccatctc cagaacccga gccagcggca gcagaagagc cggttagcac   134520
cgccgtttac atcttaaacg agtgggtggc cccaatgctt ggacattttc tcgcaatgta   134580
tgtgtatgat ttgcttttta attaaaccaa agattgtcac cacaatattt agttgtttgt   134640
tttatatgca agcgctaaac ccaacactaa agggttatat attatcccgg gggacttttg   134700
cagtaatata tattttgctg ccagtgttca ctggtgctca gtgcgcccaa ccagcacagc   134760
ccgtttaat ctctatacgc tctgtctatt ttccttaccc cgctccgtaa cacctcactt   134820
tctctcatac taccgccttt ttcacgctac tccaacagct cctacaactt acagttacca   134880
ccacaccatc gcccttaacc accaagccac atgggtgagc ctgaacctgt ggtagcgttg   134940
actgaagacg ctccactgtc cgtgtacaac cccaactaca ggagtgataa cgcactcata   135000
gccgatggtg attccagccc cattgggggg gattgttgtc cggcagaggc ggtggctgcc   135060
gctgaggagg tagctacggc tgctttggct tctgaagaaa tctacgagat gcatatcaaa   135120
tcctgcattt cttccaccac atgcggtgac cataataact caatcggcgt aacatcgggg   135180
cttactgttt gcgcggctga gtgtcacccc ccgtccccag aggccgtagg tattgaggat   135240
gtggtggttg tgcaaactgc ggctaccact aatggcccct cagatacagt acccgccagt   135300
gctgcggcct cagtgattag cgatgataac ggctgtgtac cgctgctagg gtcacgcctg   135360
gaactagaaa actatgactt ggagtctggc tgctactaca gcgaaagcga caacgaaacc   135420
gccagcctgt tcatccagag ggtcggccgg cggcaggcgc ggcgacacag gcggcgacgc   135480
gtggccctca cggtcgccgg cgtcgtgctc gtcgctgtcc tgtgcgcgat atccgggatc   135540
gtcggggcgt tcctcgcgcg cgtatttcag tgacgcgaac ccgcggacgc ggccatcgcc   135600
tctaccgcca cgatttccca ccctgctgtc ccgcacccgc cagtcaataa aacctcatag   135660
tagagaaccc cagcctctgc gcgtttgttc gatggcccgg gtagcttgtt cccaccccc   135720
tatcggaggt ggggaggtgg ggaggtgggg aggtggggag gtggggaggt ggggaggtgg   135780
ggaggtgggg aggtggggag gtggggaggt ggggaggtgg ggaggtgggg aggtggggag   135840
gtggggaggt ggggaggtgg ggaggtgggg aggtggggag gtacttgaac gctttggttt   135900
atgcaatata gaaagtttaa aagtttattg attgactggc caccgatacc gtcgcggaac   135960
ccgcctgtgg gggcagggg agcgggagct ttcggcctcg ggtacgcagg tacgcggcgg   136020
cggcggcgtg tcggggaaat agctccggat cggcccccgc catgtccagc agcgccaccc   136080
agtagcgctc cgagtcggct gggggggtct ccccgatccc gagtctcgct tcgaaaaacc   136140
gtgcgcactc gcgctcgtac atggcctggc gggaacagcc gaacgcgtgc ccaggcagc   136200
accagtgggc gcaaaaaagg aggcgggtgc tgagctcagc gtgggtctcc accggcgcgg   136260
cgcctaggtc taccaggtac ctccccaccg cgcggcgtag cgggtccgcc gagtggaaaa   136320
cgggcatggg gctgaccgca tatcggccga atagttcgca gaacatgcgg tacgcgcgcg   136380
gccagatttc gggggaggc cccgctcctc tcctgagcgc gtcagcggca tccgcggaca   136440
tagcgcgcac cgctgacgcg aattcgccca ctgagcgggg aagcgacacc gcgtgcgcgg   136500
ccgtgtccgt gctggtgggg tacagcccct caccgcctcc gcagtctccc ccggttctca   136560
caccccccgtc taccgccatg ggggaaccgt acgcgcagtc cataactctc gggagcgtgg   136620
```

```
agcctaggcg cactgaccgg gcgcggccgg gtaccagggg tatttcctcg gcggggcggg    136680
gaatcgcatg tgccatagcc ccgcccgtgc ctctatccta ttgttcttcc atcatgcctt    136740
ccggcacaca tctcaccccg gccggccgt ttgcgtgggt gctgttatcg ctcttcacat     136800
attcatacgg cgataaaggg gcaccgttgg gcgtacgcac acggcttgca cgtttaacgg    136860
ggaacgcgtg ttacgacggc gggggagatc ttctgtatag cgctcgccca accccaatac    136920
cacccaccgt ttgctgcatg cacgcgacaa acacgagatt gtgctcgatg aaggttagtc    136980
aacgatttat ttggttataa gcggggatag acgcgcattg atgctacata tgaattaact    137040
gcggcgtgtt gggggttatg gtgggaacta atagggctac taaaaacggt aactacctat    137100
gcggttttgg ttgcgtgtgc ttttaatcac cggcgagcgc ttttggccgg gcgcccgcct    137160
ttggggacag ggcgcccgcg gcgcttttga gcagcgcggg cacgtgtggt gggagggttg    137220
gtggggacat ctgcctcgct atcgctttcg ctgctagacc actttcccgt gcaacaagag    137280
tcgtcttcct cgtccgaaaa gctttcaaag tcgctgctgg cgctctcttc ctcgggacta    137340
aactctgaaa tggtgctatt tccgctagcc tcttcctcct ctgacggaga ctcgtcgccg    137400
ctaacttcgc actcttcccc aaagagggtt ttgggtggct tgctgggcgg atcaagaaac    137460
ctctgctcgt acttgtcttc cgagtttatg gcacgcagcg tggcccgcag cggaaggctc    137520
tgctccggca tcagctgcaa aagggcctgc caacattcta gggtagggcg tgcatgcgtg    137580
taccccatag cgtaaaagtc caacagcacc ctgcgcagga cgcgcgagtc ttctgttacg    137640
tgaatagatg aagtagatat accctaaac aagcgattga cgtccccggc gaggcggttt     137700
acgtctgggc gccacggcgg agcgcagaac gctcccggcc cccgagacag gtacgggcgc    137760
agcgacctcg gcgagagcgg caggccgtat tccggatggt cagagccgcc gggaagcctg    137820
gcgggcacgc gcacggagtc tatgcgctgg ctggagcgtg gggatgggtt cccaccagat    137880
gaggggggaca gggagggtat gatggggctg gtggacggcg cccccgctg tgacatgcgg     137940
caggatccgt cgcacgcccc acatggctgg ccgtgtggca tggttgctgc ggtctgggct    138000
cgcttggcgc aaatcgagta gacacggggc gttttgttcg gccaaaacga ggcggggtc     138060
gcgattggcg ctcgagccta taagcgaatg agaaaaatgg tcacgaccac ccccacgacc    138120
accccacga ccacccccac gaccaccccc acgaccaccc ccacgaccac ccccacgacc     138180
accccacga ccacccccac gaccaccccc acgaccaccc ccacgaccac ccccacgacc     138240
accccacga ccacccccac gaccaccccc acgaccaccc ccacgaccac ccccacgacg     138300
gtacgccaca cctacctcga taggttttgc agtggatgcg tatcaaacgg cttgagtttt    138360
ggagctgcgt gtgtcccttc acatggtgag gcgctggcta atatatacac tagtcccatg    138420
ttccacgcct tccagaaggc gtatacatgt acttcaccac gccttcttta ataataggtt    138480
atcgattatc ggacaaaatt ggaaacatgg cacgtggttt ttatactcaa tcctgattgg    138540
gtataggtgc cgttcgcacc aatcactaat aagttataat acttattgta acaaagtgcg    138600
aacactacat gttcgcactt cttatccggg ttacgtaata tctcgggagc gcgcatggca    138660
ctgtgccagc tagcaaccta cccaaccact ctcgccatac gctggggtgc gttagtaacc    138720
gtatttagt gcgcccccc cacacgcaca ccgtaaaccg tacgttgccg tttatatcgt      138780
aaaaactttt attgccccccc cccatatcca tacccgccgt atatcaccca cgttttttt    138840
ttcgcgcaaa aattttttagt gcccccccc ccttgtttgt actggggca tgggcaggt     138900
ttacgcatta gcaataaaaa aaactaagg ggggtcgtt taattataaa tggcagaccc     138960
gcaagatgta tgtcgtggag ttactgatgg gtggttgaat cttattttc tactacattc     139020
```

```
tcacacctgt agtaaaacgt aaagcgctta accgcttaca cggttctacg gttttacttt 139080
ttagttggcc gataaacaga aatcaaattg gatggggtgg gggcgggagg tgaaaatggg 139140
cgtgtatatt tcccccggt accccctccc attgatctta atagaccaa cccacatact 139200
tatttgaata tagggtggga aatgtgttac gtagagggg cgtgggttgt actgagtgta 139260
tagcgtcata gaatgtcgtt acgatggact gcgatctaga gcaccacatg gtggttatct 139320
gtataaactg cacctgttaa cgtgtaactg cgccaccaca agggcgtata taaaagtgca 139380
tgtaaatcga gtgtttaaaa aatagcgcca tcatgcggtt agttttcata taatatgcaa 139440
attggtccac gtagatagta tcccgcccat ttcatacaca aaaaacgata cgtgttttaa 139500
ttggttaaac tttaatgaga ttcacaggaa attacaaaac aaatgagtta ccgcccaccg 139560
cccattgccc cctccctttg caggtgcgcc atttccgctt ccttgggaaa taacgcacgc 139620
gccattttta ttaaaattaa tttcgcatac aactccccgt gctcctccca ggctcatttg 139680
tatgcagatg atatttacca ggaagtgtcg tggcaccaca gcgccttcct ctttatgcat 139740
atgagatgtg agatacggac cctagttggt gcgacgctct accggggagg agatgcatgc 139800
aaatgatata tgcacggaag tgtcatggcg gcagttggcg tccatcttta tgcatatgag 139860
atgtgctcgg ctacctcctg ttggtgcgac gcgcttccct gggaggaaac acatgcaaat 139920
taaaaatgac ataccaattg ccattgggta gagctagggg aaggcgttag gcgcatgtaa 139980
atgaaaattg tacactagtg tatcattggt tggaacggat acacgccac cgcccatcgc 140040
agccagccaa tccaaacggc ctttgtgggt tggcccctcc cattgggga ggtacaaacc 140100
ccatcgttgt agtatatagc acctgttgct cactcatcgt agcatcgcag actagagagc 140160
ctctcagctc aactagacca accatctcct caaaggacat cgatttactc ttggcaggct 140220
tgcccgcttt tggtgctccc ttctcggctt gtggaggtaa gagctcccgg gggacggctt 140280
accaacttgg cttcatactt atctgctctc ttctccttcg ctgttctcga gccaaaacta 140340
cggcgctact ccggctctgc cgcttgaggc atcactctgc gggcatactc ggcctgcgtc 140400
tgcccggccg agcttagggt gctggctttt gggtttctag tggggcggag ctaccacccc 140460
agctgggaga ggccatggcc cgcgttccct tttaccatta ggcgccgctc caaccaagca 140520
ttttgtccgc ccttgccttt tcagggtaga gagctccagc agcgtctaac ctcggttcga 140580
gcgcgcacct cacccgttct cctctaaaac ccgggagaga gcgagccatg ccagccagc 140640
gcagcgattt tgctccggac ctctacgact tcatcgagag caacaacctg gacgaggaca 140700
acctcatccg cgcagccagc gcggccgaag aggggttcca taccccggcc gccccggatc 140760
tgctgtacgg aagccagggg atgtttgggg tggacgacgc gcccttggcc accccggcgg 140820
tagtcatccc gccgccttcc ccggccccg agcccgcgg cgggaaggca aagcggtctc 140880
cggccagagc agcagtgccg gcatcgcccg ctcataaccc cgctccgggg ctcgccgaga 140940
tgctgaagat ggttcactcg tccgcggcta caggggccgg tcgcagggac accggatcat 141000
cgggcggagg tgcctataac cagggcaccg ggagcgacac cgagacctgc ccgggtctc 141060
ccggggccga gtttccaccc tcggcctccc ccgaggggag gccggcgcca aggggccgga 141120
gcatctccat atcatcgtcg tcctcgtcct cctcatcgac ggaagaccaa gccgatggtg 141180
cgggggcgag cagctcgtct tcgtcttcct ccgaagacag tgacagcgat gatgggggcg 141240
aagagaaaac tcctcgcccc catccctcgc cgagcgccgc aaaaacccaa ccggccaccg 141300
ggtcccctgg gcagattagc ggggatcgta tagcccctgg atcgtacacc ccaaagagcg 141360
```

```
gacgctcaga gaaggggcac caaagccccg tcggcgcttt tgcggcttca accggcgctc  141420
ccaccccgag taacccgggc gggcccctcg ccccgggagc tcgcatttta gagtacctgg  141480
aggggggttag ggacgccaat ctggccaaga cgctggagaa gcccgacccg agaatgtctc  141540
ctccagggca gagcccacac agagctccca aggaccagcg gcccaagtct gcgttggccg  141600
gggcctctaa gcgcaagcgc tgccaccaa gacccatacc ccagaccgcc gccacaaccg   141660
gggccgaaga ggccctcccg ggatgcgcgt gggacctgtt ggacatgaac tgctcctctc  141720
aggcccagg gctcggaacc tgccagcgcg agccgctgct cacaccatcc ggagacccat    141780
ggcccgggtc ggacgcccca ccaccgggga gggtgcgcta tggggaacc ggggactcgc    141840
gggacgggct ctgggatgac cccgaaatag ttctggccgc ctcgcgctac gccgaagccc  141900
agaccgccgt acctgtattt gtgcccgaga tgggggactc caccaagcag tacaacgctc  141960
tggtgcgcat ggtgtttgag aaccgcgagg ccatgtcttg gctgcaaaac tccaagctcg  142020
gcggggccga ccagaacctg gcccagttct gccagaagtt catacacgct ccccgcggac  142080
atgggtcctt catcacgggg agcgttgcta accccctgcc ccacatcggg gacgccatgg  142140
cggccgggaa tgctctatgg gcccttccgc acgcggcagc ctcggtgcc atgagccgcc    142200
gctacgaccg cacgcaaaag agcttcatac tccagagcct cagacgggcg tacgcggaca  142260
tggcctaccc gcgcgacgac gccggcggc aggactccca ctcggcgcc ggggtcacgg      142320
ctagctaccc ggcccaagca caggctgcct ctcaacagcc ggatccccg gccacatctg    142380
ctagggtccg cgaggagtac accagggtgt gcgcggccct cgggcacgg cgcaagacgg    142440
cggccgcggg tcctggtacc agaaccccca agcctaccgc cttcaggctc agggaactcg  142500
gagacgtctg cgtactggcc tgccaggccg ttttcgaagc cctacttcgc ctccgcggcg  142560
gagcgtccgc tgtccccggg cttgacccaa gcagagatcc ctctcccgcc tgccctcccg  142620
aagcgctgtg ctccaacccc gctgggctcg agactgctgc ctgcgccctc tacgaactca  142680
gggacctggt cgagcgtgcc aggctactcg gggactctga ccctatccac cgcctgggcc  142740
ccgacgagct gcgcctcgcg gtccgcgcgg ttctggttgt ggccagaacc gtcgcacccc  142800
tggtgcgcta caacgcggag ggagcccggg cccgggcctc ggcctggacc atcacccagg  142860
ccgtgtttag catacccagt ctggccgggg gcatgttggg ggaagccgtg ggcctgcttg  142920
cgcctcctcg gtcacagtct tcatcgtctg tcggcggcga cgttgggcag cagcagtccc  142980
tctcctcctc cgagggaagc cagacctccc gcatccccgc cttgtggccc actgttcccg  143040
ggaagcctct cgtggtgccg gccacgtctc actctcagtc ttcttcccg cagcaccaga    143100
gcagcggggg gccgacaacc tgctcccggg ccacccagac ccaggctcgc ccctcggggc  143160
agaaggctcg ctccccaccg gctgcctccc aggctatcct cggccaggag atgccggtct  143220
cctcgcaggg aggggcgga ccggcaccct acgcctcccc gaacgaccgt cccgtcaacg    143280
ggcgccccag gggcaagagc gggaagcggc gctccgagcc cctggagccg gcggcgggggg 143340
agctcccggg gtcccgcgga ggatacgacc cggtcgctcc ggtagagagc cctcctgccc  143400
caaagcgcag ggtgggtact caggcccctc gagctttggg gcccatgccg cccgagggc    143460
cacaccgccg gggaggcttc agacgcgttc cccatggaga ctgccacacg ccaccccccg  143520
gggactctgc ccgcgctgct tactgtcccc cagagctcgt ggctgagctg atagaccacc  143580
cgctgttccc cgaggcctgg cgcccccgc ttaccttcga ccccccaggcc ctggctacca  143640
tcgcagcccg ctgcaacggg cctccggcca gggagggcgc gcgctttgga gagctggctg  143700
ccagcggacc gctccgccgc cgggctgcct ggatgaacca gatccccgac cccgaagacg  143760
```

```
tgaaggtggt ggtgctctac tccccgctac cggacgagga cctgctgggt ggactcccaa    143820
ccacccgacc cggcggctcg cgccgggagc ccctctggtc cgacatcaag gggggctct     143880 cggcgctgct ggcggccctg gggaaccggg tactcacaaa gcggtcccac gcctgggctg    143940
gcaactggac tgggccccc  gacgtgtctg ccctaaacgc ccagggagtc ctgctcctct    144000
ccacggggga cttggccttt acaggctgca tcgagtactt gtgccttcgc ctgggctccg    144060
ccagacgcaa gctcctagtg ctggacgcgg tctccctaga ggactggccc caggacggtc    144120
ccgccatcag ccagtaccac atctacatgc gggccaccct caccctcgg  gtcgcctgcg    144180 ccgttcgctg gccccgggag cgccacctca gccgcgcggt cctcacttcc agcaccctct    144240
tcgggcccgg actgttcgcg agggccgagg ccgcgtttgc gcgcctctac ccgaactcgg    144300
agcccctgaa gctgtgtcgg gcggccaacg tggcctacac ggtggacacc cgggccggag    144360
agcgcacccg cgttccactg ccacctaggg agtaccgcca gcgggttctg ccagactacg    144420
acggctgcaa ggacatgaga gcccaggccg aggggctcgg gttccacgac ccagactttg    144480
aggagggcgc agcccagagc caccgcgcgg ccaaccgatg gggccttggg gcatggctgc    144540
gcccggtgta cctcgcctgc ggacggcgcg gagccggggc cgtggagccc gccgagctgc    144600
tgatcccaga actgctgagc gagttctgca gggtcgcgct gctggagccc gacgccgagg    144660
ctgaacccct ggtgatgccc atcacggagg ctcctcgccg ccgagccct  cgggttgagt    144720 gggagccggg gttcggtcag cgctcgacct cggtcctcca catgggcgcg ctggagctgt    144780
gccttcccga gtccgacgat gagcttgaga tcgacgacc  gggggacgtg gagctggttg    144840
cagatcaccc tggggtgagc ccggcagcgc agttgatccg acgcgccccc atcaagatag    144900
aggtggtatc ggacgaggag gacggagaag actggtgcaa cccctatctc acctaaacaa    144960
cagctccacc ctatggacac accaaaacaa aaatcagcac atccacaact atgtgttcgc    145020
ccgtcacaac gcaaactcca ccccaatcca tccccaaacg cgcccctgt  tgcttgcttc    145080 acaaaattac attaataaaa catgtttta  attattaatt ccggtgtggt ttgtgttagt    145140
gggcgggtta gtgggcgggt tagtgggcgg gttagtgggc gggttagtgg gcgggttagt    145200
gggcgggtta gtgggcgggt tagtgggcgg gttagtgggc gggttagtgg gcgggttagt    145260
gggcgggtta gtgggcgggt tagtgggcgg gttagtgggc gggttagtgg gcgggttagt    145320
gggcgggtta gtgggcgggt tagtgggcgg gttagtgggc gggttagtgg gcgggttagt    145380
gggcgggtta gtgggcgggt tagtgggcgg gttagtgggc gggttagtgg gcgggttagt    145440
gggcgggtta gtgggcgggt tagtgggtcc tgctcctccc cttcctgctc ctccccttcc    145500
gcttgcgtca cttccgcttc cggtcacacc cactttaagc cccccccaaa aagccacgcc    145560
ccctatttga atgagggccc gcgttatggg cggtggg                            145597
```